US006335016B1

(12) United States Patent
Baker et al.

(10) Patent No.: US 6,335,016 B1
(45) Date of Patent: *Jan. 1, 2002

(54) CHICKEN EMBRYO LETHAL ORPHAN (CELO) VIRUS

(75) Inventors: Adam Baker; Matthew Cotten, both of Vienna (AT); Susanna Chiocca, Milan (IT); Robert Kurzbauer, Kirchberg; Gotthold Schaffner, Vienna, both of (AT)

(73) Assignee: Boehringer Ingelheim International GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 10 days.

(21) Appl. No.: 09/171,461
(22) PCT Filed: Apr. 18, 1997
(86) PCT No.: PCT/EP97/01944
  § 371 Date: Jan. 12, 1999
  § 102(e) Date: Jan. 12, 1999
(87) PCT Pub. No.: WO97/40180
  PCT Pub. Date: Oct. 30, 1997

(30) Foreign Application Priority Data

Apr. 20, 1996 (DE) .......................... 196 15 803

(51) Int. Cl.[7] .................. A61K 39/12; A61K 39/23; C12N 15/00; C12N 1/12; C07H 21/04
(52) U.S. Cl. .................. 424/199.1; 424/184.1; 424/204.1; 424/185.1; 424/186.1; 424/233.1; 436/320.1; 436/235.1; 536/23.72; 536/23.1
(58) Field of Search .................. 424/199.1, 184.1, 424/204.1, 185.1, 186.1, 233.1, 130.1; 435/320.1, 235.1; 536/23.72, 23.1

(56) References Cited

FOREIGN PATENT DOCUMENTS

| WO | WO 93/07283 | 4/1993 |
| WO | WO 94/24268 | 10/1994 |
| WO | WO 94/24299 | 10/1994 |
| WO | WO 95/33062 | 12/1995 |
| WO | WO 96/03517 | 2/1996 |

OTHER PUBLICATIONS

Akopian, T.A. et al., "Sequence of an avian adenovirus (CELO) DNA fragment (0–11.2%)," *Nucl. Acids. Res.* 18:2825 (May 1990).
Akopian, T.A. et al., "Analysis of the Nucleotide Sequence of a Genome Fragment (92–100%) of Avian Adenovirus CELO," *Mol. Genet. Microbiol. & Virol.* 12:1–7 (1992).
Aleström, P. et al., "Sequence Homology Between Avian and Human Adenoviruses," *J. Virol.* 42:306–310 (Apr. 1982).
Aleström, P. et al., "A common sequence in the inverted terminal repetitions of human and avian adenoviruses," *Gene* 18:193–197 (1982).
Anderson, C.W. et al., "Characterization of the Adenovirus 2 Virion Protein, Mu," *Virol.* 172:506–512 (1989).
Bailey, A. and V. Mautner, "Phylogenetic Relationships among Adenovirus Serotypes," *Virol.* 205:438–452 (1994).
Bennett, D.D. and S. E. Wright, "Immunization with envelope glycoprotein of an avian RNA tumor virus protects against sarcoma virus tumor induction: role of subgroup," *Virus Res.* 8:73–77 (1987).
Bett, A. J. et al., "Packaging Capacity and Stability of Human Adenovirus Type 5 Vectors," *J. Virol.* 67:5911–5921 (Oct. 1993).
Both, G. W. et al., "Protective Immunity to Rotavirus–Induced Diarrhoea Is Passively Transferred to Newborn Mice from Naive Dams Vaccinated with a Single Dose of a Recombinant Adenovirus Expressing Rotavirus VP7sc," *Virol.* 193:940–950 (1993).
Bridge, E. and G. Ketner, "Redundant Control of Adenovirus Late Gene Expression by Early Region 4," *J. Virol.* 63:631–638 (1989).
Brown, P. H. et al., "Mechanism of action of a dominant–negative mutant of c–Jun," *Oncogene* 9:791–799 (1994).
Cai, F. and J. M. Weber, "Organization of the Avian Adenovirus Genome and the Structure of its Endopeptidase," *Virol.* 196:358–362 (1993).
Calnek, B. W. and B. S. Cowen, "Adenoviruses of Chickens: Serologic Groups," *Avian Dis.* 19:91–103 (1975).
Capaldo–Kimball, F. and S. D. Barbour, "Involvement of Recombination Genes in Growth and Viability of *Escherichia coli* K–12," *J. Bacteriol.* 106:204–212 (1971).
Caravokyri, C. and K. N. Leppard, "Constitutive Episomal Expression of Polypeptide IX (pIX) in a 293–Based Cell Line Complements the Deficiency of pIX Mutant Adenovirus Type 5," *J. Virol.* 69:6627–6633 (Nov. 1995).
Cavanagh, D. et al., "Amino Acids within hypervariable region 1 of avian coronavirus IBV (Massachusetts serotype) spike glycoprotein are associated with neutralization epitopes," *Virus Res.* 11:141–150 (1988).
Charlton, K. M. et al., "Oral rabies vaccination of skunks and foxes with a recombinant human adenovirus vaccine," *Arch. Virol.* 123:169–179 (1992).
Chartier, C. et al., "Efficient Generation of Recombinant Adenovirus Vectors by Homologous Recombination in *Escherichia coli,*" *J. Virol.* 70:4805–4810 (Jul. 1996).

(List continued on next page.)

Primary Examiner—Ali R. Salimi
(74) Attorney, Agent, or Firm—Sterne, Kessler, Goldstein & Fox PLLC

(57) ABSTRACT

A CELO virus obtained by in vitro manipulation of a plasmid-cloned CELO virus DNA is suitable for the production of vectors for gene therapy and as a vaccine against infectious diseases in humans and animals, particularly birds.

166 Claims, 11 Drawing Sheets

OTHER PUBLICATIONS

Cheng, S.-M. et al., "Coexpression of the Simian Immunodeficiency Virus Env and Rev Proteins by a Recombinant Human Adenovirus Host Range Mutant," *J. Virol.* 66:6721–6727 (Nov. 1992).

Chengalvala, M. V. et al., "Immunogenicity of high expression adenovirus—hepatitis B virus recombinant vaccines in dogs," *J. Gen. Virol.* 75:125–131 (1994).

Chiocca, S. et al., "The Complete DNA Sequence and Genomic Organization of the Avian Adenovirus CELO," *J. Virol.* 70:2939–2949 (May 1996).

Chroboczek, J. et al., "The Sequence of the Genome of Adenovirus Type 5 and Its Comparison with the Genome of Adenovirus Type 2," *Virol.* 186:280–285 (1992).

Cosset, F. -L. et al., "Newcastle Disease Virus (NDV) Vaccine Based on Immunization with Avian Cells Expressing the NDV Hemagglutinin–Neuraminidase Glycoprotein," *Virol.* 185:862–866 (1991).

Cotten, M. et al., "Chicken Adenovirus (CELO Virus) Particles Augment Receptor–Mediated DNA Delivery to Mammalian Cells and Yield Exceptional Levels of Stable Transformants," *J. Virol.* 67:3777–3785 (Jul. 1993).

Cotten, M. et al., "Lipopolysaccharide is a frequent contaminant of plasmid DNA preparations and can be toxic to primary human cells in the presence of Adenovirus," *Gene Ther.* 1:239–246 (1994).

Cotten, M. et al., "Psoralen Treatment of Adenovirus Particles Eliminates Virus Replication and Transcription While Maintaining the Endosomolytic Activity of the Virus Capsid," *Virol.* 205:254–261 (1994).

Cowen, B. et al., "Avian Adenoviruses: Effect on Egg Production, Shell Quality, and Feed Consumption," *Avian Dis.* 22:459–470 (1978).

Cunningham, C. H., "Immunity to Avian Infectious Bronchitis," *Develop. Biol. Standard* 28:546–562 (1975).

Degryse, E., "In vivo intermolecular recombination in *Escherichia coli*: application to plasmid constructions" *Gene* 170:45–50 (Apr. 17, 1996).

Denisova, T. S. et al., "Study of the Fragmentation of Chicken Adenovirus CELO DNA with Specific Endonucleases," *Molec. Biol.* 13:780–792 (1980).

Descombes, P. and U. Schibler, "A Liver–Enriched Transcriptional Activator Protein, LAP, and a Transcriptional Inhibitory Protein, LIP, Are Translated from the Same mRNA," *Cell* 67:569–579 (1991).

Deshmukh, D. R. et al., "Duration of Immunity in Recycled Turkey Breeder Hens Vaccinated with a Single Dose of Avian Encephalomyelitis Virus Vaccine," *Amer. J. Vet. Res.* 35:1463–1464 (1974).

Eloit, M. et al., "Construction of a defective adenovirus vector expressing the pseudorabies virus glycoprotein gp50 and its use as a live vaccine," *J. Gen. Virol.* 71:2425–2431 (1990).

Estes, M. K. and D. Y. Graham, "Rotavirus Antigens," in: *Immunobiology of Proteins and Peptides III: Viral and Bacterial Antigens,* Atassi, M. Z and H. L. Bachrach, eds., Plenum Press, New York, New York, pp. 201–214 (1985).

Fooks, A. R. et al., "High–Level Expression of the Measles Virus Nucleocapsid Protein by Using a Replication–Deficient Adenovirus Vector: Induction of an MHC–1–Restricted CTL Response and Protection in a Murine Model," *Virol.* 210:456–465 (1995).

Fynan, E. F. et al., "Use of DNA Encoding Influenza Hemagglutinin as an Avian Influenza Vaccine," *DNA & Cell Biol.* 12:785–789 (1993).

Gallichan, W. S. et al., "Mucosal Immunity and Protection after Intranasal Immunization with Recombinant Adenovirus Expressing Herpes Simplex Glycoprotein B," *J. Infect. Dis.* 168:622–629 (1993).

Gelderblom, H. and I. Maichle–Lauppe, "The Fibers of Fowl Adenoviruses," *Arch. Virol.* 72:289–298 (1982).

Ghosh–Choudhury, G. et al., "Protein IX, a minor component of the human adenovirus capsid, is essential for the packaging of full length genomes," *EMBO J.* 6:1733–1739 (1987).

Goldsmith, K. T. et al., "Trans Complementation of an E1A–Deleted Adenovirus with Codelivered E1A Sequences to Make Recombinant Adenoviral Producer Cells," *Human Gene Ther.* 5:1341–1348 (Nov. 1994).

Gooding, L. R., "Virus Proteins That Counteract Host Immune Defenses," *Cell* 71:5–7 (1992).

Gouvea, V. and T. J. Schnitzer, "Pathogenicity of Avian Reoviruses: Examination of Six Isolates and a Vaccine Strain," *Infect. & Immun.* 38:731–738 (1982).

Govea, V. et al., "In Vitro Characterization of an Avian Reovirus Vaccine Strain," *Virol.* 126:240–247 (1983).

Gräble, M. and P. Hearing, "cis and trans Requirements for the Selective Packaging of Adenovirus Type 5 DNA," *J. Virol.* 66:723–731 (1992).

Graham, F. L. et al., "Studies on In Vitro Transformation by DNA and DNA Fragments of Human Adenoviruses and Simian Virus 40," *Cold Spring Harbor Symp Quant. Biol.* 39:637–650 (1975).

Graham, F. L. et al., "Characteristics of a Human Cell Line Transformed by DNA from Human Adenovirus Type 5," *J. gen. Virol.* 36:59–72 (1977).

Graham, F. L., "Adenoviruses as expression vectors and recombinant vaccines," *Tibtech* 8:85–87 (Apr. 1990).

Green, M. et al., "Adenovirus DNA, I. Molecular Weight and Conformation," *Proc. Natl. Acad. Sci. U.S.A.* 57:1302–1309 (1967).

Guilhot, C. et al., "The 12S adenoviral E1A protein immortalizes avian cells and interacts with the avian RB Product," *Oncogene* 8:619–624 (1993).

Guo, P. et al., "Construction of Recombinant Avian Infectious Laryngotracheitis Virus Expressing the β–Galactosidase Gene and DNA Sequencing of the Insertion Region," *Virol.* 202:771–778 (1994).

Haffer, K., "In Vitro and In Vivo Studies with an Avian Reovirus Derived from a Temperature–Sensitive Mutant Clone," *Avian Dis.* 28:669–676 (1984).

Hanahan, D., "Studies on Transformation of *Escherichia coli* with Plasmids," *J. Mol. Biol.* 166:557–580 (1983).

Hay, R.T. et al., "Replication of Adenovirus Mini–chromosomes," *J. Mol. Biol.* 175:493–510 (1984).

Hertman, I. et al., "Attenuated Live Fowl Cholera Vaccine I. Development of Vaccine Strain M3G of *Pasteurella multocida,*" *Avian Dis.* 24:863–869 (1979).

Hertman, I. et al., "A Vaccine Strain of *Pasteurella Multocida* Obtained by Mutagenesis," *Prog. Clin. Biol. Res.* 47:125–132 (1980).

Hess, M. et al., "The Avian Adenovirus Penton: Two Fibres and One Base," *J. Mol. Biol.* 252:379–385 (1995).

Hosakawa, K. and M. T. Sung, "Isolation and Characterization of an Extremely Basic Protein from Adenovirus Type 5," *J. Virol* 17:924–934 (1976).

Hsu, K.–M. et al., "Efficacy of adenovirus–vectored respiratory syncytial virus vaccines in a new ferret model," *Vaccine* 12:607–612 (1994).

Huang, D. D. et al., "Association of Avian Reovirus M and S Genes with Viral Behavior in vivo. II. Viral Pathogenicity," *Avian Dis.* 31:446–454 (1987).

Ignjatovic, J. and P. G. McWaters, "Monoclonal antibodies to three structural proteins of avian infectious bronchitis virus: characterization of epitopes and antigenic differentiation of australian strains," *J. Gen. Virol.* 72: 2915–2922 (1991).

Jestin, V. et al., "Characterization of French avian paramyxovirus type 1 (PMV1) isolates with a panel of monoclonal antibodies to the ploufragan strain of Newcastle disease virus," *Arch. Virol.* 105:189–198 (1989).

Jestin, V. et al., "An ELISA blocking test using a peroxidase–labelled anti–HN monoclonal antibody for the specific titration of antibodies to avian paramyxovirus type 1 (PMV1)," *Arch. Virol.* 105:199–208 (1989).

Jia, W. et al., "A novel variant of avian infectious bronchitis virus resulting from recombination among three different strains," *Arch. Virol.* 140:259–271 (1995).

Jones, N. and T. Shenk, "Isolation of Deletion and Substitution Mutants of Adenovirus Type 5," *Cell* 13:181–188 (1978).

Jones, R. F. et al., "On the Oncogenic Properties of Chicken Embryo Lethal Orphan Virus, an Avian Adenovirus," *Can. Res.* 30:1580–1585 (1970).

Kalicharran, K. K. et al., "Studies on the Stability of a Human Adenovirus–Rabies Recombinant Vaccine," *Can. J. Vet. Res.* 56:28–33 (1992).

Kawaguchi, T. et al., "Establishment and Characterization of a Chicken Hepatocellular Carcinoma Cell Line, LMH," *Can. Res.* 47:4460–4464 (1987).

Keeler Jr., C. L. et al., "Identification of the Thymidine Kinase Gene of Infectious Laryngotracheitis Virus," *Avian Dis.* 35:920–929 (1991).

Kodihalli, S. et al., "A type–specific avian influenza virus subunit vaccine for turkeys: induction of protective immunity to challenge infection," *Vaccine* 12:1467–1472 (1994).

Kozarsky, K. F. et al., "Gene therapy: adenovirus vectors," *Curr. Opin. Genet. & Develop.* 3:499–503 (1993).

Kusters, J. G. et al., "Sequence evidence for RNA recombination in field isolates of avian coronavirus infectious bronchitis virus," *Vaccine* 8:605–608 (1990).

Larsson, S. et al., "VA RNAs from Avian and Human Adenoviruses: Dramatic Differences in Length, Sequence, and Gene Location," *J. Virol.* 58:600–609 (1986).

Laver, W. G. et al., "Purification and Properties of Chick Embryo Lethal Orphan Virus (an Avian Adenovirus)," *Virol.* 45:598–614 (1971).

Lee, M. D. et al., "A survey of potential virulence markers from avian strains of *Pasteurella Multocida*," *Vet. Microbiol.* 26:213–225 (1991).

Lenstra, J. A. et al., "Antigenicity of the Peplomer Protein of Infectious Bronchitis Virus," *Molec. Immunol.* 26:7–15 (1989).

Li, P. et al., "A Comparison of the Terminal Protein on Hexon Polypeptides of Avian and Human Adenovirus," *J. gen. Virol.* 64:1375–1379 (1983).

Li, P. et al., "The Structural Proteins of Chick Embryo Lethal Orphan Virus (Fowl Adenovirus Type 1)," *J. gen. Virol.* 65:1803–1815 (1984).

Li, P. et al., "Structural Organization and Polypeptide Composition of the Avian Adenovirus Core," *J. Virol.* 52:52:638–649 (1984).

Li, P. et al., "DNA–binding Proteins of Chick Embryo Lethal Orphan Virus: Lack of Complementation between Early Proteins of Avian and Human Adenovirus," *J. gen. Virol.* 65:1817–1825 (1984).

Malkinson, M. et al., "Antigen B of the vaccine strains of Marek's disease virus and herpesvirus of turkeys presents heat–labile group and serotype specific epitopes," *Arch. Virol.* 127:169–184 (1992).

Marshall, G. S. et al., "An Adenovirus Recombinant that Expresses the Human Cytomegalovirus Major Envelope Glycoprotein and Induces Neutralizing Antibodies," *J. Infect. Dis.* 162:1177–1181 (1990).

McFerran, J. B. and B. McC. Adair, "Avian Adenoviruses—A Review," *Avian Pathol.* 6:189–217 (1977).

McMillen, J. K. et al., "The Safe and Effective Use of Fowlpox Virus as a Vector for Poultry Vaccines," *Dev. Biol. Standard* 82:137–145 (1994).

Morrison, T. et al., "Retroviral expressed hemagglutinin–neuraminidase protein protects chickens from Newcastle disease virus induced disease," *Microbial Pathogenesis* 9:387–396 (1990).

Nascimento, E. R. et al., "Mycoplasma gallisepticum F–Vaccine Strain–Specific Polymerase Chain Reaction," *Avian Dis.* 37:203–211 (1993).

Natuk, R. J. et al., "Immunogenicity of Recombinant Human Adenovirus—Human Immunodeficiency Virus Vaccines in Chimpanzees," *AIDS Res. Human Retrovir.* 9:395–404 (May 1993).

Ni, Y. and M. C. Kemp, "Strain–specific selection of genome segments in avian reovirus coinfections," *J. Gen. Virol.* 73:3107–3113 (1992).

Nichols, R. A. J. et al., "Replication of avian encephalomyelitis virus in chick embryo neuroglial cell cultures," *Arch. Virol.* 96:283–287 (1987).

Oliner, J. D. et al., "In vivo cloning of PCR products in *E. coli*," *Nucl. Acids. Res.* 21:5192–5197 (1993).

Plank, C. et al., "Gene Transfer into Hepatocytes Using Asialoglycoprotein Receptor Mediated Endocytosis of DNA Complexed with an Artificial Tetra–Antennary Galactose Ligand," *Bioconjug. Chem.* 3:533–539 (1992).

Precious, B. and W. C. Russell, "Growth, Purification, and Titration of Adenoviruses," in: *Virology: A Practical Approach*, B. W. J. Mahy, ed., IRL Press, Washington, DC, pp. 193–205 (1985).

Scaria, A. et al., "Complementation of a human adenovirus early region 4 deletion mutant in 293 cells using adenovirus–polylysine–DNA complexes," *Gene Ther.* 2:295–298 (1995).

Schnitzlein, W. M. et al., "Genomic and antigenic characterization of avipoxviruses," *Virus. Res.* 10:65–76 (1988).

Scholz, E. et al., "Transactivation of the early SV40 promoter by avian infectious laryngotracheitis virus in avian hepatoma cells," *J. Virol. Meth.* 45:291–301 (1993).

Scott, S. D. et al., "Nucleotide and Predicted Amino Acid Sequences of the Marek's Disease Virus and Turkey Herpesvirus Thymidine Kinase Genes: Comparison with Thymidine Kinase Genes of Other Herpesviruses," *J. gen. Virol.* 70:3055–3065 (1989).

Shafren, D. R. and G. A. Tannock, "Pathogenesis of avian encephalomyelitis viruses," *J. Gen. Virol.* 72:2713–2719 (1991).

Sheppard, M. and H. Trist, "Characterization of the Avian Adenovirus Penton Base," *Virol.* 188:881–886 (1992).

Shinagawa, M. et al., "Comparative Sequence Analysis of the Inverted Terminal Repetition in the Genomes of Animal and Avian Adenoviruses," *Virol.* 125:491–495 (1983).

Tagaya, Y. et al., "ATL–derived Factor (ADF), an IL–2 receptor/TAC inducer homologous to thioredoxin; possible involvement of dithiol–reduction in the IL–2 receptor induction," *EMBO J.* 8:757–764 (1989).

Traencker, E. B. –M. et al., "Phosphorylation of human LkB–α on serine 32 and 36 controls LkB–α proteolysis and NF–kB activation in response to diverse stimuli," *EMBO J.* 14:2876–2883 (1995).

Trapnell, B. C. and M. Gorziglia, "Gene therapy using adenoviral vectors," *Curr. Opin. Biotech.* 5:617–625 (1994).

Treanor, J. J. et al., "Characterization of the attenuating M and NP gene segments of the avian influenza A/Mallard/78 Virus during in vitro production of avian–human reassortant vaccine viruses and after replication in humans and primates," *Vaccine 9*:495–501 (1991).

Tripathy, D. N. and W. M. Schnitzlein, "Expression of Avian Influenza Virus Hemagglutinin by Recombinant Fowlpox Virus," *Avian Dis. 35*:186–191 (1991).

Wagner, E. et al., "Coupling of adenovirus to transferrin–polylysine/DNA complexes greatly enhances receptor–mediated gene delivery and expression of transfected genes," *Proc. Natl. Acad. Sci. USA 89*:6099–6103 (Jul. 1992).

Weber, J. M. and C. W. Anderson, "Identification of the Gene Coding for the Precursor of Adenovirus Core Protein X," *J. Virol. 62*:1741–1745 (May 1988).

Weinberg, D. H. and G. Ketner, "A cell line that supports the growth of a defective early region 4 deletion mutant of human adenovirus type 2," *Proc. Natl. Acad. Sci. USA 80*:5383–5386 (Sep. 1983).

Wilson, M. A. et al., "Comparison of DNA Fingerprinting and Serotyping for Identification of Avian *Pasteurella multocida* Isolates," *J. Clin. Microbiol. 31*:255–259 (Feb. 1993).

Wold, W. S. M. and L. R. Gooding, "Region E3 of Adenovirus: A Cassette of Genes Involved in Host Immunosurveillance and Virus–Cell Interactions," *Virol. 184*:1–8 (1991).

Yates, V. J. and D. E. Fry, "Observations on a Chicken Embryo Lethal Orphan (CELO) Virus," *Amer. J. Vet. Res. 18*:657–660 (1957).

Zakharchuk, A. N. et al., "The fowl adenovirus type 1 (CELO) virus–associated RNA–encoding gene: a new ribozyme–expression vector," *Gene 161*:189–193 (1995).

Zheng, B. et al., "Immunogenicity in mice of tandem repeats of an epitope from herpes simplex gD protein when expressed by recombinant adenovirus vectors," *Vaccine 11*:1191–1198 (1993).

Derwent Database, WPI Accession No. 96–086063.

Derwent Database, WPI Accession No. 95–391457.

Michou, A.–I. et al., "Mutational Analysis of the Avian Adenovirus CELO, Which Provides a Basis for Gene Delivery Vectors," *J. Virol. 73*:1399–1410, American Society for Microbiology (Feb., 1999).

SEQUENCE LISTING

```
<160> NUMBER OF SEQ ID NOS: 54

<210> SEQ ID NO 1
<211> LENGTH: 43804
<212> TYPE: DNA
<213> ORGANISM: CELO Virus
<220> FEATURE:
<221> NAME/KEY: gene
<222> LOCATION: (12193)..(15043)
<223> OTHER INFORMATION: /gene: L1
<220> FEATURE:
<221> NAME/KEY: misc_feature
```

```
<222> LOCATION: (15080)
<223> OTHER INFORMATION: /note= L2 region penton base splice acceptor
      site
<220> FEATURE:
<221> NAME/KEY: gene
<222> LOCATION: (15110)..(17495)
<223> OTHER INFORMATION: /gene: L2
<220> FEATURE:
<221> NAME/KEY: polyA_site
<222> LOCATION: (17526)
<220> FEATURE:
<221> NAME/KEY: gene
<222> LOCATION: (17559)..(21754)
<223> OTHER INFORMATION: /gene: L3
<220> FEATURE:
<221> NAME/KEY: misc_feature
<222> LOCATION: (18261)
<223> OTHER INFORMATION: /gene: L3 /note= hexon splice acceptor site
<220> FEATURE:
<221> NAME/KEY: misc_feature
<222> LOCATION: (21102)
<223> OTHER INFORMATION: /gene: L3 /note= protease splice acceptor site
<220> FEATURE:
<221> NAME/KEY: misc_feature
<222> LOCATION: (21123)
<223> OTHER INFORMATION: /gene: L3 /note= protease splice acceptor site
<220> FEATURE:
<221> NAME/KEY: polyA_site
<222> LOCATION: (21767)
<220> FEATURE:
<221> NAME/KEY: polyA_site
<222> LOCATION: (21824)
<220> FEATURE:
<221> NAME/KEY: polyA_site
<222> LOCATION: (21836)
<220> FEATURE:
<221> NAME/KEY: polyA_site
<222> LOCATION: (21882)
<220> FEATURE:
<221> NAME/KEY: misc_feature
<222> LOCATION: (23608)
<223> OTHER INFORMATION: /note= 100K splice acceptor site
<220> FEATURE:
<221> NAME/KEY: misc_feature
<222> LOCATION: (23649)
<223> OTHER INFORMATION: /note= 100K splice acceptor site
<220> FEATURE:
<221> NAME/KEY: gene
<222> LOCATION: (23680)..(27886)
<223> OTHER INFORMATION: /gene: L4
<220> FEATURE:
<221> NAME/KEY: polyA_site
<222> LOCATION: (27920)
<220> FEATURE:
<221> NAME/KEY: misc_feature
<222> LOCATION: (28315)
<223> OTHER INFORMATION: /note= fibre splice acceptor site
<220> FEATURE:
<221> NAME/KEY: misc_feature
<222> LOCATION: (28341)
<223> OTHER INFORMATION: / note= fibre splice acceptor site
<220> FEATURE:
<221> NAME/KEY: gene
<222> LOCATION: (28363)..(31768)
<223> OTHER INFORMATION: /gene: L5
<220> FEATURE:
<221> NAME/KEY: misc_feature
<222> LOCATION: (30511)
<223> OTHER INFORMATION: /gene: L5 /note= fibre splice acceptor site
<220> FEATURE:
<221> NAME/KEY: polyA_site
<222> LOCATION: (31770)

<400> SEQUENCE: 1
gatgatgtat aataacctca aaaactaacg cagtcataac cggccataac cgcacggtgt      60
cactcgggta caaattatga attcgatctt tggactttc gacgcgccca gtgactgtac    120
```

-continued

| | |
|---|---|
| tttattgcgc caattcacca cgcccgggag atttcgaaat tgctatttcc gtgcagttcc | 180 |
| gcattccgaa gtacaatttta accggttttta tgggtgttcg gtgttttct agcttaatca | 240 |
| ttgttttag acgacacagt gggtatctgt tttcgcttgg acttggctcc gctttgtgaa | 300 |
| aattcaactc gatccaacat tttccttatt gatggaaggc ttttattatt tgcacaacag | 360 |
| acatcgcgct atttacacag aacgcaaagt gctgtctttt ttattccttg ttccgggtac | 420 |
| atcttttatt gctagtgcct cgcctatttt tagtcacgta tcttccttgt tctatagcta | 480 |
| tatattcacg cggttttcgg tctctcctca ctcggcagat gacttcggaa gagaagctgc | 540 |
| agagttcgtc tccggagacc ggcctcgccg ctgtcgtcct gcaaagcccc cttgaggtac | 600 |
| gtgtgcctgc cgttcttcct cctccagtgc gaattgacat ctaccgctac ccaggctttc | 660 |
| cgccaacgga gaccatctgg cacggtctca tcacgcagac tgagttaaac caggctttgg | 720 |
| agagcatcgt tgagcaattg tagtaagtgt cagtccctat ttttctgttt ttcttgtat | 780 |
| ttcctcttag acgatggacc cgttcggttc ttcttcagtc cctccgtgct ctacatcaga | 840 |
| ccttcccgaa cccaagctct atttcgtccg cttgtcaccc catgcagtgc ctccagttag | 900 |
| ggctacgcac ggagctgcag gatacgattt gtttagcgct tacgacatta aagtgcctgc | 960 |
| tcgcggtcgg gcgctagttc ccacagattt agttttcaa tttccgcccg gctgttacgg | 1020 |
| tcggattgct cctcgctcgg gcttggccgc caaattttc attgacgtcg gagcgggtgt | 1080 |
| tatcgatccc gattaccgcg ggaacgttag cgtggttttg ttcaatttct ccgagagctc | 1140 |
| gttcaacatc aggcgaggcg ataggtagc acagcttatt ctggagcgta ttatggttcc | 1200 |
| ggagctgtcg gaactgacgc agctaggcga gacagaccgc ggggcgtcgg gtttcgggtc | 1260 |
| cacaggtatg ggtgctgtag accgcaatca gcgctctgtg ttggaatggc tgaccctgg | 1320 |
| ttcccgttga taggaccctt gcgacgaagt cgacttcgct gtacgcttgc aagcagattt | 1380 |
| tgagggggac gacgacacat acggacattg tctgtgcgaa ggcagcacca gcaagaggcc | 1440 |
| ctgctgtacg ctctgtaaca gttactgcgt gcttctttag gtatgattgt gagcgtgtgg | 1500 |
| cagctcgcga ccatcgcgat tgagttttgc gataagtggg tggggaaata ctacagattc | 1560 |
| cgaccgtatc atgagagact tttgcttatg cagagtcggc aagctttgga aaggagcttg | 1620 |
| cgccgctgcg taagtgaagt tggacctccg ccagagcctc tagaatagcg atggagtccg | 1680 |
| gcgcacgtgg tgcttcctga ctttctgcac cattaccgtg gtgtttctgg ccttctttct | 1740 |
| gcagaaactt ctcaactaca tagatttcag agatagcgac tgcacagaat gttttttttgt | 1800 |
| gtagttgaca ggactatgga ccagacagca acccatacag ctttgattct tctgatcgtc | 1860 |
| ttgacggtgt tcacgggcgc ggtggtagct ttgatgttgt atattgcgat aactggactt | 1920 |
| ccttgctcta tgctttgctc tcaataaaga ttttcagaat ggtgattcta tggtatttg | 1980 |
| tctttttttct agacagtcat gtcgcgtgag tctgaacgtt actggacttt ggtgcacgct | 2040 |
| ctgattgatc ggggtgtagt cagccgtgaa cagtggcaaa tggttgaccc tgcgcaatac | 2100 |
| cagttctacc accgctccaa acagaggggt ttaaggtcc gtcacattct tcgtgatgtg | 2160 |
| attcgccaca tgtgttggtc tcggactctg ttagattata tgtcctcggc tcgacacct | 2220 |
| agtccggacg atgtattacg caatcccctg tatcagttgc tgttatgtaa tggatataac | 2280 |
| cccgctgttg tggggacagc gctgatccgg tgggcgggcc atcagagcaa ccgtaacact | 2340 |
| gtttggattc gaggcacccc tatgtccgga gctccgtact tggcacaggc tatcgcgtac | 2400 |
| tgctctcccc tcgtagggag cgttgattgg cgcaacaagt ctaacccatt cgaagggtgt | 2460 |
| ccagatagtc tggtgttttg gtgggacggc ggttatgttt atgattgttg tgtgggtctg | 2520 |

-continued

```
gtgaagcagg tgttccgggg agaacatgtt attttgcctc ctgagggctt gcgtggcccc    2580
aacccgtgct ctgaactctt caggaccccca gtcttgatgt acagccaggc ggatatttgt    2640
atgactaggc tgagatcagg ggaactaagt gcagagcatg cggtgggcct cagggattgt    2700
atgtacctga tccgtttgac agaagatttt gactgcgcgg gtggtatatc gtgtgcagat    2760
gtcaaacagt ttgtggcgtg gagccgcgaa caccctgggg aggttcgcga gacccacgaa    2820
ctcaaataaa aattcgggac ttctgtgtac gttccttttc atgtttatta aacactgttc    2880
tttcgagtga gtcatatcac gtggaagtta attgcgactg ggagccgcag aagcaggtgg    2940
taaaagcaag ctatgcaggg atagtttacg atgtcccttg aagacagac atagagtgtt     3000 tgtccttcca gtcgcgtgta ggcgccttgg cgccgcgcaa cggttactgc tgtatatatt    3060
tgttcgaggg cagggttcaa gttgcataac ctgcagtgag tagcatatgt gtataagatg    3120
agattaagag ggagttgggg ctggtggtcg tgttgagcaa cgaaattgac gaccgttttg    3180
gcccagtgag ctgtaagcac tcggatgagg gataaacaaa agagggaacg gggtgtctcg    3240
cagctgcaga tgtactggat agtccagtcg gtacatcgca tctcaataac tcttatccag    3300
ctgcagaatg acctgagctg gaggtcacac tcttcgtccg taatgcagtg gggcgagtgc    3360 ttgaagggt acatctgtct tttaaggaga aagagtagga aatcgggatc tgtgattagg     3420
gtaatgccca cgcgcgtgaa caggggctcg atgtagatat gccaactgtg ttggggctcg    3480
tcctcatcgt tgtcactatc ccaaacaagg tcgcacgact cgaatgtctg taaaacatca    3540 aagtttatt actgattttg aagagggta cgtatacagg ggttacagag tttattatcg      3600
cgtttgcaat gcagtgtcat taagcaagca caagcggcag cattagcaac aaagtcgcgt    3660
agctctttgc gcgggtggta gcatggaggg gtcttggtgt ggtctcctgt gaggaagaag    3720
acgaccgtgt tccgcgccgt gaactcgttg gcgagcgaga ggtccgcgca gtggattagc    3780 atggggtcg agggatgtg gaacgttttc ttattcagcc tgcaggtggc agcattgcct      3840
tccataaagt gcagcatcaa cgggtccggc ttctcgtcta cgaagggcag acagtataga    3900
gaggcgtggg gtgcgatttc gcccagtgat agtatggagt tgattcggct gtcggagatc    3960
gcgagcggga aacacgcgca taaggcatta aagagactct tggcgttgga aagtcttcct    4020
ccgcagagca cgagggtgtt tagttctcct cggagccatc ggaggatggc gttagctgcc    4080
acttttccct cgtagccttc ggcttccatc atctgatgga accagttgtc gcagacgttg    4140
tagaacgcag ccttgagggt gtcgggctct tcggagggta actggttaat gaggctctgt    4200
ccgggtccga accgttcctt gagggcttcg agtacacgct ctcgttcgta ggtgggtatg    4260
aggttcttgg acgggaagtt ccactggact tcgtgtgcta caccttcgac aaacaaccgt    4320
tcaaccaact gatccatggg ggacgtggac ggaaataagc agggtgaagg ggtgtctgga    4380
atgcaggatg ctatttgctc ctcttcgcta cttaaagacg actgagactc gcgtcgcctc    4440
ttggtgcact gtgggagaga attatatgtc atgtgatgag tgacaagcat gcatgggga    4500 ggtccacgag cgggaacaga gcattccttt gttctcgcat aggagagcgc gcaaggcgtc    4560
gttgtcatta tctgcctgta attggtgtat gcgatgaatg tagcgggaga gctctcccag    4620
aaagaacccg cagccgttgg cgggttcgta gaacctaata atgatatgtt cgtcgggagc    4680
agtgggcaga tgttcgggat gggggagctg atataagcgg acgaggcatt ttttctcact    4740
gatgtccacg agaccgtcgc gggtcattgt ggtgaatgac ctgcctttca gcagctggtt    4800
agcaacggga tctttgaacg tgttacaatg agctgtgcag gggaaataaa gcatcttgac    4860
```

-continued

```
taaatcttgc tgtctggcgt actggccaaa gtcgaacgcg ttaatgttgg cagtgaggac    4920
aaattggaat aatctgagga tggatgcagt gaatatatct gcggcagagg aaggttctcc    4980
tacgacatag agcgtgttag tataatggca caggcgacta atgctcatgg cagacatcca    5040
cagataaatg gcgtagatgg ctaccggagc attgtaacct tcggcttcta gcatggctcg    5100
gagatctctt tgtgaggaca gctcgaagcc ttgcagattg aaattgatcg tttgactgag    5160
cccgtagctg cagtataatt tgcgcgcttc ttccagaagc gcggggcgga ccgattcgaa    5220
tagttcagca tcttggggat accgagtgag ccaatctttg taggtaaaga tgttgtttcg    5280
ctggagatcg aatattagcc tgtgtgtgac taaatcgtcg tcgtcttctc ccgtgtggcg    5340
gttcctgagt ctcttaacgc tatccttaag tttcctgaaa cgttcctggg ggagaaagtt    5400
tttcgagatc ggttagtttg gggtttctct ctaactgctt tctatgtgtt tcgctaaatt    5460
tgatgataga tttggctgtt ttcaggaatc tctcctgaat gttaacattg agagggatga    5520
tcgagtactg ctgatctata ctgcaccacc taaaggactc ggatactggg tccggagtgt    5580
acatgaccca gctgaaccgc tggttctgct gcaggaagga aaagtaagct ttgagaagga    5640
caacgaggtc cttcgagatg ttgtgtgcga acgcatagag gaacctagcg aactggaatt    5700
ggggaatatg acaggatagg atgtgcattt tcgcgttcac tttgagggtg ggaacgtttc    5760
ctatcgcggt gcgcggtgcc atgttgtgca agactacgaa aatgtagaag gctgtacagt    5820
gggcagagcg agcaaagagc ttagaaggaa gggcgtgaaa gaggacagag acgctggagc    5880
ctgaacagag cttatccatg cactcgtcca tgataatggc gacgggtccc cgcttggaga    5940
ctttcacgta aatgttgtct ggatggtcga tgttgagatg ttcgggtgcg gtggcctcct    6000
cgtaagtcat ctccataaat tcgggacgga acgtgcttgt cttaggggcg atggtgccgt    6060
cttccctgca gtcgaaattg gcctcgacca gctgcaggtt ccaggacgtc tgttcgatgg    6120
gtggaatcat gttcttttcc ggagtgatga agatgaccgt ttcggggatc gggtccaaca    6180
tgttgcacga gatgagcgcc cgcagcagat gcgacttgcc ggatccggtg ggtccgtaga    6240 tgacccccgat gatgggctgc ttgcccatgt tgatggacgg cagctgtccg tgttggaggt    6300
agcgactgtc catctgttcc tgggctttaa cttcttcgtg ggcttcgaga aacttctcat    6360
taacgccccc taggctgtag aactcgtcgt aggaggggaa gtgttgctcg cggaagagct    6420
gcggtgctag gtcgacagct ccgtcgtacc agctggtgac gcgctggtag aagtcccgcg    6480
aggcttcgta ctcttcttcc tcatactccc aggctttccg cttcctggga gctatcatct    6540
gcgaagagta ggtcgtgaac ttgcccgcat tcctcttcgg ataggaacgc gtagggttcc    6600
catcgtaggg gtgcgagggg gtcttcgtgc ccgacgattg ggacgggtcg tacgtctcct    6660
gtcgtgcggg gatttgggtg ctcattgtcg tagggggtaca ggtagtcccc gtgctcgtat    6720
agggtgaggt ccttccacgg acgcagcact cgcgtgagct gctcgttgtg aatggtgaaa    6780
gggtcgtagc gactgaccct tgttcagaagc gtggttttaa agatggttct ccgcgtgtgt    6840
agctctggga tgttgctctg cgctccgaat tgcacgtcct cgtgtctacg ccaacagcgc    6900
agcagcgtgt cgtagatgag ttcggactgc ctgtgtccct tcgatctgat tttcccgggt    6960
cctaccgtgc ggcactgttc gttgacgcag attgagtttt tcagtccgta cagttttggc    7020
gctaggaaga tggtttccga gctgtacgtg tcacttccgc aggctttgca cttgatgtcg    7080
caatcgcagg cccagtagag gccgggattt tctggatcga aagtcagtcg agtggattct    7140
gttttgattc ggtgcgcgcc gcggcttttc atgcgatgat agcctgtttc tgtgacgaac    7200
aggctgtcgg tatcgccata gaggctgcgc ggctcctccc ttcgcaggat gtgcactcct    7260
```

```
ctgtccggtc cgtacaggat gtcacaccac tcgctgaaga aggccctcga ccagcccagc   7320
acgaagcagg cgatttgcgt ggcgtatctt ttgtttgcca cctgcttgtc caggcttttcc  7380 agatggagca cggttagggc ttctggtgtg gcttcgagga cacgcatagg tttaaaccgg   7440
gtctcgttag cgcgagcgta gtgggcggag cttagctccc cctcgggtat ataagggccc   7500
gtcgcgaggg tcgcctcgac ttccaggtct acggcgacga gaggatcgtc ttcggtaagt   7560 gcgttttttcg gcttacgggc actctcgcga tcgctgtcgt ctccttcttc ttccccatcc  7620
tcttctgctt cgggctcttc ctgttcgggg tcgtctgcgt agcggaactg ttgtcgtaga   7680
ctctcctcac tgaaggggtt aggcgcgttt tcgagggtga cttccgttcc gttgaacgag   7740
tcgtcattga gcagcgtgac gtgtttgacg atttcagtgc cttcgtagat gttttttctta 7800 tctgcttccg agaggtcctg ttcaaagatg atgcgcgtgg tgtccatgtt ggtggcaaac   7860
gcaccgtaca gcgcgttgct cagcattttg agatggatc gaatcacttc gttcttctcg    7920
cgatcggctt tttctttggc gaggatgttt ttcgtgacgt agtcggcaca tagcgttttc   7980
cattccggaa aaacaatgtt catctcgtca tggaggacct ggactcgcca tccccggttg   8040
tgcagcgtga ggatatctat gacggtgacc acctcgtcgt agagagcctc gttggtccag   8100
accagtctgc ctcccctccg ggagcagatg ggagggagtg ggtctaacat ttcgggcggg   8160
ggagggtagg cttctatttt caggatggaa ggcttgatac gcgcatcgaa gtagctcaga   8220
tgcgattcgt tggtcagcag ccggttgagc tcctccacgt gctgcgcggt aaattttgga   8280
tctaggggca ttccgtgggg catggggtgg gtgagggcgg aagcgtacat gccgcagatg   8340
tcaaagacgt agacgggttt caggtaaggt ccgagcacgt tggggtagca tcgtccgccg   8400
cggagcgctt ggcgtatgta tttgaacatg gggcggtggg gggcgtagac ttcggccacg   8460
tagtcggggg agggttgttt tttctttttg gttcgacctt tcttttttggg gggttcgggg  8520 acggagggag ggcatgtcgc acgctgttcg cggacgtaat tggaaaaggt aagttgcttc   8580
caaaaggcat gagtgttgct ggggatggtg ggccgcacga agatgttaaa atggccttcc   8640
atccctagtt ctcgttggaa ataggcgtcg tagctgtcgt gtaacgtgtg ggccagcttt   8700
tgggtgacgc ggacgtcctg catgcagtat tcgaggcacg cttggacgat gtcgtactgc   8760
tggcccgggt gttctttctg ccatagattc ttctgttcag cgatgacgga tgggtcttcc   8820
cagtaccttt cgacaggaaa gccgtcggcg tccgcgtgaa agcgccccgt ggaaatgaat   8880
tcgttgatgg cctcgtatgg gcaatgtccc ttgcagaggt ctagcgcgta ggctgccgcg   8940
gctttggaga gtttgccccc gctggtgagc tgtagagtgt ctcgcaccat gaaccgcaca   9000
aataccgagc gcgcatcctg atgggacacg atcccgcgag accagcgttc tacgcgggag   9060
gcgtctttct tcacgtagtt ggggtttggc atgcggaaaa tgatatcatt gaacagaagg   9120
cgaccgacgc gaggcatgaa ggatcgatca catttgcacg cttccgggaa taggtccctg   9180
cgctcgacga gttccgtggc taagaggagt tcatcgaact tacatatgtt gtgacctagc   9240
actacgatgt ctacggaata aaagttatcc gggagggaga gggggaggt gggtttctcg    9300 aagagctcgt acggtatttt gtgaacggag ccgtactttc cgtccttgac tagctggtcg   9360
caataatctc ggttggcagc cgcgtagcgg tcgactagat tttgggcaaa ttctatttgc   9420
agacgggacc tgaagttgcg aaaccttctg gcaacctcgc ccggatggct gtctagccaa   9480
tagaagcctt cgtcgagggc tttgagacgt tcgtcctgcc gtgctaagcg ttcggcgcgg   9540
gagaccagct gggggtctcc gctgagcatg aagcacaaca taaacggatg catgcgcttg   9600
```

| | | | | | |
|---|---|---|---|---|---|
| cctttctttt | cgaacacggt | atacgtctcg | atatcgtagg | tgatgtacaa | ctgacgtatg | 9660 |
| tgggggtgtt | gggctggaca | ggagaagtgg | acgtgctgcc | acaaatcgct | gcccgatccc | 9720 |
| tggacggcgt | ggtagtagaa | ggcagagcgg | cgttcgttgc | acgagtgtcg | tctgacccag | 9780 |
| tgtcggccgc | agtgtgggaca | ctgttgaacc | ggagtgcggc | tggtgatcca | gacccattct | 9840 |
| ccggtgacgt | ttttggcgat | gagcatgggg | ggaagggcgg | gatgttcgga | gatgtgcacg | 9900 |
| gtccgcaggc | gcgctgtttt | gcctttaaag | ttgatgacgg | tgacctgggc | gggcttaaag | 9960 |
| tcggggaggg | agcgttcggg | gtctcgggca | tagtgcagat | agtctattcg | gtcgtagcct | 10020 |
| ctggctctct | tagacagcag | gaagcggtgg | gtgcgtagga | atttcttgag | acctatgggg | 10080 |
| aatacagtgg | gttggaagcg | gaaggctgt | tcctcgatgt | aatagacgtt | tgtgcgtagg | 10140 |
| gggttgcccc | ggaagctctt | gaagtacttt | cgggtctctt | ccagccgttt | agcggaaatg | 10200 |
| gttcggatga | cgtgcgaatc | gggccccagc | acgctgtccg | tgaggggagg | cccgcgtct | 10260 |
| gcttccattt | acagaggctg | acctcgtcgc | gccgccgctt | cgatgtcttc | gcggcggtgg | 10320 |
| cggagcacgc | gtctgaggtt | ggctttgatc | tcctcgttgg | tagcgatggc | tacgatgcct | 10380 |
| ttaaatttga | tgcggaaact | gatgtcgatg | ctatcgatca | gctcttcgct | gaggttgagc | 10440 |
| tgcttcagca | cttcttcgat | gtcaccggag | cggtctctgt | attgaatatc | agagagaaac | 10500 |
| agttgttggt | ccgcatcgtc | catgccttcg | aattgacccg | tccgttcgac | catcataaga | 10560 |
| aaatcgcgta | atatcgttc | ccacaggggtt | tcgaatatgg | tggcggggtt | ggattgctcg | 10620 |
| ctccatatgc | gtttaaaaac | ctgctgcgcg | ttgacgtccc | atcccacgac | gagtacttgt | 10680 |
| aaggtcagga | cgtcgacgta | ccggcggaac | tcgcggttgg | cgatgaagtg | gctgtacagg | 10740 |
| tagtagagtg | tagaggcgat | atgttcggct | aagaagaagt | acagcaccca | cttgcgcagg | 10800 |
| aacgactctc | ccatgagtcc | cgcgtcgcgc | gcggtcagga | gcatgcggta | gaagtcgttg | 10860 |
| gcaaacctga | agagttcgtg | tctccgggcg | gccccgctga | gctcgtcttg | cagtgccccg | 10920 |
| atggcttcga | gcgctgtgcg | aatcacctcg | tctaacagct | cttcttcctc | ctcttctggt | 10980 |
| tcttctactt | ccatggcggc | ttcttctatt | tcttcgggag | ggggcgcggg | ggagggggt | 11040 |
| ctccgtcgcc | gccgcgtgac | gcggggcagg | cggtctacga | aggcccgcac | ggcacggggc | 11100 |
| ctaatgcggc | gcgcttcgga | cgcggtgatg | gctctgccgt | ggcggtctct | agggcgcagg | 11160 |
| ccggtgcggt | cggttacccg | ccggctgcag | agggtgatgg | cgcctcctga | cagacccgtt | 11220 |
| cctgctaagg | aaacggcgtc | gctcgctaga | gtgctcatga | acatctcgc | cattgtttcc | 11280 |
| gtaggttcct | ctacgtcccg | tcttcctcga | aacttgcgct | cggcatcccg | caccagttgc | 11340 |
| tgggtgtcta | gctccgcgaa | ggcttccgcg | aagtaggaga | gccagtttgg | ttcaaggaac | 11400 |
| acatcggatc | caggtaagaa | ccgatatctt | tcttccgttt | gaaatagatc | atatgcgtag | 11460 |
| cagaatagat | agtggcagag | ggcgactctt | agttggcgga | tggcggcgag | cagttcggcg | 11520 |
| tcggcggcag | aggccgttcg | catgaggacg | ccttcttgca | agccacccgc | tccgttgccc | 11580 |
| gacagtaggc | tgtggtgttc | ggcgtcgagc | tgcggcaaca | cttgtccgtg | acggcctacg | 11640 |
| tcgattcccc | tacctcgcag | atgcgcccgg | cccatgtccg | cggccacgcg | gtccatgagt | 11700 |
| acggcgttgt | gcatctgcgt | gaacgtaccg | tgaaagttgt | cgagatcgag | aaatcgcatg | 11760 |
| tactgcccta | cattgacggc | gtaggagcag | tcggtcagac | aggtccaaaa | gaggcgtctg | 11820 |
| ggtctttggg | gtgggctatc | gtaacctatc | tgcataaaaa | cgcggttgtc | gaaaaggtaa | 11880 |
| tcgttgagcg | cgcggtgcat | agcttggtac | ccgaggagaa | ggtgcggcgg | cggcaatccg | 11940 |
| ttgtagggcg | gcgcggcgac | gttcggcgat | cgcggcgcga | ggtctcggag | ttgcattaaa | 12000 |

-continued

```
cggtagtcgt acacccggct gacgagaaac acgcttcggg ggtggaccag ggctggttct   12060
tcccgaacga ggacatagtc agcggtgatg acgggttcgc agaagcggac ggtggctaga   12120
ctctgtccgg tgagatccgc gaagactctg taagcctgaa attgagcccc tgacgttttt   12180
agaccgctcg taatgcaccc cgtcctgcaa agcgttcgaa acgcgagcgt gagcgccgga   12240
ggaccccatc aacagcaacc gcagcagcaa cagcacggtg tgtcgtcggt ccgtcgtcct   12300
ccttcaccac cccgatatcc cgcacaacat gcctatcccg gcgcgggcgc gacacccacg   12360
gcaggacgag gcgatttcga cggcgcgctt gatcccgatg aaggaccggt cgcgtgcggg   12420
ctggcggccg gggccggtgt ggacgaagtt agaatgaggg agcgggacgc cgcgcggcga   12480
gccacggtgc ccgagatcaa tcttttaag gctcgacgtg acgtggtgcc caatggggat   12540
tacgagaggg atctgatgta ccactcggga caggcaatcg atatcgatcg caacgtgtg   12600 ctcactccgg aagactttaa ggggtccgag ccggctttca cgccggctgt caaccatatg   12660
cgcgcggccg agttgaagag ggcggctgag cagacggcat ttggggagga attgaggaat   12720
acctgccatc agacccgcat ccgcacggct ctgttaaggc ccgagatcgg agcgggaatc   12780
tactatctgt acgatttcgt ccagacttat ctggagcatc cggacggtcg ggtgaagctc   12840
aatcctcagc tggtgttggt ggctcagcac gcgggcaata ctatgctggc gcagcgcttg   12900
tgggccatcg cagaggagaa gaatgcgtgg ttgagagatt tgatagagat ggcgtacatg   12960
atcgtgaacg atccgtacct caatacgagg cagcagctgt cggccatctg cacgacggtg   13020
gtcgagttga gcatgaaata cgccaagttg gccgccaaga acggttaccc gtccatggcg   13080
cagatggcta aggcgcagga atttttctac cgggtcatgc aagcggtgct cgatttaggt   13140
gtccaagtgg gggtgtataa caaccgacca gctcggtacc gtcagaagcg catgagcgag   13200
attccgcaga tgactgacgc cgagtacatg ttcggtttga cccaggcgct ggagagcagg   13260
cctccgcagg gcgaatcttt tgccgacgag gggccgtcag aatcggacga cgaggatgac   13320
ttcatctgat acgtttctgg ctcttgcgcc ctacgggcgt caggaggtgg cggacgccct   13380
cagttcgctc ccagatggca aggacgcgcg gtcgctacgt catgcaccct acgcaaatcg   13440
cctcatcaaa ctccagagcg ccatggtgcc tccaaaagtg gacggtactt ccgagcgggt   13500
ggccgaaatc gtgaaagggc tagccgagca aggcgccatc taccccgatc agatgggcgc   13560
gatccactca gatttgctta atcgagctta cacgtggaat tccatggggg tgcaggagag   13620
catccaggcg ctggtcaacg acgtgatcca cggacagaac cggacattgc aagacgagct   13680
tgcgcggacg aaagaaatag cgaatgcttc gctcttgacc caattttttcg attccctgta   13740 caaaacggtg gatcgtgggc agcgaaattt tgagggcttt aagaaacttt tgcgtctttt   13800
cgtgaataac gtgccgaatg ccgaagtgta cgggtcttcg gggtcccttta gcgtgcagat   13860 aaatcttggc ggatcagtc aaaacatcaa tctgaccaat gcgtttgaga atttgaagcc   13920 gatatgggc gcacggtggg acgcggtgaa taatcctcgc atcggggcgc ttctgacacc   13980
caacactcga gcgttgttgt ttttcgtgag ctcttttttac gactacgggg ctatggagcc   14040
cggtagttac ttggacaata tcatgaggct gtacaaggag gctatcagag ccgatgtgga   14100
cgcggagggt gatgccatta tggagctcgg ggaggcgggc gcaaatctca acttgcggtt   14160
caacgattac aaggacacac taaactacct cctgcaaaat cgagaggttg tacccgacac   14220
ggctccgctg gagctgagcg cggagcagga aatgctcttg aagtacctga tgaggcaact   14280
acgacaggct cttaaggacg gggtcccggc ggacatttct atcagtacca tgactcagta   14340
```

```
cctagatcct aggctgtatc agacgaacaa ggtgttcgtg gagaaattgc aaaactacct   14400
gttggcggct caggcgcgca atcctgtgta ttaccgactg ttggtgctgg accccaactg   14460
gcggcctccg gcaggcctat atacgggtaa ttacgtgata cccgaccgct acgactttga   14520
ggacgtgcag agcgagcttg aatacgcggg tccctccaga gacgagtatt tcgatgattc   14580
tttgttcgca ccaggtcctc agcgccgctt aaattcggcc gaggaggctc aattggagcg   14640
tgacatcgaa tctttgaccg gccacattga cgaagagctg ggcgtccaat ctcaggctgg   14700
ctggctcgcc gatcaccgcc tgcctgtcgc gttcgatggc gctctcagcc ttaccgaacg   14760
caacgcctac aacacgccgt tgccccccga ttcccacatg cgtagccgtt ctagctccgt   14820
cgctagcgat cttgggctat tgaacctatc tgggacgggg gaccgggct ttttcgctag    14880 tctgcggcct ccatcggca gccgtcaacc gaccggcacg gccgtgggcc tccgcccgac    14940
gacaccgtac agcggttcgg ggtgtatgag gggcaccggt ctggcgcgca agttttaaa    15000 cccggccgcg tcgcgccggg ggcgcaagct acggttctac tgaaccctag actctgacga   15060
agaaacttaa aaacgcttac cgccatttcg ccgcgcagaa gttggaagga tgtaccggag   15120
cctgcgaccg ccgacgtcga ttcctcctcc gcctccctct ggtccctcgc cttatccggc   15180
gatgatcaac ggatatcccc cggatgtgcc ggtgggtca cctgccaacg gagatgcgga    15240
gctgttcgtg ccgctccaga gggtgatgcc gcctacgggt ggacggaaca gcattagata   15300
ccggaattat gcgccgtgcc aaaacaccac caagttttttt tacgtagaca ataagctgag   15360
cgacttagac acctacaacg aggacgcgaa tcacagcaat tttaggacga cagtcattca   15420
taatcaggac ttagacccgt caacggccgc cacagagacc attcagctcg acaataggtc   15480 gtgttgggc ggagagctaa aaacagcggt gaaaaccaat tgcccgaaca tcagctcgtt    15540
tttccaaagt gatacagtgc gcgtgcgtct gatgagcaag cgcgatccgg ggggtaccga   15600
cccagacgcg gggtgaaca acccacccgg ggccgagtac aagtggtatg atctgaggat    15660
tcccgaaggt aactacgcgt tgaacgagat cattgacctt ttgaacgaag gcatcgtcca   15720
gctgtacctg caggaggggc gccaaaacaa tgtgctcaag agcgatatcg gggttaagtt   15780
cgatacgcgg tatctggatt tgctgaagga ccccgtgacg gggctggtga cgcccggcac   15840
ctacgtttac aaaggatacc atcccgacat catcctcctc cccggctgcg cggtcgactt   15900
tacgttcagc aggcttagtc ttctgctcgg tatcgcgaag cgcgagccct actcgaaggg   15960
gtttacgatt acttacgaag atcttcaagg agggaacgtg cccgcgctgc tcgatctgtc   16020
ctccgtgcag gtagacgatc aagacgagga cgtgatcgtg gtggcagacg caaggcctct   16080
tttaaaagac tccaagggcg tttcctataa cgtgatcacc actggcgtga ctcaaccgca   16140
aaccgcttat cggtcttggc tccttgccta ccacaccctg gactccccg cgcgcaataa   16200 aacgttattg actgttccgg atatggcagg tggtatcggc gctatgtaca catcgatgcc   16260
ggacacgttt accgcacctg ccggatttaa ggaagacaat acgaccaacc tttgtcctgt   16320
ggtggccatg aacctgttcc cgagtttcaa taaggtattt taccagggcg cgtccgccta   16380
cgtgcagcgc ttagaaaatg ccacgcaatc cgcaacggcc gctttcaacc ggtttcccga   16440
aaacgaaatt ctaaagcagg ccccacccat gaatgtttcc tcggtgtgtg ataaccaacc   16500
cgccgtcgtt cagcagggtg tgctaccgct gaagaattct ctgtctggcc tacagcgcgt   16560
gttgatcacc gacgaccggc gccgtcccat tccatacgtg tacaaaacca tcgccaccgt   16620
gcaaccgcgc gttttgagca gttcaaccct gcagtgagga gcggaaggat tttcaaacat   16680
gtccattctg atttcaccca gtgataacag aggttgggga gcaaacatgc gttaccgccg   16740
```

```
tagagcatcc atgcgcgggg tcggtcgccg tcgtctcacc ctgaggcagc tattgggtct    16800
ggggtctcgc cggagacggc gatccaggcc cacgaccgtc agtaaccgtt tggtggttgt    16860
gagcacccgc cgccgctctt cccgaagacg ccgatgaagc aagcagctga tgagatgttc    16920
ttctgactat gtgtgccgtc gctatacaca ggagcgacgt cgttatgcct tccgttcttt    16980
tgaccggcgg gcggaccgcc aagggcaaga agagagcctc tcgtcgtcga gtgaaagtgc    17040
ctaagttgcc taagggagcg cgccgaaagc gtgcgtcggt gacgccggtc cctaccgtag    17100
ctaccgcgac cgcttccgag cgcgcggctc tgacgaacct agccagacgg ctccagcgcg    17160
gcgactacgc cgcttggagg cccgccgact acacgtcacc ggccgtttcc gaggcggctc    17220
gcgcagccgc ctcgtccggc accccgcgca ccgcgaggga tctcgcgacg gaaccctcg     17280 ctcgcgccgt gcccatgacg ggtaccggcg aaggcggcg caagcgcacc gctacccgcc      17340
gccgatctct gaagggggc ttcctgccgg ctctgatacc tatcattgcg gccgctatcg      17400
gcgccattcc gggcatcgca ggaccgccg tgggcatcgc caatctgaag gagcagcaga      17460
gacagtttaa taagatttac ggggacaaaa agtgatgctg actggacgca ctaaaaggcc     17520 cttttcaataa acgcgttttt gtagaaccgg ctcgcgtcat ggactacgct gcgctatcac    17580
cgcatctcgg tgggtgggcc ctgagagacc accacatcgg cgactctagc ttgagagggg    17640
gagccatcaa ctgggcaac ctcgggtcgc gcataaccag cgcgctgaac tccaccggtc      17700
gctggctgta taacaccggc aaccgcttcg tgcattcgaa cactttcaac cagattaaac     17760
aaggcataca agacagcggg gtcatacgca acgtggctaa tttggccgga gagacgctgg    17820
gggccctgac cgacatcggc cggttgaagt tgcaacagga tctggagaag ctgcggcgta    17880
aagctttggg ggaggaaggt ccagcgaccc aggccgaact gcaggctctc attcaggccc    17940
tgcaggcgca agtggctgcc ggagagccgc ccgccgcacc cgcggcgccg cgcgcggccc    18000
cgccgctcgt gcccaccact cgtcctattc ccgaaatggt aacggaggtt aagcctcccg    18060
ttacgtcttc ggcgccagcc gtccccgtag acgtgccgac cacgctggaa atgcgacctc    18120
cgccgcccaa gcgcaggcgc aagagggcac gaccgggaca atggagggca cgcttggaca    18180
gcctctcggg taccggagta gcgaccgcca ctagacgtat gtgttactaa aattccgtcg    18240
ttccgctatg tctaattttt agctcaccgg ttgtctcccg aaggcgtcat gactgcgctt    18300
actcccgacc tgaccacggc gacgccgcg ctgcagtact ttcatatcgc gggccctggc     18360
acccgagagt atctatccga ggatctccag cagtttatct cggccacggg gagctacttt    18420
gacttgaaaa acaaattcag gcagacggtc gtagctccca ctcgcaatgt caccaccgaa    18480
aaggcacaac gtctgcagat cagattctac ccgatccaga cggatgacac gccaaacagc    18540
tatcgcgtgc gctacagcgt caacgttggg gacagctggg tgttggacat ggggggcgacc   18600 tacttcgaca taaagggtgt gctggaccgc ggaccttcct tcaagccgta cggcggaacg    18660
gcttataatc cccttgcgcc aagagaagct attttcaaca cctgggtgga gagcactggt    18720
cctcagacca atgtggtggg acagatgacc aacgtgtaca caaatcagac caggaacgac    18780
aagacggcca cgcttcagca ggtcaatagc atctccgggg tggttcccaa cgtcaacctg    18840
ggacccggcc tcagtcaact agcatcccgg gccgacgtgg ataatattgg cgtggtggga    18900
cgtttcgcca aggtagactc agcgggcgtg aagcaggcgt acggagccta tgtcaagccc    18960
gtgaaggacg acgggtctca gtctctgaac cagaccgcgt actggctgat ggacaacgga    19020
ggtaccaact atctgggtgc cctggctgtg gaagactaca ctcagaccct gagttacccc    19080
```

-continued

```
gataccgtgc tcgtgacccc tcccaccgct taccagcaag tcaactccgg caccatgcgg    19140
gcatgcaggc ccaactacat cggcttccga gacaacttta tcaacctact gtaccacgac    19200
tcgggcgtct gcagcggaac gctcaactcc gagcgctccg gcatgaacgt ggtcgtggaa    19260
ctccaggaca gaaacacaga actgagttac cagtacatgc tggcggacat gatgtcccgt    19320
catcactact tcgcgctgtg gaaccaggcc gtcgaccagt acgaccacga cgtgcgcgtc    19380
ttcaacaacg acggctacga agagggcgtg cctacttacg ccttcctgcc cgacgggcac    19440
ggggcgggcg aagacaacgg tcccgacctc agcaatgtca aaatttacac caacggacag    19500
caagataagg gcaacgtggt ggccggaacg gtttccacac agctcaattt cggtaccatt    19560
ccctcctacg agatcgacat tgctgctgcc accaggcgca acttcatcat gagcaacatt    19620
gccgactacc tgcccgacaa atacaagttt agcattcgcg gtttcgaccc tgttacagac    19680
aacatcgacc ctaccaccta cttttacatg aatcgcaggg ttcccttgac caacgtggta    19740
gacctgttta ccaacattgg tgccagatgg tccgtggacc agatggacaa cgtcaatccc    19800
ttcaaccacc accgtaactg ggggttgaag tacaggtctc agctgctcgg aaacagcaga    19860
tactgccgtt tccatattca ggtgccgcag aaatactttg ccatcaagaa tctgctcctg    19920
ttgcccggca cctacactta cgagtgggtc ctcagaaagg atcccaacat gattctgcag    19980
tccagccttg gcaacgactt gcgcgcggac ggcgcgcaga tcgtgtatac cgaggtgaac    20040
cttatggcca atttcatgcc catggaccac aataccagca accagctgga gctgatgttg    20100
cgcaacgcta ccaacgacca gaccttcgcg gactacttgg gcgccaagaa cgctctctac    20160
aacgttccgg ccggctccac gctgctgacc atcaatattc ccgccagaac atgggagggt    20220
atgcggggct ggtcttttac ccgcctcaag gcctcggaga cgccccagct gggcgctcag    20280
tacgacgtcg gtttcaagta ttcaggctcc attccctatt cggatggcac cttttacctg    20340
tcccacacgt tccgcagtat gagcgtgttg tttgatacct ctatcaactg gcctggcaac    20400
gaccgtctgc tcacacctaa cctgttcgag atcaagaggc cagtggccac cgacagcgaa    20460
ggcttcacta tgtcgcagtg cgacatgacc aaggactggt tcctcgtgca gatggccacc    20520
aactacaact acgtgtacaa cggttatagg ttctggcctg acagacacta cttccactat    20580
gacttcctac gcaacttcga ccccatgtcg cgtcagggcc ccaacttcct ggacaccacg    20640
ctgtacgacc tggtgtccag cactcccgtt gttaacgaca ccggctcaca gccgtctcag    20700
gacaacgtgg gtaacaactc cggctttatc gcccctcgca gctggcccgt atggaccgca    20760
cagcagggcg aagcctggcc cgctaactgg ccgtacccgc tgatcgggaa cgacgccatc    20820
agttccaacc aaaccgtcaa ctacaagaag ttcctgtgcg ataactacct ctggaccgtg    20880
ccgttcagct cggactttat gtatatggga gagctgaccg atctgggtca gaaccccatg    20940
tacacaaaca actcccatag catggttatc aactttgagt tggaccccat ggatgagaat    21000
acttacgtgt acatgctgta cggggtattt gataccgttc gcgtgaacca gcccgagcgt    21060
aacgtgctag ccatggctta cttccgtacg ccttttcgcca caggcaacgc tgtgtaaaaa    21120
aaagacggct gggatgtcgg gaaccaccga gacccaactg cgggacctgc tgtcctctat    21180
gcacctgcgg caccgcttcc tgggtgtttt tgacaaaagt ttcccaggat ttctcgatcc    21240
gcacgtgccc gcctcagcta tcgtcaacac cggctcccgg gcctccggag gtatgcactg    21300
gatcgggttc gcgttcgacc ctgccgcagg acgatgttac atgtttgacc ctttcgggtg    21360
gtcagaccag aagctgtggg agttatacag agtcaagtac aacgctttca tgcgtcggac    21420
cggcttacgg cagcccgatc gctgttttac cctggtccgt tctaccgagg ccgtgcagtg    21480
```

-continued

```
ccctgctcg gccgcttgtg ggcttttttag tgccctttttt atcgtctctt tcgaccgtta    21540
ccggtcgaag cccatggatg gcaatcccgt gatcgacacc gtagtcggtg tgaagcacga    21600
aaatatgaat tctccgccct accgcgacat cctgcaccgt aaccaagagc gcacctatta    21660
ctggtggacc aagaatagcg cctattttcg tgctcatcaa gaggaactcc gacgagaaac    21720
ggcccttaac gccctacctg aaaatcacgt ttaatgaccg actgtaaata agaacgacg     21780
cacacacgta ctgtacatat ttgtgaatag agcaaccgtt tattagataa acgtcaataa    21840
atgccgaccg atagaccgac aaggctcttc actggcttta tttaaagaaa caaaaggatt    21900
aagcgaacgg gtcgtcactg gcgatgggcg agactggcgc caacacctcc gttttaaagg    21960
cgtacgactc gttccaacgg aactcaggca catgtgtggg ctctgaagaa cccatcacgg    22020
cagtaaacag ctccgtagca aagacgtacg cgtagcgcag atccatggcc gacagacgcc    22080
aggcgcaggt ttttcggtc ttcttcagac cgcggcctgc tccgcccgac gccgcctgcg     22140
ggttgcagca ggtgaacacc atggtatgcg ggttttttctt gtgagccttc atatcgggcc    22200
tgctctcgac catgtcgcga gtaatgtcgt ctgtgccgtt gagcttataa ggagtcattt    22260
tacagaactg tctccctgaa atggctcgat cggaggcgta gttgcagttg caattggttg    22320
agatgaggac acattcctct gcccggcgct tgtccgcgtt ggggtaaagc gccttcgtcc    22380
agtctatgtc gtgacgcatc gcgctgaccg ccttggcggc gtcggaaaag accatggcgc    22440
aactgccgtg cgcgtgggga tgagggaagc cgctgtgctc ctgatccttg tagcacaccg    22500
cgttcgcgtc gaacctgagc accaccacct gtcgtccaaa ccggttcttc tcgattacgc    22560
cgttctgttc ggccagagcc ctctttcccg cctcgctaga cgggttcaac tccacggtac    22620
gaggtttcgt caccatgtcc acaccgtgca tgcatttcgg gaagggctcc tggagcgctg    22680
ggaaccagcc atggcgccaa acgtgcgccc ctccgggcac gaacttgggc tccagacccg    22740
cgcggctgta gataacggct gccaggaacc gccctacctg agcgttgaaa gagtcgtagc    22800
tagaaaaggt caggcgaaat tcgggatgct ttttgcgaac gtatgtaccc cccatttttgg   22860
tccaaatgga gtcgtcgggg cgcacgctgg ctccctgcca ctgtaggtcg agagcttcgc    22920
agatgctggc gacggtggcc atggcgcgtt gcgcgccgta gaccacgggg tctgacagag    22980
gggcctccgg ggattcctcg tcgctggcgt tttcttcgtc atcgacaacg gtttcccgcc    23040
ggcgggtaac tcgccttacg ggggatgggg actcctcgcg gcggctgacc ttcttgcgag    23100
tcgcgcctcg gcccggggcg accacttcca cttcttcctc ctcctcttcc atcatgactt    23160
ctgccgttct cttgacaggc ttggtgctgc gaaagccatg agctcttttc ggggttcttt    23220
ccatgacttc tgcttcggtg acgggatctc gcgtttcaaa aagttcttgc tctccctcct    23280
cttcagagtc aggactact gccggagagg gtggaagcgt cttttgaagc ttcctgggac     23340
ctatagggta aagttaacgc ccatcgtcag cgagaccacg cctcgctggc cgatgggatc    23400
acgagacacg ataaaagacc gcgaccaaaa cactcttggg gctagtatcc ctacccgggt    23460
gcgagcgtgg cagatcttcg ctcttctgct tctccagtgg attctcgggg tctttcggcc    23520
ccgtcggtct ctggggtggg agaggcctgc tcctccctct gtttgacttg attaccgtcg    23580
acggcccggg ctcttcgagg tccacgaagt ccgccacgtc ttcgtcgctg ctgatcgtct    23640
ctgggtgaag cgtttctgcc atcgtggctg tcatcgaaaa tggcagacaa gattacccga    23700
gaggaaaaaa ccatagcgac gctggacctc gtgttacgac tggtcgtcga tgctggtaac    23760
tgggacgtgt tctcgaaacg tttggttcgc tacacacgcg aacagtacgg aatcgagctg    23820
```

```
cccgaagata tcggggactt accggacaca tctgaggtct cgaaagtgct gttgagtcat    23880
ttgggggaag acaaggcggt actgtccgcg taccgaatcg cggaactgac gcaaccttcc    23940
gaaatggacc gcgctaaggt cacagaggga ggcctggccg tacttaacgc gagtcgcgat    24000
gaaagcgaag ctcagaaccc ctcgaacccc gaacccgaga gcatcgagag cgacgccgta    24060
gaggatctcg gcgttgcagc agagagcgac cctagcgatg acgaacccga cccagaaccc    24120
gagtatgacc atcgagaggc ggatcatgac tctgatgcgg atagcggata ctattcggca    24180
gatgggggac gacctggaac accagtggac gaggagcccc aggacgattc tccctcttcc    24240
gaggagaccg catccactgt catcgaagaa gcgcagacta gcgctagcaa cgattctcat    24300
gacgacgaca ctcaccgcga cgacggcagt gcttctgaag aggatctcga gcgggacgcc    24360
ctcgtggccc cggccgatcc ttttcccaac ttgcggaagt gtttcgagcg ccaagccatg    24420
atgctgaccg gggcgttaaa agacgccgcg gacacggctg atccgccaga aacgctctcc    24480
gtcgacagcg tgcaaaggca gctcgaacgc ttcgtcttta accccgaccg ccgcgtgccc    24540
gccgaacact tggaggtacg ctacaatttc taccctcctt tcctcacccc caaggccatc    24600
gcgagctatc acatctttgc cgtcaccgct tccatccctc taagctgcaa agccaaccgc    24660
agcggcagcg accttctagc caaagcaaaa gagagcactt tcttcaaacg cttacctaaa    24720
tggcgtctcg ggatagagat cgacgacggg ttgggaacgg aagtcacggc ggtaacagag    24780
ctggaagagg caaaaatggt tccgttaaag gacgacgtgt ctcgtctgca gtgggcaaaa    24840
atgcgcggcg agcacattcg cttcttcagc tacccgtcgc tgcacatgcc tcccaaaatt    24900
tcccgcatgc tgatggaaac gctgttgcaa ccgttcgcgg acgaaaacca aaaggcggaa    24960
gaggcacttc cctgtctgtc ggacgaggaa gtgctggcca tcgtggaccc gacagggcgc    25020
ctccacggcg aggacgcgct caaggccgtg gaaaagcgga gggccgcggt cactatggcg    25080
gtacgctaca ccgcgaccct cgaactcatg gaacgcgtgt tccgcgaacc gtctatggtc    25140
aaaaagatgc aggaggtcct ccaccatacc ttccaccacg gcttcgtcgc cctggtacgc    25200
gaaaccgcaa aagtcaacct gagcaactat gcgaccttcc atgggcttac ctacaacaac    25260
cccctgaaca actgcatcat gtccaagctc ctagaaggag cagacaagga ggactatgtg    25320
gtggactcga tctacctttt cttggtcctg acgtggcaaa cggctatggg tatgtggcag    25380
caggccatag acgatatgac tatccagatg tacaccgagg tctttaccaa gaataagtac    25440
aggctgtact cgctgcccaa cccgaccgcc atcggcaagg ccatcgtgga catcctcatg    25500
gactacgacc ggctcaccga ggaaatgcgg aaagcgctgc ccaacttcac ctgtcagagc    25560
cagattactg ccttccgcca ttttctactg gaacggtcca acatcccagc ggtcgccgcg    25620
cctttcatgc caagcgactt tgtgcctctg gcttacaagc agagccctcc cctcctctgg    25680
gaccaggtct atctgctgca gctggccttc tatctcacta gcacggagg ctacctgtgg    25740 gaagccccgg aggaagaggc caacaacccg tccaaccgga cttactgtcc ttgcaatctc    25800
tgcagtccgc accggatgcc aggtcacaat gcggcattgc acaacgagat tctggctatc    25860
ggaacgttcg agatccgcag tccggacggg aagaccttca agctcacgcc tgagctgtgg    25920
accaacgcat acctcgacaa atttgacgcc gaggacttcc acccgttcac ggtgttccac    25980
tatcccgaga acgcatcgcg gttcgcatcc actctaaaag catgcgtcac gcagagcccc    26040
gaaatcttga gcctgattcg ccagattcag gaatcgaggg aggagtttct gctcaccaag    26100 ggcaagggg tgtacaaaga cccgaacacc ggagaaacca tctccagaca gccccgggac    26160
actgcccgcg cgcagcacgc tggagacggt caagctctac cagcccctgg agcctatacc    26220
```

```
accggaggaa atagagcgga gacagcgcct gctggagctg tacggcttgc cccggactac    26280
caagacgggc agtttcctat cgcgaaagtc ggcccgcact accatggccc aagaatgtt     26340 agacgagaag accagggtta cagaggcggg cccgaggtg tacggggaga gcgcgaggtc     26400
gtcctttcac gaagagcagg aggaagacgt tcggacgga gaaacactag gcagtcagga    26460
tacaacgaac gggctaaccg atatttcgga agaggaggag gaggatctgt tcgagggcaa   26520
caaggagaac atcccaccac ctcgccgtcc gcctcggaac cgccggctcc gagccgcata   26580
ctcgctcgag gaaccctcc ttcccccgag cgccgcgacc gacaagaaga gtaagaaagt    26640
cccaaaaagg cgaggtaaat atcgcagctg ggctaagcac cgcgtggcga tatgccaggc   26700
acttcgcgat gcggtctttg accgcaaaaa ggcgggcgaa atcctcaagc ggggtcaccg   26760
gctcttcgtg cccgctactg tcataggcta ctatgctcgc aaactctctc cctcatttct   26820
cgctcctctc tccagccaca ccgcaccct cctcccacca aaaaacacc ggcgctaagg     26880 ctgtgcgtct gcgccaagat ccggtgccgc agcacatcgc ggacctcaga ggggaaatac   26940
tcgacatcct gttggaaatc gagtcgtacg cccgccgccg tcccgaccgc cacgtgtcca   27000
ttcgcaacag aacgcgcgaa agcatcaccc gaaaactgca ttacgagaaa aatgaagata   27060
agcttacccg tatgaagagc gatgctatca agttgctcgc tctctggcag accgtttaac   27120
tcgtgttcct ttatagccct tcggaaccat gaacctgatg aacgccacac ccaccgaata   27180
cgtatggaag tacaacccag tctccggcat tcccgccggc gcgcaacaga attacgcgc    27240 cactatagac tgggtgttgc caggaggaac cggtttcgca atagcaacca acgacattcg   27300
aagacaaacc cttaacccgg ccgtgacccg tgcaattacc gcgcgttttg aagctgagtc   27360
agaccagcaa ccgtacgcta gccctcacga gaccaatgtt atcgcggcca atgtcctcga   27420
ctcgggttat cccaaatccg gtctctaccc attagagctc agcggcaatc agcgcgtaca   27480
gctggcaggc ggcctaatgg taggtcgcac tgagggcagg atgcaattag cgggcggttt   27540
aacagaagga agagtgcaac tttctggagg tttccacgga cggccgttgg ttagagggcg   27600
gagcagaaga ccgcccagat ggtgcggcgc cgaactgact gggaacggac tgcccgagca   27660
agccgaagtc acttctgaca cttacaagta cttcctgaga acacagggtc ccagccaagt   27720
ggttgaagag cccggcgtct tttcgcaaag acaatttatg actaccttcc tcccctccgt   27780
tgtccctcat cccttcgaca gcaccaaccc cggcgatttc cccgcgcagt acagtgccat   27840
ctacaaaggc cgcacggcct tcgaagacac cttttgggac tggtgaagcg cacctttttgt  27900 tggcgatgct ccgtttcgca ataaatttct tccaattctc tgtcgttaaa cggctcccgt   27960
ctggtcactg tcacgcgctc gccgcccteg ctcgtcaccc gcgcgcggta ccgtcgcctc   28020
agccagaata caaaaccggg gttcaggggt tcgtcgaacc gtaccacagc ctggtcgttt   28080
aatctcaacc aatattttct agggttcgac atcatgaacg aggaggttcc cctaaagcgt   28140
gtcagccctg acgaaaccga gacggttccc aaaaaaccgc gaaccgacgt tcgcgacacc   28200
gtcagggccg gcactgacga cacggtagat ctcgtgtacc ctttttggtg gaatctcgga   28260
acgggagggg gcggaggagg aggaggcggg ggcggcggca gtggaacctc tctccagccc   28320 aatgaccccgc tttacgccgc cagcgggacc atcaacctac gcatgacatc cccgctaacg   28380
ttgtcacaac gagccttggc tctcaaaacg gacagcaccc tcaccctcaa cacgcaaggc   28440 cagctggggcg tcagcctcac ccccgagac gggctcgtcc tcaacaccaa cgggctcagc   28500
atcaacgcag acccgcaaac cctcgcattc aacaacagcg gggcgctcga agtcaaccta   28560
```

```
gaccccgacg gaccctggtc taaaaccgcc acgggatcg atctgcgtct agatccgacg    28620
acgctcgaag tagacaattg ggaactagga gtcaagctcg atcccgacga agccatcgat    28680
tccgggcccg acggtctctg cctcaacctg gacgagactc tgctgctcgc caccaacagc    28740
acatccggca aaacggagct cggggtacac ctcaacacca gcggtcccat tactgcggac    28800
gaccagggca tcgacctgga cgtcgatccc aacaccatgc aggtgaacac aggaccttcc    28860
ggaggcatgc tggccgtcaa actcaaatct ggcggcgggc tcaccgctga ccccgacggt    28920
atctcggtca cggccaccgt cgcgcctccg tccatcagtg cgacagctcc tctcacctac    28980
accagcggca ccattgcact cactacggat acgcaaacga tgcaagtcaa cagcaaccaa    29040
ctggccgtga agctcaaaac gggaggcggt ctgacggctg acgcggacgg aatctccgtt    29100
tcggttgcac cgaccccgac gatcagcgct tctcccccgc taacctacac caacgggcaa    29160
atagggctct ctatcggaga ccaaagcctc caagtcagct ctggacagct ccaagtcaaa    29220
ctgaaaagcc agggcggtat tcaacagagc acgcaggggc tgggagtggc ggttgatcaa    29280
acccttaaga ttgtgtctaa cacgctcgag gtcaacacgg acccgagcgg accctcacc    29340 agcggcaaca acggtctcag cttagcggcc gtcacacccc tagcagtgtc ttccgccggc    29400
gtcaccctga actatcagtc ccctcttaca gtcacgagta actctctcgg gctctccata    29460
gccgcgccac tccaggcggg tgcgcaaggc ttgacgtaa acacgatgga acccttgagc    29520
gcctcggcgc agggcatcca gctgcactac ggacagggat ttcaggtcgt cgcgggcacg    29580
ctgcagctgc tcactaatcc ccccatcgtt gtctcatccc gcgggttcac cttactctac    29640
actcccgcct tcacggtgag caacaatatg ttggggttga atgtagacgc cactgactgc    29700
gtggctatca gttcagccgg cctacagatc cgtaaggaag cccgctgta cgtgacctcg    29760 ggaagcactc cagcattagc ccttaagtac agctccgact ttaccattac caatggtgcg    29820
ctcgcgttag cgaacagcgg cggaggagga agttccacac ccgaggtggc cacctatcac    29880
tgcggggata acctactcga gtcctacgac atcttcgcct ctctacccaa caccaacgcg    29940
gctaaggtgg cggcttactg ccgtttagct gctgcaggtg gcgtggtcag cgggaccatt    30000
caagtgacaa gctatgccgg acgatggcct aaagtgggca acagcgttac ggacggcatc    30060
aaatttgcca tcgtcgtgtc tcccccccatg gacaaagacc cacgatcgaa cctcagtcag    30120
tggctgggtg ccaccgtatt ccctgcgggc gcgactactg ctctcttctc acccaacccg    30180
tacggctccc tcaacaccat caccacactg ccatccatcg cctcggactg gtacgtgccc    30240
gagtccaacc tggtcacgta taccaagatc cattttaaac caacggggtc gcagcagctg    30300
cagctcgcga gcgagaact cgttgttgca gcggcgaaat cgcccgtgca gacgacgaaa    30360
tacgaattga tctatctggg atttacgctt aagcagaact cctcgggtac caacttcttc    30420
gatcccaatg cctcctccga tctatccttt ctgacaccac cgattccgtt tacttatctg    30480
gggtactatc aatgaacttg ttaactcctg cagcagcagc agcagcagca gcagcatggc    30540
tgaccagaaa aggaagctgg cggatccgga tgccgaggct ccgacgggca agatggcccg    30600
cgcgggtccg ggagaactgg acctcgtcta cccttcttgg taccaagtag ccgctcccac    30660
ggaaatcaca cctccgttct tggacccgaa cggtcccctg tactccacgg acggcttgtt    30720
gaacgtcagg ctcacggcac ccctcgttat catccgtcaa tctaacggca acgcgatcgg    30780
ggtcaagacc gacggaagca ttaccgtcaa tgcggacggc gcgctgcaga tcggaatcag    30840
cacggccgga cctctcacca ctaccgccaa cggcatcgat cttaatatcg atcccaaaac    30900
cctggtcgtt gacggtagca gcggcaagaa cgtcttggga gtgcttctga aaggacaggg    30960
```

```
ggcgctacag agcagcgcgc aaggcatagg cgttgccgtc gacgagtctc tacaaatcgt   31020
cgataacacc ttggaagtga aggtagatgc tgcaggtccg ctcgccgtca cagcagccgg   31080 cgtaggggttg cagtacgaca acacccaatt taaagtcacg aatgggactt tgcaactgta   31140
ccaagcgccc actagcagcg tggccgcatt tacatccggg acgatcggct tgtcctcccc   31200
tacgggcaat tttgtgagct ctagcaacaa cccgtttaac gggagctact tcctgcagca   31260
gatcaatacc atgggcatgc tgactacctc gctctacgtc aaagtcgaca caaccaccat   31320
gggtacgcgt cccacgggcg cggtaaacga gaacgcgcga tactttaccg tctgggtgag   31380
ctccttcctc acgcagtgca acccctcgaa catcggtcaa gggaccctag agccaagcaa   31440
catcagtatg acctcttttg aacccgccag aaacccatc tcacctcccg tgttcaatat   31500
gaaccaaaac ataccctact acgcttcccg attcggggta ctggagtctt accggcctat   31560
cttcaccggc tcgctcaaca cgggaagtat cgacgtacgg atgcaagtga cgcccgtcct   31620
cgccaccaac aacacgacct acaatctcat cgcctttacc ttccaatgcg ccagtgccgg   31680
actgttcaat cccaccgtga acggcaccgt ggccatcgga ccggtggtgc atacctgtcc   31740
cgctgcccgc gcccccgtta cggtctgaac aataaagaca aggtgaacca tttatacagt   31800
ctcacgtctc tttattgcat acgctccgct aaatgtttcc attcgctcat tgccagtaa    31860 tacagcagat tcgcaaactc actgaaccaa tcttctgtat aaaaatgtac gcgctgcgtg   31920
tccaaatcaa catcaatttt cctcatatac agacaggggc tgccacccgc ctcccccaag   31980
cgcgacaccg caattaggaa tggtagcctg ctgtgcaggt ccacgtgaat taacatcccg   32040
cacacgttcc cgatcggtcg ctgcataaat actggagaga aatcgctaaa ccccggtgac   32100
gcccacatag ccacgaagta caccctgcc acattcaagt catcctccaa cctggcccaa    32160
acataagtgg ccaaatcgga aggagccagg tggcaagccg ataacccat acgatgcaaa    32220 ggtaacccgt ggcaagcgca tcccccgaaa tgaagttcga aagaatcgta acacagtagc   32280
tgataggcat gaagcggcgt cggcatctga agaccgtcat catcttcgtc gtcttccatg   32340
tcatccccaa cttcctcctc gcgctccgct tcctgttggc ggcgctgctg gtgctgcagc   32400
accatctcca ggatctgctc gtcgttcatc ttaatccgga attatcgcgt acggatgttc   32460
ctcgtcgtcc gaactgacaa cagaaggcgg aggagctgtc agtggtgctg tagaggctaa   32520
cgatgctgca gcaccggtct cttgcaattc gaaataccaa gggttgctac tgacggtcca   32580
gttcccgccc cgtgaaccag gccagcggga aatcggtgca ggtaggggat ccggtgaagg   32640
agaccgggaa tggagggaag gaactgcgag atccttatcc actcgataca aaccgtataa   32700
cagggagccc aacgccaggt acaccaggaa cgtactacaa acgaacacgc tgattacaaa   32760
gtttaacgaa gacagatggt tctgtaggaa caggaagctg cacaggatga tgctgctgta   32820
ggacagggcg accaggaggg ccaagaactc gcgccaatag cgtccacaac actgcaaaat   32880
caaacacgta attagctata cggacgttca ccagcgactc tcgcgcgtcg ttccataaac   32940
acattgcgca gataagccaa ctgagcagaa cagaacagag agagaggttg ccgcgtcgaa   33000
cactgtttgc actgtccgaa acactcggga tgagactccc cgtacttccc gtgcacatga   33060
aatacccact cttcgacgtt agcgtaggac aaccgacggt aaccggggaa gtaacacagt   33120
ccctgcgaca cgatcggcca cagttccggc gacaccatca cgcggagcat gcttctcagg   33180
cagacgggtt gggtcacggc gctgctgcga gaaatagttt ccaccatgat ggtggccgtc   33240
acggtcacgc gacacgcatt catgagaaca accggagacc gcacaaaagg aacagacgaa   33300
```

```
ggcacttgcg aaaaggacac ctcaaagctc atcgagcgga gagccatctt tacggatatc    33360
ttctccgcaa tcagaaagcc tgtggtgaaa aacttaaaat ctgtcttcct gcgagcaagc    33420
atccacggtt ccaagtcgta cttcatccca ggtgtaataa aaagcaacct acgtgagagg    33480
tagtgcagca gggcggtctt ctctgcccgg ttcaggtgaa gggcactcac aatccggact    33540
atgcaattca tgagtacgta gtctcgccgt ttgaaacaca caaactttgc gctgcgtacc    33600
gtcactagca ccgtgacaga actatgcaat cgcctcatca gatcattatc gaaacaccgc    33660
aagctagcca cggctctatt tatgcggtac tcgttcagtc tctccatttc ctcctgtcga    33720
caagttggat cgtgacgtag gagaaaacta aaccatatta ctcctacttc gttatgaaag    33780
ccacaagctc tgctgacggt taaagactcc ttaagaaaga aaggtagta cagtcaagct     33840 gacccataca ggtgaacccg ccccaagtca cgtaagtcaa ctcaccgaaa gaggacacag    33900
agccatatcc gctgcttcaa agctttattg acgggtctaa aggcgtaaag aaaagaagaa    33960
tttaccgttc tgcatctcaa accccaccac cacgcgaaaa agtccgaacg atgctgcagc    34020
accgttcacg caaagtcccc ggacgcgcac aaataaaccc ttaatcccga taacggtgct    34080
gcagcaccgt cacgctgctg cagcatcgtc agacgtttat gacatgcagc cgattccgtg    34140
cggatttatg gtcccataac ggttccaggt cctttcgttg ctgcagcacc gtttcacgta    34200
aagaagctgt acaggtcaaa ctggtccgga ttactgatta ttcgggggag agccacgtga    34260
cgtagactcg aacgacgtcc acttccgata caaaccacat ctctctggac acaggcttgt    34320
ccgccttgag ccaaaccatg tgattcttcc ggtccgttct gacgtcaatg ccgacacgcc    34380
tcttggtgtt tgaacaggca tcccagtacg tagccaggac cactcggtga cgtcgaggtt    34440
gaggtttaaa ggtcactacg gcctgtaacc cggtactcca gggccctaaa ctaacatatt    34500
ctccggccct gcccactaca ttcgggtgat caaatatgac ataatcctta aacaatttgg    34560
ggaacttcaa acagccacat ttgggcggga caggaagatg gtgcgcagaa acattgatat    34620
gagagcgcca tctagggaca tcaaagcggt gcccgcctgg atggcaatcg tacttcttag    34680
ttccggtaaa gtaataggtg tgagtccgga aacacgtaaa ctccgtcact tcctgtgtcg    34740
tcattgccct cgcccctagt gacgtcagag tgccacgccc cttgtacagt ctaataaatt    34800
ttaatacacc cccgccccta gcatataaaa caatgggagc ctcgcccaca ttcctatccc    34860
taataaaata ccatctgacc gaataccgt gttccatccc tattgtttta gtataataag    34920
ggtcataagt ccacaactcc gcggcattgc cctctgtcac caccaacagc aaataggaag    34980
atgccatgtc atcctctcgt aaaagcatcc tccaatcagc tacctcttcc gtgtagtact    35040
gagttggctg actgtaatca cgccccgtga cgtaggctga ccacgcggaa ggaacacttc    35100
cgtgcatgct cagtagctgg tcagcctggt gagtatccag ggccttcata aggtcaaag    35160 gcgccataat gtgataacac agtccatccg atcggaggaa atcaaaggga atatgtacat    35220
cttcacaatg gcgcctccca gaataagacc atgcacagat ttgacctttc caccaagcac    35280
gtgactcgca agcctcatgt ttttgaccag tcagatcgct ccgtatatac tcgtctccta    35340
ttggtcgatc aaaaccgtac gaaccaatac tagacgcaat caccactacg taatccgcgt    35400
catccctaga gataacacta tccgcatccc tattggctga ccaatgacca ccggaagaca    35460
gcaaaaggtt taacccttt tgtgtgtaagt ccatcctata accctggaaa ctttccaatg    35520
ggggatctag cgccactatg cggccaacct tttttgaccc tctgtccgga ctagaagttg    35580
gcgggacaaa gccgcgcata cagtgcccc tagcgacatc cctatgcaat gaattcgatg    35640
gtccttgaac tccgtaaaaa aatgagcagt ggtcctgact gcgtaatagg ccggccccct    35700
```

```
cacatcctgc ccccacaaaa gggcgtctac cttcttacaa atatctctca gctgattggt    35760
ccagtccaac agaatgaccg gggactctgg cgtcataatg gtatgcatac gcaaaatctt    35820
tctcatcatt tcactggtcc atttatatgt gccgtcatag cgcgccctat taataagcgg    35880
acacacatcg ggatacatgt cctgaaccag aataatgagc tccccgctat ctttaccatc    35940 caatacccccg agccgccgca tttgactgac aacccagggg ccgtccgaaa aagtcaaaaa    36000
agtctcattc caccatacaa ttaacttggg ccacgaagga aaatccggcg aataggtgcc    36060
catcaagcgc ctgacgtcag ccttaggata tggcggatcc catctggaat ccgacccatt    36120
aaagcacgaa gatagggcag acatcggcca atggccagga gaatgggtag aattaataag    36180
gactccgcct ccatttccga gcttttaaaa aaagagaaaa atggaaatca gccaagagac    36240
caccaccccg tgattggatg attggtcatc agaagatcga taagggaatt tattttctgg    36300 gagcccccccc cccccctact cctatttaaa aaataaccct ttcctcacca agctcagaag    36360
acagaggagg agagtagagc gccgctcaga ggtcatccgc cgagagaaaa tcccgcgcag    36420
agaacagagc tctcaggtag gggtctggag ctctctggaa aaatcgcggg ctcttataca    36480
cttactctcc gcccattcga aagccgcgcc tgactagagt acacactata aattccattc    36540
cggtgactta ctactaggcg ctggccactt atcaaaagaa acagttctaa gaataggaca    36600
aagtccaacc gcaataaaac acccttgtca aacatgataa gagtgttctc gagaaggtac    36660
tggaaaagca aacagtccaa ctcccaagtt aaatattacg caaagaggcg taacgagaaa    36720
agactagaaa gtgtaaacac acctctccta gttatatata aacccagcgg ggcagtccct    36780
agaagaacac tacctcaatc cagttacaca ttaacccggg aacctattat tgattaacta    36840
gacagtactt cctcattttc tactggaact ttccactgcc ctccggggat tttccattgg    36900
caatcattaa cttgactttg tactttatgt ttactctcca tagcaacgca ccttatatgg    36960
aaaatatgct cctccccgga ccgcccatcg taccacctga gcaggtaggc tgtacctttt    37020
cctattggcc cattatgagc tcacctggtt aatcatatac ccgctccgcc tatataggta    37080
gcataccggg acaggttccc tcacagtcta ttgcagactg ccgaagagag aggagctccg    37140
cataggactg ggaccagaac cccgagactc tgccggtaat atttttaattt catttaatcg    37200 aatcaaataa atcaaaaatc aactcaaacc catgattctc aatggaaatt tcttgtgatt    37260
ttctttcgcg cgcgaccacc ccctatggca ccccccctgta cacccccctg tacaccccccc    37320 tgtacaaggg aacctaccccc cctgtacagc gaccaccccc catggacacc cccctgtaca    37380
ttctacaggt atggcccgca acccattccg catgttccct ggggaccttc catactacat    37440
ggggaccatt tcctttactt cggtggtccc tgtggaccct agccagcgga atcccaccac    37500
tagccttaga gaaatggtga ccaccggcct gattttttaac cctaacctga ccggcgagca    37560
actgcgggaa tactcattca gccccctagt gtccatgggg agaaaggcaa tcttcgcaga    37620
ctacgagggt ccccagcgca ttatccacgt taccattagg gggcgctccg cggaacccaa    37680 gaccccccagt gaggccctca ttatgatgga gaaggcggtc cgtggcgcgt tcgcggttcc    37740
tgattgggtg gccagggaat actcggatcc cctcccccac ggcataaccc acgtggggga    37800
cctgggcttc cccattggtt ccgtgcatgc cctgaagatg gcgctagaca cactgaagat    37860
ccatgtccct cgcggagtgg gggtccctgg ctatgagggt ctctgtggga ccaccaccat    37920
caaagccccc cgacaatatc ggctcctgac cactggagtt ttcaccaaaa aagatctgaa    37980
aagaacactt ccagaaccat tcttcagccg attttttaac caaactcccg aagtttgtgc    38040
```

```
catcaagact ggcaaaaatc cgttttctac agaaatttgg tgtatgactc tcggcgggga    38100
tagccccgcc cccgagagaa atgaacccag aaatccccat tctctccaag attgggcaag    38160
actgggtgtc atggaaacct gcctacgtat gagtaggcgg ggactcgggt ctcggcacca    38220
cccctaccat tctctgtaac caatccctga ataaagattt gcataacaga actttgactc    38280
ctccttttat gtgggtgggg taatgggcgg cacttggggg taatggcggt tcctattgga    38340
tgggtaacac cgactccgcc ctacaaagtt aatgattgat ttttcggact tagaaaaatt    38400
tcgactgtca cctggatgtt tttccccact taacctctag ggggagatag atcgcgtcca    38460
aggggaggag ctcaataccg gaccgcctat taggtgtggc ttcgggctcc gcctagtggg    38520
aggagacagg aaaaccacgc ctagtgacgc tgggtcaaag tccaagggga gtggtttatg    38580
cgcaccgcct tggggcgtgg tttgggcggc gcaaggtaac ccttggactg ggaggagact    38640
tctgtccctt gggcgtgtca acaggtaaa ccccacccgc gcgattaatg attaattttt    38700
cggacttaga aaattttcaa cctgatactt tattttcaag cttttcccgc cgacgggcaa    38760
gcctcctatc tctccgtcta tgactccaca gagcctcatc tgaatatgta aatgtgctga    38820
accgcaaccc cgtagaccgc gcccacccca gcatcaaagg taacgccccc gatgccacaa    38880
tgtaattacc cactgttaaa ttaggatcct tacaccaatc atttctgtac aatttaaacc    38940
accgcccacg cgggactttc ccgtggtggt agaaaaaggt tttgaaaaac gcgcgcatta    39000
ttttcgtggc ttcattaata gcggacatgc gcagatccag aaaggtcaga cacaccacca    39060
cggtcacatg acatttgcat ggagacaggg attggatacc gacacaatac gccatcggat    39120
actgaatgtc cacattggtc cgtgcatata cagtgtgcca cctcctcttg accgcagcca    39180
cgaatcccca gaagagttct tcccgccaca aaatcgaaac cggggcggcg gccccaaagc    39240
acaaatacaa aggcatcctc ctgaggctct agaaaaaaca actcattaac aggcatcccg    39300 ctataggta cattcgtgta aacagggctg catgccaacc aatgccccgc gttttacaaa    39360
gtgacgggcc accctattgg cggagggggt ccacgtattg cgcaccgcgt aaatagaagc    39420 caccccctcgc ggaacctgtg tacattcaaa tctcctccaa atacattcgc gcagtaaagc    39480
caccgccctt ttcaagaaag tccaatcaac cttatgcgtg ggcaaaaaaa tagaagctga    39540 atatacccccc gcaaactcct ccaatcggaa caggtaatct acactatagt gggacagcat    39600
ctcaacagtt aaactttccc aggcatttat caccgtcaat ttcagatcat ggaatacggc    39660
caagttaggc tccatcaagg tcacgcggag gtggaagtaa tacatcccga ataccctgt    39720 taaaaaaat agaaaatga actaaccgac aataagatcg gcagtaccca gtttcgatct    39780
ggggacctcc ggagtgcaag tccgacgctc ttacggctga gctacactgt cgatcttgat    39840
ccgctagggt acgcagtccg gagaagaaat atactaagtg agacccggtc ctatatatac    39900
aggttggttc aaaggaacct ttgtacccat taaaacaggt gcgtgactgt agaagccaca    39960 ccctacctg taccgataag gcacaccctg agcaaacaaa ccataaaggt atacttcctt    40020
attcagacag gtataaatgg aacctccgca caacagtccg gtaccatttt ccatcgcgaa    40080
aatgggcaac cctactctgc tccttctttc aggtctcctt tctctgaccc aggccatttc    40140
catcggagaa cacgaaaaca aaaccccggca tgtgattgta tggcggcact cctcctccca    40200
ccaatgctct gattggagaa cagtcacgga atggttcccg ccccaaaaag gcaacccggt    40260
gagaccaccc tacacccagc gggtttccct ggatacggca acaatacccc tcacggtaaa    40320
acccttcgag acaaacaacg ggtgttggga aactacgtca caaggcatta accatccacc    40380
aaccaccatt cagtaccggg tatggaacat caccaccacg cccaccatac agacaatcaa    40440
```

```
cattaccaaa ataactgttc gggaggggga ggactttacc ttatacggac ctgtgtccga    40500
aaccatgagt attatcgaat gggaattcat caaggatgtc acgccccagt tcatcctcca    40560
atactatctc tccattaact ctactattgt gtacgcaagc taccaaggga gagttacctt    40620 taacccggt aaaacacac taaccttaaa aggcgcgaag accaccgaca gcggcaccta     40680
caagtccacg gtgaacctcg accaggtatc cgtccacaac ttccgagtag gagtcacgcc    40740
catcgagaaa aaagaagaag ctaccgcaga gacacctgcc agcaagccca cgcccatacc    40800
acgtgtccga gcggatgctc gaagtactgc cctatgggtt ggacttgccc tttgcatcct    40860
gactgttata cccgcccta ttgggtggta cttcagagat aggctctgtg ttcccgatcc     40920
aatcattgaa ctggaaatcc ccggacaacc ccatgtaaca atacacatat tgaaaggtcc    40980
cgatgatgat tgcgaaactt aatgattgac aaacgtaata aaaagctgt gacgcacata      41040 agtacgtgtc tgtgtcattc atccatacct atatatggtg atagccccctt cctcaataca    41100 caccgagccg cgatggaccc cagaccactt gttctgctcc tcctcctagc gtcccatata    41160
agtacattcc ggcaaatgta ctttgaaggg gaaaccatcc atttccctat ggcatatat     41220 ggaaatgaga ccaccctcta tatgaatgac atcatcctgg aaggaacacg cgccaatacg    41280
accacccgta caatcagcct cacgaccacc aagaagaatg cgggaactaa cctgtacact    41340
gtgatctccg aaacgggaca caacgccacc tatctgataa ctgtacaacc gctgggacaa    41400
tcgatacacc acgcctacac ttgggctgga atacttttta ccttacaagg acaggtattt    41460
gaacacggta attatacacg atgggtgcgg ctggagaatg cggaaccgaa actcattatc    41520
agctgggcat tgtccaacag aacaataaac aaaggaccgg cctatactgc aaacatggac    41580
tttgatcccg gaaacaacac cctcactctc caccctgtgc tgataacaga tgccgggatt    41640
ttccaatgcg tcattgatca gcaaacaaac ctaaccctca ccataaactt tacagtctcc    41700
gagaatccac caatcgtagc acacctggat atccataaaa ctatttctag aacaattgcc    41760
atttgtagct gtttgcttat cgcggtaatt gcggtcttgt gttgcctacg tcagctcaat    41820
gtaaacgggc ggggaaattc cgaaatgata taaaacaata aagcagtgtg cgtcatggaa    41880 actttctca ggtgcttcct cattcacaca ggtatatata gggaatggaa aattagacag      41940
atacccacac cggaacaatg ctacttctca cagtagttct gttggtgggg gtcaccctcg     42000
ctgcggacca tcctactcta tacgctccga aaggggcag tatagaattg ggtgtggggg      42060
ctaaacagaa agggcaatac aaatttgaat ggcggtttgg aaatctaaaa attgtgatag    42120
ccgaaatgtc atccactaac caattagaaa tcaaatttcc cgataacggt ttccaaaatc    42180
gatccgagtt taaccccacc aaacataact taaccattca taatgccagc tacgaggaca    42240
gcggaaccta ctcactccac caggaagaaa atgatggcac ggaacacacg gacaacttca    42300
aagtgattgt tcaaggtatg tcattatata catatttaca atatgcatta atatcaccta    42360
tctaatagag cattaattat ccagacccga ttccacgccc tgaagtcaag ggaaccacta    42420
tgcaaatcaa cggaaaaact ttcaccaata tatcctgcca tctaccggcc ggttcctacg    42480
gcaatgtctc ctggcattgg aattataccg acccaatcat agtcgggtac gaaaatcaga    42540
gcatgctcgt tggaccttta ggggtaatgt attcatgtac ggcatccaat caagtctcaa    42600
aaaactccag tgcaataagt atggacaccg ccgaaccatc agagagtaag tagcgccctc    42660
tatagacatt atatagaata taactgaaca cattaagaaa cctctgtaat tatttatagg    42720
agcggagtgc gcatatacag gatacattgc gggcattata atcttaggag tgctttgcat    42780
```

-continued

```
attgttcatt tacctatatg caaatacccc tgaagtgcgg cagagaataa ccgaccaatt    42840
agaaaagctt ctcggaacat tctgtgacgt cagtatagaa gacggaatac cggaacgcac    42900
cagaagaaac aaaaaaagaa tcatcttaaa ggagccctcc cataggtgga tctggattca    42960
gtcatttgca taatatgctg tgtcataacc gccaccatca ccatagcaat cattgggcgt    43020
aagtattgtg acgtaagaaa aggcatgtct aaaaaaacgg tcactcacca taatgctgcc    43080
cccgataggt tgcgaccgcc ttccggagtt tgacgtagta tgcccgcgag actggatcgg    43140
atttcaaagc aagtgctact acttttcgga gtcagagtcc aattggagtg aagccgaaaa    43200
attttgtaga cagcaagagg cggagctagc agttcggcgt tccgaggagg aaaaggtaaa    43260
aagttaaatt ccaggaaact cctaattccc cgaaaaatta caaaaattaa cggagaccct    43320
ttacaggagt tccttctgcg ccaatgcgga acaggaacta actggctggg cgtaaccagg    43380
aagtcgaagg acggagctga ttgggtggat gcatcgtacg atgattacgt accatggtga    43440
gtcatgttat acgtcacatc cgggatgtga cgtatgcgga agttgatccg ggagtgaaaa    43500
cccggaagta acctgttaat ttgcatacag gtatgaaatt cggggaggcg gagactgcgt    43560
gtatttaaat ggagaccgag tgacgtcagc ctactgtgat acccagaagc tatttgtctg    43620
ttcctgtcaa gattcgtatt cgtattggtt agaaaacaaa taaatcaata aactaattta    43680
tgatatcatt catatttatg ggtgtggttt tattatgcgt cataaaacta ttttgcgtat    43740
agcgacacgc tgcggttatg gccggttatg actgcgttag tttttgaggt tattatacat    43800
catc                                                                43804
```

<210> SEQ ID NO 2
<211> LENGTH: 178
<212> TYPE: PRT
<213> ORGANISM: CELO Virus
<220> FEATURE:
<223> OTHER INFORMATION: Position: 794..1330 /note=ORF1

<400> SEQUENCE: 2

```
Met Asp Pro Phe Gly Ser Ser Val Pro Cys Ser Thr Ser Asp
  1               5                  10                  15

Leu Pro Glu Pro Lys Leu Tyr Phe Val Arg Leu Ser Pro His Ala Val
                 20                  25                  30

Pro Pro Val Arg Ala Thr His Gly Ala Ala Gly Tyr Asp Leu Phe Ser
             35                  40                  45

Ala Tyr Asp Ile Lys Val Pro Ala Arg Gly Arg Ala Leu Val Pro Thr
         50                  55                  60

Asp Leu Val Phe Gln Phe Pro Gly Cys Tyr Gly Arg Ile Ala Pro
 65                  70                  75                  80

Arg Ser Gly Leu Ala Ala Lys Phe Phe Ile Asp Val Gly Ala Gly Val
                 85                  90                  95

Ile Asp Pro Asp Tyr Arg Gly Asn Val Ser Val Leu Phe Asn Phe
            100                 105                 110

Ser Glu Ser Ser Phe Asn Ile Arg Arg Gly Asp Arg Val Ala Gln Leu
        115                 120                 125

Ile Leu Glu Arg Ile Met Val Pro Glu Leu Ser Glu Leu Thr Gln Leu
    130                 135                 140

Gly Glu Thr Asp Arg Gly Ala Ser Gly Phe Gly Ser Thr Gly Met Gly
145                 150                 155                 160

Ala Val Asp Arg Asn Gln Arg Ser Val Leu Glu Trp Leu Thr Pro Gly
                165                 170                 175
```

Ser Arg

<210> SEQ ID NO 3
<211> LENGTH: 276
<212> TYPE: PRT
<213> ORGANISM: CELO Virus
<220> FEATURE:
<223> OTHER INFORMATION: Position: 1999..2829 /note=ORF2

<400> SEQUENCE: 3

```
Met Ser Arg Glu Ser Glu Arg Tyr Trp Thr Leu Val His Ala Leu Ile
 1               5                  10                  15

Asp Arg Gly Val Val Ser Arg Glu Gln Trp Gln Met Val Asp Pro Ala
            20                  25                  30

Gln Tyr Gln Phe Tyr His Arg Ser Lys Gln Arg Gly Phe Lys Val Arg
        35                  40                  45

His Ile Leu Arg Asp Val Ile Arg His Met Cys Trp Ser Arg Thr Leu
    50                  55                  60

Leu Asp Tyr Met Ser Ser Ala Ser Thr Pro Ser Pro Asp Asp Val Leu
65                  70                  75                  80

Arg Asn Pro Leu Tyr Gln Leu Leu Cys Asn Gly Tyr Asn Pro Ala
                85                  90                  95

Val Val Gly Thr Ala Leu Ile Arg Trp Ala Gly His Gln Ser Asn Arg
            100                 105                 110

Asn Thr Val Trp Ile Arg Gly Thr Pro Met Ser Gly Ala Pro Tyr Leu
        115                 120                 125

Ala Gln Ala Ile Ala Tyr Cys Ser Pro Leu Val Gly Ser Val Asp Trp
    130                 135                 140

Arg Asn Lys Ser Asn Pro Phe Glu Gly Cys Pro Asp Ser Leu Val Phe
145                 150                 155                 160

Trp Trp Asp Gly Gly Tyr Val Tyr Asp Cys Cys Val Gly Leu Val Lys
                165                 170                 175

Gln Val Phe Arg Gly Glu His Val Ile Leu Pro Pro Glu Gly Leu Arg
            180                 185                 190

Gly Pro Asn Pro Cys Ser Glu Leu Phe Arg Thr Pro Val Leu Met Tyr
        195                 200                 205

Ser Gln Ala Asp Ile Cys Met Thr Arg Leu Arg Ser Gly Glu Leu Ser
    210                 215                 220

Ala Glu His Ala Val Gly Leu Arg Asp Cys Met Tyr Leu Ile Arg Leu
225                 230                 235                 240

Thr Glu Asp Phe Asp Cys Ala Gly Gly Ile Ser Cys Ala Asp Val Lys
                245                 250                 255

Gln Phe Val Ala Trp Ser Arg Glu His Pro Gly Glu Val Arg Glu Thr
            260                 265                 270

His Glu Leu Lys
        275
```

<210> SEQ ID NO 4
<211> LENGTH: 104
<212> TYPE: PRT
<213> ORGANISM: CELO Virus
<220> FEATURE:
<223> OTHER INFORMATION: Position: 3781..4095 /note=ORF3

<400> SEQUENCE: 4

```
Met Gly Val Glu Gly Met Trp Asn Val Phe Leu Phe Ser Leu Gln Val
 1               5                  10                  15
```

-continued

```
Ala Ala Leu Pro Ser Ile Lys Cys Ser Ile Asn Gly Ser Gly Phe Ser
            20                  25                  30

Ser Thr Lys Gly Arg Gln Tyr Arg Glu Ala Trp Gly Ala Ile Ser Pro
        35                  40                  45

Ser Asp Ser Met Glu Leu Ile Arg Leu Ser Glu Ile Ala Ser Gly Lys
    50                  55                  60

His Ala His Lys Ala Leu Lys Arg Leu Leu Ala Leu Glu Ser Leu Pro
 65                  70                  75                  80

Pro Gln Ser Thr Arg Val Phe Ser Ser Pro Arg Ser His Arg Arg Met
                85                  90                  95

Ala Leu Ala Ala Thr Phe Pro Ser
                100

<210> SEQ ID NO 5
<211> LENGTH: 136
<212> TYPE: PRT
<213> ORGANISM: CELO Virus
<220> FEATURE:
<223> OTHER INFORMATION: Position: 5963..6373 /note=ORF4

<400> SEQUENCE: 5

Met Val Asp Val Glu Met Phe Gly Cys Gly Gly Leu Leu Val Ser His
  1               5                  10                  15

Leu His Lys Phe Gly Thr Glu Arg Ala Cys Leu Arg Gly Asp Gly Ala
            20                  25                  30

Val Phe Pro Ala Val Glu Ile Gly Leu Asp Gln Leu Gln Val Pro Gly
        35                  40                  45

Arg Leu Phe Asp Gly Trp Asn His Val Leu Phe Arg Ser Asp Glu Asp
    50                  55                  60

Asp Arg Phe Gly Asp Arg Val Gln His Val Ala Arg Asp Glu Arg Pro
 65                  70                  75                  80

Gln Gln Met Arg Leu Ala Gly Ser Gly Ser Val Asp Asp Pro Asp
                85                  90                  95

Asp Gly Leu Leu Ala His Val Asp Gly Arg Gln Leu Ser Val Leu Glu
                100                 105                 110

Val Ala Thr Val His Leu Phe Leu Gly Phe Asn Phe Phe Val Gly Phe
            115                 120                 125

Glu Lys Leu Leu Ile Asn Ala Pro
    130                 135

<210> SEQ ID NO 6
<211> LENGTH: 378
<212> TYPE: PRT
<213> ORGANISM: CELO Virus
<220> FEATURE:
<223> OTHER INFORMATION: Position: 12193..13329 /gene: L1 /Product: L1
      52K

<400> SEQUENCE: 6

Met His Pro Val Leu Gln Ser Val Arg Asn Ala Ser Val Ser Ala Gly
  1               5                  10                  15

Gly Pro His Gln Gln Gln Pro Gln Gln Gln His Gly Val Ser Ser
            20                  25                  30

Val Arg Arg Pro Pro Ser Pro Pro Arg Tyr Pro Ala Gln His Ala Tyr
        35                  40                  45

Pro Gly Ala Gly Ala Thr Pro Thr Ala Gly Arg Gly Asp Phe Asp Gly
    50                  55                  60

Ala Leu Asp Pro Asp Glu Gly Pro Val Ala Cys Gly Leu Ala Ala Gly
```

```
                65                  70                  75                  80
Ala Gly Val Asp Glu Val Arg Met Arg Glu Arg Asp Ala Ala Arg Arg
                        85                  90                  95

Ala Thr Val Pro Glu Ile Asn Leu Phe Lys Ala Arg Arg Asp Val Val
                100                 105                 110

Pro Asn Gly Asp Tyr Glu Arg Asp Leu Met Tyr His Ser Gly Gln Ala
                115                 120                 125

Ile Asp Ile Asp Arg Gln Arg Val Leu Thr Pro Glu Asp Phe Lys Gly
        130                 135                 140

Ser Glu Pro Ala Phe Thr Pro Ala Val Asn His Met Arg Ala Ala Glu
145                 150                 155                 160

Leu Lys Arg Ala Ala Glu Gln Thr Ala Phe Gly Glu Glu Leu Arg Asn
                165                 170                 175

Thr Cys His Gln Thr Arg Ile Arg Thr Ala Leu Leu Arg Pro Glu Ile
                180                 185                 190

Gly Ala Gly Ile Tyr Tyr Leu Tyr Asp Phe Val Gln Thr Tyr Leu Glu
                195                 200                 205

His Pro Asp Gly Arg Val Lys Leu Asn Pro Gln Leu Val Leu Val Ala
        210                 215                 220

Gln His Ala Gly Asn Thr Met Leu Ala Gln Arg Leu Trp Ala Ile Ala
225                 230                 235                 240

Glu Glu Lys Asn Ala Trp Leu Arg Asp Leu Ile Glu Met Ala Tyr Met
                245                 250                 255

Ile Val Asn Asp Pro Tyr Leu Asn Thr Glu Gln Gln Leu Ser Ala Ile
                260                 265                 270

Cys Thr Thr Val Val Glu Leu Ser Met Lys Tyr Ala Lys Leu Ala Ala
        275                 280                 285

Lys Asn Gly Tyr Pro Ser Met Ala Gln Met Ala Lys Ala Gln Glu Phe
290                 295                 300

Phe Tyr Arg Val Met Gln Ala Val Leu Asp Leu Gly Val Gln Val Gly
305                 310                 315                 320

Val Tyr Asn Asn Arg Pro Ala Arg Tyr Arg Gln Lys Arg Met Ser Glu
                325                 330                 335

Ile Pro Gln Met Thr Asp Ala Glu Tyr Met Phe Gly Leu Thr Gln Ala
                340                 345                 350

Leu Glu Ser Arg Pro Pro Gln Gly Glu Ser Phe Ala Asp Glu Gly Pro
                355                 360                 365

Ser Glu Ser Asp Asp Glu Asp Phe Ile
        370                 375

<210> SEQ ID NO 7
<211> LENGTH: 575
<212> TYPE: PRT
<213> ORGANISM: CELO Virus
<220> FEATURE:
<223> OTHER INFORMATION: Position: 13316..15043 /gene: L1 /product: L1
      IIIa

<400> SEQUENCE: 7

Met Thr Ser Ser Asp Thr Phe Leu Ala Leu Ala Pro Tyr Gly Arg Gln
1               5                   10                  15

Glu Val Ala Asp Ala Leu Ser Ser Leu Pro Asp Gly Lys Asp Ala Arg
                20                  25                  30

Ser Leu Arg His Ala Pro Tyr Ala Asn Arg Leu Ile Lys Leu Gln Ser
        35                  40                  45
```

-continued

```
Ala Met Val Pro Pro Lys Val Asp Gly Thr Ser Glu Arg Val Ala Glu
     50                  55                  60

Ile Val Lys Gly Leu Ala Glu Gln Gly Ala Ile Tyr Pro Asp Gln Met
 65                  70                  75                  80

Gly Ala Ile His Ser Asp Leu Leu Asn Arg Ala Tyr Thr Trp Asn Ser
                 85                  90                  95

Met Gly Val Gln Glu Ser Ile Gln Ala Leu Val Asn Asp Val Ile His
            100                 105                 110

Gly Gln Asn Arg Thr Leu Gln Asp Glu Leu Ala Arg Thr Lys Glu Ile
            115                 120                 125

Ala Asn Ala Ser Leu Leu Thr Gln Phe Phe Asp Ser Leu Tyr Lys Thr
130                 135                 140

Val Asp Arg Gly Gln Arg Asn Phe Glu Gly Phe Lys Lys Leu Leu Arg
145                 150                 155                 160

Leu Phe Val Asn Asn Val Pro Asn Ala Glu Val Tyr Gly Ser Ser Gly
                165                 170                 175

Ser Phe Ser Val Gln Ile Asn Leu Gly Gly Ser Gln Asn Ile Asn
            180                 185                 190

Leu Thr Asn Ala Phe Glu Asn Leu Lys Pro Ile Trp Gly Ala Arg Trp
        195                 200                 205

Asp Ala Val Asn Asn Pro Arg Ile Gly Ala Leu Leu Thr Pro Asn Thr
    210                 215                 220

Arg Ala Leu Leu Phe Phe Val Ser Ser Phe Tyr Asp Tyr Gly Ala Met
225                 230                 235                 240

Glu Pro Gly Ser Tyr Leu Asp Asn Ile Met Arg Leu Tyr Lys Glu Ala
                245                 250                 255

Ile Arg Ala Asp Val Asp Ala Glu Gly Asp Ala Ile Met Glu Leu Gly
            260                 265                 270

Glu Ala Gly Ala Asn Leu Asn Leu Arg Phe Asn Asp Tyr Lys Asp Thr
        275                 280                 285

Leu Asn Tyr Leu Leu Gln Asn Arg Glu Val Val Pro Asp Thr Ala Pro
    290                 295                 300

Leu Glu Leu Ser Ala Glu Gln Glu Met Leu Leu Lys Tyr Leu Met Arg
305                 310                 315                 320

Gln Leu Arg Gln Ala Leu Lys Asp Gly Val Pro Ala Asp Ile Ser Ile
                325                 330                 335

Ser Thr Met Thr Gln Tyr Leu Asp Pro Arg Leu Tyr Gln Thr Asn Lys
            340                 345                 350

Val Phe Val Glu Lys Leu Gln Asn Tyr Leu Leu Ala Gln Ala Arg
        355                 360                 365

Asn Pro Val Tyr Tyr Arg Leu Leu Val Leu Asp Pro Asn Trp Arg Pro
    370                 375                 380

Pro Ala Gly Leu Tyr Thr Gly Asn Tyr Val Ile Pro Asp Arg Tyr Asp
385                 390                 395                 400

Phe Glu Asp Val Gln Ser Glu Leu Glu Tyr Ala Gly Pro Ser Arg Asp
                405                 410                 415

Glu Tyr Phe Asp Asp Ser Leu Phe Ala Pro Gly Pro Gln Arg Arg Leu
            420                 425                 430

Asn Ser Ala Glu Glu Ala Gln Leu Glu Arg Asp Ile Glu Ser Leu Thr
        435                 440                 445

Gly His Ile Asp Glu Glu Leu Gly Val Gln Ser Gln Ala Gly Trp Leu
    450                 455                 460

Ala Asp His Arg Leu Pro Val Ala Phe Asp Gly Ala Leu Ser Leu Thr
```

-continued

```
465                 470                 475                 480
Glu Arg Asn Ala Tyr Asn Thr Pro Leu Pro Pro Asp Ser His Met Arg
                485                 490                 495

Ser Arg Ser Ser Val Ala Ser Asp Leu Gly Leu Leu Asn Leu Ser
            500                 505                 510

Gly Thr Gly Gly Pro Gly Phe Phe Ala Ser Leu Arg Pro Ser Ile Gly
            515                 520                 525

Ser Arg Gln Pro Thr Gly Thr Ala Val Gly Leu Arg Pro Thr Thr Pro
            530                 535                 540

Tyr Ser Gly Ser Gly Cys Met Arg Gly Thr Gly Leu Ala Arg Lys Val
545                 550                 555                 560

Leu Asn Pro Ala Ala Ser Arg Arg Gly Arg Lys Leu Arg Phe Tyr
                565                 570                 575

<210> SEQ ID NO 8
<211> LENGTH: 515
<212> TYPE: PRT
<213> ORGANISM: CELO Virus
<220> FEATURE:
<223> OTHER INFORMATION: Position: 15110..16657 /gene: L2 /product:
      penton base

<400> SEQUENCE: 8

Met Tyr Arg Ser Leu Arg Pro Pro Thr Ser Ile Pro Pro Pro Pro Pro
  1               5                  10                  15

Ser Gly Pro Ser Pro Tyr Pro Ala Met Ile Asn Gly Tyr Pro Pro Asp
                 20                  25                  30

Val Pro Val Gly Ser Pro Ala Asn Gly Asp Ala Glu Leu Phe Val Pro
             35                  40                  45

Leu Gln Arg Val Met Pro Pro Thr Gly Gly Arg Asn Ser Ile Arg Tyr
         50                  55                  60

Arg Asn Tyr Ala Pro Cys Gln Asn Thr Thr Lys Phe Phe Tyr Val Asp
 65                  70                  75                  80

Asn Lys Leu Ser Asp Leu Asp Thr Tyr Asn Glu Asp Ala Asn His Ser
                 85                  90                  95

Asn Phe Arg Thr Thr Val Ile His Asn Gln Asp Leu Asp Pro Ser Thr
             100                 105                 110

Ala Ala Thr Glu Thr Ile Gln Leu Asp Asn Arg Ser Cys Trp Gly Gly
         115                 120                 125

Glu Leu Lys Thr Ala Val Lys Thr Asn Cys Pro Asn Ile Ser Ser Phe
     130                 135                 140

Phe Gln Ser Asp Thr Val Arg Val Arg Leu Met Ser Lys Arg Asp Pro
145                 150                 155                 160

Gly Gly Thr Asp Pro Asp Ala Gly Val Asn Asn Pro Pro Gly Ala Glu
                165                 170                 175

Tyr Lys Trp Tyr Asp Leu Arg Ile Pro Glu Gly Asn Tyr Ala Leu Asn
            180                 185                 190

Glu Ile Ile Asp Leu Leu Asn Glu Gly Ile Val Gln Leu Tyr Leu Gln
        195                 200                 205

Glu Gly Arg Gln Asn Asn Val Leu Lys Ser Asp Ile Gly Val Lys Phe
    210                 215                 220

Asp Thr Arg Tyr Leu Asp Leu Leu Lys Asp Pro Val Thr Gly Leu Val
225                 230                 235                 240

Thr Pro Gly Thr Tyr Val Tyr Lys Gly Tyr His Pro Asp Ile Ile Leu
                245                 250                 255
```

```
Leu Pro Gly Cys Ala Val Asp Phe Thr Phe Ser Arg Leu Ser Leu Leu
            260                 265                 270

Leu Gly Ile Ala Lys Arg Glu Pro Tyr Ser Lys Gly Phe Thr Ile Thr
        275                 280                 285

Tyr Glu Asp Leu Gln Gly Gly Asn Val Pro Ala Leu Leu Asp Leu Ser
    290                 295                 300

Ser Val Gln Val Asp Asp Gln Asp Glu Asp Val Ile Val Val Ala Asp
305                 310                 315                 320

Ala Arg Pro Leu Leu Lys Asp Ser Lys Gly Val Ser Tyr Asn Val Ile
                325                 330                 335

Thr Thr Gly Val Thr Gln Pro Gln Thr Ala Tyr Arg Ser Trp Leu Leu
            340                 345                 350

Ala Tyr His Thr Leu Asp Ser Pro Ala Arg Asn Lys Thr Leu Leu Thr
        355                 360                 365

Val Pro Asp Met Ala Gly Gly Ile Gly Ala Met Tyr Thr Ser Met Pro
    370                 375                 380

Asp Thr Phe Thr Ala Pro Ala Gly Phe Lys Glu Asp Asn Thr Thr Asn
385                 390                 395                 400

Leu Cys Pro Val Val Ala Met Asn Leu Phe Pro Ser Phe Asn Lys Val
                405                 410                 415

Phe Tyr Gln Gly Ala Ser Ala Tyr Val Gln Arg Leu Glu Asn Ala Thr
            420                 425                 430

Gln Ser Ala Thr Ala Ala Phe Asn Arg Phe Pro Glu Asn Glu Ile Leu
        435                 440                 445

Lys Gln Ala Pro Pro Met Asn Val Ser Ser Val Cys Asp Asn Gln Pro
    450                 455                 460

Ala Val Val Gln Gln Gly Val Leu Pro Leu Lys Asn Ser Leu Ser Gly
465                 470                 475                 480

Leu Gln Arg Val Leu Ile Thr Asp Asp Arg Arg Pro Ile Pro Tyr
                485                 490                 495

Val Tyr Lys Thr Ile Ala Thr Val Gln Pro Arg Val Leu Ser Ser Ser
            500                 505                 510

Thr Leu Gln
        515

<210> SEQ ID NO 9
<211> LENGTH: 72
<212> TYPE: PRT
<213> ORGANISM: CELO Virus
<220> FEATURE:
<223> OTHER INFORMATION: Position: 16679..16897 /gene: L2 /product:
      L2pVII

<400> SEQUENCE: 9

Met Ser Ile Leu Ile Ser Pro Ser Asp Asn Arg Gly Trp Gly Ala Asn
1               5                   10                  15

Met Arg Tyr Arg Arg Arg Ala Ser Met Arg Gly Val Gly Arg Arg Arg
            20                  25                  30

Leu Thr Leu Arg Gln Leu Leu Gly Leu Gly Ser Arg Arg Arg Arg Arg
        35                  40                  45

Ser Arg Pro Thr Thr Val Ser Asn Arg Leu Val Val Val Ser Thr Arg
    50                  55                  60

Arg Arg Ser Ser Arg Arg Arg
65                  70

<210> SEQ ID NO 10
```

-continued

```
<211> LENGTH: 188
<212> TYPE: PRT
<213> ORGANISM: CELO Virus
<220> FEATURE:
<223> OTHER INFORMATION: Position: 16929..17495 /gene: L2 /product: L2
      mu (pX, 11K)

<400> SEQUENCE: 10

Met Cys Ala Val Ala Ile His Arg Ser Asp Val Val Met Pro Ser Val
 1               5                   10                  15

Leu Leu Thr Gly Gly Arg Thr Ala Lys Gly Lys Lys Arg Ala Ser Arg
            20                  25                  30

Arg Arg Val Lys Val Pro Lys Leu Pro Lys Gly Ala Arg Arg Lys Arg
        35                  40                  45

Ala Ser Val Thr Pro Val Pro Thr Val Ala Thr Ala Thr Ala Ser Glu
    50                  55                  60

Arg Ala Ala Leu Thr Asn Leu Ala Arg Arg Leu Gln Arg Gly Asp Tyr
65                  70                  75                  80

Ala Ala Trp Arg Pro Ala Asp Tyr Thr Ser Pro Ala Val Ser Glu Ala
                85                  90                  95

Ala Arg Ala Ala Ala Ser Ser Gly Thr Pro Ala Thr Ala Arg Asp Leu
            100                 105                 110

Ala Thr Gly Thr Leu Ala Arg Ala Val Pro Met Thr Gly Thr Gly Gly
        115                 120                 125

Arg Arg Arg Lys Arg Thr Ala Thr Arg Arg Ser Leu Lys Gly Gly
    130                 135                 140

Phe Leu Pro Ala Leu Ile Pro Ile Ile Ala Ala Ala Ile Gly Ala Ile
145                 150                 155                 160

Pro Gly Ile Ala Gly Thr Ala Val Gly Ile Ala Asn Leu Lys Glu Gln
                165                 170                 175

Gln Arg Gln Phe Asn Lys Ile Tyr Gly Asp Lys Lys
            180                 185

<210> SEQ ID NO 11
<211> LENGTH: 223
<212> TYPE: PRT
<213> ORGANISM: CELO Virus
<220> FEATURE:
<223> OTHER INFORMATION: Position: 17559..18230 /gene: L3 /product: L3
      pVI

<400> SEQUENCE: 11

Met Asp Tyr Ala Ala Leu Ser Pro His Leu Gly Gly Trp Ala Leu Arg
 1               5                   10                  15

Asp His His Ile Gly Asp Ser Ser Leu Arg Gly Gly Ala Ile Asn Trp
            20                  25                  30

Gly Asn Leu Gly Ser Arg Ile Thr Ser Ala Leu Asn Ser Thr Gly Arg
        35                  40                  45

Trp Leu Tyr Asn Thr Gly Asn Arg Phe Val His Ser Asn Thr Phe Asn
    50                  55                  60

Gln Ile Lys Gln Gly Ile Gln Asp Ser Gly Val Ile Arg Asn Val Ala
65                  70                  75                  80

Asn Leu Ala Gly Glu Thr Leu Gly Ala Leu Thr Asp Ile Gly Arg Leu
                85                  90                  95

Lys Leu Gln Gln Asp Leu Glu Lys Leu Arg Arg Lys Ala Leu Gly Glu
            100                 105                 110

Glu Gly Pro Ala Thr Gln Ala Glu Leu Gln Ala Leu Ile Gln Ala Leu
        115                 120                 125
```

-continued

```
Gln Ala Gln Val Ala Ala Gly Glu Pro Pro Ala Ala Pro Ala Ala Pro
    130                 135                 140

Ala Pro Ala Pro Pro Leu Val Pro Thr Thr Arg Pro Ile Pro Glu Met
145                 150                 155                 160

Val Thr Glu Val Lys Pro Pro Val Thr Ser Ser Ala Pro Ala Val Pro
                165                 170                 175

Val Asp Val Pro Thr Thr Leu Glu Met Arg Pro Pro Pro Lys Arg
                180                 185                 190

Arg Arg Lys Arg Ala Arg Pro Gly Gln Trp Arg Ala Arg Leu Asp Ser
            195                 200                 205

Leu Ser Gly Thr Gly Val Ala Thr Ala Thr Arg Met Cys Tyr
    210                 215                 220
```

<210> SEQ ID NO 12
<211> LENGTH: 942
<212> TYPE: PRT
<213> ORGANISM: CELO Virus
<220> FEATURE:
<223> OTHER INFORMATION: Position: 18289..21117 /gene: L3 /product: L3 hexon

<400> SEQUENCE: 12

```
Met Thr Ala Leu Thr Pro Asp Leu Thr Thr Ala Thr Pro Arg Leu Gln
1               5                   10                  15

Tyr Phe His Ile Ala Gly Pro Gly Thr Arg Glu Tyr Leu Ser Glu Asp
                20                  25                  30

Leu Gln Gln Phe Ile Ser Ala Thr Gly Ser Tyr Phe Asp Leu Lys Asn
            35                  40                  45

Lys Phe Arg Gln Thr Val Val Ala Pro Thr Arg Asn Val Thr Thr Glu
    50                  55                  60

Lys Ala Gln Arg Leu Gln Ile Arg Phe Tyr Pro Ile Gln Thr Asp Asp
65                  70                  75                  80

Thr Pro Asn Ser Tyr Arg Val Arg Tyr Ser Val Asn Val Gly Asp Ser
                85                  90                  95

Trp Val Leu Asp Met Gly Ala Thr Tyr Phe Asp Ile Lys Gly Val Leu
                100                 105                 110

Asp Arg Gly Pro Ser Phe Lys Pro Tyr Gly Gly Thr Ala Tyr Asn Pro
            115                 120                 125

Leu Ala Pro Arg Glu Ala Ile Phe Asn Thr Trp Val Glu Ser Thr Gly
    130                 135                 140

Pro Gln Thr Asn Val Val Gly Gln Met Thr Asn Val Tyr Thr Asn Gln
145                 150                 155                 160

Thr Arg Asn Asp Lys Thr Ala Thr Leu Gln Gln Val Asn Ser Ile Ser
                165                 170                 175

Gly Val Val Pro Asn Val Asn Leu Gly Pro Gly Leu Ser Gln Leu Ala
                180                 185                 190

Ser Arg Ala Asp Val Asp Asn Ile Gly Val Val Gly Arg Phe Ala Lys
            195                 200                 205

Val Asp Ser Ala Gly Val Lys Gln Ala Tyr Gly Ala Tyr Val Lys Pro
    210                 215                 220

Val Lys Asp Asp Gly Ser Gln Ser Leu Asn Gln Thr Ala Tyr Trp Leu
225                 230                 235                 240

Met Asp Asn Gly Gly Thr Asn Tyr Leu Gly Ala Leu Ala Val Glu Asp
                245                 250                 255

Tyr Thr Gln Thr Leu Ser Tyr Pro Asp Thr Val Leu Val Thr Pro Pro
```

-continued

```
                260                 265                 270
Thr Ala Tyr Gln Gln Val Asn Ser Gly Thr Met Arg Ala Cys Arg Pro
            275                 280                 285
Asn Tyr Ile Gly Phe Arg Asp Asn Phe Ile Asn Leu Leu Tyr His Asp
290                 295                 300
Ser Gly Val Cys Ser Gly Thr Leu Asn Ser Glu Arg Ser Gly Met Asn
305                 310                 315                 320
Val Val Val Glu Leu Gln Asp Arg Asn Thr Glu Leu Ser Tyr Gln Tyr
            325                 330                 335
Met Leu Ala Asp Met Met Ser Arg His His Tyr Phe Ala Leu Trp Asn
            340                 345                 350
Gln Ala Val Asp Gln Tyr Asp His Asp Val Arg Val Phe Asn Asn Asp
            355                 360                 365
Gly Tyr Glu Glu Gly Val Pro Thr Tyr Ala Phe Leu Pro Asp Gly His
            370                 375                 380
Gly Ala Gly Glu Asp Asn Gly Pro Asp Leu Ser Asn Val Lys Ile Tyr
385                 390                 395                 400
Thr Asn Gly Gln Gln Asp Lys Gly Asn Val Val Ala Gly Thr Val Ser
            405                 410                 415
Thr Gln Leu Asn Phe Gly Thr Ile Pro Ser Tyr Glu Ile Asp Ile Ala
            420                 425                 430
Ala Ala Thr Arg Arg Asn Phe Ile Met Ser Asn Ile Ala Asp Tyr Leu
            435                 440                 445
Pro Asp Lys Tyr Lys Phe Ser Ile Arg Gly Phe Asp Pro Val Thr Asp
            450                 455                 460
Asn Ile Asp Pro Thr Thr Tyr Phe Tyr Met Asn Arg Arg Val Pro Leu
465                 470                 475                 480
Thr Asn Val Val Asp Leu Phe Thr Asn Ile Gly Ala Arg Trp Ser Val
            485                 490                 495
Asp Gln Met Asp Asn Val Asn Pro Phe Asn His His Arg Asn Trp Gly
            500                 505                 510
Leu Lys Tyr Arg Ser Gln Leu Leu Gly Asn Ser Arg Tyr Cys Arg Phe
            515                 520                 525
His Ile Gln Val Pro Gln Lys Tyr Phe Ala Ile Lys Asn Leu Leu Leu
            530                 535                 540
Leu Pro Gly Thr Tyr Thr Tyr Glu Trp Val Leu Arg Lys Asp Pro Asn
545                 550                 555                 560
Met Ile Leu Gln Ser Ser Leu Gly Asn Asp Leu Arg Ala Asp Gly Ala
            565                 570                 575
Gln Ile Val Tyr Thr Glu Val Asn Leu Met Ala Asn Phe Met Pro Met
            580                 585                 590
Asp His Asn Thr Ser Asn Gln Leu Glu Leu Met Leu Arg Asn Ala Thr
            595                 600                 605
Asn Asp Gln Thr Phe Ala Asp Tyr Leu Gly Ala Lys Asn Ala Leu Tyr
            610                 615                 620
Asn Val Pro Ala Gly Ser Thr Leu Leu Thr Ile Asn Ile Pro Ala Arg
625                 630                 635                 640
Thr Trp Glu Gly Met Arg Gly Trp Ser Phe Thr Arg Leu Lys Ala Ser
            645                 650                 655
Glu Thr Pro Gln Leu Gly Ala Gln Tyr Asp Val Gly Phe Lys Tyr Ser
            660                 665                 670
Gly Ser Ile Pro Tyr Ser Asp Gly Thr Phe Tyr Leu Ser His Thr Phe
            675                 680                 685
```

-continued

```
Arg Ser Met Ser Val Leu Phe Asp Thr Ser Ile Asn Trp Pro Gly Asn
    690                 695                 700

Asp Arg Leu Leu Thr Pro Asn Leu Phe Glu Ile Lys Arg Pro Val Ala
705                 710                 715                 720

Thr Asp Ser Glu Gly Phe Thr Met Ser Gln Cys Asp Met Thr Lys Asp
                725                 730                 735

Trp Phe Leu Val Gln Met Ala Thr Asn Tyr Asn Tyr Val Tyr Asn Gly
            740                 745                 750

Tyr Arg Phe Trp Pro Asp Arg His Tyr Phe His Tyr Asp Phe Leu Arg
        755                 760                 765

Asn Phe Asp Pro Met Ser Arg Gln Gly Pro Asn Phe Leu Asp Thr Thr
    770                 775                 780

Leu Tyr Asp Leu Val Ser Ser Thr Pro Val Val Asn Asp Thr Gly Ser
785                 790                 795                 800

Gln Pro Ser Gln Asp Asn Val Arg Asn Asn Ser Gly Phe Ile Ala Pro
                805                 810                 815

Arg Ser Trp Pro Val Trp Thr Ala Gln Gln Gly Glu Ala Trp Pro Ala
            820                 825                 830

Asn Trp Pro Tyr Pro Leu Ile Gly Asn Asp Ala Ile Ser Ser Asn Gln
        835                 840                 845

Thr Val Asn Tyr Lys Lys Phe Leu Cys Asp Asn Tyr Leu Trp Thr Val
    850                 855                 860

Pro Phe Ser Ser Asp Phe Met Tyr Met Gly Glu Leu Thr Asp Leu Gly
865                 870                 875                 880

Gln Asn Pro Met Tyr Thr Asn Asn Ser His Ser Met Val Ile Asn Phe
                885                 890                 895

Glu Leu Asp Pro Met Asp Glu Asn Thr Tyr Val Tyr Met Leu Tyr Gly
            900                 905                 910

Val Phe Asp Thr Val Arg Val Asn Gln Pro Glu Arg Asn Val Leu Ala
        915                 920                 925

Met Ala Tyr Phe Arg Thr Pro Phe Ala Thr Gly Asn Ala Val
    930                 935                 940

<210> SEQ ID NO 13
<211> LENGTH: 206
<212> TYPE: PRT
<213> ORGANISM: CELO Virus
<220> FEATURE:
<223> OTHER INFORMATION: Position: 21134..21754 /gene: L3 /product: L3
      protease

<400> SEQUENCE: 13

Met Ser Gly Thr Thr Glu Thr Gln Leu Arg Asp Leu Ser Ser Met
  1               5                  10                  15

His Leu Arg His Arg Phe Leu Gly Val Phe Asp Lys Ser Phe Pro Gly
            20                  25                  30

Phe Leu Asp Pro His Val Pro Ala Ser Ala Ile Val Asn Thr Gly Ser
        35                  40                  45

Arg Ala Ser Gly Gly Met His Trp Ile Gly Phe Ala Phe Asp Pro Ala
    50                  55                  60

Ala Gly Arg Cys Tyr Met Phe Asp Pro Phe Gly Trp Ser Asp Gln Lys
65                  70                  75                  80

Leu Trp Glu Leu Tyr Arg Val Lys Tyr Asn Ala Phe Met Arg Arg Thr
                85                  90                  95

Gly Leu Arg Gln Pro Asp Arg Cys Phe Thr Leu Val Arg Ser Thr Glu
```

-continued

```
                  100                 105                 110
Ala Val Gln Cys Pro Cys Ser Ala Ala Cys Gly Leu Phe Ser Ala Leu
            115                 120                 125

Phe Ile Val Ser Phe Asp Arg Tyr Arg Ser Lys Pro Met Asp Gly Asn
130                 135                 140

Pro Val Ile Asp Thr Val Val Gly Val Lys His Glu Asn Met Asn Ser
145                 150                 155                 160

Pro Pro Tyr Arg Asp Ile Leu His Arg Asn Gln Glu Arg Thr Tyr Tyr
            165                 170                 175

Trp Trp Thr Lys Asn Ser Ala Tyr Phe Arg Ala His Gln Glu Glu Leu
            180                 185                 190

Arg Arg Glu Thr Ala Leu Asn Ala Leu Pro Glu Asn His Val
            195                 200                 205

<210> SEQ ID NO 14
<211> LENGTH: 984
<212> TYPE: PRT
<213> ORGANISM: CELO Virus
<220> FEATURE:
<223> OTHER INFORMATION: Position: 23680..26634 /gene: L4 /product: L4
      100K

<400> SEQUENCE: 14

Met Ala Asp Lys Ile Thr Arg Glu Glu Lys Thr Ile Ala Thr Leu Asp
  1               5                  10                  15

Leu Val Leu Arg Val Val Asp Ala Gly Asn Trp Asp Val Phe Ser
                 20                  25                  30

Lys Arg Leu Val Arg Tyr Thr Arg Glu Gln Tyr Gly Ile Glu Leu Pro
             35                  40                  45

Glu Asp Ile Gly Asp Leu Pro Asp Thr Ser Glu Val Ser Lys Val Leu
         50                  55                  60

Leu Ser His Leu Gly Glu Asp Lys Ala Val Leu Ser Ala Tyr Arg Ile
 65                  70                  75                  80

Ala Glu Leu Thr Gln Pro Ser Glu Met Asp Arg Ala Lys Val Thr Glu
                 85                  90                  95

Gly Gly Leu Ala Val Leu Asn Ala Ser Arg Asp Glu Ser Glu Ala Gln
            100                 105                 110

Asn Pro Ser Asn Pro Glu Pro Glu Ser Ile Glu Ser Asp Ala Val Glu
            115                 120                 125

Asp Leu Gly Val Ala Ala Glu Ser Asp Pro Ser Asp Glu Pro Asp
            130                 135                 140

Pro Glu Pro Glu Tyr Asp His Arg Glu Ala Asp His Asp Ser Asp Ala
145                 150                 155                 160

Asp Ser Gly Tyr Tyr Ser Ala Asp Gly Gly Arg Pro Gly Thr Pro Val
            165                 170                 175

Asp Glu Glu Pro Gln Asp Asp Ser Pro Ser Ser Glu Glu Thr Ala Ser
            180                 185                 190

Thr Val Ile Glu Glu Ala Gln Thr Ser Ala Ser Asn Asp Ser His Asp
            195                 200                 205

Asp Asp Thr His Arg Asp Asp Gly Ser Ala Ser Glu Glu Asp Leu Glu
            210                 215                 220

Arg Asp Ala Leu Val Ala Pro Ala Asp Pro Phe Pro Asn Leu Arg Lys
225                 230                 235                 240

Cys Phe Glu Arg Gln Ala Met Met Leu Thr Gly Ala Leu Lys Asp Ala
            245                 250                 255
```

-continued

Ala Asp Thr Ala Asp Pro Pro Glu Thr Leu Ser Val Asp Ser Val Gln
            260                 265                 270

Arg Gln Leu Glu Arg Phe Val Phe Asn Pro Asp Arg Arg Val Pro Ala
        275                 280                 285

Glu His Leu Glu Val Arg Tyr Asn Phe Tyr Pro Pro Phe Leu Thr Pro
    290                 295                 300

Lys Ala Ile Ala Ser Tyr His Ile Phe Ala Val Thr Ala Ser Ile Pro
305                 310                 315                 320

Leu Ser Cys Lys Ala Asn Arg Ser Gly Ser Asp Leu Leu Ala Lys Ala
                325                 330                 335

Lys Glu Ser Thr Phe Phe Lys Arg Leu Pro Lys Trp Arg Leu Gly Ile
            340                 345                 350

Glu Ile Asp Asp Gly Leu Gly Thr Glu Val Thr Ala Val Thr Glu Leu
        355                 360                 365

Glu Glu Ala Lys Met Val Pro Leu Lys Asp Asp Val Ser Arg Leu Gln
    370                 375                 380

Trp Ala Lys Met Arg Gly Glu His Ile Arg Phe Phe Ser Tyr Pro Ser
385                 390                 395                 400

Leu His Met Pro Pro Lys Ile Ser Arg Met Leu Met Glu Thr Leu Leu
                405                 410                 415

Gln Pro Phe Ala Asp Glu Asn Gln Lys Ala Glu Ala Leu Pro Cys
            420                 425                 430

Leu Ser Asp Glu Glu Val Leu Ala Ile Val Asp Pro Thr Gly Arg Leu
        435                 440                 445

His Gly Glu Asp Ala Leu Lys Ala Val Glu Lys Arg Arg Ala Ala Val
    450                 455                 460

Thr Met Ala Val Arg Tyr Thr Ala Thr Leu Glu Leu Met Glu Arg Val
465                 470                 475                 480

Phe Arg Glu Pro Ser Met Val Lys Lys Met Gln Glu Val Leu His His
                485                 490                 495

Thr Phe His His Gly Phe Val Ala Leu Val Arg Glu Thr Ala Lys Val
            500                 505                 510

Asn Leu Ser Asn Tyr Ala Thr Phe His Gly Leu Thr Tyr Asn Asn Pro
        515                 520                 525

Leu Asn Asn Cys Ile Met Ser Lys Leu Leu Glu Gly Ala Asp Lys Glu
    530                 535                 540

Asp Tyr Val Val Asp Ser Ile Tyr Leu Phe Leu Val Leu Thr Trp Gln
545                 550                 555                 560

Thr Ala Met Gly Met Trp Gln Gln Ala Ile Asp Asp Met Thr Ile Gln
                565                 570                 575

Met Tyr Thr Glu Val Phe Thr Lys Asn Lys Tyr Arg Leu Tyr Ser Leu
            580                 585                 590

Pro Asn Pro Thr Ala Ile Gly Lys Ala Ile Val Asp Ile Leu Met Asp
        595                 600                 605

Tyr Asp Arg Leu Thr Glu Glu Met Arg Lys Ala Leu Pro Asn Phe Thr
    610                 615                 620

Cys Gln Ser Gln Ile Thr Ala Phe Arg His Phe Leu Leu Glu Arg Ser
625                 630                 635                 640

Asn Ile Pro Ala Val Ala Ala Pro Phe Met Pro Ser Asp Phe Val Pro
                645                 650                 655

Leu Ala Tyr Lys Gln Ser Pro Pro Leu Leu Trp Asp Gln Val Tyr Leu
            660                 665                 670

Leu Gln Leu Ala Phe Tyr Leu Thr Lys His Gly Gly Tyr Leu Trp Glu

-continued

```
                        675                 680                 685
Ala Pro Glu Glu Ala Asn Asn Pro Ser Asn Arg Thr Tyr Cys Pro
        690                 695                 700

Cys Asn Leu Cys Ser Pro His Arg Met Pro Gly His Asn Ala Ala Leu
705                 710                 715                 720

His Asn Glu Ile Leu Ala Ile Gly Thr Phe Glu Ile Arg Ser Pro Asp
                725                 730                 735

Gly Lys Thr Phe Lys Leu Thr Pro Glu Leu Trp Thr Asn Ala Tyr Leu
                740                 745                 750

Asp Lys Phe Asp Ala Glu Asp Phe His Pro Phe Thr Val Phe His Tyr
                755                 760                 765

Pro Glu Asn Ala Ser Arg Phe Ala Ser Thr Leu Lys Ala Cys Val Thr
770                 775                 780

Gln Ser Pro Glu Ile Leu Ser Leu Ile Arg Gln Ile Gln Glu Ser Arg
785                 790                 795                 800

Glu Glu Phe Leu Leu Thr Lys Gly Lys Gly Val Tyr Lys Asp Pro Asn
                805                 810                 815

Thr Gly Glu Thr Ile Ser Arg Gln Pro Arg Asp Thr Ala Arg Ala Gln
                820                 825                 830

His Ala Gly Asp Gly Gln Ala Leu Pro Ala Pro Gly Ala Tyr Thr Thr
                835                 840                 845

Gly Gly Asn Arg Ala Glu Thr Ala Pro Ala Gly Ala Val Arg Leu Ala
850                 855                 860

Pro Asp Tyr Gln Asp Gly Gln Phe Pro Ile Ala Lys Val Gly Pro His
865                 870                 875                 880

Tyr His Gly Pro Lys Asn Val Arg Arg Glu Asp Gln Gly Tyr Arg Gly
                885                 890                 895

Gly Pro Gly Gly Val Arg Gly Glu Arg Glu Val Val Leu Ser Arg Arg
                900                 905                 910

Ala Gly Gly Arg Arg Phe Gly Arg Arg Asn Thr Arg Gln Ser Gly Tyr
                915                 920                 925

Asn Glu Arg Ala Asn Arg Tyr Phe Gly Arg Gly Gly Gly Gly Ser Val
930                 935                 940

Arg Gly Gln Gln Gly Glu His Pro Thr Thr Ser Pro Ser Ala Ser Glu
945                 950                 955                 960

Pro Pro Ala Pro Ser Arg Ile Leu Ala Arg Gly Thr Pro Pro Ser Pro
                965                 970                 975

Glu Arg Arg Asp Arg Gln Glu Glu
                980
```

```
<210> SEQ ID NO 15
<211> LENGTH: 245
<212> TYPE: PRT
<213> ORGANISM: CELO Virus
<220> FEATURE:
<223> OTHER INFORMATION: Position: 27149..27886 /gene: L4 /product: L4
      pVIII

<400> SEQUENCE: 15

Met Asn Leu Met Asn Ala Thr Pro Thr Glu Tyr Val Trp Lys Tyr Asn
1               5                   10                  15

Pro Val Ser Gly Ile Pro Ala Gly Ala Gln Gln Asn Tyr Gly Ala Thr
                20                  25                  30

Ile Asp Trp Val Leu Pro Gly Gly Thr Gly Phe Ala Ile Ala Thr Asn
                35                  40                  45
```

```
Asp Ile Arg Arg Gln Thr Leu Asn Pro Ala Val Thr Arg Ala Ile Thr
     50                  55                  60

Ala Arg Phe Glu Ala Glu Ser Asp Gln Gln Pro Tyr Ala Ser Pro His
 65                  70                  75                  80

Glu Thr Asn Val Ile Ala Ala Asn Val Leu Asp Ser Gly Tyr Pro Lys
                 85                  90                  95

Ser Gly Leu Tyr Pro Leu Glu Leu Ser Gly Asn Gln Arg Val Gln Leu
                100                 105                 110

Ala Gly Gly Leu Met Val Gly Arg Thr Glu Gly Arg Met Gln Leu Ala
            115                 120                 125

Gly Gly Leu Thr Glu Gly Arg Val Gln Leu Ser Gly Gly Phe His Gly
        130                 135                 140

Arg Pro Leu Val Arg Gly Arg Ser Arg Arg Pro Arg Trp Cys Gly
145                 150                 155                 160

Ala Glu Leu Thr Gly Asn Gly Leu Pro Glu Gln Ala Glu Val Thr Ser
                165                 170                 175

Asp Thr Tyr Lys Tyr Phe Leu Arg Thr Gln Gly Pro Ser Gln Val Val
            180                 185                 190

Glu Glu Pro Gly Val Phe Ser Gln Arg Gln Phe Met Thr Thr Phe Leu
        195                 200                 205

Pro Ser Val Val Pro His Pro Phe Asp Ser Thr Asn Pro Gly Asp Phe
    210                 215                 220

Pro Ala Gln Tyr Ser Ala Ile Tyr Lys Gly Arg Thr Ala Phe Glu Asp
225                 230                 235                 240

Thr Phe Trp Asp Trp
                245

<210> SEQ ID NO 16
<211> LENGTH: 710
<212> TYPE: PRT
<213> ORGANISM: CELO Virus
<220> FEATURE:
<223> OTHER INFORMATION: Position: 28363..30495 /gene: L5 /product: L5
      fibre 1

<400> SEQUENCE: 16

Met Thr Ser Pro Leu Thr Leu Ser Gln Arg Ala Leu Ala Leu Lys Thr
 1               5                  10                  15

Asp Ser Thr Leu Thr Leu Asn Thr Gln Gly Gln Leu Gly Val Ser Leu
             20                  25                  30

Thr Pro Gly Asp Gly Leu Val Leu Asn Thr Asn Gly Leu Ser Ile Asn
         35                  40                  45

Ala Asp Pro Gln Thr Leu Ala Phe Asn Asn Ser Gly Ala Leu Glu Val
     50                  55                  60

Asn Leu Asp Pro Asp Gly Pro Trp Ser Lys Thr Ala Thr Gly Ile Asp
 65                  70                  75                  80

Leu Arg Leu Asp Pro Thr Thr Leu Glu Val Asp Asn Trp Glu Leu Gly
                 85                  90                  95

Val Lys Leu Asp Pro Asp Glu Ala Ile Asp Ser Gly Pro Asp Gly Leu
                100                 105                 110

Cys Leu Asn Leu Asp Glu Thr Leu Leu Ala Thr Asn Ser Thr Ser
            115                 120                 125

Gly Lys Thr Glu Leu Gly Val His Leu Asn Thr Ser Gly Pro Ile Thr
        130                 135                 140

Ala Asp Asp Gln Gly Ile Asp Leu Asp Val Asp Pro Asn Thr Met Gln
145                 150                 155                 160
```

```
Val Asn Thr Gly Pro Ser Gly Gly Met Leu Ala Val Lys Leu Lys Ser
                165                 170                 175
Gly Gly Gly Leu Thr Ala Asp Pro Asp Gly Ile Ser Val Thr Ala Thr
            180                 185                 190
Val Ala Pro Pro Ser Ile Ser Ala Thr Ala Pro Leu Thr Tyr Thr Ser
        195                 200                 205
Gly Thr Ile Ala Leu Thr Thr Asp Thr Gln Thr Met Gln Val Asn Ser
    210                 215                 220
Asn Gln Leu Ala Val Lys Leu Lys Thr Gly Gly Gly Leu Thr Ala Asp
225                 230                 235                 240
Ala Asp Gly Ile Ser Val Ser Val Ala Pro Thr Pro Thr Ile Ser Ala
                245                 250                 255
Ser Pro Pro Leu Thr Tyr Thr Asn Gly Gln Ile Gly Leu Ser Ile Gly
                260                 265                 270
Asp Gln Ser Leu Gln Val Ser Ser Gly Gln Leu Gln Val Lys Leu Lys
            275                 280                 285
Ser Gln Gly Gly Ile Gln Gln Ser Thr Gln Gly Leu Gly Val Ala Val
        290                 295                 300
Asp Gln Thr Leu Lys Ile Val Ser Asn Thr Leu Glu Val Asn Thr Asp
305                 310                 315                 320
Pro Ser Gly Pro Leu Thr Ser Gly Asn Asn Gly Leu Ser Leu Ala Ala
                325                 330                 335
Val Thr Pro Leu Ala Val Ser Ser Ala Gly Val Thr Leu Asn Tyr Gln
                340                 345                 350
Ser Pro Leu Thr Val Thr Ser Asn Ser Leu Gly Leu Ser Ile Ala Ala
            355                 360                 365
Pro Leu Gln Ala Gly Ala Gln Gly Leu Thr Val Asn Thr Met Glu Pro
        370                 375                 380
Leu Ser Ala Ser Ala Gln Gly Ile Gln Leu His Tyr Gly Gln Gly Phe
385                 390                 395                 400
Gln Val Val Ala Gly Thr Leu Gln Leu Leu Thr Asn Pro Pro Ile Val
                405                 410                 415
Val Ser Ser Arg Gly Phe Thr Leu Leu Tyr Thr Pro Ala Phe Thr Val
                420                 425                 430
Ser Asn Asn Met Leu Gly Leu Asn Val Asp Gly Thr Asp Cys Val Ala
            435                 440                 445
Ile Ser Ser Ala Gly Leu Gln Ile Arg Lys Glu Ala Pro Leu Tyr Val
        450                 455                 460
Thr Ser Gly Ser Thr Pro Ala Leu Ala Leu Lys Tyr Ser Ser Asp Phe
465                 470                 475                 480
Thr Ile Thr Asn Gly Ala Leu Ala Leu Ala Asn Ser Gly Gly Gly Gly
                485                 490                 495
Ser Ser Thr Pro Glu Val Ala Thr Tyr His Cys Gly Asp Asn Leu Leu
            500                 505                 510
Glu Ser Tyr Asp Ile Phe Ala Ser Leu Pro Asn Thr Asn Ala Ala Lys
        515                 520                 525
Val Ala Ala Tyr Cys Arg Leu Ala Ala Ala Gly Gly Val Val Ser Gly
        530                 535                 540
Thr Ile Gln Val Thr Ser Tyr Ala Gly Arg Trp Pro Lys Val Gly Asn
545                 550                 555                 560
Ser Val Thr Asp Gly Ile Lys Phe Ala Ile Val Val Ser Pro Pro Met
                565                 570                 575
```

-continued

```
Asp Lys Asp Pro Arg Ser Asn Leu Ser Gln Trp Leu Gly Ala Thr Val
            580                 585                 590

Phe Pro Ala Gly Ala Thr Thr Ala Leu Phe Ser Pro Asn Pro Tyr Gly
            595                 600                 605

Ser Leu Asn Thr Ile Thr Thr Leu Pro Ser Ile Ala Ser Asp Trp Tyr
            610                 615                 620

Val Pro Glu Ser Asn Leu Val Thr Tyr Thr Lys Ile His Phe Lys Pro
625                 630                 635                 640

Thr Gly Ser Gln Gln Leu Gln Leu Ala Ser Gly Glu Leu Val Val Ala
                    645                 650                 655

Ala Ala Lys Ser Pro Val Gln Thr Thr Lys Tyr Glu Leu Ile Tyr Leu
            660                 665                 670

Gly Phe Thr Leu Lys Gln Asn Ser Ser Gly Thr Asn Phe Phe Asp Pro
            675                 680                 685

Asn Ala Ser Ser Asp Leu Ser Phe Leu Thr Pro Pro Ile Pro Phe Thr
            690                 695                 700

Tyr Leu Gly Tyr Tyr Gln
705                 710

<210> SEQ ID NO 17
<211> LENGTH: 410
<212> TYPE: PRT
<213> ORGANISM: CELO Virus
<220> FEATURE:
<223> OTHER INFORMATION: Position: 30536..31768 /gene: L5 /product: L5
      fibre 2

<400> SEQUENCE: 17

Met Ala Asp Gln Lys Arg Lys Leu Ala Asp Pro Asp Ala Glu Ala Pro
1               5                   10                  15

Thr Gly Lys Met Ala Arg Ala Gly Pro Gly Glu Leu Asp Leu Val Tyr
            20                  25                  30

Pro Phe Trp Tyr Gln Val Ala Ala Pro Thr Glu Ile Thr Pro Pro Phe
            35                  40                  45

Leu Asp Pro Asn Gly Pro Leu Tyr Ser Thr Asp Gly Leu Leu Asn Val
        50                  55                  60

Arg Leu Thr Ala Pro Leu Val Ile Ile Arg Gln Ser Asn Gly Asn Ala
65                  70                  75                  80

Ile Gly Val Lys Thr Asp Gly Ser Ile Thr Val Asn Ala Asp Gly Ala
                85                  90                  95

Leu Gln Ile Gly Ile Ser Thr Ala Gly Pro Leu Thr Thr Thr Ala Asn
            100                 105                 110

Gly Ile Asp Leu Asn Ile Asp Pro Lys Thr Leu Val Val Asp Gly Ser
            115                 120                 125

Ser Gly Lys Asn Val Leu Gly Val Leu Leu Lys Gly Gln Gly Ala Leu
        130                 135                 140

Gln Ser Ser Ala Gln Gly Ile Gly Val Ala Val Asp Glu Ser Leu Gln
145                 150                 155                 160

Ile Val Asp Asn Thr Leu Glu Val Lys Val Asp Ala Ala Gly Pro Leu
                165                 170                 175

Ala Val Thr Ala Ala Gly Val Gly Leu Gln Tyr Asp Asn Thr Gln Phe
            180                 185                 190

Lys Val Thr Asn Gly Thr Leu Gln Leu Tyr Gln Ala Pro Thr Ser Ser
            195                 200                 205

Val Ala Ala Phe Thr Ser Gly Thr Ile Gly Leu Ser Ser Pro Thr Gly
        210                 215                 220
```

```
Asn Phe Val Ser Ser Asn Asn Pro Phe Asn Gly Ser Tyr Phe Leu
225                 230                 235                 240

Gln Gln Ile Asn Thr Met Gly Met Leu Thr Thr Ser Leu Tyr Val Lys
            245                 250                 255

Val Asp Thr Thr Thr Met Gly Thr Arg Pro Thr Gly Ala Val Asn Glu
            260                 265                 270

Asn Ala Arg Tyr Phe Thr Val Trp Val Ser Ser Phe Leu Thr Gln Cys
        275                 280                 285

Asn Pro Ser Asn Ile Gly Gln Gly Thr Leu Glu Pro Ser Asn Ile Ser
    290                 295                 300

Met Thr Ser Phe Glu Pro Ala Arg Asn Pro Ile Ser Pro Pro Val Phe
305                 310                 315                 320

Asn Met Asn Gln Asn Ile Pro Tyr Tyr Ala Ser Arg Phe Gly Val Leu
            325                 330                 335

Glu Ser Tyr Arg Pro Ile Phe Thr Gly Ser Leu Asn Thr Gly Ser Ile
            340                 345                 350

Asp Val Arg Met Gln Val Thr Pro Val Leu Ala Thr Asn Asn Thr Thr
        355                 360                 365

Tyr Asn Leu Ile Ala Phe Thr Phe Gln Cys Ala Ser Ala Gly Leu Phe
        370                 375                 380

Asn Pro Thr Val Asn Gly Thr Val Ala Ile Gly Pro Val Val His Thr
385                 390                 395                 400

Cys Pro Ala Ala Arg Ala Pro Val Thr Val
                405                 410

<210> SEQ ID NO 18
<211> LENGTH: 148
<212> TYPE: PRT
<213> ORGANISM: CELO Virus
<220> FEATURE:
<223> OTHER INFORMATION: Position: 33030..33476 /note=ORF5

<400> SEQUENCE: 18

Met Arg Leu Pro Val Leu Pro Val His Met Lys Tyr Pro Leu Phe Asp
  1               5                  10                  15

Val Ser Val Gly Gln Pro Thr Val Thr Gly Glu Val Thr Gln Ser Leu
             20                  25                  30

Arg His Asp Arg Pro Gln Phe Arg Arg His His Ala Glu His Ala
            35                  40                  45

Ser Gln Ala Asp Gly Leu Gly His Gly Ala Ala Arg Asn Ser Phe
        50                  55                  60

His His Asp Gly Gly Arg His Gly His Ala Thr Arg Ile His Glu Asn
 65                  70                  75                  80

Asn Arg Arg Pro His Lys Arg Asn Arg Arg His Leu Arg Lys Gly
                85                  90                  95

His Leu Lys Ala His Arg Ala Glu Ser His Leu Tyr Gly Tyr Leu Leu
            100                 105                 110

Arg Asn Gln Lys Ala Cys Gly Glu Lys Leu Lys Ile Cys Leu Pro Ala
        115                 120                 125

Ser Lys His Pro Arg Phe Gln Val Val Leu His Pro Arg Cys Asn Lys
    130                 135                 140

Lys Gln Pro Thr
145

<210> SEQ ID NO 19
```

```
<211> LENGTH: 104
<212> TYPE: PRT
<213> ORGANISM: CELO Virus
<220> FEATURE:
<223> OTHER INFORMATION: Position: 33169..33483 /note=ORF6

<400> SEQUENCE: 19
```

Met Leu Leu Arg Gln Thr Gly Trp Val Thr Ala Leu Leu Arg Glu Ile
1               5                   10                  15

Val Ser Thr Met Met Val Ala Val Thr Val Thr Arg His Ala Phe Met
            20                  25                  30

Arg Thr Thr Gly Asp Arg Thr Lys Gly Thr Asp Glu Gly Thr Cys Glu
        35                  40                  45

Lys Asp Thr Ser Lys Leu Ile Glu Arg Arg Ala Ile Phe Thr Asp Ile
    50                  55                  60

Phe Ser Ala Ile Arg Lys Pro Val Val Lys Asn Leu Lys Ser Val Phe
65                  70                  75                  80

Leu Arg Ala Ser Ile His Gly Ser Lys Ser Tyr Phe Ile Pro Gly Val
                85                  90                  95

Ile Lys Ser Asn Leu Arg Glu Arg
            100

```
<210> SEQ ID NO 20
<211> LENGTH: 131
<212> TYPE: PRT
<213> ORGANISM: CELO Virus
<220> FEATURE:
<223> OTHER INFORMATION: Position: 35629..36024 /note= ORF7

<400> SEQUENCE: 20
```

Met Asn Ser Met Val Leu Glu Leu Arg Lys Lys Met Ser Ser Gly Pro
1               5                   10                  15

Asp Cys Val Ile Gly Arg Pro Pro His Ile Leu Pro Pro Gln Lys Gly
            20                  25                  30

Val Tyr Leu Leu Thr Asn Ile Ser Gln Leu Ile Gly Pro Val Gln Gln
        35                  40                  45

Asn Asp Arg Gly Leu Trp Arg His Asn Gly Met His Thr Gln Asn Leu
    50                  55                  60

Ser His His Phe Thr Gly Pro Phe Ile Cys Ala Val Ile Ala Arg Pro
65                  70                  75                  80

Ile Asn Lys Arg Thr His Ile Gly Ile His Val Leu Asn Gln Asn Asn
                85                  90                  95

Glu Leu Pro Ala Ile Phe Thr Ile Gln Tyr Pro Glu Pro Pro His Leu
            100                 105                 110

Thr Asp Asn Pro Gly Ala Val Arg Lys Ser Gln Lys Ser Leu Ile Pro
        115                 120                 125

Pro Tyr Asn
    130

```
<210> SEQ ID NO 21
<211> LENGTH: 282
<212> TYPE: PRT
<213> ORGANISM: CELO Virus
<220> FEATURE:
<223> OTHER INFORMATION: Position:  37391..38239 /note=ORF8

<400> SEQUENCE: 21
```

Met Ala Arg Asn Pro Phe Arg Met Phe Pro Gly Asp Leu Pro Tyr Tyr
1               5                   10                  15

-continued

```
Met Gly Thr Ile Ser Phe Thr Ser Val Pro Val Asp Pro Ser Gln
             20                  25                  30

Arg Asn Pro Thr Thr Ser Leu Arg Glu Met Val Thr Thr Gly Leu Ile
         35                  40                  45

Phe Asn Pro Asn Leu Thr Gly Glu Gln Leu Arg Glu Tyr Ser Phe Ser
     50                  55                  60

Pro Leu Val Ser Met Gly Arg Lys Ala Ile Phe Ala Asp Tyr Glu Gly
 65                  70                  75                  80

Pro Gln Arg Ile Ile His Val Thr Ile Arg Gly Arg Ser Ala Glu Pro
                 85                  90                  95

Lys Thr Pro Ser Glu Ala Leu Ile Met Met Glu Lys Ala Val Arg Gly
             100                 105                 110

Ala Phe Ala Val Pro Asp Trp Val Ala Arg Glu Tyr Ser Asp Pro Leu
         115                 120                 125

Pro His Gly Ile Thr His Val Gly Asp Leu Gly Phe Pro Ile Gly Ser
    130                 135                 140

Val His Ala Leu Lys Met Ala Leu Asp Thr Leu Lys Ile His Val Pro
145                 150                 155                 160

Arg Gly Val Gly Val Pro Gly Tyr Glu Gly Leu Cys Gly Thr Thr Thr
                165                 170                 175

Ile Lys Ala Pro Arg Gln Tyr Arg Leu Leu Thr Thr Gly Val Phe Thr
            180                 185                 190

Lys Lys Asp Leu Lys Arg Thr Leu Pro Glu Pro Phe Phe Ser Arg Phe
        195                 200                 205

Phe Asn Gln Thr Pro Glu Val Cys Ala Ile Lys Thr Gly Lys Asn Pro
    210                 215                 220

Phe Ser Thr Glu Ile Trp Cys Met Thr Leu Gly Gly Asp Ser Pro Ala
225                 230                 235                 240

Pro Glu Arg Asn Glu Pro Arg Asn Pro His Ser Leu Gln Asp Trp Ala
                245                 250                 255

Arg Leu Gly Val Met Glu Thr Cys Leu Arg Met Ser Arg Arg Gly Leu
            260                 265                 270

Gly Ser Arg His His Pro Tyr His Ser Leu
        275                 280

<210> SEQ ID NO 22
<211> LENGTH: 321
<212> TYPE: PRT
<213> ORGANISM: CELO Virus
<220> FEATURE:
<223> OTHER INFORMATION: Position: 40037..41002 /note=ORF9

<400> SEQUENCE: 22

Met Glu Pro Pro His Asn Ser Pro Val Pro Phe Ser Ile Ala Lys Met
  1               5                  10                  15

Gly Asn Pro Thr Leu Leu Leu Ser Gly Leu Leu Ser Leu Thr Gln
             20                  25                  30

Ala Ile Ser Ile Gly Glu His Glu Asn Lys Thr Arg His Val Ile Val
         35                  40                  45

Trp Arg His Ser Ser Ser His Gln Cys Ser Asp Trp Arg Thr Val Thr
     50                  55                  60

Glu Trp Phe Pro Pro Gln Lys Gly Asn Pro Val Arg Pro Pro Tyr Thr
 65                  70                  75                  80

Gln Arg Val Ser Leu Asp Thr Ala Asn Asn Thr Leu Thr Val Lys Pro
                 85                  90                  95
```

```
Phe Glu Thr Asn Asn Gly Cys Trp Glu Thr Thr Ser Gln Gly Ile Asn
                100                 105                 110
His Pro Pro Thr Thr Ile Gln Tyr Arg Val Trp Asn Ile Thr Thr Thr
            115                 120                 125
Pro Thr Ile Gln Thr Ile Asn Ile Thr Lys Ile Thr Val Arg Glu Gly
        130                 135                 140
Glu Asp Phe Thr Leu Tyr Gly Pro Val Ser Glu Thr Met Ser Ile Ile
145                 150                 155                 160
Glu Trp Glu Phe Ile Lys Asp Val Thr Pro Gln Phe Ile Leu Gln Tyr
                165                 170                 175
Tyr Leu Ser Ile Asn Ser Thr Ile Val Tyr Ala Ser Tyr Gln Gly Arg
            180                 185                 190
Val Thr Phe Asn Pro Gly Lys Asn Thr Leu Thr Leu Lys Gly Ala Lys
        195                 200                 205
Thr Thr Asp Ser Gly Thr Tyr Lys Ser Thr Val Asn Leu Asp Gln Val
210                 215                 220
Ser Val His Asn Phe Arg Val Gly Val Thr Pro Ile Glu Lys Lys Glu
225                 230                 235                 240
Glu Ala Thr Ala Glu Thr Pro Ala Ser Lys Pro Thr Pro Ile Pro Arg
                245                 250                 255
Val Arg Ala Asp Ala Arg Ser Thr Ala Leu Trp Val Gly Leu Ala Leu
            260                 265                 270
Cys Ile Leu Thr Val Ile Pro Ala Leu Ile Gly Trp Tyr Phe Arg Asp
        275                 280                 285
Arg Leu Cys Val Pro Asp Pro Ile Ile Glu Leu Glu Ile Pro Gly Gln
    290                 295                 300
Pro His Val Thr Ile His Ile Leu Lys Gly Pro Asp Asp Cys Glu
305                 310                 315                 320
Thr

<210> SEQ ID NO 23
<211> LENGTH: 283
<212> TYPE: PRT
<213> ORGANISM: CELO Virus
<220> FEATURE:
<223> OTHER INFORMATION: Position: 41002..41853 /note=ORF10

<400> SEQUENCE: 23

Met Ile Asp Lys Arg Asn Lys Lys Ala Val Thr His Ile Ser Thr Cys
  1                 5                  10                  15
Leu Cys His Ser Ser Ile Pro Ile Tyr Gly Asp Ser Pro Phe Leu Asn
                 20                  25                  30
Thr His Arg Ala Ala Met Asp Pro Arg Pro Leu Val Leu Leu Leu Leu
             35                  40                  45
Leu Ala Ser His Ile Ser Thr Phe Arg Gln Met Tyr Phe Glu Gly Glu
         50                  55                  60
Thr Ile His Phe Pro Met Gly Ile Tyr Gly Asn Glu Thr Thr Leu Tyr
 65                  70                  75                  80
Met Asn Asp Ile Ile Leu Glu Gly Thr Arg Ala Asn Thr Thr Thr Arg
                 85                  90                  95
Thr Ile Ser Leu Thr Thr Thr Lys Lys Asn Ala Gly Thr Asn Leu Tyr
                100                 105                 110
Thr Val Ile Ser Glu Thr Gly His Asn Ala Thr Tyr Leu Ile Thr Val
            115                 120                 125
Gln Pro Leu Gly Gln Ser Ile His His Ala Tyr Thr Trp Ala Gly Asn
```

```
            130                 135                 140
Thr Phe Thr Leu Gln Gly Gln Val Phe Glu His Gly Asn Tyr Thr Arg
145                 150                 155                 160

Trp Val Arg Leu Glu Asn Ala Glu Pro Lys Leu Ile Ile Ser Trp Ala
                165                 170                 175

Leu Ser Asn Arg Thr Ile Asn Lys Gly Pro Ala Tyr Thr Ala Asn Met
            180                 185                 190

Asp Phe Asp Pro Gly Asn Asn Thr Leu Thr Leu His Pro Val Leu Ile
        195                 200                 205

Thr Asp Ala Gly Ile Phe Gln Cys Val Ile Asp Gln Gln Thr Asn Leu
    210                 215                 220

Thr Leu Thr Ile Asn Phe Thr Val Ser Glu Asn Pro Pro Ile Val Ala
225                 230                 235                 240

His Leu Asp Ile His Lys Thr Ile Ser Arg Thr Ile Ala Ile Cys Ser
                245                 250                 255

Cys Leu Ile Ala Val Ile Ala Val Leu Cys Cys Leu Arg Gln Leu
            260                 265                 270

Asn Val Asn Gly Arg Gly Asn Ser Glu Met Ile
        275                 280
```

<210> SEQ ID NO 24
<211> LENGTH: 135
<212> TYPE: PRT
<213> ORGANISM: CELO Virus
<220> FEATURE:
<223> OTHER INFORMATION: Position: 41958..42365 /note= ORF11

<400> SEQUENCE: 24

```
Met Leu Leu Leu Thr Val Val Leu Val Gly Val Thr Leu Ala Ala
 1               5                   10                  15

Asp His Pro Thr Leu Tyr Ala Pro Lys Gly Gly Ser Ile Glu Leu Gly
                20                  25                  30

Val Gly Ala Lys Gln Lys Gly Gln Tyr Lys Phe Glu Trp Arg Phe Gly
            35                  40                  45

Asn Leu Lys Ile Val Ile Ala Glu Met Ser Ser Thr Asn Gln Leu Glu
        50                  55                  60

Ile Lys Phe Pro Asp Asn Gly Phe Gln Asn Arg Ser Glu Phe Asn Pro
65                  70                  75                  80

Thr Lys His Asn Leu Thr Ile His Asn Ala Ser Tyr Glu Asp Ser Gly
                85                  90                  95

Thr Tyr Ser Leu His Gln Glu Glu Asn Asp Gly Thr Glu His Thr Asp
            100                 105                 110

Asn Phe Lys Val Ile Val Gln Gly Met Ser Leu Tyr Thr Tyr Leu Gln
        115                 120                 125

Tyr Ala Leu Ile Ser Pro Ile
    130                 135
```

<210> SEQ ID NO 25
<211> LENGTH: 1326
<212> TYPE: DNA
<213> ORGANISM: CELO VIRUS
<220> FEATURE:
<221> NAME/KEY: CDS
<222> LOCATION: (1)..(1326)

<400> SEQUENCE: 25

```
atg gaa aga acc ccg aaa aga gct cat ggc ttt cgc agc acc aag cct    48
Met Glu Arg Thr Pro Lys Arg Ala His Gly Phe Arg Ser Thr Lys Pro
```

-continued

```
  1                   5                  10                  15 gtc aag aga acg gca gaa gtc atg atg gaa gag gag gaa gaa gtg      96
Val Lys Arg Thr Ala Glu Val Met Met Glu Glu Glu Glu Glu Val
             20                  25                  30 gaa gtg gtc gcc ccg ggc cga ggc gcg act cgc aag aag gtc agc cgc  144
Glu Val Val Ala Pro Gly Arg Gly Ala Thr Arg Lys Lys Val Ser Arg
                 35                  40                  45 cgc gag gag tcc cca tcc ccc gta agg cga gtt acc cgc cgg cgg gaa  192
Arg Glu Glu Ser Pro Ser Pro Val Arg Arg Val Thr Arg Arg Arg Glu
     50                  55                  60 acc gtt gtc gat gac gaa gaa aac gcc agc gac gag gaa tcc ccg gag  240
Thr Val Val Asp Asp Glu Glu Asn Ala Ser Asp Glu Glu Ser Pro Glu
 65                  70                  75                  80 gcc cct ctg tca gac ccc gtg gtc tac ggc gcg caa cgc gcc atg gcc  288
Ala Pro Leu Ser Asp Pro Val Val Tyr Gly Ala Gln Arg Ala Met Ala
                 85                  90                  95 acc gtc gcc agc atc tgc gaa gct ctc gac cta cag tgg cag gga gcc  336
Thr Val Ala Ser Ile Cys Glu Ala Leu Asp Leu Gln Trp Gln Gly Ala
             100                 105                 110 agc gtg cgc ccc gac gac tcc att tgg acc aaa atg ggg ggt aca tac  384
Ser Val Arg Pro Asp Asp Ser Ile Trp Thr Lys Met Gly Gly Thr Tyr
         115                 120                 125 gtt cgc aaa aag cat ccc gaa ttt cgc ctg acc ttt tct agc tac gac  432
Val Arg Lys Lys His Pro Glu Phe Arg Leu Thr Phe Ser Ser Tyr Asp
     130                 135                 140 tct ttc aac gct cag gta ggg cgg ttc ctg gca gcc gtt atc tac agc  480
Ser Phe Asn Ala Gln Val Gly Arg Phe Leu Ala Ala Val Ile Tyr Ser
145                 150                 155                 160 cgc gcg ggt ctg gag ccc aag ttc gtg ccc gga ggg gcg cac gtt tgg  528
Arg Ala Gly Leu Glu Pro Lys Phe Val Pro Gly Gly Ala His Val Trp
                 165                 170                 175 cgc cat ggc tgg ttc cca gcg ctc cag gag ccc ttc ccg aaa tgc atg  576
Arg His Gly Trp Phe Pro Ala Leu Gln Glu Pro Phe Pro Lys Cys Met
             180                 185                 190 cac ggt gtg gac atg gtg acg aaa cct cgt acc gtg gag ttg aac ccg  624
His Gly Val Asp Met Val Thr Lys Pro Arg Thr Val Glu Leu Asn Pro
         195                 200                 205 tct agc gag gcg gga aag agg gct ctg gcc gaa cag aac ggc gta atc  672
Ser Ser Glu Ala Gly Lys Arg Ala Leu Ala Glu Gln Asn Gly Val Ile
     210                 215                 220 gag aag aac cgg ttt gga cga cag gtg gtg gtg ctc agg ttc gac gcg  720
Glu Lys Asn Arg Phe Gly Arg Gln Val Val Val Leu Arg Phe Asp Ala
225                 230                 235                 240 aac gcg gtg tgc tac aag gat cag gag cac agc ggc ttc cct cat ccc  768
Asn Ala Val Cys Tyr Lys Asp Gln Glu His Ser Gly Phe Pro His Pro
                 245                 250                 255 cac gcg cac ggc agt tgc gcc atg gtc ttt tcc gac gcc gcc aag gcg  816
His Ala His Gly Ser Cys Ala Met Val Phe Ser Asp Ala Ala Lys Ala
             260                 265                 270 gtc agc gcg atg cgt cac gac ata gac tgg acg aag gcg ctt tac ccc  864
Val Ser Ala Met Arg His Asp Ile Asp Trp Thr Lys Ala Leu Tyr Pro
         275                 280                 285 aac gcg gac aag cgc cgg gca gag gaa tgt gtc ctc atc tca acc aat  912
Asn Ala Asp Lys Arg Arg Ala Glu Glu Cys Val Leu Ile Ser Thr Asn
     290                 295                 300 tgc aac tgc aac tac gcc tcc gat cga gcc att tca ggg aga cag ttc  960
Cys Asn Cys Asn Tyr Ala Ser Asp Arg Ala Ile Ser Gly Arg Gln Phe
305                 310                 315                 320 tgt aaa atg act cct tat aag ctc aac ggc aca gac gac att act cgc  1008
```

```
                                                                    -continued Cys Lys Met Thr Pro Tyr Lys Leu Asn Gly Thr Asp Asp Ile Thr Arg
            325                 330                 335 gac atg gtc gag agc agg ccc gat atg aag gct cac aag aaa aac ccg   1056
Asp Met Val Glu Ser Arg Pro Asp Met Lys Ala His Lys Lys Asn Pro
            340                 345                 350 cat acc atg gtg ttc acc tgc tgc aac ccg cag gcg gcg tcg ggc gga   1104
His Thr Met Val Phe Thr Cys Cys Asn Pro Gln Ala Ala Ser Gly Gly
            355                 360                 365 gca ggc cgc ggt ctg aag aag acc gaa aaa acc tgc gcc tgg cgt ctg   1152
Ala Gly Arg Gly Leu Lys Lys Thr Glu Lys Thr Cys Ala Trp Arg Leu
370                 375                 380 tcg gcc atg gat ctg cgc tac gcg tac gtc ttt gct acg gag ctg ttt   1200
Ser Ala Met Asp Leu Arg Tyr Ala Tyr Val Phe Ala Thr Glu Leu Phe
385                 390                 395                 400 act gcc gtg atg ggt tct tca gag ccc aca cat gtg cct gag ttc cgt   1248
Thr Ala Val Met Gly Ser Ser Glu Pro Thr His Val Pro Glu Phe Arg
            405                 410                 415 tgg aac gag tcg tac gcc ttt aaa acg gag gtg ttg gcg cca gtc tcg   1296
Trp Asn Glu Ser Tyr Ala Phe Lys Thr Glu Val Leu Ala Pro Val Ser
            420                 425                 430 ccc atc gcc agt gac gac ccg ttc gct taa                           1326
Pro Ile Ala Ser Asp Asp Pro Phe Ala
            435                 440

<210> SEQ ID NO 26
<211> LENGTH: 441
<212> TYPE: PRT
<213> ORGANISM: CELO VIRUS
<220> FEATURE:
<223> OTHER INFORMATION: Position: 21899..23224/Product: E2a DBP

<400> SEQUENCE: 26

Met Glu Arg Thr Pro Lys Arg Ala His Gly Phe Arg Ser Thr Lys Pro
1               5                   10                  15

Val Lys Arg Thr Ala Glu Val Met Met Glu Glu Glu Glu Glu Glu Val
            20                  25                  30

Glu Val Ala Pro Gly Arg Gly Ala Thr Arg Lys Lys Val Ser Arg
        35                  40                  45

Arg Glu Glu Ser Pro Ser Pro Val Arg Arg Val Thr Arg Arg Glu
    50                  55                  60

Thr Val Val Asp Asp Glu Glu Asn Ala Ser Asp Glu Glu Ser Pro Glu
65                  70                  75                  80

Ala Pro Leu Ser Asp Pro Val Tyr Gly Ala Gln Arg Ala Met Ala
                85                  90                  95

Thr Val Ala Ser Ile Cys Glu Ala Leu Asp Leu Gln Trp Gln Gly Ala
                100                 105                 110

Ser Val Arg Pro Asp Asp Ser Ile Trp Thr Lys Met Gly Gly Thr Tyr
            115                 120                 125

Val Arg Lys Lys His Pro Glu Phe Arg Leu Thr Phe Ser Ser Tyr Asp
130                 135                 140

Ser Phe Asn Ala Gln Val Gly Arg Phe Leu Ala Ala Val Ile Tyr Ser
145                 150                 155                 160

Arg Ala Gly Leu Glu Pro Lys Phe Val Pro Gly Gly Ala His Val Trp
                165                 170                 175

Arg His Gly Trp Phe Pro Ala Leu Gln Glu Pro Phe Pro Lys Cys Met
            180                 185                 190

His Gly Val Asp Met Val Thr Lys Pro Arg Thr Val Glu Leu Asn Pro
        195                 200                 205
```

-continued

```
Ser Ser Glu Ala Gly Lys Arg Ala Leu Ala Glu Gln Asn Gly Val Ile
    210                 215                 220
Glu Lys Asn Arg Phe Gly Arg Gln Val Val Leu Arg Phe Asp Ala
225                 230                 235                 240
Asn Ala Val Cys Tyr Lys Asp Gln Glu His Ser Gly Phe Pro His Pro
                245                 250                 255
His Ala His Gly Ser Cys Ala Met Val Phe Ser Asp Ala Ala Lys Ala
            260                 265                 270
Val Ser Ala Met Arg His Asp Ile Asp Trp Thr Lys Ala Leu Tyr Pro
        275                 280                 285
Asn Ala Asp Lys Arg Arg Ala Glu Glu Cys Val Leu Ile Ser Thr Asn
290                 295                 300
Cys Asn Cys Asn Tyr Ala Ser Asp Arg Ala Ile Ser Gly Arg Gln Phe
305                 310                 315                 320
Cys Lys Met Thr Pro Tyr Lys Leu Asn Gly Thr Asp Asp Ile Thr Arg
                325                 330                 335
Asp Met Val Glu Ser Arg Pro Asp Met Lys Ala His Lys Lys Asn Pro
            340                 345                 350
His Thr Met Val Phe Thr Cys Cys Asn Pro Gln Ala Ala Ser Gly Gly
        355                 360                 365
Ala Gly Arg Gly Leu Lys Lys Thr Glu Lys Thr Cys Ala Trp Arg Leu
370                 375                 380
Ser Ala Met Asp Leu Arg Tyr Ala Tyr Val Phe Ala Thr Glu Leu Phe
385                 390                 395                 400
Thr Ala Val Met Gly Ser Ser Glu Pro Thr His Val Pro Glu Phe Arg
                405                 410                 415
Trp Asn Glu Ser Tyr Ala Phe Lys Thr Glu Val Leu Ala Pro Val Ser
            420                 425                 430
Pro Ile Ala Ser Asp Asp Pro Phe Ala
        435                 440

<210> SEQ ID NO 27
<211> LENGTH: 3366
<212> TYPE: DNA
<213> ORGANISM: CELO VIRUS
<220> FEATURE:
<221> NAME/KEY: CDS
<222> LOCATION: (1)..(3366)

<400> SEQUENCE: 27 atg ctc atc gcc aaa aac gtc acc gga gaa tgg gtc tgg atc acc agc      48
Met Leu Ile Ala Lys Asn Val Thr Gly Glu Trp Val Trp Ile Thr Ser
  1               5                  10                  15 cgc act ccg gtt caa cag tgt ccc acc tgc ggc cga cac tgg gtc aga      96
Arg Thr Pro Val Gln Gln Cys Pro Thr Cys Gly Arg His Trp Val Arg
             20                  25                  30 cga cac tcg tgc aac gaa cgc cgc tct gcc ttc tac tac cac gcc gtc     144
Arg His Ser Cys Asn Glu Arg Arg Ser Ala Phe Tyr Tyr His Ala Val
         35                  40                  45 cag gga tcg ggc agc gat ttg tgg cag cac gtc cac ttc tcc tgt cca     192
Gln Gly Ser Gly Ser Asp Leu Trp Gln His Val His Phe Ser Cys Pro
     50                  55                  60 gcc caa cac ccc cac ata cgt cag ttg tac atc acc tac gat atc gag     240
Ala Gln His Pro His Ile Arg Gln Leu Tyr Ile Thr Tyr Asp Ile Glu
 65                  70                  75                  80 acg tat acc gtg ttc gaa aag aaa ggc aag cgc atg cat ccg ttt atg     288
Thr Tyr Thr Val Phe Glu Lys Lys Gly Lys Arg Met His Pro Phe Met
                 85                  90                  95
```

-continued

|  |  |  |  |  |  |  | 85 |  |  |  |  |  | 90 |  |  |  |  |  | 95 |  |  |  |
|---|---|---|---|---|---|---|---|---|---|---|---|---|---|---|---|---|---|---|---|---|---|---|

```
ttg tgc ttc atg ctc agc gga gac ccc cag ctg gtc tcc cgc gcc gaa     336
Leu Cys Phe Met Leu Ser Gly Asp Pro Gln Leu Val Ser Arg Ala Glu
            100                 105                 110 cgc tta gca cgg cag gac gac cgt ctc aaa gcc ctc gac gaa ggc ttc     384
Arg Leu Ala Arg Gln Asp Asp Arg Leu Lys Ala Leu Asp Glu Gly Phe
        115                 120                 125 tat tgg cta gac agc cat ccg ggc gag gtt gcc aga agg ttt cgc aac     432
Tyr Trp Leu Asp Ser His Pro Gly Glu Val Ala Arg Arg Phe Arg Asn
130                 135                 140 ttc agg tcc cgt ctg caa ata gaa ttt gcc caa aat cta gtc gac cgc     480
Phe Arg Ser Arg Leu Gln Ile Glu Phe Ala Gln Asn Leu Val Asp Arg
145                 150                 155                 160 tac gcg gct gcc aac cga gat tat tgc gac cag cta gtc aag gac gga     528
Tyr Ala Ala Ala Asn Arg Asp Tyr Cys Asp Gln Leu Val Lys Asp Gly
            165                 170                 175 aag tac ggc tcc gtt cac aaa ata ccg tac gag ctc ttc gag aaa ccc     576
Lys Tyr Gly Ser Val His Lys Ile Pro Tyr Glu Leu Phe Glu Lys Pro
        180                 185                 190 acc tcc ccc ctc tcc ctc ccg gat aac ttt tat tcc gta gac atc gta     624
Thr Ser Pro Leu Ser Leu Pro Asp Asn Phe Tyr Ser Val Asp Ile Val
        195                 200                 205 gtg cta ggt cac aac ata tgt aag ttc gat gaa ctc ctc tta gcc acg     672
Val Leu Gly His Asn Ile Cys Lys Phe Asp Glu Leu Leu Leu Ala Thr
210                 215                 220 gaa ctc gtc gag cgc agg gac cta ttc ccg gaa gcg tgc aaa tgt gat     720
Glu Leu Val Glu Arg Arg Asp Leu Phe Pro Glu Ala Cys Lys Cys Asp
225                 230                 235                 240 cga tcc ttc atg cct cgc gtc ggt cgc ctt ctg ttc aat gat atc att     768
Arg Ser Phe Met Pro Arg Val Gly Arg Leu Leu Phe Asn Asp Ile Ile
            245                 250                 255 ttc cgc atg cca aac ccc aac tac gtg aag aaa gac gcc tcc cgc gta     816
Phe Arg Met Pro Asn Pro Asn Tyr Val Lys Lys Asp Ala Ser Arg Val
        260                 265                 270 gaa cgc tgg tct cgc ggg atc gtg tcc cat cag gat gcg cgc tcg gta     864
Glu Arg Trp Ser Arg Gly Ile Val Ser His Gln Asp Ala Arg Ser Val
        275                 280                 285 ttt gtg cgg ttc atg gtg cga gac act cta cag ctc acc agc ggg gcc     912
Phe Val Arg Phe Met Val Arg Asp Thr Leu Gln Leu Thr Ser Gly Ala
290                 295                 300 aaa ctc tcc aaa gcc gcg gca gcc tac gcg cta gac ctc tgc aag gga     960
Lys Leu Ser Lys Ala Ala Ala Ala Tyr Ala Leu Asp Leu Cys Lys Gly
305                 310                 315                 320 cat tgc cca tac gag gcc atc aac gaa ttc att tcc acg ggg cgc ttt    1008
His Cys Pro Tyr Glu Ala Ile Asn Glu Phe Ile Ser Thr Gly Arg Phe
            325                 330                 335 cac gcg gac gcc gac ggc ttt cct gtc gaa agg tac tgg gaa gac cca    1056
His Ala Asp Ala Asp Gly Phe Pro Val Glu Arg Tyr Trp Glu Asp Pro
        340                 345                 350 tcc gtc atc gct gaa cag aag aat cta tgg cag aaa gaa cac ccg ggc    1104
Ser Val Ile Ala Glu Gln Lys Asn Leu Trp Gln Lys Glu His Pro Gly
        355                 360                 365 cag cag tac gac atc gtc caa gcg tgc ctc gaa tac tgc atg cag gac    1152
Gln Gln Tyr Asp Ile Val Gln Ala Cys Leu Glu Tyr Cys Met Gln Asp
370                 375                 380 gtc cgt gtc acc caa aag ctg gcc cac acg tta cac gac agc tac gac    1200
Val Arg Val Thr Gln Lys Leu Ala His Thr Leu His Asp Ser Tyr Asp
385                 390                 395                 400 gcc tat ttc caa cga gaa cta ggg atg gaa ggc cat ttt aac atc ttc    1248
```

```
                                                                -continued

Ala Tyr Phe Gln Arg Glu Leu Gly Met Glu Gly His Phe Asn Ile Phe
                405                 410                 415 gtg cgg ccc acc atc ccc agc aac act cat gcc ttt tgg aag caa ctt    1296
Val Arg Pro Thr Ile Pro Ser Asn Thr His Ala Phe Trp Lys Gln Leu
            420                 425                 430 acc ttt tcc aat tac gtc cgc gaa cag cgt gcg aca tgc cct ccc tcc    1344
Thr Phe Ser Asn Tyr Val Arg Glu Gln Arg Ala Thr Cys Pro Pro Ser
            435                 440                 445 gtc ccc gaa ccc ccc aaa aag aaa ggt cga acc aaa aag aaa aaa caa    1392
Val Pro Glu Pro Pro Lys Lys Lys Gly Arg Thr Lys Lys Lys Lys Gln
450                 455                 460 ccc tcc ccc gac tac gtg gcc gaa gtc tac gcc ccc cac cgc ccc atg    1440
Pro Ser Pro Asp Tyr Val Ala Glu Val Tyr Ala Pro His Arg Pro Met
465                 470                 475                 480 ttc aaa tac ata cgc caa gcg ctc cgc ggc gga cga tgc tac ccc aac    1488
Phe Lys Tyr Ile Arg Gln Ala Leu Arg Gly Gly Arg Cys Tyr Pro Asn
                485                 490                 495 gtg ctc gga cct tac ctg aaa ccc gtc tac gtc ttt gac atc tgc ggc    1536
Val Leu Gly Pro Tyr Leu Lys Pro Val Tyr Val Phe Asp Ile Cys Gly
            500                 505                 510 atg tac gct tcc gcc ctc acc cac ccc atg ccc cac gga atg ccc cta    1584
Met Tyr Ala Ser Ala Leu Thr His Pro Met Pro His Gly Met Pro Leu
            515                 520                 525 gat cca aaa ttt acc gcg cag cac gtg gag gag ctc aac cgg ctg ctg    1632
Asp Pro Lys Phe Thr Ala Gln His Val Glu Glu Leu Asn Arg Leu Leu
530                 535                 540 acc aac gaa tcg cat ctg agc tac ttc gat gcg cgt atc aag cct tcc    1680
Thr Asn Glu Ser His Leu Ser Tyr Phe Asp Ala Arg Ile Lys Pro Ser
545                 550                 555                 560 atc ctg aaa ata gaa gcc tac cct ccc ccg ccc gaa atg tta gac cca    1728
Ile Leu Lys Ile Glu Ala Tyr Pro Pro Pro Pro Glu Met Leu Asp Pro
                565                 570                 575 ctc cct ccc atc tgc tcc cgg agg gga ggc aga ctg gtc tgg acc aac    1776
Leu Pro Pro Ile Cys Ser Arg Arg Gly Gly Arg Leu Val Trp Thr Asn
            580                 585                 590 gag gct ctc tac gac gag gtg gtc acc gtc ata gat atc ctc acg ctg    1824
Glu Ala Leu Tyr Asp Glu Val Val Thr Val Ile Asp Ile Leu Thr Leu
            595                 600                 605 cac aac cgg gga tgg cga gtc cag gtc ctc cat gac gag atg aac att    1872
His Asn Arg Gly Trp Arg Val Gln Val Leu His Asp Glu Met Asn Ile
610                 615                 620 gtt ttt ccg gaa tgg aaa acg cta tgt gcc gac tac gtc acg aaa aac    1920
Val Phe Pro Glu Trp Lys Thr Leu Cys Ala Asp Tyr Val Thr Lys Asn
625                 630                 635                 640 atc ctc gcc aaa gaa aaa gcc gat cgc gag aag aac gaa gtg att cga    1968
Ile Leu Ala Lys Glu Lys Ala Asp Arg Glu Lys Asn Glu Val Ile Arg
                645                 650                 655 tcc atc tcc aaa atg ctg agc aac gcg ctg tac ggt gcg ttt gcc acc    2016
Ser Ile Ser Lys Met Leu Ser Asn Ala Leu Tyr Gly Ala Phe Ala Thr
            660                 665                 670 aac atg gac acc acg cgc atc atc ttt gaa cag gac ctc tcg gaa gca    2064
Asn Met Asp Thr Thr Arg Ile Ile Phe Glu Gln Asp Leu Ser Glu Ala
            675                 680                 685 gat aag aaa aac atc tac gaa ggc act gaa atc gtc aaa cac gtc acg    2112
Asp Lys Lys Asn Ile Tyr Glu Gly Thr Glu Ile Val Lys His Val Thr
690                 695                 700 ctg ctc aat gac gac tcg ttc aac gga acg gaa gtc acc ctc gaa aac    2160
Leu Leu Asn Asp Asp Ser Phe Asn Gly Thr Glu Val Thr Leu Glu Asn
705                 710                 715                 720
```

```
                                        -continued gcg cct aac ccc ttc agt gag gag agt cta cga caa cag ttc cgc tac    2208
Ala Pro Asn Pro Phe Ser Glu Glu Ser Leu Arg Gln Gln Phe Arg Tyr
            725                 730                 735 gca gac gac ccc gaa cag gaa gag ccc gaa gca gaa gag gat ggg gaa    2256
Ala Asp Asp Pro Glu Gln Glu Glu Pro Glu Ala Glu Glu Asp Gly Glu
            740                 745                 750 gaa gaa gga gac gac agc gat cgc gag agt gcc cgt aag ccg aaa aac    2304
Glu Glu Gly Asp Asp Ser Asp Arg Glu Ser Ala Arg Lys Pro Lys Asn
            755                 760                 765 gca ctt acc gaa gac gat cct ctc gtc gcc gta gac ctg gaa gtc gag    2352
Ala Leu Thr Glu Asp Asp Pro Leu Val Ala Val Asp Leu Glu Val Glu
770                 775                 780 gcg acc ctc gcg acg ggc cct tat ata ccc gag ggg gag cta agc tcc    2400
Ala Thr Leu Ala Thr Gly Pro Tyr Ile Pro Glu Gly Glu Leu Ser Ser
785                 790                 795                 800 gcc cac tac gct cgc gct aac gag acc cgg ttt aaa cct atg cgt ctc    2448
Ala His Tyr Ala Arg Ala Asn Glu Thr Arg Phe Lys Pro Met Arg Leu
                805                 810                 815 ctc gaa gcc aca cca gaa gcc cta acc gtg ctc cat ctg gaa agc ctg    2496
Leu Glu Ala Thr Pro Glu Ala Leu Thr Val Leu His Leu Glu Ser Leu
            820                 825                 830 gac aag cag gtg gca aac aaa aga tac gcc acg caa atc gcc tgc ttc    2544
Asp Lys Gln Val Ala Asn Lys Arg Tyr Ala Thr Gln Ile Ala Cys Phe
            835                 840                 845 gtg ctg ggc tgg tcg agg gcc ttc ttc agc gag tgg tgt gac atc ctg    2592
Val Leu Gly Trp Ser Arg Ala Phe Phe Ser Glu Trp Cys Asp Ile Leu
850                 855                 860 tac gga ccg gac aga gga gtg cac atc ctg cga agg gag gag ccg cgc    2640
Tyr Gly Pro Asp Arg Gly Val His Ile Leu Arg Arg Glu Glu Pro Arg
865                 870                 875                 880 agc ctc tat ggc gat acc gac agc ctg ttc gtc aca gaa aca ggc tat    2688
Ser Leu Tyr Gly Asp Thr Asp Ser Leu Phe Val Thr Glu Thr Gly Tyr
                885                 890                 895 cat cgc atg aaa agc cgc ggc gcg cac cga atc aaa aca gaa tcc act    2736
His Arg Met Lys Ser Arg Gly Ala His Arg Ile Lys Thr Glu Ser Thr
            900                 905                 910 cga ctg act ttc gat cca gaa aat ccc ggc ctc tac tgg gcc tgc gat    2784
Arg Leu Thr Phe Asp Pro Glu Asn Pro Gly Leu Tyr Trp Ala Cys Asp
            915                 920                 925 tgc gac atc aag tgc aaa gcc tgc gga agt gac acg tac agc tcg gaa    2832
Cys Asp Ile Lys Cys Lys Ala Cys Gly Ser Asp Thr Tyr Ser Ser Glu
930                 935                 940 acc atc ttc cta gcg cca aaa ctg tac gga ctg aaa aac tca atc tgc    2880
Thr Ile Phe Leu Ala Pro Lys Leu Tyr Gly Leu Lys Asn Ser Ile Cys
945                 950                 955                 960 gtc aac gaa cag tgc cgc acg gta gga ccc ggg aaa atc aga tcg aag    2928
Val Asn Glu Gln Cys Arg Thr Val Gly Pro Gly Lys Ile Arg Ser Lys
                965                 970                 975 gga cac agg cag tcc gaa ctc atc tac gac acg ctg ctg cgc tgt tgg    2976
Gly His Arg Gln Ser Glu Leu Ile Tyr Asp Thr Leu Leu Arg Cys Trp
            980                 985                 990 cgt aga cac gag gac gtg caa ttc gga gcg cag agc aac atc cca gag    3024
Arg Arg His Glu Asp Val Gln Phe Gly Ala Gln Ser Asn Ile Pro Glu
            995                 1000                1005 cta cac acg cgg aga acc atc ttt aaa acc acg ctt ctg aac aag gtc    3072
Leu His Thr Arg Arg Thr Ile Phe Lys Thr Thr Leu Leu Asn Lys Val
            1010                1015                1020 agt cgc tac gac cct ttc acc att cac aac gag cag ctc acg cga gtg    3120
Ser Arg Tyr Asp Pro Phe Thr Ile His Asn Glu Gln Leu Thr Arg Val
1025                1030                1035                1040
```

-continued

| | | | | | | | | | | | | |
|---|---|---|---|---|---|---|---|---|---|---|---|---|
| ctg | cgt | ccg | tgg | aag | gac | ctc | acc | cta | tac | gag | cac | ggg | gac | tac | ctg | 3168 |
| Leu | Arg | Pro | Trp | Lys | Asp | Leu | Thr | Leu | Tyr | Glu | His | Gly | Asp | Tyr | Leu | |
| | | | | 1045 | | | | 1050 | | | | | 1055 | | | |

| tac | ccc | tac | gac | aat | gag | cac | cca | aat | ccc | cgc | acg | aca | gga | gac | gta | 3216 |
| Tyr | Pro | Tyr | Asp | Asn | Glu | His | Pro | Asn | Pro | Arg | Thr | Thr | Gly | Asp | Val | |
| | | | 1060 | | | | 1065 | | | | | 1070 | | | | |

| cga | ccc | gtc | cca | atc | gtc | ggg | cac | gaa | gac | ccc | ctc | gca | ccc | cta | cga | 3264 |
| Arg | Pro | Val | Pro | Ile | Val | Gly | His | Glu | Asp | Pro | Leu | Ala | Pro | Leu | Arg | |
| | | 1075 | | | | | 1080 | | | | | 1085 | | | | |

| tgg | gaa | ccc | tac | gcg | ttc | cta | tcc | gaa | gag | gaa | tgc | ggg | caa | gtt | cac | 3312 |
| Trp | Glu | Pro | Tyr | Ala | Phe | Leu | Ser | Glu | Glu | Glu | Cys | Gly | Gln | Val | His | |
| | 1090 | | | | | 1095 | | | | | 1100 | | | | | |

| gac | cta | ctc | ttc | gca | gat | gat | agc | tcc | cag | gaa | gcg | gaa | agc | ctg | gga | 3360 |
| Asp | Leu | Leu | Phe | Ala | Asp | Asp | Ser | Ser | Gln | Glu | Ala | Glu | Ser | Leu | Gly | |
| 1105 | | | | 1110 | | | | 1115 | | | | 1120 | | | | |

| gta | tga | | | | | | | | | | | | | | | 3366 |
| Val | | | | | | | | | | | | | | | | |

<210> SEQ ID NO 28
<211> LENGTH: 1121
<212> TYPE: PRT
<213> ORGANISM: CELO VIRUS
<220> FEATURE:
<223> OTHER INFORMATION: Position: 6501..9866/Product: E2b pol

<400> SEQUENCE: 28

```
Met Leu Ile Ala Lys Asn Val Thr Gly Glu Trp Val Trp Ile Thr Ser
  1               5                  10                  15

Arg Thr Pro Val Gln Gln Cys Pro Thr Cys Gly Arg His Trp Val Arg
             20                  25                  30

Arg His Ser Cys Asn Glu Arg Ser Ala Phe Tyr Tyr His Ala Val
         35                  40                  45

Gln Gly Ser Gly Ser Asp Leu Trp Gln His Val His Phe Ser Cys Pro
     50                  55                  60

Ala Gln His Pro His Ile Arg Gln Leu Tyr Ile Thr Tyr Asp Ile Glu
 65                  70                  75                  80

Thr Tyr Thr Val Phe Glu Lys Lys Gly Lys Arg Met His Pro Phe Met
                 85                  90                  95

Leu Cys Phe Met Leu Ser Gly Asp Pro Gln Leu Val Ser Arg Ala Glu
            100                 105                 110

Arg Leu Ala Arg Gln Asp Asp Arg Leu Lys Ala Leu Asp Glu Gly Phe
        115                 120                 125

Tyr Trp Leu Asp Ser His Pro Gly Glu Val Ala Arg Phe Arg Asn
    130                 135                 140

Phe Arg Ser Arg Leu Gln Ile Glu Phe Ala Gln Asn Leu Val Asp Arg
145                 150                 155                 160

Tyr Ala Ala Ala Asn Arg Asp Tyr Cys Asp Gln Leu Val Lys Asp Gly
                165                 170                 175

Lys Tyr Gly Ser Val His Lys Ile Pro Tyr Glu Leu Phe Glu Lys Pro
            180                 185                 190

Thr Ser Pro Leu Ser Leu Pro Asp Asn Phe Tyr Ser Val Asp Ile Val
        195                 200                 205

Val Leu Gly His Asn Ile Cys Lys Phe Asp Glu Leu Leu Ala Thr
    210                 215                 220

Glu Leu Val Glu Arg Arg Asp Leu Phe Pro Glu Ala Cys Lys Cys Asp
225                 230                 235                 240
```

```
Arg Ser Phe Met Pro Arg Val Gly Arg Leu Leu Phe Asn Asp Ile Ile
            245                 250                 255

Phe Arg Met Pro Asn Pro Asn Tyr Val Lys Lys Asp Ala Ser Arg Val
            260                 265                 270

Glu Arg Trp Ser Arg Gly Ile Val Ser His Gln Asp Ala Arg Ser Val
            275                 280                 285

Phe Val Arg Phe Met Val Arg Asp Thr Leu Gln Leu Thr Ser Gly Ala
            290                 295                 300

Lys Leu Ser Lys Ala Ala Ala Tyr Ala Leu Asp Leu Cys Lys Gly
305                 310                 315                 320

His Cys Pro Tyr Glu Ala Ile Asn Glu Phe Ile Ser Thr Gly Arg Phe
            325                 330                 335

His Ala Asp Ala Asp Gly Phe Pro Val Glu Arg Tyr Trp Glu Asp Pro
            340                 345                 350

Ser Val Ile Ala Glu Gln Lys Asn Leu Trp Gln Lys Glu His Pro Gly
            355                 360                 365

Gln Gln Tyr Asp Ile Val Gln Ala Cys Leu Glu Tyr Cys Met Gln Asp
            370                 375                 380

Val Arg Val Thr Gln Lys Leu Ala His Thr Leu His Asp Ser Tyr Asp
385                 390                 395                 400

Ala Tyr Phe Gln Arg Glu Leu Gly Met Glu Gly His Phe Asn Ile Phe
            405                 410                 415

Val Arg Pro Thr Ile Pro Ser Asn Thr His Ala Phe Trp Lys Gln Leu
            420                 425                 430

Thr Phe Ser Asn Tyr Val Arg Glu Gln Arg Ala Thr Cys Pro Pro Ser
            435                 440                 445

Val Pro Glu Pro Pro Lys Lys Lys Gly Arg Thr Lys Lys Lys Lys Gln
450                 455                 460

Pro Ser Pro Asp Tyr Val Ala Glu Val Tyr Ala Pro His Arg Pro Met
465                 470                 475                 480

Phe Lys Tyr Ile Arg Gln Ala Leu Arg Gly Gly Arg Cys Tyr Pro Asn
            485                 490                 495

Val Leu Gly Pro Tyr Leu Lys Pro Val Tyr Val Phe Asp Ile Cys Gly
            500                 505                 510

Met Tyr Ala Ser Ala Leu Thr His Pro Met Pro His Gly Met Pro Leu
            515                 520                 525

Asp Pro Lys Phe Thr Ala Gln His Val Glu Glu Leu Asn Arg Leu Leu
            530                 535                 540

Thr Asn Glu Ser His Leu Ser Tyr Phe Asp Ala Arg Ile Lys Pro Ser
545                 550                 555                 560

Ile Leu Lys Ile Glu Ala Tyr Pro Pro Pro Glu Met Leu Asp Pro
            565                 570                 575

Leu Pro Pro Ile Cys Ser Arg Arg Gly Gly Arg Leu Val Trp Thr Asn
            580                 585                 590

Glu Ala Leu Tyr Asp Glu Val Val Thr Val Ile Asp Ile Leu Thr Leu
            595                 600                 605

His Asn Arg Gly Trp Arg Val Gln Val Leu His Asp Glu Met Asn Ile
            610                 615                 620

Val Phe Pro Glu Trp Lys Thr Leu Cys Ala Asp Tyr Val Thr Lys Asn
625                 630                 635                 640

Ile Leu Ala Lys Glu Lys Ala Asp Arg Glu Lys Asn Glu Val Ile Arg
            645                 650                 655

Ser Ile Ser Lys Met Leu Ser Asn Ala Leu Tyr Gly Ala Phe Ala Thr
```

-continued

```
                 660                      665                       670
Asn Met Asp Thr Thr Arg Ile Ile Phe Glu Gln Asp Leu Ser Glu Ala
                675                      680                      685
Asp Lys Lys Asn Ile Tyr Glu Gly Thr Glu Ile Val Lys His Val Thr
690                      695                      700
Leu Leu Asn Asp Asp Ser Phe Asn Gly Thr Glu Val Thr Leu Glu Asn
705                      710                      715                      720
Ala Pro Asn Pro Phe Ser Glu Glu Ser Leu Arg Gln Gln Phe Arg Tyr
                725                      730                      735
Ala Asp Asp Pro Glu Gln Glu Glu Pro Glu Ala Glu Asp Gly Glu
                740                      745                      750
Glu Glu Gly Asp Asp Ser Asp Arg Glu Ser Ala Arg Lys Pro Lys Asn
                755                      760                      765
Ala Leu Thr Glu Asp Asp Pro Leu Val Ala Val Asp Leu Glu Val Glu
770                      775                      780
Ala Thr Leu Ala Thr Gly Pro Tyr Ile Pro Glu Gly Glu Leu Ser Ser
785                      790                      795                      800
Ala His Tyr Ala Arg Ala Asn Glu Thr Arg Phe Lys Pro Met Arg Leu
                805                      810                      815
Leu Glu Ala Thr Pro Glu Ala Leu Thr Val Leu His Leu Glu Ser Leu
                820                      825                      830
Asp Lys Gln Val Ala Asn Lys Arg Tyr Ala Thr Gln Ile Ala Cys Phe
                835                      840                      845
Val Leu Gly Trp Ser Arg Ala Phe Phe Ser Glu Trp Cys Asp Ile Leu
                850                      855                      860
Tyr Gly Pro Asp Arg Gly Val His Ile Leu Arg Arg Glu Glu Pro Arg
865                      870                      875                      880
Ser Leu Tyr Gly Asp Thr Asp Ser Leu Phe Val Thr Glu Thr Gly Tyr
                885                      890                      895
His Arg Met Lys Ser Arg Gly Ala His Arg Ile Lys Thr Glu Ser Thr
                900                      905                      910
Arg Leu Thr Phe Asp Pro Glu Asn Pro Gly Leu Tyr Trp Ala Cys Asp
                915                      920                      925
Cys Asp Ile Lys Cys Lys Ala Cys Gly Ser Asp Thr Tyr Ser Ser Glu
930                      935                      940
Thr Ile Phe Leu Ala Pro Lys Leu Tyr Gly Leu Lys Asn Ser Ile Cys
945                      950                      955                      960
Val Asn Glu Gln Cys Arg Thr Val Gly Pro Gly Lys Ile Arg Ser Lys
                965                      970                      975
Gly His Arg Gln Ser Glu Leu Ile Tyr Asp Thr Leu Leu Arg Cys Trp
                980                      985                      990
Arg Arg His Glu Asp Val Gln Phe Gly Ala Gln Ser Asn Ile Pro Glu
                995                     1000                     1005
Leu His Thr Arg Arg Thr Ile Phe Lys Thr Thr Leu Leu Asn Lys Val
               1010                     1015                     1020
Ser Arg Tyr Asp Pro Phe Thr Ile His Asn Glu Gln Leu Thr Arg Val
1025                     1030                     1035                     1040
Leu Arg Pro Trp Lys Asp Leu Thr Leu Tyr Glu His Gly Asp Tyr Leu
               1045                     1050                     1055
Tyr Pro Tyr Asp Asn Glu His Pro Asn Pro Arg Thr Thr Gly Asp Val
               1060                     1065                     1070
Arg Pro Val Pro Ile Val Gly His Glu Asp Pro Leu Ala Pro Leu Arg
               1075                     1080                     1085
```

```
Trp Glu Pro Tyr Ala Phe Leu Ser Glu Glu Cys Gly Gln Val His
    1090            1095                1100

Asp Leu Leu Phe Ala Asp Asp Ser Ser Gln Glu Ala Glu Ser Leu Gly
1105            1110                1115                1120

Val

<210> SEQ ID NO 29
<211> LENGTH: 1728
<212> TYPE: DNA
<213> ORGANISM: CELO VIRUS
<220> FEATURE:
<221> NAME/KEY: CDS
<222> LOCATION: (1)..(1728)

<400> SEQUENCE: 29 atg caa ctc cga gac ctc gcg ccg cga tcg ccg aac gtc gcc gcg ccg      48
Met Gln Leu Arg Asp Leu Ala Pro Arg Ser Pro Asn Val Ala Ala Pro
 1               5                  10                  15 ccc tac aac gga ttg ccg ccg ccg cac ctt ctc ctc ggg tac caa gct      96
Pro Tyr Asn Gly Leu Pro Pro Pro His Leu Leu Leu Gly Tyr Gln Ala
             20                  25                  30 atg cac cgc gcg ctc aac gat tac ctt ttc gac aac cgc gtt ttt atg     144
Met His Arg Ala Leu Asn Asp Tyr Leu Phe Asp Asn Arg Val Phe Met
         35                  40                  45 cag ata ggt tac gat agc cca ccc caa aga ccc aga cgc ctc ttt tgg     192
Gln Ile Gly Tyr Asp Ser Pro Pro Gln Arg Pro Arg Arg Leu Phe Trp
     50                  55                  60 acc tgt ctg acc gac tgc tcc tac gcc gtc aat gta ggg cag tac atg     240
Thr Cys Leu Thr Asp Cys Ser Tyr Ala Val Asn Val Gly Gln Tyr Met
 65                  70                  75                  80 cga ttt ctc gat ctc gac aac ttt cac ggt acg ttc acg cag atg cac     288
Arg Phe Leu Asp Leu Asp Asn Phe His Gly Thr Phe Thr Gln Met His
                 85                  90                  95 aac gcc gta ctc atg gac cgc gtg gcc gcg gac atg ggc cgg gcg cat     336
Asn Ala Val Leu Met Asp Arg Val Ala Ala Asp Met Gly Arg Ala His
            100                 105                 110 ctg cga ggt agg gga atc gac gta ggc cgt cac gga caa gtg ttg ccg     384
Leu Arg Gly Arg Gly Ile Asp Val Gly Arg His Gly Gln Val Leu Pro
        115                 120                 125 cag ctc gac gcc gaa cac cac agc cta ctg tcg ggc aac gga gcg ggt     432
Gln Leu Asp Ala Glu His His Ser Leu Leu Ser Gly Asn Gly Ala Gly
    130                 135                 140 ggc ttg caa gaa ggc gtc ctc atg cga acg gcc tct gcc gcc gac gcc     480
Gly Leu Gln Glu Gly Val Leu Met Arg Thr Ala Ser Ala Ala Asp Ala
145                 150                 155                 160 gaa ctg ctc gcc gcc atc cgc caa cta aga gtc gcc ctc tgc cac tat     528
Glu Leu Leu Ala Ala Ile Arg Gln Leu Arg Val Ala Leu Cys His Tyr
                165                 170                 175 cta ttc tgc tac gca tat gat cta ttt caa acg gaa gaa aga tat cgg     576
Leu Phe Cys Tyr Ala Tyr Asp Leu Phe Gln Thr Glu Glu Arg Tyr Arg
            180                 185                 190 ttc tta cct gga tcc gat gtg ttc ctt gaa cca aac tgg ctc tcc tac     624
Phe Leu Pro Gly Ser Asp Val Phe Leu Glu Pro Asn Trp Leu Ser Tyr
        195                 200                 205 ttc gcg gaa gcc ttc gcg gag cta gac acc cag caa ctg gtg cgg gat     672
Phe Ala Glu Ala Phe Ala Glu Leu Asp Thr Gln Gln Leu Val Arg Asp
    210                 215                 220 gcc gag cgc aag ttt cga gga aga cgg gac gta gag gaa cct acg gaa     720
Ala Glu Arg Lys Phe Arg Gly Arg Arg Asp Val Glu Glu Pro Thr Glu
225                 230                 235                 240
```

```
aca atg gcg aga tgt ttc atg agc act cta gcg agc gac gcc gtt tcc      768
Thr Met Ala Arg Cys Phe Met Ser Thr Leu Ala Ser Asp Ala Val Ser
            245                 250                 255 tta gca gga acg ggt ctg tca gga ggc gcc atc acc ctc tgc agc cgg      816
Leu Ala Gly Thr Gly Leu Ser Gly Gly Ala Ile Thr Leu Cys Ser Arg
            260                 265                 270 cgg gta acc gac cgc acc ggc ctg cgc cct aga gac cgc cac ggc aga      864
Arg Val Thr Asp Arg Thr Gly Leu Arg Pro Arg Asp Arg His Gly Arg
            275                 280                 285 gcc atc acc gcg tcc gaa gcg cgc cgc att agg ccc cgt gcc gtg cgg      912
Ala Ile Thr Ala Ser Glu Ala Arg Arg Ile Arg Pro Arg Ala Val Arg
            290                 295                 300 gcc ttc gta gac cgc ctg ccc cgc gtc acg cgg cgg cga cgg aga ccc      960
Ala Phe Val Asp Arg Leu Pro Arg Val Thr Arg Arg Arg Arg Arg Pro
305                 310                 315                 320 ccc tcc ccc gcg ccc cct ccc gaa gaa ata gaa gaa gcc gcc atg gaa     1008
Pro Ser Pro Ala Pro Pro Pro Glu Glu Ile Glu Glu Ala Ala Met Glu
                325                 330                 335 gta gaa gaa cca gaa gag gag gaa gaa gag ctg tta gac gag gtg att     1056
Val Glu Glu Pro Glu Glu Glu Glu Glu Leu Leu Asp Glu Val Ile
            340                 345                 350 cgc aca gcg ctc gaa gcc atc ggg gca ctg caa gac gag ctc agc ggg     1104
Arg Thr Ala Leu Glu Ala Ile Gly Ala Leu Gln Asp Glu Leu Ser Gly
            355                 360                 365 gcc gcc cgg aga cac gaa ctc ttc agg ttt gcc aac gac ttc tac cgc     1152
Ala Ala Arg Arg His Glu Leu Phe Arg Phe Ala Asn Asp Phe Tyr Arg
            370                 375                 380 atg ctc ctg acc gcg cgc gac gcg gga ctc atg gga gag tcg ttc ctg     1200
Met Leu Leu Thr Ala Arg Asp Ala Gly Leu Met Gly Glu Ser Phe Leu
385                 390                 395                 400 cgc aag tgg gtg ctg tac ttc ttc tta gcc gaa cat atc gcc tct aca     1248
Arg Lys Trp Val Leu Tyr Phe Phe Leu Ala Glu His Ile Ala Ser Thr
                405                 410                 415 ctc tac tac ctg tac agc cac ttc atc gcc aac cgc gag ttc cgc cgg     1296
Leu Tyr Tyr Leu Tyr Ser His Phe Ile Ala Asn Arg Glu Phe Arg Arg
            420                 425                 430 tac gtc gac gtc ctg acc tta caa gta ctc gtc gtg gga tgg gac gtc     1344
Tyr Val Asp Val Leu Thr Leu Gln Val Leu Val Val Gly Trp Asp Val
            435                 440                 445 aac gcg cag cag gtt ttt aaa cgc ata tgg agc gag caa tcc aac ccc     1392
Asn Ala Gln Gln Val Phe Lys Arg Ile Trp Ser Glu Gln Ser Asn Pro
450                 455                 460 gcc acc ata ttc gaa acc ctg tgg gaa cgt ata tta cgc gat ttt ctt     1440
Ala Thr Ile Phe Glu Thr Leu Trp Glu Arg Ile Leu Arg Asp Phe Leu
465                 470                 475                 480 atg atg gtc gaa cgg acg ggt caa ttc gaa ggc atg gac gat gcg gac     1488
Met Met Val Glu Arg Thr Gly Gln Phe Glu Gly Met Asp Asp Ala Asp
                485                 490                 495 caa caa ctg ttt ctc tct gat att caa tac aga gac cgc tcc ggt gac     1536
Gln Gln Leu Phe Leu Ser Asp Ile Gln Tyr Arg Asp Arg Ser Gly Asp
            500                 505                 510 atc gaa gaa gtg ctg aag cag ctc aac ctc agc gaa gag ctg atc gat     1584
Ile Glu Glu Val Leu Lys Gln Leu Asn Leu Ser Glu Glu Leu Ile Asp
            515                 520                 525 agc atc gac atc agt ttc cgc atc aaa ttt aaa ggc atc gta gcc atc     1632
Ser Ile Asp Ile Ser Phe Arg Ile Lys Phe Lys Gly Ile Val Ala Ile
530                 535                 540 gct acc aac gag gag atc aaa gcc aac ctc aga cgc gtg ctc cgc cac     1680
Ala Thr Asn Glu Glu Ile Lys Ala Asn Leu Arg Arg Val Leu Arg His
```

```
545                 550                 555                 560
cgc cgc gaa gac atc gaa gcg gcg gcg cga cga ggt cag cct ctg taa       1728
Arg Arg Glu Asp Ile Glu Ala Ala Ala Arg Arg Gly Gln Pro Leu
                565                 570                 575
```

<210> SEQ ID NO 30
<211> LENGTH: 575
<212> TYPE: PRT
<213> ORGANISM: CELO VIRUS
<220> FEATURE:
<223> OTHER INFORMATION: Position: 10269..11996/Product: E2b pTP

<400> SEQUENCE: 30

```
Met Gln Leu Arg Asp Leu Ala Pro Arg Ser Pro Asn Val Ala Ala Pro
  1               5                  10                  15

Pro Tyr Asn Gly Leu Pro Pro His Leu Leu Gly Tyr Gln Ala
                 20                  25                  30

Met His Arg Ala Leu Asn Asp Tyr Leu Phe Asp Asn Arg Val Phe Met
                 35                  40                  45

Gln Ile Gly Tyr Asp Ser Pro Pro Gln Arg Pro Arg Arg Leu Phe Trp
     50                  55                  60

Thr Cys Leu Thr Asp Cys Ser Tyr Ala Val Asn Val Gly Gln Tyr Met
 65                  70                  75                  80

Arg Phe Leu Asp Leu Asp Asn Phe His Gly Thr Phe Thr Gln Met His
                 85                  90                  95

Asn Ala Val Leu Met Asp Arg Val Ala Ala Asp Met Gly Arg Ala His
                100                 105                 110

Leu Arg Gly Arg Gly Ile Asp Val Gly Arg His Gly Gln Val Leu Pro
            115                 120                 125

Gln Leu Asp Ala Glu His His Ser Leu Leu Ser Gly Asn Gly Ala Gly
        130                 135                 140

Gly Leu Gln Glu Gly Val Leu Met Arg Thr Ala Ser Ala Ala Asp Ala
145                 150                 155                 160

Glu Leu Leu Ala Ala Ile Arg Gln Leu Arg Val Ala Leu Cys His Tyr
                165                 170                 175

Leu Phe Cys Tyr Ala Tyr Asp Leu Phe Gln Thr Glu Glu Arg Tyr Arg
                180                 185                 190

Phe Leu Pro Gly Ser Asp Val Phe Leu Glu Pro Asn Trp Leu Ser Tyr
            195                 200                 205

Phe Ala Glu Ala Phe Ala Glu Leu Asp Thr Gln Gln Leu Val Arg Asp
        210                 215                 220

Ala Glu Arg Lys Phe Arg Gly Arg Arg Asp Val Glu Pro Thr Glu
225                 230                 235                 240

Thr Met Ala Arg Cys Phe Met Ser Thr Leu Ala Ser Asp Ala Val Ser
                245                 250                 255

Leu Ala Gly Thr Gly Leu Ser Gly Gly Ala Ile Thr Leu Cys Ser Arg
                260                 265                 270

Arg Val Thr Asp Arg Thr Gly Leu Arg Pro Arg Asp Arg His Gly Arg
            275                 280                 285

Ala Ile Thr Ala Ser Glu Ala Arg Arg Ile Arg Pro Arg Ala Val Arg
        290                 295                 300

Ala Phe Val Asp Arg Leu Pro Arg Val Thr Arg Arg Arg Arg Pro
305                 310                 315                 320

Pro Ser Pro Ala Pro Pro Pro Glu Glu Ile Glu Glu Ala Ala Met Glu
                325                 330                 335
```

```
Val Glu Glu Pro Glu Glu Glu Glu Leu Leu Asp Glu Val Ile
            340                 345                 350

Arg Thr Ala Leu Glu Ala Ile Gly Ala Leu Gln Asp Glu Leu Ser Gly
        355                 360                 365

Ala Ala Arg Arg His Glu Leu Phe Arg Phe Ala Asn Asp Phe Tyr Arg
    370                 375                 380

Met Leu Leu Thr Ala Arg Asp Ala Gly Leu Met Gly Glu Ser Phe Leu
385                 390                 395                 400

Arg Lys Trp Val Leu Tyr Phe Phe Leu Ala Glu His Ile Ala Ser Thr
                405                 410                 415

Leu Tyr Tyr Leu Tyr Ser His Phe Ile Ala Asn Arg Glu Phe Arg Arg
            420                 425                 430

Tyr Val Asp Val Leu Thr Leu Gln Val Leu Val Val Gly Trp Asp Val
        435                 440                 445

Asn Ala Gln Gln Val Phe Lys Arg Ile Trp Ser Glu Gln Ser Asn Pro
450                 455                 460

Ala Thr Ile Phe Glu Thr Leu Trp Glu Arg Ile Leu Arg Asp Phe Leu
465                 470                 475                 480

Met Met Val Glu Arg Thr Gly Gln Phe Glu Gly Met Asp Asp Ala Asp
                485                 490                 495

Gln Gln Leu Phe Leu Ser Asp Ile Gln Tyr Arg Asp Arg Ser Gly Asp
            500                 505                 510

Ile Glu Glu Val Leu Lys Gln Leu Asn Leu Ser Glu Glu Leu Ile Asp
        515                 520                 525

Ser Ile Asp Ile Ser Phe Arg Ile Lys Phe Lys Gly Ile Val Ala Ile
    530                 535                 540

Ala Thr Asn Glu Glu Ile Lys Ala Asn Leu Arg Arg Val Leu Arg His
545                 550                 555                 560

Arg Arg Glu Asp Ile Glu Ala Ala Ala Arg Arg Gly Gln Pro Leu
                565                 570                 575

<210> SEQ ID NO 31
<211> LENGTH: 1320
<212> TYPE: DNA
<213> ORGANISM: CELO VIRUS
<220> FEATURE:
<221> NAME/KEY: CDS
<222> LOCATION: (1)..(1320)

<400> SEQUENCE: 31 atg agc acc caa atc ccc gca cga cag gag acg tac gac ccg tcc caa      48
Met Ser Thr Gln Ile Pro Ala Arg Gln Glu Thr Tyr Asp Pro Ser Gln
1               5                   10                  15 tcg tcg ggc acg aag acc ccc tcg cac ccc tac gat ggg aac cct acg      96
Ser Ser Gly Thr Lys Thr Pro Ser His Pro Tyr Asp Gly Asn Pro Thr
            20                  25                  30 cgt tcc tat ccg aag agg aat gcg ggc aag ttc acg acc tac tct tcg     144
Arg Ser Tyr Pro Lys Arg Asn Ala Gly Lys Phe Thr Thr Tyr Ser Ser
        35                  40                  45 cag atg ata gct ccc agg aag cgg aaa gcc tgg gag tat gag gaa gaa     192
Gln Met Ile Ala Pro Arg Lys Arg Lys Ala Trp Glu Tyr Glu Glu Glu
    50                  55                  60 gag tac gaa gcc tcg cgg gac ttc tac cag cgc gtc acc agc tgg tac     240
Glu Tyr Glu Ala Ser Arg Asp Phe Tyr Gln Arg Val Thr Ser Trp Tyr
65                  70                  75                  80 gac gga gct gtc gac cta gca ccg cag ctc ttc gcg gag caa cac ttc     288
Asp Gly Ala Val Asp Leu Ala Pro Gln Leu Phe Arg Glu Gln His Phe
                85                  90                  95
```

-continued

```
ccc tcc tac gac gag ttc tac agc cta ggg ggc gtt aat gag aag ttt        336
Pro Ser Tyr Asp Glu Phe Tyr Ser Leu Gly Gly Val Asn Glu Lys Phe
            100                 105                 110 ctc gaa gcc cac gaa gaa gtt aaa gcc cag gaa cag atg gac agt cgc        384
Leu Glu Ala His Glu Glu Val Lys Ala Gln Glu Gln Met Asp Ser Arg
            115                 120                 125 tac ctc caa cac gga cag ctg ccg tcc atc aac atg ggc aag cag ccc        432
Tyr Leu Gln His Gly Gln Leu Pro Ser Ile Asn Met Gly Lys Gln Pro
        130                 135                 140 atc atc ggg gtc atc tac gga ccc acc gga tcc ggc aag tcg cat ctg        480
Ile Ile Gly Val Ile Tyr Gly Pro Thr Gly Ser Gly Lys Ser His Leu
145                 150                 155                 160 ctg cgg gcg ctc atc tcg tgc aac atg ttg gac ccg atc ccc gaa acg        528
Leu Arg Ala Leu Ile Ser Cys Asn Met Leu Asp Pro Ile Pro Glu Thr
                165                 170                 175 gtc atc ttc atc act ccg gaa aag aac atg att cca ccc atc gaa cag        576
Val Ile Phe Ile Thr Pro Glu Lys Asn Met Ile Pro Pro Ile Glu Gln
                180                 185                 190 acg tcc tgg aac ctg cag ctg gtc gag gcc aat ttc gac tgc agg gaa        624
Thr Ser Trp Asn Leu Gln Leu Val Glu Ala Asn Phe Asp Cys Arg Glu
            195                 200                 205 gac ggc acc atc gcc cct aag aca agc acg ttc cgt ccc gaa ttt atg        672
Asp Gly Thr Ile Ala Pro Lys Thr Ser Thr Phe Arg Pro Glu Phe Met
        210                 215                 220 gag atg act tac gag gag gcc acc gca ccc gaa cat ctc aac atc gac        720
Glu Met Thr Tyr Glu Glu Ala Thr Ala Pro Glu His Leu Asn Ile Asp
225                 230                 235                 240 cat cca gac aac att tac gtg aaa gtc tcc aag cgg gga ccc gtc gcc        768
His Pro Asp Asn Ile Tyr Val Lys Val Ser Lys Arg Gly Pro Val Ala
                245                 250                 255 att atc atg gac gag tgc atg gat aag ctc tgt tca ggc tcc agc gtc        816
Ile Ile Met Asp Glu Cys Met Asp Lys Leu Cys Ser Gly Ser Ser Val
                260                 265                 270 tct gtc ctc ttt cac gcc ctt cct tct aag ctc ttt gct cgc tct gcc        864
Ser Val Leu Phe His Ala Leu Pro Ser Lys Leu Phe Ala Arg Ser Ala
            275                 280                 285 cac tgt aca gcc ttc tac att ttc gta gtc ttg cac aac atg gca ccg        912
His Cys Thr Ala Phe Tyr Ile Phe Val Val Leu His Asn Met Ala Pro
        290                 295                 300 cgc acc gcg ata gga aac gtt ccc acc ctc aaa gtg aac gca aaa atg        960
Arg Thr Ala Ile Gly Asn Val Pro Thr Leu Lys Val Asn Ala Lys Met
305                 310                 315                 320 cac atc cta tcc tgt cat att ccc caa ttc cag ttc gct agg ttc ctc       1008
His Ile Leu Ser Cys His Ile Pro Gln Phe Gln Phe Ala Arg Phe Leu
                325                 330                 335 tat gcg ttc gca cac aac atc tcg aag gac ctc gtt gtc ctt ctc aaa       1056
Tyr Ala Phe Ala His Asn Ile Ser Lys Asp Leu Val Val Leu Leu Lys
            340                 345                 350 gct tac ttt tcc ttc ctg cag cag aac cag cgg ttc agc tgg gtc atg       1104
Ala Tyr Phe Ser Phe Leu Gln Gln Asn Gln Arg Phe Ser Trp Val Met
        355                 360                 365 tac act ccg gac cca gta tcc gag tcc ttt agg tgg tgc agt ata gat       1152
Tyr Thr Pro Asp Pro Val Ser Glu Ser Phe Arg Trp Cys Ser Ile Asp
370                 375                 380 cag cag tac tcg atc atc cct ctc aat gtt aac att cag gag aga ttc       1200
Gln Gln Tyr Ser Ile Ile Pro Leu Asn Val Asn Ile Gln Glu Arg Phe
385                 390                 395                 400 ctg aaa aca gcc aaa tct atc atc aaa ttt agc gaa aca cat aga aag       1248
Leu Lys Thr Ala Lys Ser Ile Ile Lys Phe Ser Glu Thr His Arg Lys
```

```
                      405                 410                 415
cag tta gag aga aac ccc aaa cta acc gat ctc gaa aaa ctt tct ccc      1296
Gln Leu Glu Arg Asn Pro Lys Leu Thr Asp Leu Glu Lys Leu Ser Pro
            420                 425                 430 cca gga acg ttt cag gaa act taa                                      1320
Pro Gly Thr Phe Gln Glu Thr
        435                 440
```

<210> SEQ ID NO 32
<211> LENGTH: 439
<212> TYPE: PRT
<213> ORGANISM: CELO VIRUS
<220> FEATURE:
<223> OTHER INFORMATION: Position: 5366..6685/Product:IVa2

<400> SEQUENCE: 32

```
Met Ser Thr Gln Ile Pro Ala Arg Gln Glu Thr Tyr Asp Pro Ser Gln
 1               5                  10                  15

Ser Ser Gly Thr Lys Thr Pro Ser His Pro Tyr Asp Gly Asn Pro Thr
            20                  25                  30

Arg Ser Tyr Pro Lys Arg Asn Ala Gly Lys Phe Thr Thr Tyr Ser Ser
        35                  40                  45

Gln Met Ile Ala Pro Arg Lys Arg Lys Ala Trp Glu Tyr Glu Glu Glu
    50                  55                  60

Glu Tyr Glu Ala Ser Arg Asp Phe Tyr Gln Arg Val Thr Ser Trp Tyr
65                  70                  75                  80

Asp Gly Ala Val Asp Leu Ala Pro Gln Leu Phe Arg Glu Gln His Phe
                85                  90                  95

Pro Ser Tyr Asp Glu Phe Tyr Ser Leu Gly Gly Val Asn Glu Lys Phe
            100                 105                 110

Leu Glu Ala His Glu Glu Val Lys Ala Gln Glu Gln Met Asp Ser Arg
        115                 120                 125

Tyr Leu Gln His Gly Gln Leu Pro Ser Ile Asn Met Gly Lys Gln Pro
    130                 135                 140

Ile Ile Gly Val Ile Tyr Gly Pro Thr Gly Ser Gly Lys Ser His Leu
145                 150                 155                 160

Leu Arg Ala Leu Ile Ser Cys Asn Met Leu Asp Pro Ile Pro Glu Thr
                165                 170                 175

Val Ile Phe Ile Thr Pro Glu Lys Asn Met Ile Pro Ile Glu Gln
            180                 185                 190

Thr Ser Trp Asn Leu Gln Leu Val Glu Ala Asn Phe Asp Cys Arg Glu
        195                 200                 205

Asp Gly Thr Ile Ala Pro Lys Thr Ser Thr Phe Arg Pro Glu Phe Met
    210                 215                 220

Glu Met Thr Tyr Glu Glu Ala Thr Ala Pro Glu His Leu Asn Ile Asp
225                 230                 235                 240

His Pro Asp Asn Ile Tyr Val Lys Val Ser Lys Arg Gly Pro Val Ala
                245                 250                 255

Ile Ile Met Asp Glu Cys Met Asp Lys Leu Cys Ser Gly Ser Ser Val
            260                 265                 270

Ser Val Leu Phe His Ala Leu Pro Ser Lys Leu Phe Ala Arg Ser Ala
        275                 280                 285

His Cys Thr Ala Phe Tyr Ile Phe Val Val Leu His Asn Met Ala Pro
    290                 295                 300

Arg Thr Ala Ile Gly Asn Val Pro Thr Leu Lys Val Asn Ala Lys Met
305                 310                 315                 320
```

```
His Ile Leu Ser Cys His Ile Pro Gln Phe Gln Phe Ala Arg Phe Leu
                325                 330                 335

Tyr Ala Phe Ala His Asn Ile Ser Lys Asp Leu Val Val Leu Leu Lys
            340                 345                 350

Ala Tyr Phe Ser Phe Leu Gln Gln Asn Gln Arg Phe Ser Trp Val Met
            355                 360                 365

Tyr Thr Pro Asp Pro Val Ser Glu Ser Phe Arg Trp Cys Ser Ile Asp
    370                 375                 380

Gln Gln Tyr Ser Ile Ile Pro Leu Asn Val Asn Ile Gln Glu Arg Phe
385                 390                 395                 400

Leu Lys Thr Ala Lys Ser Ile Ile Lys Phe Ser Glu Thr His Arg Lys
                405                 410                 415

Gln Leu Glu Arg Asn Pro Lys Leu Thr Asp Leu Glu Lys Leu Ser Pro
            420                 425                 430

Pro Gly Thr Phe Gln Glu Thr
            435

<210> SEQ ID NO 33
<211> LENGTH: 633
<212> TYPE: DNA
<213> ORGANISM: CELO VIRUS
<220> FEATURE:
<221> NAME/KEY: CDS
<222> LOCATION: (1)..(633)

<400> SEQUENCE: 33 atg cta gaa gcc gaa ggt tac aat gct ccg gta gcc atc tac gcc att        48
Met Leu Glu Ala Glu Gly Tyr Asn Ala Pro Val Ala Ile Tyr Ala Ile
 1               5                  10                  15 tat ctg tgg atg tct gcc atg agc att agt cgc ctg tgc cat tat act       96
Tyr Leu Trp Met Ser Ala Met Ser Ile Ser Arg Leu Cys His Tyr Thr
             20                  25                  30 aac acg ctc tat gtc gta gga gaa cct tcc tct gcc gca gat ata ttc      144
Asn Thr Leu Tyr Val Val Gly Glu Pro Ser Ser Ala Ala Asp Ile Phe
         35                  40                  45 act gca tcc atc ctc aga tta ttc caa ttt gtc ctc act gcc aac att      192
Thr Ala Ser Ile Leu Arg Leu Phe Gln Phe Val Leu Thr Ala Asn Ile
     50                  55                  60 aac gcg ttc gac ttt ggc cag tac gcc aga cag caa gat tta gtc aag      240
Asn Ala Phe Asp Phe Gly Gln Tyr Ala Arg Gln Gln Asp Leu Val Lys
 65                  70                  75                  80 atg ctt tat ttc ccc tgc aca gct cat tgt aac acg ttc aaa gat ccc      288
Met Leu Tyr Phe Pro Cys Thr Ala His Cys Asn Thr Phe Lys Asp Pro
                 85                  90                  95 gtt gct aac cag ctg ctg aaa ggc agg tca ttc acc aca atg acc cgc      336
Val Ala Asn Gln Leu Leu Lys Gly Arg Ser Phe Thr Thr Met Thr Arg
            100                 105                 110 gac ggt ctc gtg gac atc agt gag aaa aaa tgc ctc gtc cgc tta tat      384
Asp Gly Leu Val Asp Ile Ser Glu Lys Lys Cys Leu Val Arg Leu Tyr
        115                 120                 125 cag ctc ccc cat ccc gaa cat ctg ccc act gct ccc gac gaa cat atc      432
Gln Leu Pro His Pro Glu His Leu Pro Thr Ala Pro Asp Glu His Ile
    130                 135                 140 att att agg ttc tac gaa ccc gcc aac ggc tgc ggg ttc ttt ctg gga      480
Ile Ile Arg Phe Tyr Glu Pro Ala Asn Gly Cys Gly Phe Phe Leu Gly
145                 150                 155                 160 gag ctc tcc cgc tac att cat cgc ata cac caa tta cag gca gat aat      528
Glu Leu Ser Arg Tyr Ile His Arg Ile His Gln Leu Gln Ala Asp Asn
                165                 170                 175
```

```
gac aac gac gcc ttg cgc gct ctc cta tgc gag aac aaa gga atg ctc    576
Asp Asn Asp Ala Leu Arg Ala Leu Leu Cys Glu Asn Lys Gly Met Leu
            180                 185                 190 tgt tcc cgc tcg tgg acc tcc cca tgc aat gct tgt cac tca tca cat    624
Cys Ser Arg Ser Trp Thr Ser Pro Cys Asn Ala Cys His Ser Ser His
        195                 200                 205 gac ata taa                                                        633
Asp Ile
    210

<210> SEQ ID NO 34
<211> LENGTH: 210
<212> TYPE: PRT
<213> ORGANISM: CELO VIRUS
<220> FEATURE:
<223> OTHER INFORMATION: Position: 4462..5094/note=ORF12

<400> SEQUENCE: 34

Met Leu Glu Ala Glu Gly Tyr Asn Ala Pro Val Ala Ile Tyr Ala Ile
  1               5                  10                  15

Tyr Leu Trp Met Ser Ala Met Ser Ile Ser Arg Leu Cys His Tyr Thr
             20                  25                  30

Asn Thr Leu Tyr Val Val Gly Glu Pro Ser Ser Ala Ala Asp Ile Phe
         35                  40                  45

Thr Ala Ser Ile Leu Arg Leu Phe Gln Phe Val Leu Thr Ala Asn Ile
     50                  55                  60

Asn Ala Phe Asp Phe Gly Gln Tyr Ala Arg Gln Gln Asp Leu Val Lys
 65                  70                  75                  80

Met Leu Tyr Phe Pro Cys Thr Ala His Cys Asn Thr Phe Lys Asp Pro
                 85                  90                  95

Val Ala Asn Gln Leu Leu Lys Gly Arg Ser Phe Thr Thr Met Thr Arg
            100                 105                 110

Asp Gly Leu Val Asp Ile Ser Glu Lys Lys Cys Leu Val Arg Leu Tyr
        115                 120                 125

Gln Leu Pro His Pro Glu His Leu Pro Thr Ala Pro Asp Glu His Ile
    130                 135                 140

Ile Ile Arg Phe Tyr Glu Pro Ala Asn Gly Cys Gly Phe Phe Leu Gly
145                 150                 155                 160

Glu Leu Ser Arg Tyr Ile His Arg Ile His Gln Leu Gln Ala Asp Asn
                165                 170                 175

Asp Asn Asp Ala Leu Arg Ala Leu Leu Cys Glu Asn Lys Gly Met Leu
            180                 185                 190

Cys Ser Arg Ser Trp Thr Ser Pro Cys Asn Ala Cys His Ser Ser His
        195                 200                 205

Asp Ile
    210

<210> SEQ ID NO 35
<211> LENGTH: 1020
<212> TYPE: DNA
<213> ORGANISM: CELO VIRUS
<220> FEATURE:
<221> NAME/KEY: CDS
<222> LOCATION: (1)..(1020)

<400> SEQUENCE: 35 atg aca acg acg cct tgc gcg ctc tcc tat gcg aga aca aag gaa tgc    48
Met Thr Thr Thr Pro Cys Ala Leu Ser Tyr Ala Arg Thr Lys Glu Cys
  1               5                  10                  15
```

-continued

| | | | | | | | | | | | | | | | | |
|---|---|---|---|---|---|---|---|---|---|---|---|---|---|---|---|---|
| tct | gtt | ccc | gct | cgt | gga | cct | ccc | cat | gca | atg | ctt | gtc | act | cat | cac | 96 |
| Ser | Val | Pro | Ala | Arg | Gly | Pro | Pro | His | Ala | Met | Leu | Val | Thr | His | His | |
| | | | 20 | | | | 25 | | | | | 30 | | | | |
| atg | aca | tat | aat | tct | ctc | cca | cag | tgc | acc | aag | agg | cga | cgc | gag | tct | 144 |
| Met | Thr | Tyr | Asn | Ser | Leu | Pro | Gln | Cys | Thr | Lys | Arg | Arg | Arg | Glu | Ser | |
| | | | 35 | | | | 40 | | | | 45 | | | | | |
| cag | tcg | tct | tta | agt | agc | gaa | gag | gag | caa | ata | gca | tcc | tgc | att | cca | 192 |
| Gln | Ser | Ser | Leu | Ser | Ser | Glu | Glu | Gln | Ile | Ala | Ser | Cys | Ile | Pro | | |
| | 50 | | | | | 55 | | | | 60 | | | | | | |
| gac | acc | cct | tca | ccc | tgc | tta | ttt | ccg | tcc | acg | tcc | ccc | atg | gat | cag | 240 |
| Asp | Thr | Pro | Ser | Pro | Cys | Leu | Phe | Pro | Ser | Thr | Ser | Pro | Met | Asp | Gln | |
| 65 | | | | | 70 | | | | | 75 | | | | | 80 | |
| ttg | gtt | gaa | cgg | ttg | ttt | gtc | gaa | ggt | gta | gca | cac | gaa | gtc | cag | tgg | 288 |
| Leu | Val | Glu | Arg | Leu | Phe | Val | Glu | Gly | Val | Ala | His | Glu | Val | Gln | Trp | |
| | | | | 85 | | | | 90 | | | | | 95 | | | |
| aac | ttc | ccg | tcc | aag | aac | ctc | ata | ccc | acc | tac | gaa | cga | gag | cgt | gta | 336 |
| Asn | Phe | Pro | Ser | Lys | Asn | Leu | Ile | Pro | Thr | Tyr | Glu | Arg | Glu | Arg | Val | |
| | | | 100 | | | | 105 | | | | 110 | | | | | |
| ctc | gaa | gcc | ctc | aag | gaa | cgg | ttc | gga | ccc | gga | cag | agc | ctc | att | aac | 384 |
| Leu | Glu | Ala | Leu | Lys | Glu | Arg | Phe | Gly | Pro | Gly | Gln | Ser | Leu | Ile | Asn | |
| | | 115 | | | | | 120 | | | | | 125 | | | | |
| cag | tta | ccc | tcc | gaa | gag | ccc | gac | acc | ctc | aag | gct | gcg | ttc | tac | aac | 432 |
| Gln | Leu | Pro | Ser | Glu | Glu | Pro | Asp | Thr | Leu | Lys | Ala | Ala | Phe | Tyr | Asn | |
| | 130 | | | | | 135 | | | | | 140 | | | | | |
| gtc | tgc | gac | aac | tgg | ttc | cat | cag | atg | atg | gaa | gcc | gaa | ggc | tac | gag | 480 |
| Val | Cys | Asp | Asn | Trp | Phe | His | Gln | Met | Met | Glu | Ala | Glu | Gly | Tyr | Glu | |
| 145 | | | | | 150 | | | | | 155 | | | | | 160 | |
| gga | aaa | gtg | gca | gct | aac | gcc | atc | ctc | cga | tgg | ctc | cga | gga | gaa | cta | 528 |
| Gly | Lys | Val | Ala | Ala | Asn | Ala | Ile | Leu | Arg | Trp | Leu | Arg | Gly | Glu | Leu | |
| | | | | 165 | | | | 170 | | | | | 175 | | | |
| aac | acc | ctc | gtg | ctc | tgc | gga | gga | aga | ctt | tcc | aac | gcc | aag | agt | ctc | 576 |
| Asn | Thr | Leu | Val | Leu | Cys | Gly | Gly | Arg | Leu | Ser | Asn | Ala | Lys | Ser | Leu | |
| | | | 180 | | | | | 185 | | | | | 190 | | | |
| ttt | aat | gcc | tta | tgc | gcg | tgt | ttc | ccg | ctc | gcg | atc | tcc | gac | agc | cga | 624 |
| Phe | Asn | Ala | Leu | Cys | Ala | Cys | Phe | Pro | Leu | Ala | Ile | Ser | Asp | Ser | Arg | |
| | | 195 | | | | | 200 | | | | | 205 | | | | |
| atc | aac | tcc | ata | cta | tca | ctg | ggc | gaa | atc | gca | ccc | cac | gcc | tct | cta | 672 |
| Ile | Asn | Ser | Ile | Leu | Ser | Leu | Gly | Glu | Ile | Ala | Pro | His | Ala | Ser | Leu | |
| | 210 | | | | | 215 | | | | | 220 | | | | | |
| tac | tgt | ctg | ccc | ttc | gta | gac | gag | aag | ccg | gac | ccg | ttg | atg | ctg | cac | 720 |
| Tyr | Cys | Leu | Pro | Phe | Val | Asp | Glu | Lys | Pro | Asp | Pro | Leu | Met | Leu | His | |
| 225 | | | | | 230 | | | | | 235 | | | | | 240 | |
| ttt | atg | gaa | ggc | aat | gct | gcc | acc | tgc | agg | ctg | aat | aag | aaa | acg | ttc | 768 |
| Phe | Met | Glu | Gly | Asn | Ala | Ala | Thr | Cys | Arg | Leu | Asn | Lys | Lys | Thr | Phe | |
| | | | | 245 | | | | 250 | | | | | 255 | | | |
| cac | atc | ccc | tcg | acc | ccc | atg | cta | atc | cac | tgc | gcg | gac | ctc | tcg | ctc | 816 |
| His | Ile | Pro | Ser | Thr | Pro | Met | Leu | Ile | His | Cys | Ala | Asp | Leu | Ser | Leu | |
| | | | 260 | | | | | 265 | | | | | 270 | | | |
| gcc | aac | gag | ttc | acg | gcg | cgg | aac | acg | gtc | gtc | ttc | ttc | ctc | aca | gga | 864 |
| Ala | Asn | Glu | Phe | Thr | Ala | Arg | Asn | Thr | Val | Val | Phe | Phe | Leu | Thr | Gly | |
| | | 275 | | | | | 280 | | | | | 285 | | | | |
| gac | cac | acc | aag | acc | cct | cca | tgc | tac | cac | ccg | cgc | aaa | gag | cta | cgc | 912 |
| Asp | His | Thr | Lys | Thr | Pro | Pro | Cys | Tyr | His | Pro | Arg | Lys | Glu | Leu | Arg | |
| | 290 | | | | | 295 | | | | | 300 | | | | | |
| gac | ttt | gtt | gct | aat | gct | gcc | gct | tgt | gct | tgc | tta | atg | aca | ctg | cat | 960 |
| Asp | Phe | Val | Ala | Asn | Ala | Ala | Ala | Cys | Ala | Cys | Leu | Met | Thr | Leu | His | |
| 305 | | | | 310 | | | | 315 | | | | | 320 | | | |
| tgc | aaa | cgc | gat | aat | aaa | ctc | tgt | aac | ccc | tgt | ata | cgt | acc | cct | ctt | 1008 |
| Cys | Lys | Arg | Asp | Asn | Lys | Leu | Cys | Asn | Pro | Cys | Ile | Arg | Thr | Pro | Leu | |

```
                325                 330                 335 caa aat cag taa                                                              1020
Gln Asn Gln
        340

<210> SEQ ID NO 36
<211> LENGTH: 339
<212> TYPE: PRT
<213> ORGANISM: CELO VIRUS
<220> FEATURE:
<223> OTHER INFORMATION: Position: 3549..4568/note=ORF13

<400> SEQUENCE: 36

Met Thr Thr Thr Pro Cys Ala Leu Ser Tyr Ala Arg Thr Lys Glu Cys
  1               5                  10                  15

Ser Val Pro Ala Arg Gly Pro Pro His Ala Met Leu Val Thr His His
             20                  25                  30

Met Thr Tyr Asn Ser Leu Pro Gln Cys Thr Lys Arg Arg Arg Glu Ser
         35                  40                  45

Gln Ser Ser Leu Ser Ser Glu Glu Gln Ile Ala Ser Cys Ile Pro
     50                  55                  60

Asp Thr Pro Ser Pro Cys Leu Phe Pro Ser Thr Ser Pro Met Asp Gln
 65                  70                  75                  80

Leu Val Glu Arg Leu Phe Val Glu Gly Val Ala His Glu Val Gln Trp
                 85                  90                  95

Asn Phe Pro Ser Lys Asn Leu Ile Pro Thr Tyr Glu Arg Glu Arg Val
            100                 105                 110

Leu Glu Ala Leu Lys Glu Arg Phe Gly Pro Gly Gln Ser Leu Ile Asn
        115                 120                 125

Gln Leu Pro Ser Glu Glu Pro Asp Thr Leu Lys Ala Ala Phe Tyr Asn
    130                 135                 140

Val Cys Asp Asn Trp Phe His Gln Met Met Glu Ala Glu Gly Tyr Glu
145                 150                 155                 160

Gly Lys Val Ala Ala Asn Ala Ile Leu Arg Trp Leu Arg Gly Glu Leu
                165                 170                 175

Asn Thr Leu Val Leu Cys Gly Gly Arg Leu Ser Asn Ala Lys Ser Leu
            180                 185                 190

Phe Asn Ala Leu Cys Ala Cys Phe Pro Leu Ala Ile Ser Asp Ser Arg
        195                 200                 205

Ile Asn Ser Ile Leu Ser Leu Gly Glu Ile Ala Pro His Ala Ser Leu
    210                 215                 220

Tyr Cys Leu Pro Phe Val Asp Glu Lys Pro Asp Pro Leu Met Leu His
225                 230                 235                 240

Phe Met Glu Gly Asn Ala Ala Thr Cys Arg Leu Asn Lys Lys Thr Phe
                245                 250                 255

His Ile Pro Ser Thr Pro Met Leu Ile His Cys Ala Asp Leu Ser Leu
            260                 265                 270

Ala Asn Glu Phe Thr Ala Arg Asn Thr Val Val Phe Phe Leu Thr Gly
        275                 280                 285

Asp His Thr Lys Thr Pro Pro Cys Tyr His Pro Arg Lys Glu Leu Arg
    290                 295                 300

Asp Phe Val Ala Asn Ala Ala Cys Ala Cys Leu Met Thr Leu His
305                 310                 315                 320

Cys Lys Arg Asp Asn Lys Leu Cys Asn Pro Cys Ile Arg Thr Pro Leu
                325                 330                 335
```

Gln Asn Gln

<210> SEQ ID NO 37
<211> LENGTH: 483
<212> TYPE: DNA
<213> ORGANISM: CELO VIRUS
<220> FEATURE:
<221> NAME/KEY: CDS
<222> LOCATION: (1)..(483)

<400> SEQUENCE: 37

| | | | | | | | | | | | | | | | | |
|---|---|---|---|---|---|---|---|---|---|---|---|---|---|---|---|---|
| atg | tac | ccc | ttc | aag | cac | tcg | ccc | cac | tgc | att | acg | gac | gaa | gag | tgt | 48 |
| Met | Tyr | Pro | Phe | Lys | His | Ser | Pro | His | Cys | Ile | Thr | Asp | Glu | Glu | Cys | |
| 1 | | | | 5 | | | | | 10 | | | | | 15 | | |
| gac | ctc | cag | ctc | agg | tca | ttc | tgc | agc | tgg | ata | aga | gtt | att | gag | atg | 96 |
| Asp | Leu | Gln | Leu | Arg | Ser | Phe | Cys | Ser | Trp | Ile | Arg | Val | Ile | Glu | Met | |
| | | | | 20 | | | | | 25 | | | | | 30 | | |
| cga | tgt | acc | gac | tgg | act | atc | cag | tac | atc | tgc | agc | tgc | gag | aca | ccc | 144 |
| Arg | Cys | Thr | Asp | Trp | Thr | Ile | Gln | Tyr | Ile | Cys | Ser | Cys | Glu | Thr | Pro | |
| | | | 35 | | | | | 40 | | | | | 45 | | | |
| cgt | tcc | ctc | ttt | tgt | tta | tcc | ctc | atc | cga | gtg | ctt | aca | gct | cac | tgg | 192 |
| Arg | Ser | Leu | Phe | Cys | Leu | Ser | Leu | Ile | Arg | Val | Leu | Thr | Ala | His | Trp | |
| | | 50 | | | | | 55 | | | | | 60 | | | | |
| gcc | aaa | acg | gtc | gtc | aat | ttc | gtt | gct | caa | cac | gac | cac | cag | ccc | caa | 240 |
| Ala | Lys | Thr | Val | Val | Asn | Phe | Val | Ala | Gln | His | Asp | His | Gln | Pro | Gln | |
| 65 | | | | | 70 | | | | | 75 | | | | | 80 | |
| ctc | cct | ctt | aat | ctc | atc | tta | tac | aca | tat | gct | act | cac | tgc | agg | tta | 288 |
| Leu | Pro | Leu | Asn | Leu | Ile | Leu | Tyr | Thr | Tyr | Ala | Thr | His | Cys | Arg | Leu | |
| | | | | 85 | | | | | 90 | | | | | 95 | | |
| tgc | aac | ttg | aac | cct | gcc | ctc | gaa | caa | ata | tat | aca | gca | gta | acc | gtt | 336 |
| Cys | Asn | Leu | Asn | Pro | Ala | Leu | Glu | Gln | Ile | Tyr | Thr | Ala | Val | Thr | Val | |
| | | | | 100 | | | | | 105 | | | | | 110 | | |
| gcg | cgg | cgc | caa | ggc | gcc | tac | acg | cga | ctg | gaa | gga | caa | aca | ctc | tat | 384 |
| Ala | Arg | Arg | Gln | Gly | Ala | Tyr | Thr | Arg | Leu | Glu | Gly | Gln | Thr | Leu | Tyr | |
| | | | 115 | | | | | 120 | | | | | 125 | | | |
| gtc | tgt | ctt | cca | agg | gac | atc | gta | aac | tat | ccc | tgc | ata | gct | tgc | ttt | 432 |
| Val | Cys | Leu | Pro | Arg | Asp | Ile | Val | Asn | Tyr | Pro | Cys | Ile | Ala | Cys | Phe | |
| | | 130 | | | | | 135 | | | | | 140 | | | | |
| tac | cac | ctg | ctt | ctg | cgg | ctc | cca | gtc | gca | att | aac | ttc | cac | gtg | ata | 480 |
| Tyr | His | Leu | Leu | Leu | Arg | Leu | Pro | Val | Ala | Ile | Asn | Phe | His | Val | Ile | |
| 145 | | | | | 150 | | | | | 155 | | | | | 160 | |
| tga | | | | | | | | | | | | | | | | 483 |

<210> SEQ ID NO 38
<211> LENGTH: 160
<212> TYPE: PRT
<213> ORGANISM: CELO VIRUS
<220> FEATURE:
<223> OTHER INFORMATION: Position: 2892..3374/note=ORF14

<400> SEQUENCE: 38

Met Tyr Pro Phe Lys His Ser Pro His Cys Ile Thr Asp Glu Glu Cys
1               5                   10                  15

Asp Leu Gln Leu Arg Ser Phe Cys Ser Trp Ile Arg Val Ile Glu Met
            20                  25                  30

Arg Cys Thr Asp Trp Thr Ile Gln Tyr Ile Cys Ser Cys Glu Thr Pro
        35                  40                  45

Arg Ser Leu Phe Cys Leu Ser Leu Ile Arg Val Leu Thr Ala His Trp
    50                  55                  60

Ala Lys Thr Val Val Asn Phe Val Ala Gln His Asp His Gln Pro Gln
65                  70                  75                  80

```
Leu Pro Leu Asn Leu Ile Leu Tyr Thr Tyr Ala Thr His Cys Arg Leu
                85                  90                  95

Cys Asn Leu Asn Pro Ala Leu Glu Gln Ile Tyr Thr Ala Val Thr Val
            100                 105                 110

Ala Arg Arg Gln Gly Ala Tyr Thr Arg Leu Glu Gly Gln Thr Leu Tyr
        115                 120                 125

Val Cys Leu Pro Arg Asp Ile Val Asn Tyr Pro Cys Ile Ala Cys Phe
    130                 135                 140

Tyr His Leu Leu Leu Arg Leu Pro Val Ala Ile Asn Phe His Val Ile
145                 150                 155                 160

<210> SEQ ID NO 39
<211> LENGTH: 324
<212> TYPE: DNA
<213> ORGANISM: CELO VIRUS
<220> FEATURE:
<221> NAME/KEY: CDS
<222> LOCATION: (1)..(324)

<400> SEQUENCE: 39 atg gtc gcg agc tgc cac acg ctc aca atc ata cct aaa gaa gca cgc     48
Met Val Ala Ser Cys His Thr Leu Thr Ile Ile Pro Lys Glu Ala Arg
 1               5                  10                  15 agt aac tgt tac aga gcg tac agc agg gcc tct tgc tgg tgc tgc ctt     96
Ser Asn Cys Tyr Arg Ala Tyr Ser Arg Ala Ser Cys Trp Cys Cys Leu
                20                  25                  30 cgc aca gac aat gtc cgt atg tgt cgt cgt ccc cct caa aat ctg ctt    144
Arg Thr Asp Asn Val Arg Met Cys Arg Arg Pro Pro Gln Asn Leu Leu
            35                  40                  45 gca agc gta cag cga agt cga ctt cgt cgc aag ggt cct atc aac ggg    192
Ala Ser Val Gln Arg Ser Arg Leu Arg Arg Lys Gly Pro Ile Asn Gly
        50                  55                  60 aac cag ggg tca gcc att cca aca cag agc gct gat tgc ggt cta cag    240
Asn Gln Gly Ser Ala Ile Pro Thr Gln Ser Ala Asp Cys Gly Leu Gln
 65                  70                  75                  80 cac cca tac ctg tgg acc cga aac ccg acg ccc cgc ggt ctg tct cgc    288
His Pro Tyr Leu Trp Thr Arg Asn Pro Thr Pro Arg Gly Leu Ser Arg
                85                  90                  95 cta gct gcg tca gtt ccg aca gct ccg gaa cca taa                    324
Leu Ala Ala Ser Val Pro Thr Ala Pro Glu Pro
            100                 105

<210> SEQ ID NO 40
<211> LENGTH: 107
<212> TYPE: PRT
<213> ORGANISM: CELO VIRUS
<220> FEATURE:
<223> OTHER INFORMATION: Position:1191..1514/note=ORF15

<400> SEQUENCE: 40

Met Val Ala Ser Cys His Thr Leu Thr Ile Ile Pro Lys Glu Ala Arg
 1               5                  10                  15

Ser Asn Cys Tyr Arg Ala Tyr Ser Arg Ala Ser Cys Trp Cys Cys Leu
                20                  25                  30

Arg Thr Asp Asn Val Arg Met Cys Arg Arg Pro Pro Gln Asn Leu Leu
            35                  40                  45

Ala Ser Val Gln Arg Ser Arg Leu Arg Arg Lys Gly Pro Ile Asn Gly
        50                  55                  60

Asn Gln Gly Ser Ala Ile Pro Thr Gln Ser Ala Asp Cys Gly Leu Gln
 65                  70                  75                  80
```

-continued

```
His Pro Tyr Leu Trp Thr Arg Asn Pro Thr Pro Arg Gly Leu Ser Arg
                85                  90                  95
Leu Ala Ala Ser Val Pro Thr Ala Pro Glu Pro
            100                 105
```

<210> SEQ ID NO 41
<211> LENGTH: 417
<212> TYPE: DNA
<213> ORGANISM: CELO VIRUS
<220> FEATURE:
<221> NAME/KEY: CDS
<222> LOCATION: (1)..(417)

<400> SEQUENCE: 41

```
atg tat tac ttc cac ctc cgc gtg acc ttg atg gag cct aac ttg gcc      48
Met Tyr Tyr Phe His Leu Arg Val Thr Leu Met Glu Pro Asn Leu Ala
 1               5                  10                  15 gta ttc cat gat ctg aaa ttg acg gta ata aat gcc tgg gaa agt tta      96
Val Phe His Asp Leu Lys Leu Thr Val Ile Asn Ala Trp Glu Ser Leu
            20                  25                  30 act gtt gag atg ctg tcc cac tat agt gta gat tac ctg ttc cga ttg     144
Thr Val Glu Met Leu Ser His Tyr Ser Val Asp Tyr Leu Phe Arg Leu
        35                  40                  45 gag gag ttt gcg ggg gta tat tca gct tct att ttt ttg ccc acg cat     192
Glu Glu Phe Ala Gly Val Tyr Ser Ala Ser Ile Phe Leu Pro Thr His
    50                  55                  60 aag gtt gat tgg act ttc ttg aaa agg gcg gtg gct tta ctg cgc gaa     240
Lys Val Asp Trp Thr Phe Leu Lys Arg Ala Val Ala Leu Leu Arg Glu
65                  70                  75                  80 tgt att tgg agg aga ttt gaa tgt aca cag gtt ccg cga ggg gtg gct     288
Cys Ile Trp Arg Arg Phe Glu Cys Thr Gln Val Pro Arg Gly Val Ala
                85                  90                  95 tct att tac gcg gtg cgc aat acg tgg acc ccc tcc gcc aat agg gtg     336
Ser Ile Tyr Ala Val Arg Asn Thr Trp Thr Pro Ser Ala Asn Arg Val
            100                 105                 110 gcc cgt cac ttt gta aaa cgc ggg gca ttg gtt ggc atg cag ccc tgt     384
Ala Arg His Phe Val Lys Arg Gly Ala Leu Val Gly Met Gln Pro Cys
        115                 120                 125 tta cac gaa tgt acc tat gag cgg gat gcc tgt                         417
Leu His Glu Cys Thr Tyr Glu Arg Asp Ala Cys
    130                 135
```

<210> SEQ ID NO 42
<211> LENGTH: 139
<212> TYPE: PRT
<213> ORGANISM: CELO VIRUS
<220> FEATURE:
<223> OTHER INFORMATION: Position:39286..39705/note=ORF16

<400> SEQUENCE: 42

```
Met Tyr Tyr Phe His Leu Arg Val Thr Leu Met Glu Pro Asn Leu Ala
 1               5                  10                  15

Val Phe His Asp Leu Lys Leu Thr Val Ile Asn Ala Trp Glu Ser Leu
            20                  25                  30

Thr Val Glu Met Leu Ser His Tyr Ser Val Asp Tyr Leu Phe Arg Leu
        35                  40                  45

Glu Glu Phe Ala Gly Val Tyr Ser Ala Ser Ile Phe Leu Pro Thr His
    50                  55                  60

Lys Val Asp Trp Thr Phe Leu Lys Arg Ala Val Ala Leu Leu Arg Glu
65                  70                  75                  80
```

```
Cys Ile Trp Arg Arg Phe Glu Cys Thr Gln Val Pro Arg Gly Val Ala
                85                  90                  95

Ser Ile Tyr Ala Val Arg Asn Thr Trp Thr Pro Ser Ala Asn Arg Val
               100                 105                 110

Ala Arg His Phe Val Lys Arg Gly Ala Leu Val Gly Met Gln Pro Cys
           115                 120                 125

Leu His Glu Cys Thr Tyr Glu Arg Asp Ala Cys
       130                 135

<210> SEQ ID NO 43
<211> LENGTH: 540
<212> TYPE: DNA
<213> ORGANISM: CELO VIRUS
<220> FEATURE:
<221> NAME/KEY: CDS
<222> LOCATION: (1)..(540)

<400> SEQUENCE: 43 atg cct ttg tat ttg tgc ttt ggg gcc gcc gcc ccg gtt tcg att ttg      48
Met Pro Leu Tyr Leu Cys Phe Gly Ala Ala Ala Pro Val Ser Ile Leu
  1               5                  10                  15 tgg cgg gaa gaa ctc ttc tgg gga ttc gtg gct gcg gtc aag agg agg      96
Trp Arg Glu Glu Leu Phe Trp Gly Phe Val Ala Ala Val Lys Arg Arg
             20                  25                  30 tgg cac act gta tat gca cgg acc aat gtg gac att cag tat ccg atg     144
Trp His Thr Val Tyr Ala Arg Thr Asn Val Asp Ile Gln Tyr Pro Met
         35                  40                  45 gcg tat tgt gtc ggt atc caa tcc ctg tct cca tgc aaa tgt cat gtg     192
Ala Tyr Cys Val Gly Ile Gln Ser Leu Ser Pro Cys Lys Cys His Val
     50                  55                  60 acc gtg gtg gtg tgt ctg acc ttt ctg gat ctg cgc atg tcc gct att     240
Thr Val Val Val Cys Leu Thr Phe Leu Asp Leu Arg Met Ser Ala Ile
 65                  70                  75                  80 aat gaa gcc acg aaa ata atg cgc gcg ttt ttc aaa acc ttt ttc tac     288
Asn Glu Ala Thr Lys Ile Met Arg Ala Phe Phe Lys Thr Phe Phe Tyr
                 85                  90                  95 cac cac ggg aaa gtc ccg cgt ggg cgg tgg ttt aaa ttg tac aga aat     336
His His Gly Lys Val Pro Arg Gly Arg Trp Phe Lys Leu Tyr Arg Asn
            100                 105                 110 gat tgg tgt aag gat cct aat tta aca gtg ggt aat tac att gtg gca     384
Asp Trp Cys Lys Asp Pro Asn Leu Thr Val Gly Asn Tyr Ile Val Ala
        115                 120                 125 tcg ggg gcg tta cct ttg atg ctg ggg tgg gcg cgg tct acg ggg ttg     432
Ser Gly Ala Leu Pro Leu Met Leu Gly Trp Ala Arg Ser Thr Gly Leu
    130                 135                 140 cgg ttc agc aca ttt aca tat tca gat gag gct ctg tgg agt cat aga     480
Arg Phe Ser Thr Phe Thr Tyr Ser Asp Glu Ala Leu Trp Ser His Arg
145                 150                 155                 160 cgg aga gat agg agg ctt gcc cgt cgg cgg gaa aag ctt gaa aat aaa     528
Arg Arg Asp Arg Arg Leu Ala Arg Arg Arg Glu Lys Leu Glu Asn Lys
                165                 170                 175 gta tca ggt tga                                                     540
Val Ser Gly
        180

<210> SEQ ID NO 44
<211> LENGTH: 179
<212> TYPE: PRT
<213> ORGANISM: CELO VIRUS
<220> FEATURE:
<223> OTHER INFORMATION: Position:38717..39256/note=ORF17
```

<400> SEQUENCE: 44

| | | | | | | | | | | | | | | |
|---|---|---|---|---|---|---|---|---|---|---|---|---|---|---|
|Met|Pro|Leu|Tyr|Leu|Cys|Phe|Gly|Ala|Ala|Pro|Val|Ser|Ile|Leu|
|1| | | |5| | | | |10| | | | |15|

Trp Arg Glu Glu Leu Phe Trp Gly Phe Val Ala Ala Val Lys Arg Arg
     20       25       30

Trp His Thr Val Tyr Ala Arg Thr Asn Val Asp Ile Gln Tyr Pro Met
    35       40       45

Ala Tyr Cys Val Gly Ile Gln Ser Leu Ser Pro Cys Lys Cys His Val
 50       55       60

Thr Val Val Cys Leu Thr Phe Leu Asp Leu Arg Met Ser Ala Ile
65       70       75       80

Asn Glu Ala Thr Lys Ile Met Arg Ala Phe Phe Lys Thr Phe Phe Tyr
     85       90       95

His His Gly Lys Val Pro Arg Gly Arg Trp Phe Lys Leu Tyr Arg Asn
     100       105      110

Asp Trp Cys Lys Asp Pro Asn Leu Thr Val Gly Asn Tyr Ile Val Ala
    115       120      125

Ser Gly Ala Leu Pro Leu Met Leu Gly Trp Ala Arg Ser Thr Gly Leu
 130       135       140

Arg Phe Ser Thr Phe Thr Tyr Ser Asp Glu Ala Leu Trp Ser His Arg
145       150       155      160

Arg Arg Asp Arg Arg Leu Ala Arg Arg Glu Lys Leu Glu Asn Lys
     165       170      175

Val Ser Gly

<210> SEQ ID NO 45
<211> LENGTH: 609
<212> TYPE: DNA
<213> ORGANISM: CELO VIRUS
<220> FEATURE:
<221> NAME/KEY: CDS
<222> LOCATION: (1)..(609)

<400> SEQUENCE: 45

```
atg tct gcc cta tct tcg tgc ttt aat ggg tcg gat tcc aga tgg gat      48
Met Ser Ala Leu Ser Ser Cys Phe Asn Gly Ser Asp Ser Arg Trp Asp
  1               5                  10                  15 ccg cca tat cct aag gct gac gtc agg cgc ttg atg ggc acc tat tcg      96
Pro Pro Tyr Pro Lys Ala Asp Val Arg Arg Leu Met Gly Thr Tyr Ser
             20                  25                  30 ccg gat ttt cct tcg tgg ccc aag tta att gta tgg tgg aat gag act     144
Pro Asp Phe Pro Ser Trp Pro Lys Leu Ile Val Trp Trp Asn Glu Thr
         35                  40                  45 ttt ttg act ttt tcg gac ggc ccc tgg gtt gtc agt caa atg cgg cgg     192
Phe Leu Thr Phe Ser Asp Gly Pro Trp Val Val Ser Gln Met Arg Arg
     50                  55                  60 ctc ggg gta ttg gat ggt aaa gat agc ggg gag ctc att att ctg gtt     240
Leu Gly Val Leu Asp Gly Lys Asp Ser Gly Glu Leu Ile Ile Leu Val
 65                  70                  75                  80 cag gac atg tat ccc gat gtg tgt ccg ctt att aat agg gcg cgc tat     288
Gln Asp Met Tyr Pro Asp Val Cys Pro Leu Ile Asn Arg Ala Arg Tyr
                 85                  90                  95 gac ggc aca tat aaa tgg acc agt gaa atg atg aga aag att ttg cgt     336
Asp Gly Thr Tyr Lys Trp Thr Ser Glu Met Met Arg Lys Ile Leu Arg
            100                 105                 110 atg cat acc att atg acg cca gag tcc ccg gtc att ctg ttg gac tgg     384
Met His Thr Ile Met Thr Pro Glu Ser Pro Val Ile Leu Leu Asp Trp
        115                 120                 125
```

```
acc aat cag ctg aga gat att tgt aag aag gta gac gcc ctt ttg tgg    432
Thr Asn Gln Leu Arg Asp Ile Cys Lys Lys Val Asp Ala Leu Leu Trp
        130                 135                 140 ggg cag gat gtg agg ggg ccg gcc tat tac gca gtc agg acc act gct    480
Gly Gln Asp Val Arg Gly Pro Ala Tyr Tyr Ala Val Arg Thr Thr Ala
145                 150                 155                 160 cat ttt ttt acg gag ttc aag gac cat cga att cat tgc ata ggg atg    528
His Phe Phe Thr Glu Phe Lys Asp His Arg Ile His Cys Ile Gly Met
                165                 170                 175 tcg cta ggg ggc act gta tgc gcg gct ttg tcc cgc caa ctt cta gtc    576
Ser Leu Gly Gly Thr Val Cys Ala Ala Leu Ser Arg Gln Leu Leu Val
        180                 185                 190 cgg aca gag ggt caa aaa agg ttg gcc gca tag                         609
Arg Thr Glu Gly Gln Lys Arg Leu Ala Ala
            195                 200
```

<210> SEQ ID NO 46
<211> LENGTH: 202
<212> TYPE: PRT
<213> ORGANISM: CELO VIRUS
<220> FEATURE:
<223> OTHER INFORMATION: Position:35536..36144/note=ORF18

<400> SEQUENCE: 46

```
Met Ser Ala Leu Ser Ser Cys Phe Asn Gly Ser Asp Ser Arg Trp Asp
1               5                   10                  15

Pro Pro Tyr Pro Lys Ala Asp Val Arg Arg Leu Met Gly Thr Tyr Ser
            20                  25                  30

Pro Asp Phe Pro Ser Trp Pro Lys Leu Ile Val Trp Trp Asn Glu Thr
        35                  40                  45

Phe Leu Thr Phe Ser Asp Gly Pro Trp Val Val Ser Gln Met Arg Arg
    50                  55                  60

Leu Gly Val Leu Asp Gly Lys Asp Ser Gly Glu Leu Ile Ile Leu Val
65                  70                  75                  80

Gln Asp Met Tyr Pro Asp Val Cys Pro Leu Ile Asn Arg Ala Arg Tyr
                85                  90                  95

Asp Gly Thr Tyr Lys Trp Thr Ser Glu Met Met Arg Lys Ile Leu Arg
            100                 105                 110

Met His Thr Ile Met Thr Pro Glu Ser Pro Val Ile Leu Leu Asp Trp
        115                 120                 125

Thr Asn Gln Leu Arg Asp Ile Cys Lys Lys Val Asp Ala Leu Leu Trp
    130                 135                 140

Gly Gln Asp Val Arg Gly Pro Ala Tyr Tyr Ala Val Arg Thr Thr Ala
145                 150                 155                 160

His Phe Phe Thr Glu Phe Lys Asp His Arg Ile His Cys Ile Gly Met
                165                 170                 175

Ser Leu Gly Gly Thr Val Cys Ala Ala Leu Ser Arg Gln Leu Leu Val
            180                 185                 190

Arg Thr Glu Gly Gln Lys Arg Leu Ala Ala
        195                 200
```

<210> SEQ ID NO 47
<211> LENGTH: 1362
<212> TYPE: DNA
<213> ORGANISM: CELO VIRUS
<220> FEATURE:
<221> NAME/KEY: CDS
<222> LOCATION: (1)..(1362)

```
<400> SEQUENCE: 47 atg cgc ggc ttt gtc ccg cca act tct agt ccg gac aga ggg tca aaa      48
Met Arg Gly Phe Val Pro Pro Thr Ser Ser Pro Asp Arg Gly Ser Lys
 1               5                  10                  15 aag gtt ggc cgc ata gtg gcg cta gat ccc cca ttg gaa agt ttc cag      96
Lys Val Gly Arg Ile Val Ala Leu Asp Pro Pro Leu Glu Ser Phe Gln
             20                  25                  30 ggt tat agg atg gac tta cac aca aaa ggg tta aac ctt ttg ctg tct     144
Gly Tyr Arg Met Asp Leu His Thr Lys Gly Leu Asn Leu Leu Leu Ser
         35                  40                  45 tcc ggt ggt cat tgg tca gcc aat agg gat gcg gat agt gtt atc tct     192
Ser Gly Gly His Trp Ser Ala Asn Arg Asp Ala Asp Ser Val Ile Ser
     50                  55                  60 agg gat gac gcg gat tac gta gtg gtg att gcg tct agt att ggt tcg     240
Arg Asp Asp Ala Asp Tyr Val Val Val Ile Ala Ser Ser Ile Gly Ser
 65                  70                  75                  80 tac ggt ttt gat cga cca ata gga gac gag tat ata cgg agc gat ctg     288
Tyr Gly Phe Asp Arg Pro Ile Gly Asp Glu Tyr Ile Arg Ser Asp Leu
                 85                  90                  95 act ggt caa aaa cat gag gct tgc gag tca cgt gct tgg tgg aaa ggt     336
Thr Gly Gln Lys His Glu Ala Cys Glu Ser Arg Ala Trp Trp Lys Gly
            100                 105                 110 caa atc tgt gca tgg tct tat tct ggg agg cgc cat tgt gaa gat gta     384
Gln Ile Cys Ala Trp Ser Tyr Ser Gly Arg Arg His Cys Glu Asp Val
        115                 120                 125 cat att ccc ttt gat ttc ctc cga tcg gat gga ctg tgt tat cac att     432
His Ile Pro Phe Asp Phe Leu Arg Ser Asp Gly Leu Cys Tyr His Ile
    130                 135                 140 atg gcg cct ttg acc ttt atg aag gcc ctg gat act cac cag gct gac     480
Met Ala Pro Leu Thr Phe Met Lys Ala Leu Asp Thr His Gln Ala Asp
145                 150                 155                 160 cag cta ctg agc atg cac gga agt gtt cct tcc gcg tgg tca gcc tac     528
Gln Leu Leu Ser Met His Gly Ser Val Pro Ser Ala Trp Ser Ala Tyr
                165                 170                 175 gtc acg ggg cgt gat tac agt cag cca act cag tac tac acg gaa gag     576
Val Thr Gly Arg Asp Tyr Ser Gln Pro Thr Gln Tyr Tyr Thr Glu Glu
            180                 185                 190 gta gct gat tgg agg atg ctt tta cga gag gat gac atg gca tct tcc     624
Val Ala Asp Trp Arg Met Leu Leu Arg Glu Asp Asp Met Ala Ser Ser
        195                 200                 205 tat ttg ctg ttg gtg gtg aca gag ggc aat gcc gcg gag ttg tgg act     672
Tyr Leu Leu Leu Val Val Thr Glu Gly Asn Ala Ala Glu Leu Trp Thr
    210                 215                 220 tat gac cct tat tat act aaa aca ata ggg atg gaa cac ggg tat tcg     720
Tyr Asp Pro Tyr Tyr Thr Lys Thr Ile Gly Met Glu His Gly Tyr Ser
225                 230                 235                 240 gtc aga tgg tat ttt att agg gat agg aat gtg ggc gag gct ccc att     768
Val Arg Trp Tyr Phe Ile Arg Asp Arg Asn Val Gly Glu Ala Pro Ile
                245                 250                 255 gtt tta tat gct agg ggc ggg ggt gta tta aaa ttt att aga ctg tac     816
Val Leu Tyr Ala Arg Gly Gly Gly Val Leu Lys Phe Ile Arg Leu Tyr
            260                 265                 270 aag ggg cgt ggc act ctg acg tca cta ggg gcg agg gca atg acg aca     864
Lys Gly Arg Gly Thr Leu Thr Ser Leu Gly Ala Arg Ala Met Thr Thr
        275                 280                 285 cag gaa gtg acg gag ttt acg tgt ttc cgg act cac acc tat tac ttt     912
Gln Glu Val Thr Glu Phe Thr Cys Phe Arg Thr His Thr Tyr Tyr Phe
    290                 295                 300 acc gga act aag aag tac gat tgc cat cca ggc ggg cac cgc ttt gat     960
```

```
                Thr Gly Thr Lys Lys Tyr Asp Cys His Pro Gly Gly His Arg Phe Asp
                305                 310                 315                 320 gtc cct aga tgg cgc tct cat atc aat gtt tct gcg cac cat ctt cct              1008
Val Pro Arg Trp Arg Ser His Ile Asn Val Ser Ala His His Leu Pro
                325                 330                 335 gtc ccg ccc aaa tgt ggc tgt ttg aag ttc ccc aaa ttg ttt aag gat              1056
Val Pro Pro Lys Cys Gly Cys Leu Lys Phe Pro Lys Leu Phe Lys Asp
            340                 345                 350 tat gtc ata ttt gat cac ccg aat gta gtg ggc agg gcc gga gaa tat              1104
Tyr Val Ile Phe Asp His Pro Asn Val Val Gly Arg Ala Gly Glu Tyr
            355                 360                 365 gtt agt tta ggg ccc tgg agt acc ggg tta cag gcc gta gtg acc ttt              1152
Val Ser Leu Gly Pro Trp Ser Thr Gly Leu Gln Ala Val Val Thr Phe
        370                 375                 380 aaa cct caa cct cga cgt cac cga gtg gtc ctg gct acg tac tgg gat              1200
Lys Pro Gln Pro Arg Arg His Arg Val Val Leu Ala Thr Tyr Trp Asp
385                 390                 395                 400 gcc tgt tca aac acc aag agg cgt gtc ggc att gac gtc aga acg gac              1248
Ala Cys Ser Asn Thr Lys Arg Arg Val Gly Ile Asp Val Arg Thr Asp
                405                 410                 415 cgg aag aat cac atg gtt tgg ctc aag gcg gac aag cct gtg tcc aga              1296
Arg Lys Asn His Met Val Trp Leu Lys Ala Asp Lys Pro Val Ser Arg
            420                 425                 430 gag atg tgg ttt gta tcg gaa gtg gac gtc gtt cga gtc tac gtc acg              1344
Glu Met Trp Phe Val Ser Glu Val Asp Val Val Arg Val Tyr Val Thr
            435                 440                 445 tgg ctc tcc ccc gaa taa                                                      1362
Trp Leu Ser Pro Glu
        450

<210> SEQ ID NO 48
<211> LENGTH: 453
<212> TYPE: PRT
<213> ORGANISM: CELO VIRUS
<220> FEATURE:
<223> OTHER INFORMATION: Position:34238..35599/note=ORF19

<400> SEQUENCE: 48

Met Arg Gly Phe Val Pro Pro Thr Ser Ser Pro Asp Arg Gly Ser Lys
1               5                   10                  15

Lys Val Gly Arg Ile Val Ala Leu Asp Pro Pro Leu Glu Ser Phe Gln
            20                  25                  30

Gly Tyr Arg Met Asp Leu His Thr Lys Gly Leu Asn Leu Leu Leu Ser
        35                  40                  45

Ser Gly Gly His Trp Ser Ala Asn Arg Asp Ala Asp Ser Val Ile Ser
    50                  55                  60

Arg Asp Ala Asp Tyr Val Val Ile Ala Ser Ser Ile Gly Ser
65                  70                  75                  80

Tyr Gly Phe Asp Arg Pro Ile Gly Asp Glu Tyr Ile Arg Ser Asp Leu
                85                  90                  95

Thr Gly Gln Lys His Glu Ala Cys Glu Ser Arg Ala Trp Trp Lys Gly
            100                 105                 110

Gln Ile Cys Ala Trp Ser Tyr Ser Gly Arg Arg His Cys Glu Asp Val
        115                 120                 125

His Ile Pro Phe Asp Phe Leu Arg Ser Asp Gly Leu Cys Tyr His Ile
    130                 135                 140

Met Ala Pro Leu Thr Phe Met Lys Ala Leu Asp Thr His Gln Ala Asp
145                 150                 155                 160
```

```
Gln Leu Leu Ser Met His Gly Ser Val Pro Ser Ala Trp Ser Ala Tyr
                165                 170                 175
Val Thr Gly Arg Asp Tyr Ser Gln Pro Thr Gln Tyr Tyr Thr Glu Glu
            180                 185                 190
Val Ala Asp Trp Arg Met Leu Leu Arg Glu Asp Met Ala Ser Ser
        195                 200                 205
Tyr Leu Leu Val Val Thr Glu Gly Asn Ala Ala Glu Leu Trp Thr
    210                 215                 220
Tyr Asp Pro Tyr Tyr Thr Lys Thr Ile Gly Met Glu His Gly Tyr Ser
225                 230                 235                 240
Val Arg Trp Tyr Phe Ile Arg Asp Arg Asn Val Gly Glu Ala Pro Ile
                245                 250                 255
Val Leu Tyr Ala Arg Gly Gly Val Leu Lys Phe Ile Arg Leu Tyr
            260                 265                 270
Lys Gly Arg Gly Thr Leu Thr Ser Leu Gly Ala Arg Ala Met Thr Thr
                275                 280                 285
Gln Glu Val Thr Glu Phe Thr Cys Phe Arg Thr His Thr Tyr Tyr Phe
            290                 295                 300
Thr Gly Thr Lys Lys Tyr Asp Cys His Pro Gly His Arg Phe Asp
305                 310                 315                 320
Val Pro Arg Trp Arg Ser His Ile Asn Val Ser Ala His His Leu Pro
                325                 330                 335
Val Pro Pro Lys Cys Gly Cys Leu Lys Phe Pro Lys Leu Phe Lys Asp
            340                 345                 350
Tyr Val Ile Phe Asp His Pro Asn Val Val Gly Arg Ala Gly Glu Tyr
                355                 360                 365
Val Ser Leu Gly Pro Trp Ser Thr Gly Leu Gln Ala Val Val Thr Phe
    370                 375                 380
Lys Pro Gln Pro Arg Arg His Arg Val Val Leu Ala Thr Tyr Trp Asp
385                 390                 395                 400
Ala Cys Ser Asn Thr Lys Arg Arg Val Gly Ile Asp Val Arg Thr Asp
                405                 410                 415
Arg Lys Asn His Met Val Trp Leu Lys Ala Asp Lys Pro Val Ser Arg
            420                 425                 430
Glu Met Trp Phe Val Ser Glu Val Asp Val Val Arg Val Tyr Val Thr
            435                 440                 445
Trp Leu Ser Pro Glu
    450
```

<210> SEQ ID NO 49
<211> LENGTH: 816
<212> TYPE: DNA
<213> ORGANISM: CELO VIRUS
<220> FEATURE:
<221> NAME/KEY: CDS
<222> LOCATION: (1)..(816)

<400> SEQUENCE: 49

```
atg gag aga ctg aac gag tac cgc ata aat aga gcc gtg gct agc ttg     48
Met Glu Arg Leu Asn Glu Tyr Arg Ile Asn Arg Ala Val Ala Ser Leu
  1               5                  10                  15 cgg tgt ttc gat aat gat ctg atg agg cga ttg cat agt tct gtc acg     96
Arg Cys Phe Asp Asn Asp Leu Met Arg Arg Leu His Ser Ser Val Thr
                 20                  25                  30 gtg cta gtg acg gta cgc agc gca aag ttt gtg tgt ttc aaa cgg cga    144
Val Leu Val Thr Val Arg Ser Ala Lys Phe Val Cys Phe Lys Arg Arg
             35                  40                  45
```

```
gac tac gta ctc atg aat tgc ata gtc cgg att gtg agt gcc ctt cac      192
Asp Tyr Val Leu Met Asn Cys Ile Val Arg Ile Val Ser Ala Leu His
         50                  55                  60 ctg aac cgg gca gag aag acc gcc ctg ctg cac tac ctc tca cgt agg      240
Leu Asn Arg Ala Glu Lys Thr Ala Leu Leu His Tyr Leu Ser Arg Arg
 65                  70                  75                  80 ttg ctt ttt att aca cct ggg atg aag tac gac ttg gaa ccg tgg atg      288
Leu Leu Phe Ile Thr Pro Gly Met Lys Tyr Asp Leu Glu Pro Trp Met
                     85                  90                  95 ctt gct cgc agg aag aca gat ttt aag ttt ttc acc aca ggc ttt ctg      336
Leu Ala Arg Arg Lys Thr Asp Phe Lys Phe Phe Thr Thr Gly Phe Leu
                100                 105                 110 att gcg gag aag ata tcc gta aag atg gct ctc cgc tcg atg agc ttt      384
Ile Ala Glu Lys Ile Ser Val Lys Met Ala Leu Arg Ser Met Ser Phe
            115                 120                 125 gag gtg tcc ttt tcg caa gtg cct tcg tct gtt cct ttt gtg cgg tct      432
Glu Val Ser Phe Ser Gln Val Pro Ser Ser Val Pro Phe Val Arg Ser
        130                 135                 140 ccg gtt gtt ctc atg aat gcg tgt cgc gtg acc gtg acg gcc acc atc      480
Pro Val Val Leu Met Asn Ala Cys Arg Val Thr Val Thr Ala Thr Ile
145                 150                 155                 160 atg gtg gaa act att tct cgc agc agc gcc gtg acc caa ccc gtc tgc      528
Met Val Glu Thr Ile Ser Arg Ser Ser Ala Val Thr Gln Pro Val Cys
                    165                 170                 175 ctg aga agc atg ctc cgc gtg atg gtg tcg ccg gaa ctg tgg ccg atc      576
Leu Arg Ser Met Leu Arg Val Met Val Ser Pro Glu Leu Trp Pro Ile
                180                 185                 190 gtg tcg cag gga ctg tgt tac ttc ccc ggt tac cgt cgg ttg tcc tac      624
Val Ser Gln Gly Leu Cys Tyr Phe Pro Gly Tyr Arg Arg Leu Ser Tyr
            195                 200                 205 gct aac gtc gaa gag tgg gta ttt cat gtg cac ggg aag tac ggg gag      672
Ala Asn Val Glu Glu Trp Val Phe His Val His Gly Lys Tyr Gly Glu
        210                 215                 220 tct cat ccc gag tgt ttc gga cag tgc aaa cag tgt tcg acg cgg caa      720
Ser His Pro Glu Cys Phe Gly Gln Cys Lys Gln Cys Ser Thr Arg Gln
225                 230                 235                 240 cct ctc tct ctg ttc tgt tct gct cag ttg gct tat ctg cgc aat gtg      768
Pro Leu Ser Leu Phe Cys Ser Ala Gln Leu Ala Tyr Leu Arg Asn Val
                    245                 250                 255 ttt atg gaa cga cgc gcg aga gtc gct ggt gaa cgt ccg tat agc taa      816
Phe Met Glu Arg Arg Ala Arg Val Ala Gly Glu Arg Pro Tyr Ser
                260                 265                 270
```

<210> SEQ ID NO 50
<211> LENGTH: 271
<212> TYPE: PRT
<213> ORGANISM: CELO VIRUS
<220> FEATURE:
<223> OTHER INFORMATION: Position:32892..33707/note=ORF20

<400> SEQUENCE: 50

```
Met Glu Arg Leu Asn Glu Tyr Arg Ile Asn Arg Ala Val Ala Ser Leu
 1               5                  10                  15

Arg Cys Phe Asp Asn Asp Leu Met Arg Arg Leu His Ser Ser Val Thr
                20                  25                  30

Val Leu Val Thr Val Arg Ser Ala Lys Phe Val Cys Phe Lys Arg Arg
            35                  40                  45

Asp Tyr Val Leu Met Asn Cys Ile Val Arg Ile Val Ser Ala Leu His
        50                  55                  60
```

```
Leu Asn Arg Ala Glu Lys Thr Ala Leu Leu His Tyr Leu Ser Arg Arg
 65                  70                  75                  80

Leu Leu Phe Ile Thr Pro Gly Met Lys Tyr Asp Leu Glu Pro Trp Met
             85                  90                  95

Leu Ala Arg Arg Lys Thr Asp Phe Lys Phe Thr Thr Gly Phe Leu
                100                 105                 110

Ile Ala Glu Lys Ile Ser Val Lys Met Ala Leu Arg Ser Met Ser Phe
            115                 120                 125

Glu Val Ser Phe Ser Gln Val Pro Ser Ser Val Pro Phe Val Arg Ser
        130                 135                 140

Pro Val Leu Met Asn Ala Cys Arg Val Thr Val Ala Thr Ile
145                 150                 155                 160

Met Val Glu Thr Ile Ser Arg Ser Ser Ala Val Thr Gln Pro Val Cys
                165                 170                 175

Leu Arg Ser Met Leu Arg Val Met Val Ser Pro Glu Leu Trp Pro Ile
            180                 185                 190

Val Ser Gln Gly Leu Cys Tyr Phe Pro Gly Tyr Arg Arg Leu Ser Tyr
        195                 200                 205

Ala Asn Val Glu Glu Trp Val Phe His Val His Gly Lys Tyr Gly Glu
    210                 215                 220

Ser His Pro Glu Cys Phe Gly Gln Cys Lys Gln Cys Ser Thr Arg Gln
225                 230                 235                 240

Pro Leu Ser Leu Phe Cys Ser Ala Gln Leu Ala Tyr Leu Arg Asn Val
                245                 250                 255

Phe Met Glu Arg Arg Ala Arg Val Ala Gly Glu Arg Pro Tyr Ser
            260                 265                 270

<210> SEQ ID NO 51
<211> LENGTH: 324
<212> TYPE: DNA
<213> ORGANISM: CELO VIRUS
<220> FEATURE:
<221> NAME/KEY: CDS
<222> LOCATION: (1)..(324)

<400> SEQUENCE: 51 atg tgc acg gga agt acg ggg agt ctc atc ccg agt gtt tcg gac agt      48
Met Cys Thr Gly Ser Thr Gly Ser Leu Ile Pro Ser Val Ser Asp Ser
 1               5                  10                  15 gca aac agt gtt cga cgc ggc aac ctc tct ctc tgt tct gtt ctg ctc      96
Ala Asn Ser Val Arg Arg Gly Asn Leu Ser Leu Cys Ser Val Leu Leu
             20                  25                  30 agt tgg ctt atc tgc gca atg tgt tta tgg aac gac gcg cga gag tcg     144
Ser Trp Leu Ile Cys Ala Met Cys Leu Trp Asn Asp Ala Arg Glu Ser
         35                  40                  45 ctg gtg aac gtc cgt ata gct aat tac gtg ttt gat ttt gca gtg ttg     192
Leu Val Asn Val Arg Ile Ala Asn Tyr Val Phe Asp Phe Ala Val Leu
     50                  55                  60 tgg acg cta ttg gcg cga gtt ctt ggc cct cct ggt cgc cct gtc cta     240
Trp Thr Leu Leu Ala Arg Val Leu Gly Pro Pro Gly Arg Pro Val Leu
 65                  70                  75                  80 cag cag cat cat cct gtg cag ctt cct gtt cct aca gaa cca tct gtc     288
Gln Gln His His Pro Val Gln Leu Pro Val Pro Thr Glu Pro Ser Val
                 85                  90                  95 ttc gtt aaa ctt tgt aat cag cgt gtt cgt ttg tag                     324
Phe Val Lys Leu Cys Asn Gln Arg Val Arg Leu
            100                 105
```

```
<210> SEQ ID NO 52
<211> LENGTH: 107
<212> TYPE: PRT
<213> ORGANISM: CELO VIRUS
<220> FEATURE:
<223> OTHER INFORMATION: Position:32735..33058/note=ORF21

<400> SEQUENCE: 52

Met Cys Thr Gly Ser Thr Gly Ser Leu Ile Pro Ser Val Ser Asp Ser
  1               5                  10                  15

Ala Asn Ser Val Arg Arg Gly Asn Leu Ser Leu Cys Ser Val Leu Leu
             20                  25                  30

Ser Trp Leu Ile Cys Ala Met Cys Leu Trp Asn Asp Ala Arg Glu Ser
         35                  40                  45

Leu Val Asn Val Arg Ile Ala Asn Tyr Val Phe Asp Phe Ala Val Leu
     50                  55                  60

Trp Thr Leu Leu Ala Arg Val Leu Gly Pro Gly Arg Pro Val Leu
 65                  70                  75                  80

Gln Gln His His Pro Val Gln Leu Pro Val Pro Thr Glu Pro Ser Val
                 85                  90                  95

Phe Val Lys Leu Cys Asn Gln Arg Val Arg Leu
            100                 105

<210> SEQ ID NO 53
<211> LENGTH: 618
<212> TYPE: DNA
<213> ORGANISM: CELO VIRUS
<220> FEATURE:
<221> NAME/KEY: CDS
<222> LOCATION: (1)..(618)

<400> SEQUENCE: 53 atg aac gac gag cag atc ctg gag atg gtg ctg cag cac cag cag cgc      48
Met Asn Asp Glu Gln Ile Leu Glu Met Val Leu Gln His Gln Gln Arg
  1               5                  10                  15 cgc caa cag gaa gcg gag cgc gag gag gaa gtt ggg gat gac atg gaa      96
Arg Gln Gln Glu Ala Glu Arg Glu Glu Glu Val Gly Asp Asp Met Glu
             20                  25                  30 gac gac gaa gat gat gac ggt ctt cag atg ccg acg ccg ctt cat gcc     144
Asp Asp Glu Asp Asp Asp Gly Leu Gln Met Pro Thr Pro Leu His Ala
         35                  40                  45 tat cag cta ctg tgt tac gat tct ttc gaa ctt cat ttc ggg gga tgc     192
Tyr Gln Leu Leu Cys Tyr Asp Ser Phe Glu Leu His Phe Gly Gly Cys
     50                  55                  60 gct tgc cac ggg tta cct ttg cat cgt atg ggg tta tcg gct tgc cac     240
Ala Cys His Gly Leu Pro Leu His Arg Met Gly Leu Ser Ala Cys His
 65                  70                  75                  80 ctg gct cct tcc gat ttg gcc act tat gtt tgg gcc agg ttg gag gat     288
Leu Ala Pro Ser Asp Leu Ala Thr Tyr Val Trp Ala Arg Leu Glu Asp
                 85                  90                  95 gac ttg aat gtg gca ggg gtg tac ttc gtg gct atg tgg gcg tca ccg     336
Asp Leu Asn Val Ala Gly Val Tyr Phe Val Ala Met Trp Ala Ser Pro
            100                 105                 110 ggg ttt agc gat ttc tct cca gta ttt atg cag cga ccg atc ggg aac     384
Gly Phe Ser Asp Phe Ser Pro Val Phe Met Gln Arg Pro Ile Gly Asn
        115                 120                 125 gtg tgc ggg atg tta att cac gtg gac ctg cac agc agg cta cca ttc     432
Val Cys Gly Met Leu Ile His Val Asp Leu His Ser Arg Leu Pro Phe
    130                 135                 140 cta att gcg gtg tcg cgc ttg ggg gag gcg ggt ggc agc ccc tgt ctg     480
Leu Ile Ala Val Ser Arg Leu Gly Glu Ala Gly Gly Ser Pro Cys Leu
```

-continued

```
                145                 150                 155                 160
tat atg agg aaa att gat gtt gat ttg gac acg cag cgc gta cat ttt        528
Tyr Met Arg Lys Ile Asp Val Asp Leu Asp Thr Gln Arg Val His Phe
                165                 170                 175 tat aca gaa gat tgg ttc agt gag ttt gcg aat ctg ctg tat tac tgg        576
Tyr Thr Glu Asp Trp Phe Ser Glu Phe Ala Asn Leu Leu Tyr Tyr Trp
                180                 185                 190 caa atg agc gaa tgg aaa cat tta gcg gag cgt atg caa taa                618
Gln Met Ser Glu Trp Lys His Leu Ala Glu Arg Met Gln
        195                 200                 205

<210> SEQ ID NO 54
<211> LENGTH: 205
<212> TYPE: PRT
<213> ORGANISM: CELO VIRUS
<220> FEATURE:
<223> OTHER INFORMATION: Position:31812..32429/note=ORF22

<400> SEQUENCE: 54

Met Asn Asp Glu Gln Ile Leu Glu Met Val Leu Gln His Gln Gln Arg
  1               5                  10                  15

Arg Gln Gln Glu Ala Glu Arg Glu Glu Glu Val Gly Asp Asp Met Glu
                 20                  25                  30

Asp Asp Glu Asp Asp Gly Leu Gln Met Pro Thr Pro Leu His Ala
             35                  40                  45

Tyr Gln Leu Leu Cys Tyr Asp Ser Phe Glu Leu His Phe Gly Gly Cys
         50                  55                  60

Ala Cys His Gly Leu Pro Leu His Arg Met Gly Leu Ser Ala Cys His
 65                  70                  75                  80

Leu Ala Pro Ser Asp Leu Ala Thr Tyr Val Trp Ala Arg Leu Glu Asp
                 85                  90                  95

Asp Leu Asn Val Ala Gly Val Tyr Phe Val Ala Met Trp Ala Ser Pro
                100                 105                 110

Gly Phe Ser Asp Phe Ser Pro Val Phe Met Gln Arg Pro Ile Gly Asn
            115                 120                 125

Val Cys Gly Met Leu Ile His Val Asp Leu His Ser Arg Leu Pro Phe
        130                 135                 140

Leu Ile Ala Val Ser Arg Leu Gly Glu Ala Gly Gly Ser Pro Cys Leu
145                 150                 155                 160

Tyr Met Arg Lys Ile Asp Val Asp Leu Asp Thr Gln Arg Val His Phe
                165                 170                 175

Tyr Thr Glu Asp Trp Phe Ser Glu Phe Ala Asn Leu Leu Tyr Tyr Trp
            180                 185                 190

Gln Met Ser Glu Trp Lys His Leu Ala Glu Arg Met Gln
        195                 200                 205
```

CHICKEN EMBRYO LETHAL ORPHAN (CELO) VIRUS

The invention relates to adenoviruses. The large family of adenoviruses is subdivided according to its host into adenoviruses which infect mammals (the mastadenoviridae) and adenoviruses which infect birds (the aviadenoviridae). The CELO virus (Chicken Embryo Lethal Orphan; article by Mcferran, et al., 1977; McCracken and Adair, 1993) was identified as an infectious agent in 1957 (Yates and Fry, 1957). CELO virus is classified as a poultry adenovirus type 1 (FAV-1) and first aroused interest because of its property of being tumorigenic in baby hamsters. However, since infection with the CELO virus does not have any serious health and economic consequences, the interest in this virus disappeared in recent years. The FAV-1 adenoviruses can be isolated from healthy chickens and do not cause any disease when reintroduced experimentally into chickens (Cowen, et al., 1978). Their isolation from sick birds is presumably the result of adenovirus replication in a host which has an immune system weakened by other influences.

The general structural organisation of CELO virus, with an icosahedral capsid of 70–80 nm, made up of hexon and penton structures, is similar to that of the mammalian adenoviruses (Laver, et al., 1971). The CELO virus genome is a linear, double-stranded DNA molecule, the DNA being condensed inside the virion by virus-coded core proteins (Laver et al., 1971; Li, et al., 1984b). The CELO virus genome has covalently bound terminal proteins (Li, et al., 1983) and the genome has inverted terminal repeats (ITRs), although they are shorter than the mammalian ITRs (Alestrom, et al., 1982b; Sheppard and Trist, 1992). The CELO virus codes a protease with 61–69% homology for the mammalian adenovirus proteases (Cai and Weber, 1993).

There are significant differences between CELO virus and the mastadenoviruses. CELO virus has a larger genome, with sequence homology with Ad5 which can only be detected in two short regions of the CELO virus genome (by hybridisation) (Alestrom, et al., 1982a). The CELO virion has been reported to have two fibres of different lengths at each vertex. The CELO virus cannot complement the E1A functions of Ad5, and the replication of CELO virus is not made easier by the activity of Ad5E1 (Li, et al., 1984c).

Within the scope of the present invention, total sequence analysis of the CELO virus was carried out; on the one hand because it is useful for understanding the biology of adenoviruses to clarify the genomic organisation of an adenovirus which is very remote from the mammalian adenoviruses generally studied. Since the conditions for transmission and survival for a virus which infects a type of bird are presumably different than for mammalian viruses, it is possible that the bird adenoviruses have acquired new virus functions or exhibit a higher degree of variability than the mastadenoviridae. The complete CELO virus sequence also permits changes in the CELO virus genome with respect to functional analysis.

Since adenovirus vectors have proved highly effective vectors for gene transfer (see the summarising article by Graham, 1990; Kozarsky and Wilson, 1993; Trapnell and Gorziglia, 1994), the complete CELO virus sequence, on the other hands is particularly interesting as the basis for preparing new recombinant vectors for gene transfer.

Sequence analysis has shown that the CELO virus genome has 43.8 kb, being more than 8 kb longer than the human subtypes Ad2 and Ad5. The genes for the main structural proteins (hexon, penton based, IIIa, fibres, pVI, pVII, pVIII) are on the one hand both present and also located at the corresponding sites in the genome. The genes of the early region 2 (E2; DNA binding protein, DNA polymerase and terminal protein) are also present. However, the CELO virus lacks sequences homologous to the regions E1, E3 and E4 of the mammalian adenoviruses. There are approximately 5 kb at the left hand end and 15 kb at the right hand end of the CELO virus genome, where there is only restricted homology or no homology at all with the mastadenovirus genomes. These new sequences contain a number of open reading frames, and it can be assumed that these code for functions which replace the missing E1, E3 and possibly E4 regions.

Parts of the CELO virus sequence have already been published; they are listed in Table 1, as are the differences between the sequence known from the databank and the sequence determined within the scope of the present invention. From studies concentrating on specific viral genes, a homolog of the VA RNA gene of mastadenovirus was known (Larsson, et al., 1986) and part of the genome sequence which carries the endoprotease has been described (Cai and Weber, 1993). In addition, fragments of the CELO virus genome have been published (Akopian, et al., 1990; Akopian, et al., 1992; Hess, et al., 1995). The sequence of the penton base of the related virus FAV-10 has also been reported (Sheppard and Trist, 1992). Some other sequence fragments have been deposited in the databank and are also shown in Table 1. In all, about 50% of the CELO virus genome is available in the form of fragments (total about 24 kb). The sequence obtained within the scope of the present invention is complete and has the advantage of having been obtained from a single isolated material.

The total sequence of the CELO virus is shown in the sequence listing (in the sequence listing the word "complementary" indicates that the open reading frames are present in the reverse arrangement). It shows a large number of striking differences between Ad2 and the CELO virus. The organisation of the recognisable open reading frames (ORFs) of the CELO virus genome based on the sequence analysis, compared with Ad2, is shown in FIG. 1A: the Figure shows an overview of the genomic organisation of Ad2/5 and CELO virus. The arrows indicate the position of the coding regions but not the exact cleavage patterns of the gene products. The pattern of the CELO virus also (in the first 6,000 bp and in the last 13,000 bp) gives all the non-associated open reading frames which begin with a methionine and which code for more than 99 amino acid groups. The central region of the two genomes which show homology on the basis of dot matrix analysis (cf. FIG. 3) and the regions at the ends of the CELO virus genome which have no homology with other adenoviruses ("unique to CELO") are given. The abbreviations in the Figure, which also correspond to those in the Tables, have the following meanings: PB, penton base; EP, endoproteinase; DBP, DNA binding protein; bTP, preterminal protein; pol, DNA polymerase.

The sequenced CELO virus genome has a length of 43,804 bp and has a content of G+C of 54.3%. It had already been presumed at an earlier stage that the CELO virus genome is much larger than the mastadenovirus genome with 34–36 kb; it has been found that the CELO virus DNA has a weight of $30 \times 10^6$ Daltons, determined according to its sedimentation coefficient (Laver, et al., 1971), compared with $24 \times 10^6$ Daltons for Ad2 (Green, et al., 1967). The size of the CELO virus genome determined by the addition of the restriction fragments is about 43 kb (Cai and Weber, 1993; Denisova, et al., 1979). A Pulsed Field Gel Analysis of the CELO virus genome isolated from purified virions is shown in FIG. 2A and is compared with the DNA isolated from Ad5 dl1014 (34,600 bp; Bridge and Ketner, 1989) or Wild-type Ad5-virions (35,935 bp; vt300; Chroboczek, et al., 1992; Jones and Shenk, 1978); a mixture of uncleaved bacteriophage λ-DNA and γ-DNA cleaved with five different restriction enzymes (Biorad) was used as the size marker (tracks 1 and 7 show the molecular weight markers, track 2 shows the DNA of Ad5 dl1014, track 3 shows the DNA of Ad5 wt300, track 4 shows the CELO virus DNA, track 5 shows the DNA of OTE, track 6 shows the DNA of Indiana C). FIG. 2A shows that the CELO virus genome has a length of 44 kb. From this analysis it is clear that the CELO virus genome is actually substantially larger than the genome of the mammalian virus. Calculations based on the migration of fragments of the lambda bacteriophage give a size of 43 kb for the CELO virus genome. The DNA extracted from two other FAV-1 isolates, Indiana C and OTE, co-migrates with the CELO virus species, which is further evidence of the size of the CELO virus genome. FIG. 2B shows that the CELO virus sequence contained in the bacterial plasmid pBR327 has the same size.

There is no identifiable E1 region. No significant homology could be found between the CELO virus genome and the first 4,000 bp of Ad2. There are a few small open reading frames in the first 5,000 bp of CELO virus which might possibly perform some of the E1 tasks. An open reading frame at the right hand end of the virus genome (GAM-1) may replace E1B 19K in functional assays without there being any significant homology between GAM-1 and E1B 19K. In order to confirm that the left hand end originates from the Wild type CELO virus genome and is not the sequence of a cloned variant, various tests were carried out; comparison of the direct sequence analysis of CELO virions at three different sites with the corresponding sites of the cloned sequences; Southern analyses with DNA from various virus isolates which yielded the same restriction fragments; pulsed field gel electrophoresis of various virus genomes which showed no heterogenicity.

There is no identifiable E3 region; the two small open reading frames in the corresponding region of the CELO virus have no significant homology with the E3 functions described.

There is a group of small open reading frames between 36,000 and 31,000 the position of which indicates the mammalian virus E4 region, but with additional 8 kb sequence at the right hand end of the CELO virus.

Nor was any sequence resembling protein IX identified (protein IX is essential for the hexon-hexon interactions and the stability of the mammalian adenovirus virions).

A protein V gene was not identified either.

The following regions are conserved between CELO virus and Ad2: the central part of the CELO virus genome, from the IVa2 gene (approximately from nucleotide (nt) 5,000) on the left hand strand up to the fibre genes on the right hand strand (approximately up to nt 33,000) is organised as in the mastadenoviruses, and the majority of the important viral genes can be identified both by their position and by sequence homology. Earlier studies on the homology between CELO and Ad2 (Alestrõm, et al., 1982a) showed two regions of the CELO virus which cross-hybridise with the Ad2 sequence. These two fragments are nt 5,626 to 8,877 (coding for IVa2 and the carboxy terminus of DNA polymerase) and nt 17,881 to 21,607 (coding for the hexon). The dot matrix analysis shown in FIG. 3 (carried out using the UWGCG program Compare with a window of 30 and a stringency of 20; summarised in FIG. 1A) shows that the total DNA sequence homology between CELO virus and Ad5 is mapped in the central region of the CELO virus genome. This is to be expected because the capsid proteins are coded in this central region and the coarse structure of the CELO virion is comparable with the capsid of the mammalian adenovirus (Laver, et al., 1971; Li, et al., 1984a). The genes which code for proteins corresponding to the human adenovirus proteins hexon, IIIa, penton base, protein VI and protein VIII, are present, and indeed in the expected sequence and position (FIG. 1A and Table 2A; Table 2B shows non-associated open reading frames which code for gene products with more than 99 amino acid groups). Each vertex of the mastadenovirus virion contains a pentamer of the penton base protein in conjunction with a single fibre consisting of three copies of the fibre polypeptide. Ad2, like most mastadenoviruses, has a single fibre gene, some adenovirus types have two fibre genes. The CELO virus genome codes for two fibre polypeptides of different lengths and sequences.

DNA binding proteins were identified in the region E2 (Li, et al., 1984c); four proteins with similar peptide maps were described, indicating a single precursor which is then cleaved or decomposed. The left hand open reading frame of the CELO virus genome, starting at nt 23,224, is located in the expected DNA binding protein region. The genes coding for DNA polymerase and pTP (pre-terminal protein) are present and in the expected positions (FIG. 1A, Table 2A).

With a view to the preparation of vectors based on the CELO virus it is useful to identify the mechanisms which the CELO virus uses in order to package almost 44 kb of DNA into a virion which is of a similar size to the human adenoviruses which are subjected to considerable restrictions on their packaging capacity (Bett, et al., 1993; Caravokyri and Leppard, 1995; Ghosh-Choudhury, 1987). One possibility is that the CELO virion, although virtually identical in size to Ad2 and Ad5, has a sufficiently widened structure in order to accommodate the larger genome. An alternative hypothesis is that CELO has a different mechanism for condensing DNA and therefore has differences in its provision of core proteins which are responsible for DNA packaging. Laver et al., in 1971 identified two proteins in the nucleus of the CELO virus and noted the absence of a molecule resembling protein V. Li, et al., 1984b, used electrophoresis with a higher resolution and reported a nuclear structure with three polypeptides (20 kD, 12 kD and 9.5 kD). These two findings lead one to conclude that the CELO virus must lack the larger basic nuclear protein V (41 kD) which occurs in mammalian adenoviruses. Perhaps the absence of protein V and/or the presence of smaller basic proteins is responsible for the additional packaging capacity of the CELO virion. The smallest of the CELO virus core proteins identified by Li, et al., 1984b (9.5 kD) is most closely associated with the virus DNA, similar to protein VII of the human adenovirus. An open reading frame which leads one to expect a protein with 8,597 D having 72 amino acids is located at nt 16,679; the coded protein is rich in arginine (32.9 mol %) and contains two cleavage sites for protease (pVII of Ad2 has only one cleavage site). An open reading frame which leads one to expect a protein with 19,777 D having 188 amino acid groups is located at nt 16,929. The protein has protease cleavage sites after groups 22, 128 and 145, and the carboxy-terminal groups have homology with pX of mastadenovirus. FIG. 4 shows the amino acid sequences of protein VII and pX of various mastadenoviruses compared with the CELO virus and the core proteins Core 2 and Core 1 of FAV-10. The sequences were arranged using the UWGCG Bestfit Program with a gap weight of 3.0 and a weight and gap length ("Gap Length Weight") of 0.1. The protease cleavage sites of adenovirus are underlined. In connection with this it is interesting that the mastadenovirus DNA binding protein designated "mu" consisting of 19 groups is formed by two protease cleavings of the pX precursor (Hosokava and Sung, 1976; Weber and Anderson, 1988; Anderson, et al., 1989). Cleaving of the protein having 188 groups after groups 128 and 145 would produce a mu-like basic protein consisting of 17 groups (41% arginine, 12% lysine). The uncleaved form of the protein is also highly basic; the uncleaved copies of this protein could correspond to the 20 kD core protein observed by Li, et al., 1984b; a third 12 kD core protein identified by these authors could not yet be assigned.

Moreover, some new or non-assigned open reading frames were found in the CELO virus genome. A summary of these open reading frames is shown in Table 2A; these open reading frames are also given in FIG. 1A. This summary was restricted to the sequences from nt 0–6,000 and 31,000–43,804 and only ORFs which contain a methionine group and code for a protein >99 amino acid groups are mentioned. As already stated, there is an ORF at nt 1999 which codes for a protein having homology with parvovirus-REP, and an ORF at nt 794 having homology with dUTPase and Ad2 E4 ORF1. The objective of the present invention was to prepare a new CELO virus.

Thus, on the basis of the complete CELO virus genome sequence, the present invention relates to a CELO virus obtained by in vitro manipulation of a plasmid-cloned CELO virus DNA.

The CELO virus according to the invention derived from the genomic DNA contains, in a preferred embodiment, the left and right terminal repeat and the packaging signal and has modifications in the form of insertions and/or deletions and/or mutations in regions of the CELO virus DNA which are different therefrom.

The left or right terminal repeat ("Inverted Terminal Repeat", ITR) extends from nucleotides 1–68 or from nucleotides 43734–43804, the packaging signal (also referred to as "Psi") extends from nucleotides 70–200. Modifications in DNA sections other than these ensures that the genes affected by the modification are non-functional or are deleted.

Preferably, modifications of the CELO virus genome are undertaken which are located on a section of the CELO virus DNA which includes the nucleotides from about 201 to about 5,000 (following the left terminal repeat of the section at the left hand end, hereinafter referred to as "Section A") and/or on a section which includes the nucleotides from about 31,800– about 43,734 (the section at the right hand end located in front of the right terminal repeat, hereinafter referred to as "Section B") and/or on a section which includes the nucleotides from about 28,114–30,495 (the region of the fibre 1 gene, hereinafter referred to as "Section C").

A CELO virus in which certain genes are non-functional or are deleted, e.g. genes which affect the immune response of the host, such as antagonists to genes of the E3 region of mammalian adenoviruses, can be used as a vaccine.

In one embodiment of the invention the CELO virus contains one or more foreign DNA molecules, particularly a foreign DNA which is to be expressed in a host organism. In this embodiment the CELO virus acts as a vector which is capable of transporting the foreign DNA into higher eukaryotic cells, tissue or organisms, particularly mammals and birds, and expressing it therein.

Suitable insertion sites for the foreign DNA are the sections A and/or B and/or C.

The foreign DNA preferably replaces one or more sequences from these sections.

The CELO virus according to the invention is contained on a plasmid which is replicatable in bacteria or yeast and which yields virus particles after being introduced into suitable cells. Examples of suitable cells are bird embryo kidney or liver cells.

With a view to using a recombinant CELO virus vector for gene therapy, the foreign DNA may consist of one or more therapeutically active genes. Examples of these are genes coding for immunomodulators or modulators of inflammatory processes (cytokines such as IL-2, GM-CSF, IL-1, IL-6, IL-12; interferons, tumour antigens, IκB, and derivatives of IκB which lack serine phosphorylation sites (Traenckner, et al., 1995) or which lack lysine ubiquitinisation sites; glucocorticoid receptors; enzymes such as catalase, manganese superoxide dismutase, glutathione peroxidase, LIP members of the C/EBP family such as LIP or LAP (Descombes and Schibler, 1991), ADF (Tagaya, et al., 1989)), genes which influence apoptosis (members of the Bcl-2 family such as Bcl-2, adenovirus E1B19K, Mcl-2; BAX; IRF-2; members of the ICE protease family; variants of cJun, such as TAM-67 (Brown, et al., 1994); adenovirus E1A; p53) and genes which code for other therapeutic proteins (e.g. clotting factors such as factor VIII or IX; growth factors such as erythropoetin; cystic fibrosis transmembrane regulator gene (CFTR); dystrophin and derivatives thereof; globin; the LDL receptor; genes which are absent in lysosomal storage dysfunctions such as β-glucuronidase; etc.).

With regard to the production of cellular tumour vaccines or for pharmaceutical compositions with which the immune response to tumours is to be intensified, the foreign DNA codes for immunostimulating proteins or tumour antigens or fragments thereof.

The therapeutically active DNA may also code for antisense molecules which prevent the expression of genes or the transcription of specific RNA sequences in the target cell.

With regard to the use of the recombinant CELO virus vector as a vaccine, the foreign DNA codes for one or more antigens which bring about an immune response in the individual treated.

In one embodiment of the invention the foreign DNA codes for an antigen derived from a human pathogen, particularly a pathogen of infectious diseases.

Epitopes which can be expressed by recombinant CELO viruses include epitopes derived from all kinds of human viral pathogens such as HIV, hepatitis A, B, C, hanta virus, polio virus, influenza virus, respiratory syncytial virus, measles, mumps, rubella, papilloma and many other viruses. The non-viral pathogens include trypanosomes (the causal agents of sleeping sickness and Chagas' sickness), leishmania, *Plasmodium falciparum* (malaria), various bacterial pathogens such as the pathogens which cause tuberculosis, leprosy, *Pseudomonas aeruginosa* (complications in cystic fibrosis) and many others.

A summary of vaccines based on mastadenoviruses is given in Table 3; the epitopes mentioned therein by way of example can also be used for insertion in a vector based on the CELO virus.

With regard to the use of the recombinant CELO virus vector as a vaccine in the veterinary field, e.g. for birds, particularly poultry, the foreign DNA, in another preferred embodiment, codes for an antigen derived from a protein of a pathogen of animal diseases, particularly infectious diseases in birds.

Examples of pathogens of bird diseases are Avian Infectious Bronchitis Virus (IBV, a corona virus; Jia, et al., 1995; Ignjatovic and McWaters, 1991; Kusters, et al., 1990; Lenstra, et al., 1989; Cavanagh, et al., 1988; Cunningham, 1975), Avian Influenza Virus (Orthomyxovirus Type A; Kodihalli, et al., 1994; Treanor, et al., 1991; Tripathy and Schnitzlein, 1991), Fowlpox-Virus (McMillen, et al., 1994), Avian Infectious Laryngotracheitis Virus (Guo, et al., 1994; Scholz, et al., 1993; Keeler, et al., 1991), Mycoplasma Gallisepticum (Nascimento, et al., 1993), Avian Pasteurella Multocida (Wilson, et al., 1993; Lee, et al., 1991; Hertman, et al., 1980; Hertman, et al., 1979), Avian Reovirus (Ni and Kemp, 1992; Huang, et al., 1987), Marek's Disease Virus (MDV; Malkinson, et al., 1992; Scott, et al., 1989), Herpes virus of turkeys (HVT, Herpes virus of Turkeys), Newcastle Disease Virus (NDV; Cosset, et al., 1991; Morrison, et al., 1990), Avian Paramyxovirus Type 1 (Jestin, et al., 1989), Avipoxvirus Isolates (Schnitzlein, et al., 1988), such as Juncopox, Pigeon Pox, and Field-(Field) and vaccine strains of bird pox viruses, Avian Encephalomyelitis Virus (Shafren and Tannock, 1991; Nicholas, et al., 1987; Deshmukh, et al., 1974), Avian Sarcoma Virus, Rotavirus (Estes and Graham, 1985), Avian Reovirus (Haffer, 1984; Gouvea, et al., 1983; Gouvea and Schnitzer, 1982), H7 Influenza Virus (Fynan, et al., 1993).

Apart from DNA sequences which code for therapeutically active gene products or for antigens, the foreign DNA may code for proteins or protein fragments which change the behaviour of the CELO virus, particularly its ability to bind to cells, with regard to the use of mammals, particularly on mammalian cells. Examples of such proteins are fibre or penton base proteins from mammalian and other adenoviruses, surface proteins of other viruses and ligands which have the ability to bind to mammalian cells and transport the CELO virus into the cells. Suitable ligands include transferrin from various mammalian species, lectins, antibodies or antibody fragments, etc. The skilled person will be aware of ligands of this kind, other examples can be found in WO 93/07283.

The recombinant CELO virus may contain one or more foreign DNA molecules. These may be inserted either in tandem or spaced apart in different sections of the CELO virus sequence.

The foreign DNA is under the control of regulatory sequences; suitable promoters include for example the CMV immediate early promoter/enhancer, the Rous sarcoma virus LTR, the adenovirus major late promoter and the CELO virus major late promoter.

The suitability of the CELO virus for preparing vectors and the advantages of these vectors and their applications are based particularly on the following properties of the CELO virus:

i) Safety: Naturally, the CELO virus does not replicate in mammalian cells. Therefore, vectors based on this virus can be used in humans without any danger of a subsequent infection with a Wild type human adenovirus complementing the vector and possibly allowing replication. This is an advantage over the Ad2 and Ad5 vectors used at present.

ii) Increased packaging capacity: The CELO virus genome is about 44 kb long, compared with the 36 kb of the Ad5 genome. Both viruses have comparable virion sizes, so that with a CELO virus vector it is possible to expand the strict packaging limit of 35 kb which is available with Ad5. On the basis of the sequencing carried out within the scope of the present invention, DNA-packaging core proteins of the CELO virus were identified, and striking differences were found from Ad2 which could be responsible for the increased packaging capacity. There are about 13 kb at both ends of the CELO virus which would appear not to code for structural proteins (e.g. capsid components) or for proteins required directly for the virus replication (e.g. DNA polymerase). For the production of vectors, these sequences on the CELO virus genome can be removed and if necessary replaced by complementing cell lines. These sequences can be assumed to code for the immune functions or the apoptotic functions (e.g. GAM-1) of the host cell or to be involved in the activation of the host cell for virus replication (antagonists to the E1, E3 and E4 regions of Ad2). These are the gene types which are either non-essential for virus growth in the cell culture, such as the E3 genes of Ad2 (Wold and Gooding, 1991; Gooding, 1992), or which are easily removed from the virus and can be expressed by a complementing cell line, such as the E1 region in 293 cells (Graham, et al., 1977) and the E4 region in W162 cells (Weinberg and Ketner, 1983).

iii) Stability: The CELO virion is remarkably stable. Its infectivity and its ability to transport DNA withstand a 30 minute treatment at 60° C. As a comparison, Ad5 loses two powers of ten of its infectivity at 48° C. and is completely inactivated at 52° C. Presumably, the CELO virus did not develop its heat stability naturally, rather this heat stability would indicate a reaction to another type of selective pressure on the virion. The natural route of CELO virus infection is a faecal-oral route, which requires the virion to survive contact with a chemically aggressive environment with extreme pH values and with proteases. For particular applications in gene therapy, a more resistant virus would be desirable which would survive, for example, in the digestive tract or in the lungs of a patient suffering from cystic fibrosis.

iv) Targeted use: The CELO virus binds only slightly to mammalian cells on its own and for efficient entry into the cell requires the addition of a ligand (transferrin or lectin; Cotten, et al., 1993). Therefore, recombinant CELO virions are unable to penetrate into human cells, resulting in the following possible applications:

The virus may be genetically modified as stated above in order to express, on its surface, ligands which enable targeted transportation, such as for example specific peptides or fibres and/or penton bases of human adenoviruses.

Another possibility is the chemical modification of the virus in order to couple specific ligands such as transferrin thereto, as proposed for example in WO 94/24299 and additionally the virus may be biotinylated (WO 93/07283) and bound via streptavidin to biotinylated ligands such as wheatgerm agglutinin or other lectins (WO 93/07283). CELO virus vectors thus do not have the disadvantages of human adenoviruses which have good binding ability to human cells but have to be masked for a specific, targeted use mediated by the ligand.

v) Possibility of use for vaccines: The CELO virus is seldom connected to diseases in birds, indicating that it provokes a strong protective immune response in bird hosts. The CELO virus vector can easily be adapted for the expression of new vaccine epitopes.

With regard to the removal of regions of the CELO virus DNA, it was concluded from the results obtained with the mastadenovirus that, when the central sections of the CELO genome are removed, these sections have to be made available in trans, e.g. by a packaging cell line. This restriction is based on the large quantity of virion components which are necessary for the assembly of the virus and the need to produce a cell line which is capable of producing the corresponding amounts of these proteins without any toxicity.

The approaches which have hitherto proved more successful in this respect with mastadenoviruses consisted of the production of cell lines which express regulatory proteins (E1 and E4 regions) or enzymatic proteins (DNA polymerase, DNA binding protein), because these proteins are not required in large amounts during a productive virus infection.

Starting from the analysis of the known CELO genes, the sections of the genome from nt about 12,000 to about 33,000 which code for structural components of the virus are preferably not interrupted. The region from about nt 5,000 to about 12,000 codes for the E2 genes IVa2 (a viral transcription factor), viral DNA polymerase (POL) and the terminal virus protein (viral terminal protein; pTP) These genes are essential for the function of mastadenoviruses; they ought therefore to be essential for the CELO virus as well. However, it is theoretically also possible to have deletions of essential genes of this kind provided that they can be produced in trans, e.g. by a packaging line. For example, a packaging cell line was prepared which produces Ad5 DNA polymerase, thus making it possible for this gene to be deleted from the virus genome. A similar procedure may be used in the construction of CELO virus vectors, by removing sections or the entire region from nt 5,000 to 12,000 from the CELO virus and having the corresponding functions controlled in trans by a packaging cell line.

Another possible restriction exists with regard to the presumed major late promoter, which was provisionally assigned to the region at about nt 7,000 (TATA box at nt 7,488). In the mastadenoviruses, this promoter is essential for driving late gene expression. Therefore, any change in the region at nt 7,000 of the CELO genome must be carried out in a way which maintains the promoter function of this region.

Table 4 lists the sequence elements of the CELO virus genome and is divided into various categories with regard to their deletion and/or mutation in the production of CELO virus vectors (in Table 4 L1, L2, etc. denote "late message 1, 2, etc., corresponding to the nomenclature normally used for mastadenoviruses):

Category 1 includes sequence elements which are required in cis and therefore cannot be made available in trans by a complementing cell line or by a complementing plasmid. These sections are necessary and are therefore present on the CELO virus according to the invention; these are the left and right terminal repeats and the packaging signal.

Sequences of category 2 code for proteins which are required in large amounts for virion production. These proteins may optionally be produced by a gene contained in a complementing cell line or on a complementing plasmid. Other sequences of category 2 are the major later promoter, the tripartite leader sequence and also the splice acceptor sites (SA) or the polyadenylation sites (poly A sites) of genes which are essential and which cannot be made available in trans.

Fundamentally, care must be taken to ensure that, in modifications of the CELO virus DNA which are carried out at the boundaries of genes, any control signals present, e.g. polyA sites are not interrupted or affected in any other way if possible.

The genes deleted from the CELO virus or non-functional genes therein may be prepared in trans, e.g. by complementing cell lines.

Complementing cell lines ("helper cells") can be prepared by the manner known from the literature, analogously to helper cells which complement the functions of mammalian adenoviruses. To do this, the relevant CELO virus gene on a plasmid, preferably combined with a selectable marker, is introduced into cells which permit the replication of CELO virus, preferably into immortalised cell lines such as LMH (Kawaguchi, et al., 1987) or immortalised quail cell lines, as described for example by Guilhot et al., 1993. In helper cells which express the relevant CELO virus genes, optionally stably integrated, the defective CELO viruses are able to replicate.

Instead of making the regions of the CELO virus deleted in the vector available by means of a cell line, the deletions may also be complemented by a copy of the relevant gene contained on a plasmid. For this, the method described in WO 96/03517, that described by Cotten et al., 1994a and 1994b) or the one described by Wagner et al., 1992, may be used, for example, in which a CELO virus vector containing a deletion is inserted, as a component of a transfection complex, containing a conjugate of polylysine and a UV/psoralen-inactivated adenovirus (human or CELO) and optionally transferrin-polylysine, into embryonic chicken kidney cells or liver cells, embryonic or immortalised quail cells, e.g. liver or kidney cells, and the transfection complex also contains a plasmid which carries a copy of the gene or genes which lack the CELO virus vector. The combination of genes contained on the vector and genes carried by the plasmid results in a normal virus replication cycle. (Similar approaches were used in mastadenovirus systems in order to complement E1-deficient adenoviruses (Goldsmith, et al., 1994) and E4-deficient adenoviruses (Scaria, et al., 1995)). The subsequent amplification of the virus may be carried out by using the defective virus as a carrier which is dependent on the complementing plasmid using the methods described above.

Another possible way of replacing the genes missing from the CELO virus is by using helper viruses.

The helper virus used may be a CELO virus (Wild type or partly defective). In this embodiment the CELO plasmid carrying the mutation (e.g. a derivative of pCELO7), is introduced into chicken cells, e.g. using the method described in WO 96/03517 or described by Cotten et al., 1994, using as the carrier for the derivative, for example, psoralen/UV-inactivated adenovirus (human or CELO) together with an adenovirus (human or CELO) as a carrier for the plasmid or plasmids with the genes which complement the defect. Alternatively, a Wild type CELO virus may be used both as a carrier and as source for complementing gene functions. The subsequent amplification of the defective CELO viruses obtained is carried out by co-infection of the defective CELO virus with a complementing adenovirus (e.g. Wild-type CELO or a CELO which has mutations at other points of the genome).

CELO virus genes of category 3 include the sequences on Sections A, B and C. These are sequences which code for a protein or an RNA molecule which is necessary for the interaction with the host cell machinery or with the host immune system. These proteins should be required in fairly low concentrations or may be dispensable for cultivation of the virus in the tissue culture.

Thus, preferably, in the CELO virus vectors according to the invention the genes of category 3 are replaced by the gene in question; if necessary, complementary cell lines or plasmids or helper viruses can be prepared which produce the corresponding gene products.

In one embodiment of the invention the vectors according to the invention contain the gene in question instead of one of the fibre genes. The CELO virus has two fibre proteins (Laver, et al., 1971; Gelderblom and Maichle- Lauppe, 1982; Li, et al., 1984a). It can be assumed that one of the fibres of the CELO virus is not necessary for the assembly of the virion and the infectivity. This assumption is backed up by electron microscopic observations that the longer fibre (fibre 1) should associate with the penton base along the side of the complex, whilst the shorter fibre (fibre 2) projects out of the middle of the penton base, similarly to the penton/fibre complexes in the mastadenoviruses (Hess, et al., 1995). In adenoviruses with only a single fibre, the fibre molecule is required for the assembly of the virus; in the absence of fibres no stable mature viruses are formed. The CELO virion should therefore require fibre 2 for stability and as a ligand, whereas fibre 1 acts only as a ligand. Within the scope of the present invention the assumption that, of the two fibre genes of the CELO virus, fibre gene 1 located in region C is superfluous and can be replaced by the gene in question was proved correct by removing the fibre 1 gene and replacing it with a luciferase expression unit.

Other examples are inserts in region A and/or B.

Within the scope of the present invention it was found that destruction of the reading frame at nt 794 (region A) which codes for dUTPase yields viable viruses. The dUTPase gene is thus a gene which is not necessary for growth in cell culture.

In one embodiment of the invention, the recombinant CELO virus thus contains a foreign gene which is inserted in the region of the reading frame coding for dUTPase.

According to another aspect the present invention relates to a process for preparing recombinant CELO virus.

The process is characterised in that the CELO virus genome contained on a plasmid or sections thereof is or are genetically manipulated.

In one aspect of the invention the genetic manipulation consists of insertion and/or deletion. Insertions and/or deletions can be carried out by using restriction enzyme cutting sites which occur naturally in the CELO virus DNA in these sections, e.g. the FseI cutting site occurring at position 35,693 in Section B. The insertion may be carried out directly into this cutting site or beyond this cutting site or close to this cutting site, or this cutting site may be used to allow recombination in the surrounding area.

In one preferred embodiment the manipulation consists of carrying out insertions and/or deletions using standard methods of molecular biology (Maniatis, 1989). The naturally occurring restriction cutting sites can be used for this, e.g. sites located in regions of the genome which are non-essential for cultivation of the virus in the host cell, e.g. the FseI cutting site which occurs at position 35,693 in Section B. The insertion can be made directly into this cutting site or beyond this cutting site or in the vicinity of this cutting site, or the cutting site may be used to facilitate recombination in the surrounding area. Foreign DNA sequences can be inserted, e.g. marker genes or genes coding for therapeutically active proteins.

An alternative possibility is to remove CELO sequences which are flanked by two restriction sites and replace them with new sequences. (An example of this is dUTPase mutation as carried out in Example 7.) In these cases the manipulation is carried out with the entire CELO virus genome. In the event that restriction sites are present, the deletion/insertion can alternatively be carried out on a subfragment which is then re-incorporated in the entire genome by ligation and optionally recloning in bacteria.

Another possibility is to insert the foreign gene in artificial restriction enzyme cutting sites produced by conventional methods of recombinant DNA technology (Maniatis, 1989).

In one embodiment the process is characterised in that manipulations are carried out in a plasmid DNA which contains the CELO virus genome, in CELO DNA sequences, with the exception of the left and right inverted terminal repeats and the packaging signal.

In another preferred method, the manipulation of the CELO genome is carried out by recombination. For this, a subfragment of the CELO genome is manipulated in order to introduce mutations and/or new sequences. Subfragments can be prepared by various methods, specifically by PCR (polymerase chain reaction), by ligation between PCR products or between restriction fragments or by subcloning in bacteria (as described in the Examples of the previous invention; see also Chartier et al., 1996). Examples of suitable bacteria strains for recombination are BJ 5183 (Hanahan, 1983) or JC 8679 (Gillen et al., 1974) or JC 5176 (Capado-Kimball and Barbour, 1971).

For recombination using PCR products, the sequence to be inserted into the CELO genome is prepared by PCR (Oliner et al., 1993) using primers which flank the sequence plus about 15 nucleotides of the sequence complementary to the insertion site in the CELO genome. In a second round of PCR, another 15 nucleotides are hung from the sequence complementary to CELO, resulting in a PCR product which consists of the sequence to be inserted with 30 nucleotides of the CELO sequence at each end. This fragment is mixed with a plasmid which contains the CELO DNA (e.g. the plasmid pCELO7 prepared within the scope of the present invention) and which has been linearised with a restriction enzyme which cuts only between the two flanking sequences hung from the sequence by PCR.

For recombination using ligation reaction products (prepared by conventional techniques as described for example by Maniatis et al., 1989), in principle the same procedure is used as in the recombination with cloned fragments, except that the intermediate cloning step is omitted.

In every case, the manipulated product obtained is characterised and used to prepare virus by transfecting avian cells (e.g. using the method described by Wagner et al., 1992; Cotten et al., 1994; or Cotten et al., 1993) and then cultivating them, after which the virus is harvested.

For preparing recombinant CELO virus using cloned fragments, the method preferably comprises subcloning a small fragment from the relevant region of CELO virus into which the foreign gene is to be inserted on a bacterial plasmid in order to ensure that restriction sites which occur several times on the CELO virus genome occur only once on the plasmid. These restriction sites are used to remove a region from the small fragment. For preparing the CELO virus vector this region is replaced by foreign DNA. The foreign DNA may consist solely of a linker with a restriction site occurring only once or of a sequence coding for a protein or for an antigen. The sequence may also code for a reporter gene with a restriction site occurring only once. This makes further manipulation of the CELO virus easier by inserting the foreign DNA, which codes for a therapeutically active gene product or for an antigen, into this restriction site, and at the same time the reporter gene permits rapid information as to the efficiency of the vector, by introducing the plasmid into cells and monitoring the expression of the reporter gene.

Figure 1A:
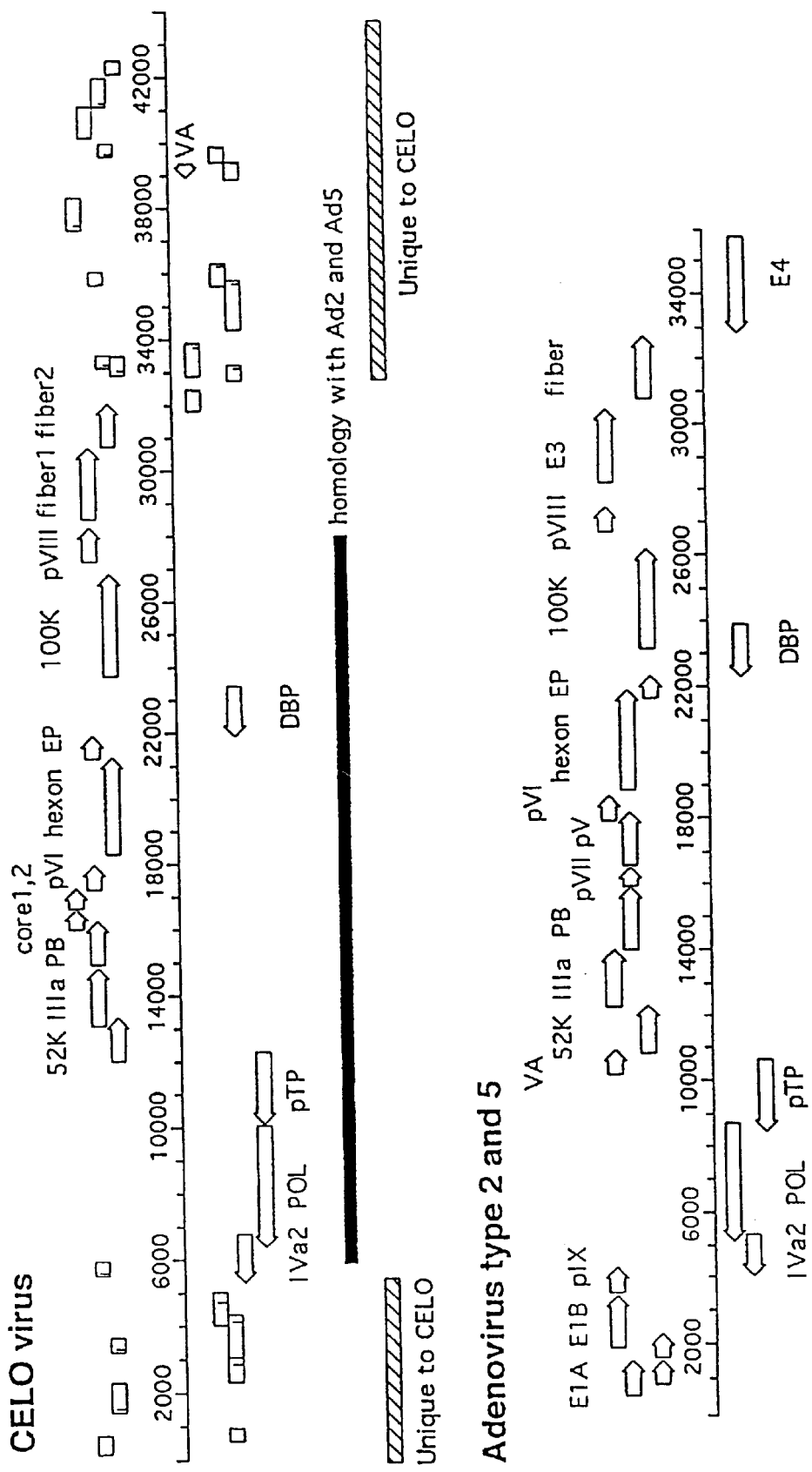
FIG. 1A: Comparison of the genomic organisation of Ad2/5 with the CELO virus

In the Examples, the following materials and methods were used unless otherwise specified:

a) Virus and virus DNA

A plate-purified isolate from CELO virus (FAV-1, Phelps strain) which was used as starting material for the DNA both for direct sequencing and for the formation of bacterial plasmid clones, was grown in 9 day old pathogen-free chicken embryos, as described by Cotten, et al., 1993. The FAV-1 isolates OTE (Kawamura, et al., 1963) and Indiana C (Calnek and Cowen, 1975; Cowen, et al., 1978) were cultivated in chicken embryo kidney cells. The virus was purified from the allantoic fluid or from infected embryo kidney cells by separation in CsCl gradients, as described by Laver, et al., 1971, and Cotten, et al., 1993. Virus DNA was isolated by treating the purified virions with proteinase K (0.1 mg/ml) and SDS (0.2%) at 56° C. for 45 min and subsequent equilibrium centrifugation of the DNA in a CsCl gradient in the presence of ethidium bromide. After the second gradient, the ethidium bromide was removed by extraction with CsCl-saturated isopropanol and the virus DNA was exhaustively dialysed against 10 mM Tris, 0.1 mM EDTA, pH 8.

b) Chicken embryo kidney cells

The kidneys of 14 day old chicken embryos were collected washed in PBS and digested with pancreas trypsin (2.5 mg/ml in PBS) at 37° C. The dispersed cells were mixed with an equal volume of foetal calf serum, the cells were collected by centrifugation, washed once with FCK medium and taken up in the same medium again. (The FCK medium is medium 199 with Earle's salts (Sigma M2154) supplemented with 10% tryptose phosphate (Sigma T8159), with 10% foetal calf serum, 2 mM glutamine, 100 µg/ml streptomycin and 100 IU/ml penicillin.) The cells were plated out in 175 cm² tissue culture flasks (2 embryo kidneys per flask), stored at 37° C. under 5% $CO_2$ and infected 24 to 48 hours later. The cells were infected with about 1,000 virus particles per cell and harvested 3 to 4 days after infection when the cytopathic effect was complete.

c) Pulsed Field Electrophoresis

Aliquots of purified adenovirus DNA (10–20 ng) were loaded onto a 1% agarose gel (BioRad, PFC agarose) and separated using a BioRad CHEF Mapper Pulsed Field Electrophoresis system (FIGE mode) for 24 hours in 0.5× TBE cooled to 14° C. The switching time, both in the forward direction and in reverse, was changed logarithmically from 0.22 seconds to 0.92 seconds with a ramp factor of 0.357 (21%). The forward voltage gradient was 9 V/cm (300 V), the reverse voltage gradient was 6 V/cm (200 V). After the run the gel was stained for 25 minutes in 0.5 µg/ml of ethidium bromide solution in water and then destained for 1 hour before the DNA pattern was made visible under UV light.

d) Sequencing methods, data analysis

For the sequencing, EcoRI and HindIII restriction fragments of CELO virus DNA were cloned in pBlueScript SK(−). Three of the EcoRI clones containing the EcoRI fragments C, D and E (see FIG. 1B) and five of the HindIII clones containing the HindIII fragments F, A, G, B and E (cf. FIG. 1B, were selected for the preparation of deletions in one direction using exonuclease III (in FIG. 1B the cleavage sites for the restriction enzymes EcoRI, HindIII, BamHI and BglII are given; the alphabetical names for the EcoRI and HindIII fragments, on the basis of their relative sizes, are also given). These deletion clones were sequenced using the Taq Dyedeoxy Terminator system with the automatic sequencing apparatus ABI 373 according to the manufacturer's instructions. The sequence analysis of the terminal 2,000 bp at the left hand end and the 1,000 bp at the right hand end of the CELO virus genome, the sequencing to close the gaps between the fragments EcoRI C/HindIII G and the fragments HindIII B/EcoRI D and the sequencing to confirm the sequence at various points of the genome were carried out by direct sequencing of the viral DNA. All the sequence data are the results of at least three sequence reactions. The sequence data were combined using the programs SeqEd (ABI) and SeqMan (Lasergene). The sequence analysis was carried out using the program GCG of the University of Wisconsin.

EXAMPLE 1

Preparation of a recombinant bacterial plasmid clone of the CELO virus genome a) Preparation of a plasmid vector with a low copy number for cloning the CELO virus The bacterial vector pBR327 (ATCC No. 37516) was chosen for this because it is retained in bacterial host strains at relatively low copy numbers (instead of this plasmid any other plasmid with a low copy number such as pBR322 could be used equally well). It was essential to create on the vector a restriction site which occurs only once and which does not appear in the CELO virus sequence. As described hereinafter, the virus sequence has to be cut from the plasmid vector sequences in order to inject a productive infection; therefore, restriction sites which flank the CELO sequence (but which are not present within the CELO sequence) have to be incorporated in the vector. In the experiments carried out, the restriction enzyme SpeI was used; however, any other enzymes which do not have recognition sites in the CELO sequence, such as AscI, PacI and SfiI, may be used instead.

The plasmid p327SpeI was prepared by ligating an SpeI linker (New England Biolabs) into the Klenow-treated EcoRI site of pBR327, thereby destroying the EcoRI site and creating an SpeI site which occurs only once.

b) Cloning the ends of CELO

The two terminal HindIII fragments were cloned. In order to do this, CsCl-purified genomic CELO DNA was digested with HindIII and separated on a low-melting agarose gel (0.7% low melting agarose in TAE). The 1601 bp left hand end fragment and the 959 bp right hand end fragment were cut from the gel, and each gel fragment was suspended in 300 µl of 10 mM Tris, 1 mM EDTA pH 7.4 and heated to 70° C. for 10 min to melt the agarose. The terminal peptides were eliminated by the addition of NaOH to 0.3 N and heating to 37° C. for 90 min. (Hay, et al., 1984). The solutions were then cooled to ambient temperature, then Tris pH 7.4 (to 0.1 M) and HCl (to 0.3 M) were added in order to neutralise the NaOH. The fragments were heated to 56° C. for 20 min. and slowly cooled (over 1 hour) to ambient temperature in order to facilitate re-annealing. Then the DNA was purified over a Qiaquick column and ligated for 4 hours at 16° C. using a Pharmacia T4 ligase reaction (New England Biolabs) to an SpeI linker (New England Biolabs). The ligase was inactivated by heating to 70° C. for 10 minutes, excess linker was removed (and an overhang complementary to SpeI was formed) by digesting for 2 hours with restriction endonuclease SpeI. The DNA fragments were in turn purified by Quiquick column chromatography and ligated to p327SpeI treated with SpeI/HindIII/calf alkaline phosphatase. The ligation product was transformed into the bacterial strain DH5alpha, and plasmid clones were identified which carried either the 1601 bp left hand end fragment or the 959 bp right hand end fragment (both released by SpeI/HindIII digestion). In order to confirm the terminal 300 bp of both fragments, DNA sequence analysis was carried out.

c) Cloning of both CELO ends on the same plasmid

The 1601 bp left hand end and the 959 bp right hand end fragment were cut from their vectors by HindIII/SpeI digestion, separated by gel electrophoresis and purified by Qiaquick chromatography. The two fragments were mixed in approximately equimolar amounts and ligated for 30 minutes using the Pharmacia T4 ligase reaction. An aliquot of SpeI/CIP-treated p327SpeI was added and ligation was continued for 4 hours. The ligation mixture was transformed in DH5alpha and plasmid clones were identified which carried the correct double insert (pWu#1 and pWu#3).

The second HindIII site was removed by cleaving pWu#3 with ClaI and BamHI, treating with Klenow enzyme, religation, transforming DH5alpha and selecting a clone which missed the ClaI/BamHI fragment (which had contained a HindIII site). The resulting plasmid designated pWu-H35 now contained a single HindIII site between the left and right hand CELO end fragments.

d) Cloning the entire CELO genome

Figure 2A:
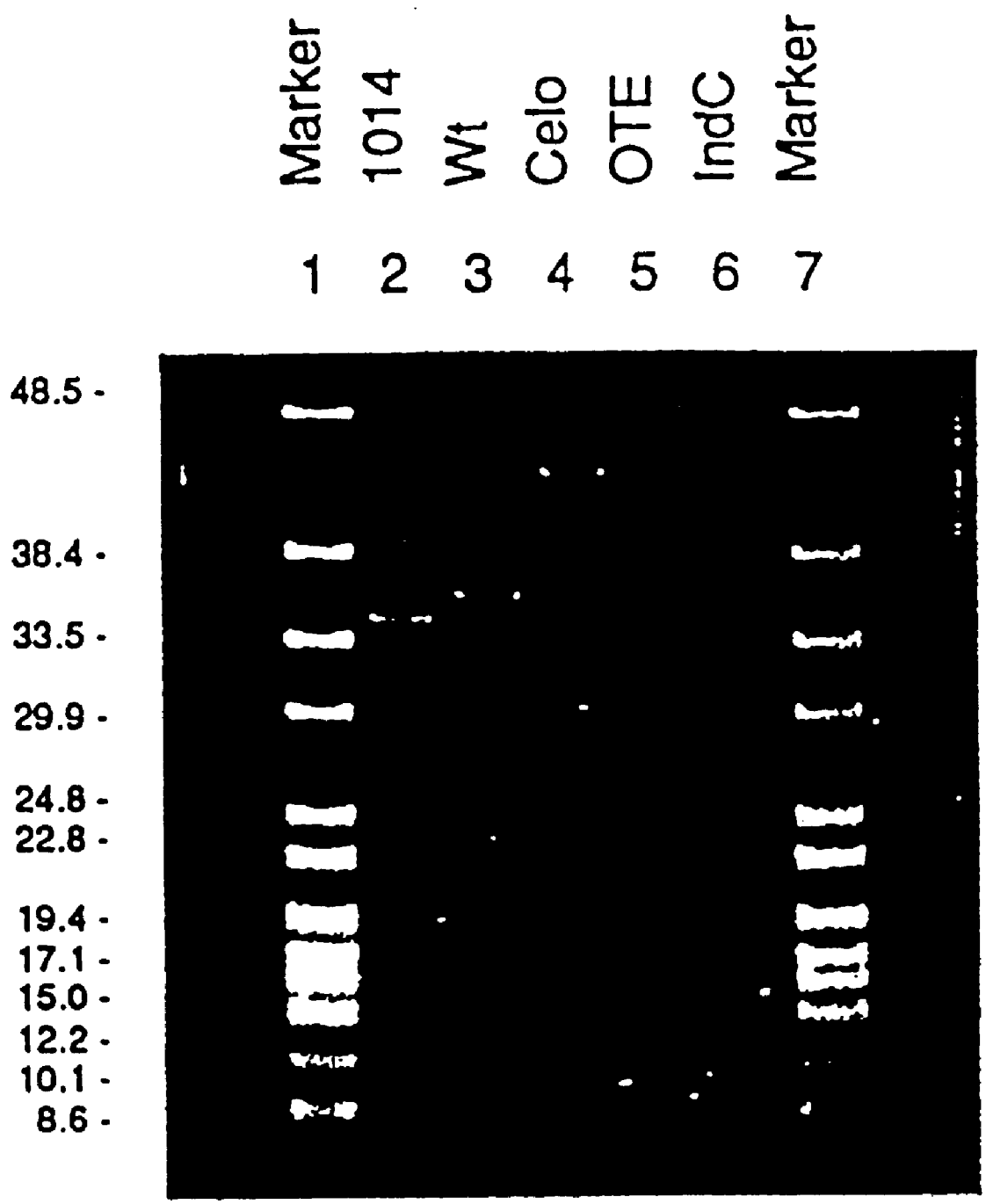
FIGS. 2A and B: Pulsed Field gel-electrophoretic analysis of the genome size of adenoviruses
Figure 2B:
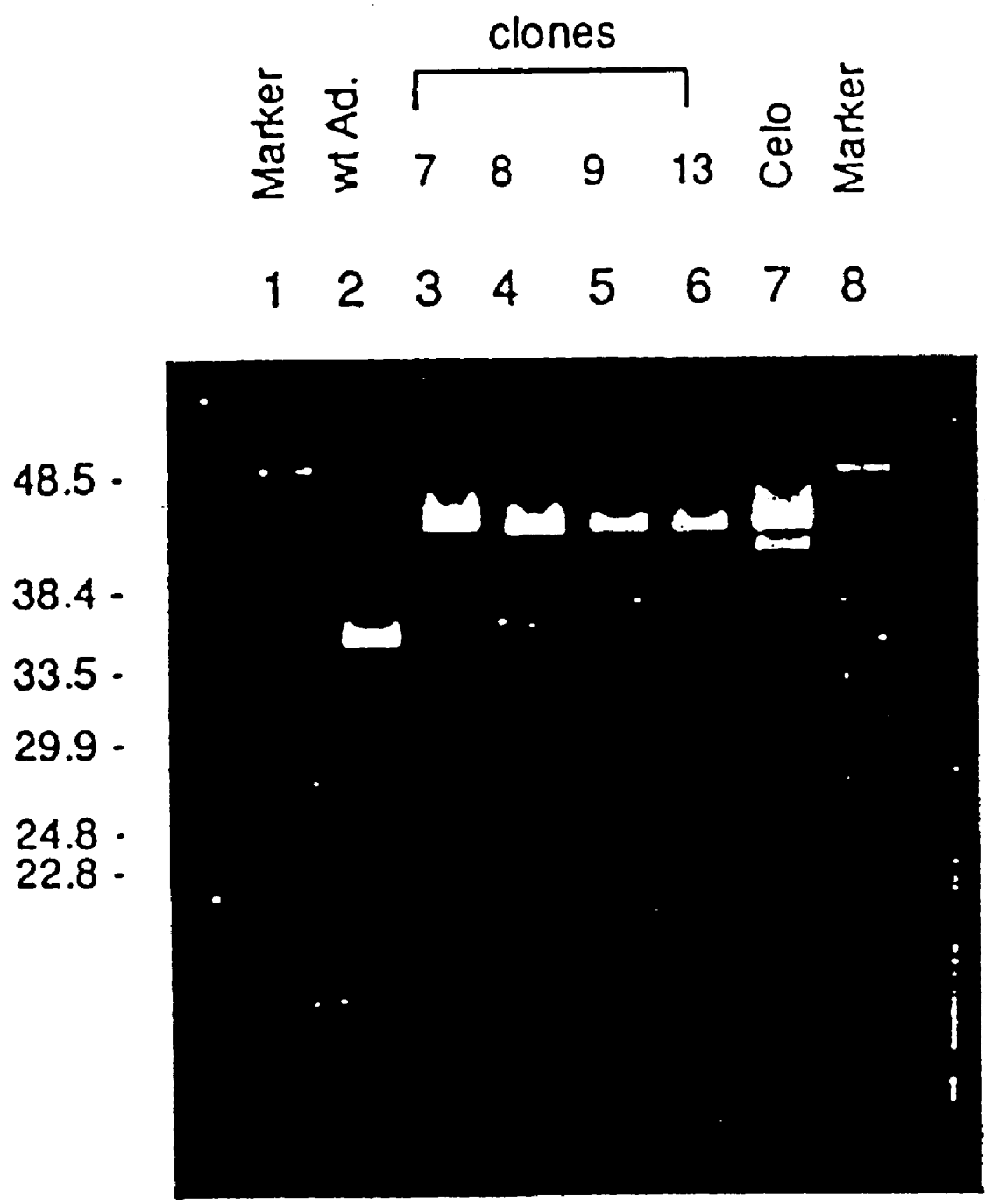
FIG. 2C: Characterisation of plasmid-cloned copies of the CELO virus genome by means of restriction endonucleases
Figure 2C:
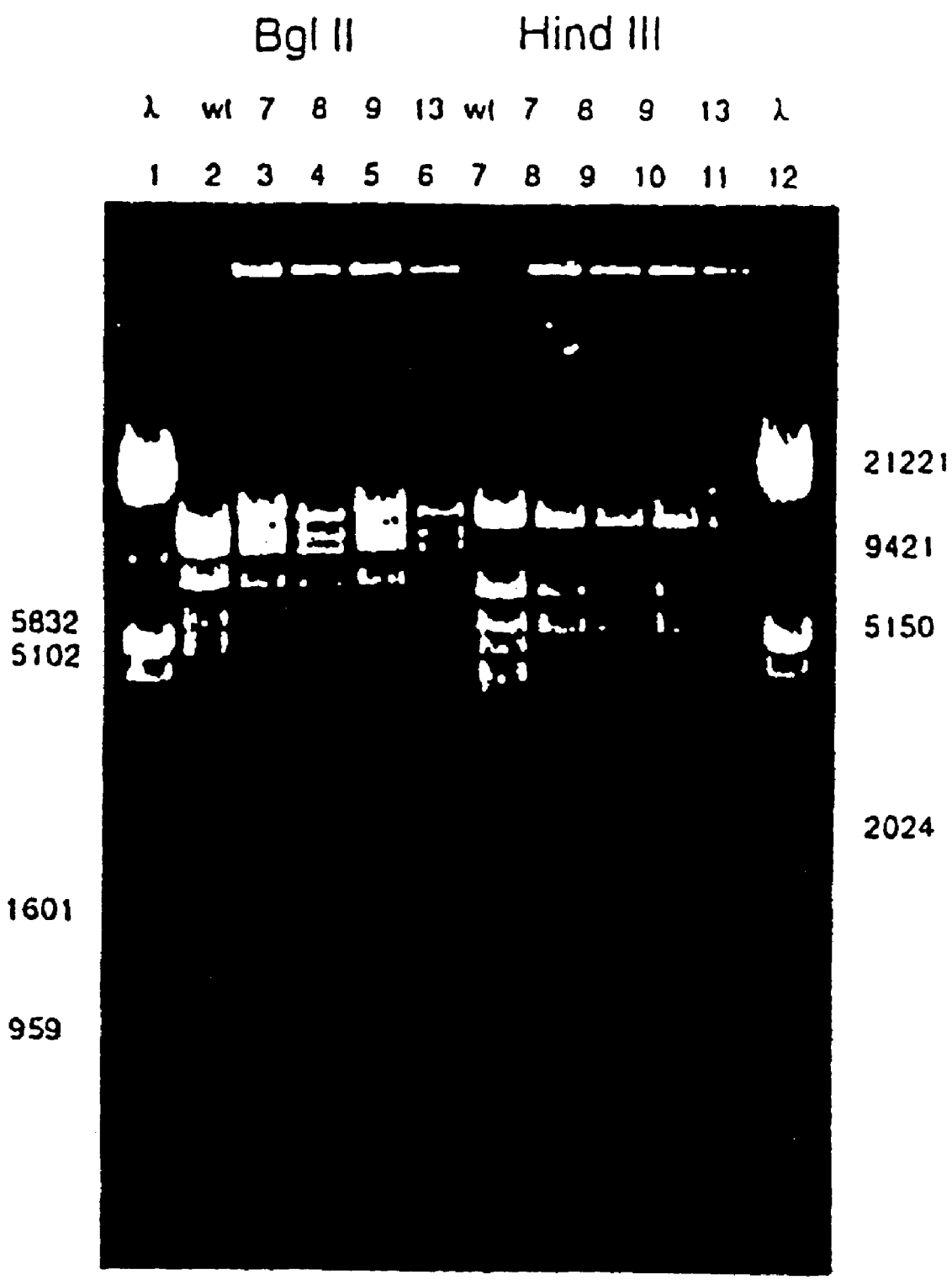
Figure 3:
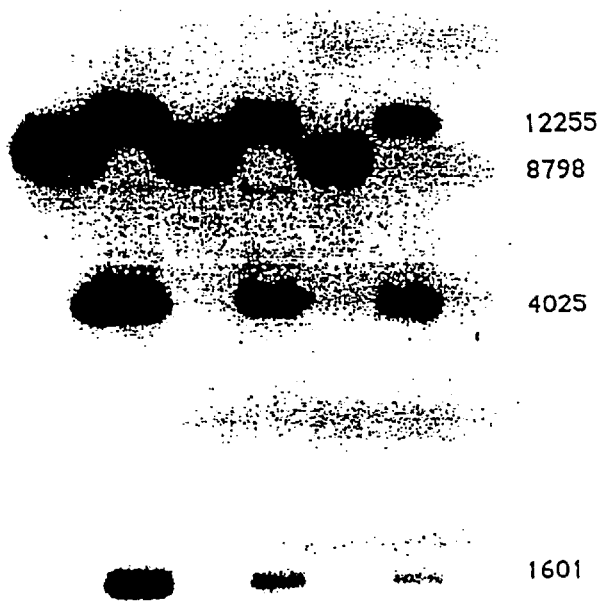
FIG. 3: Dot matrix analysis of the DNA sequence homology between CELO virus and Ad2
Figure 4:
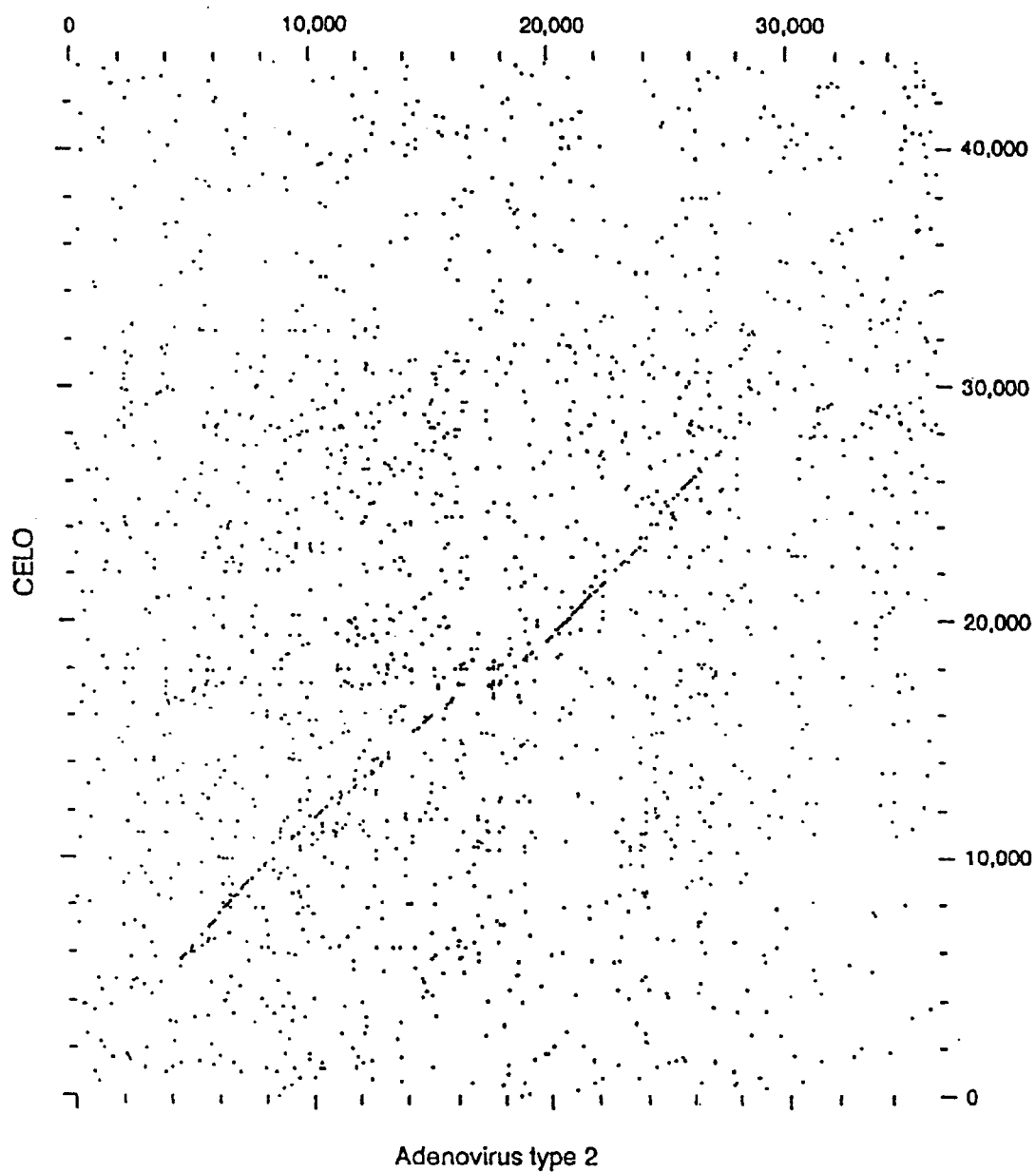
FIG. 4: Amino acid sequences of protein VII and pX from various mastadenoviruses compared with CELO virus and the core proteins core 2 and core 1

The plasmid pWu-H35 obtained in c) was treated with HindIII and CIP and purified on a low melting agarose gel following by Qiaquick chromatography. The linearised vector pWu-H35 was mixed with 0.3 μg of purified CELO virus DNA, then 30 μl of electro-competent bacterial strain JC8679 (Gillen, et al., 1974; Oliner, et al., 1993) were added to the DNA mixture on ice. 10 Minutes later the mixture was transferred into a BioRad Electroporation chamber and pulsed with an electric charge of 2.4 kV (BioRad Gene Pulser; Oliner, et al., 1993). The bacteria were then plated onto LB ampicillin plates and the ampicillin-resistant colonies were investigated for their plasmid content. Recombination between the terminal CELO sequences on pWu-H35 and the ends of the genomic CELO DNA re-establishes the circularity of the linearised plasmid and allows growth on ampicillin. A plasmid which contains the CELO genome over its full length was identified, and this plasmid, referred to as pCELO7, was used for the subsequent investigations. FIG. 2C shows the characterisation of plasmid-cloned copies of the CELO virus genome. Plasmid DNA from clones designated pCELO7, 8, 9 and 13 or DNA isolated from purified CELO virus, was digested either with BglII (tracks 2–6) or HindIII (tracks 7–11) and separated on a 0.6% agarose gel, and the DNA was shown up by ethidium bromide staining. The molecular weight marker (tracks 1 and 12) was bacteriophage λ-DNA cut with HindIII and EcoRI. The sizes of some molecular weight fragments (in base pairs) are shown on the right of the Figure. For each enzyme, the two CELO end fragments which are bound to the bacterial plasmid during cloning (and which are therefore not released after restriction digestion) are given on the left of the Figure (in base pairs). These are the fragments with 5832 and 5102 bp with BglII or 1601 and 959 with HindIII.

Figure 5:
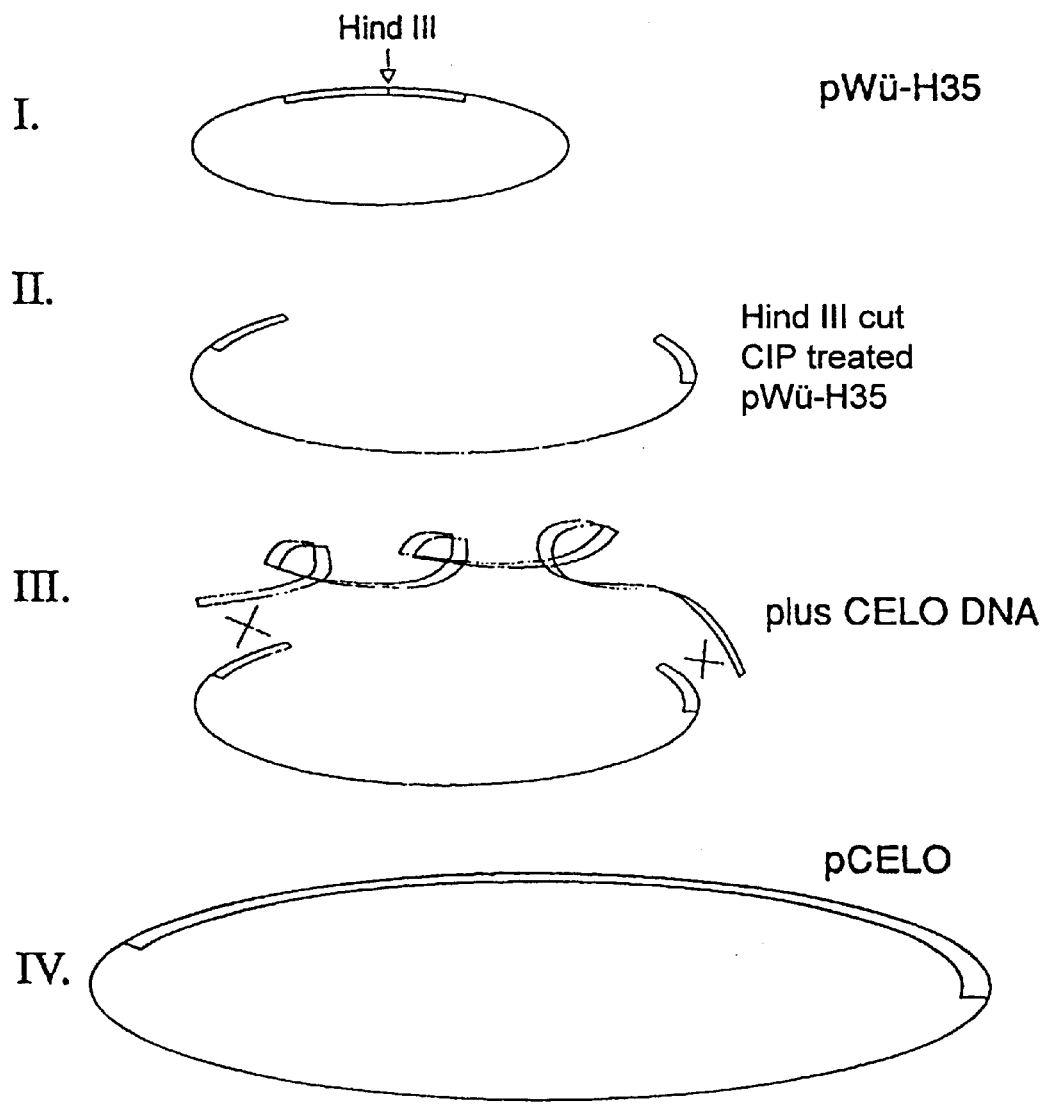
FIG. 5: Construction of a plasmid which contains the entire length of the CELO genome

The construction of pCELO7 is shown in FIG. 5.

e) Initiation of a CELO virus infection by a cloned CELO genome pCELO7 was cleaved with SpeI (which cleaves at the sites flanking the adenovirus termini), extracted with phenol/chloroform and passed over an HBS-equilibrated gel filtration column. (Pharmacia Nick column) to remove any impurities. The cleaved DNA was then incorporated in streptavidin-polylysine/transferrin-polylysine/biotin-adenovirus (UV/psoralen-inactivated) as described in WO 93/07283. Complexes containing 0.5 μg of SpeI-cleaved pCELO7 plus 5.5 μg of carrier DNA (pSP65; Boehringer Mannheim) were used to transfect primary embryonic chicken kidney cells (the complexes contain 4 mg of DNA per 180 cm$^2$ flask, containing about 3×10$^6$ cells), and the cells were investigated for the cytopathic effect caused by virus replication. Five days after transfection, when the majority of the transfected cells had been rounded off and detached from the surface of the plate, the cells were obtained by centrifuging and the CELO virus was purified as described by Cotten, et al., 1993. The virus yield from plasmid cloned CELO virus is comparable with the yields obtained by using pure CELO virus DNA (purified from virions).

EXAMPLE 2

Preparation of a CELO mutant which lacks the sequences from nt 35,870 to 42,373 at the right hand end There are no identifiable viral structural genes beyond the two fibre genes with the L5-polyadenylation site at position 31771. (There is a cryptic VA-gene at positions 39,841 to 39,751.) Investigations were therefore carried out to see whether the sequences between about 32,000 and the right ITR are necessary for the growth of the virus in cell culture. For this an accumulation of seven AseI sites were used at positions 35,870, 36,173, 38,685, 38,692, 39,015, 42,348 and 42,373, which does not appear anywhere else in the CELO virus genome. pCELO7 was digested with AseI, religated and a plasmid which lacked the inner AseI fragments was identified and designated pALMCELO_35870-42373. In connection with this it should be noted that the plasmid vector also has an AseI site; however, this is located in the ampicillin resistance gene, and selection for ampicillin resistance requires that all positive colonies have at least the two fragments which carry the right and left hand halves of the amp gene.

To aid further manipulations of the virus with the missing left hand end of the genome, pALMCELO_35870-42373 was digested with AseI (which cuts once in the ampicillin resistance gene of the plasmid and once at position 35,870) and ligated to a linker oligonucleotide TACCCTTAAT-TAAGGG which codes for a cutting site for the restriction endonuclease PacI and for ends which are complementary to those formed during AseI digestion. Religation, followed by selection for ampicillin resistance, identified plasmids which did not integrate the oligonucleotide at the AseI site of the ampicillin resistance gene. Restriction digestion identified a plasmid which carried a PacI site at the earlier AseI site of CELO at position 35,870. The plasmid was designated pALMCELO_35870-42373P.

Figure 1B:
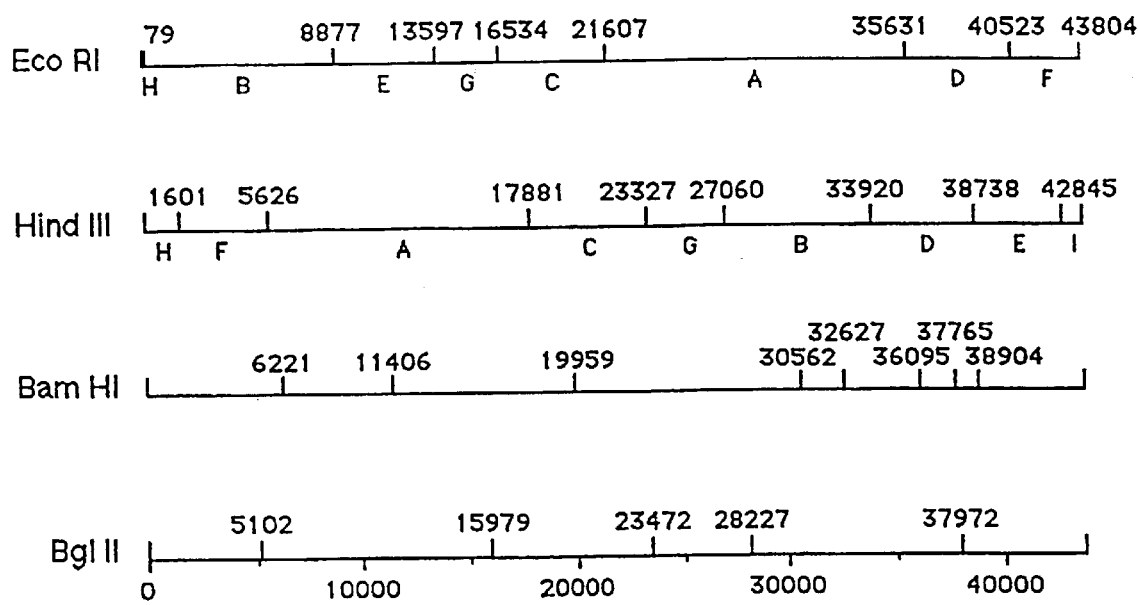
FIG. 1B: Restriction map of the CELO virus genome

EXAMPLE 3
Preparation of a CELO virus vector in which a fibre gene is missing which is replaced by a gene of interest The CELO fibre genes are contained on a HindIII fragment which extends from nt 27,060 to 33,920 (the HindIII B-fragment, cf. the restriction map in FIG. 1B). On this fragment the sequence coding for fibre 1 extends from nt 1,054 to 3,435. The 5H3 fragment was digested with BglII (which cuts at nt 1,168) and HpaI (which cuts at 3,440), the BglII end was filled with Klenow enzyme and ligated to a blunt CMV/luciferase/β-globin cleavage/polyadenylation signal fragment from the plasmid pCMVL (Plank et al., 1992) to form the plasmid p5H_28227-30502(luc) which lacks almost the entire fibre 1 sequence which is replaced by a luciferase expression unit.

The relevant restriction cutting sites in CELO are as follows:

```
BglII A'GATC_T

Cuts at:    0    5102   15979   23472   28227   37972   43804
Size:         5102  10877    7493   4755    9745    5832
HindIII A'AGCT_T Cuts at:    0    1601   5626   17881   23327   27060   33920   38738   42845
42845  43804
Size:         1601   4025  12255   5446    3733    6860    4818    4107
959
HpaI GTT'AAC Cuts at:         0    5503   20673   23355   30502   43804
Size:              5503  15170    2682    7147   13302
NotI GC'GGCC_GC Cuts at:  0   17389   43804
Size:        17389   26415
XbaI T'CTAG_A Cuts at:  0   1659   1988   28608   39268   41746   43804
Size:        1659    329   26620   10660    2478    2058
```

The modifications which were carried out on p5H_28227-30502(luc) were introduced into the entire CELO genome in the following manner: The CELO/luciferase/CELO fragment was cut from p5H_28227-30502(luc) as a HindIII fragment. This fragment was recombined with the 26 kb XbaI fragment (CELO nucleotides 1988–28608) and the terminal HpaI fragments derived from pCELO7 (obtained by cutting with HpaI, containing the left hand end of the CELO virus and pBR327 sequences, defined by the HpaI sites). The three DNA fragments (each about 50 ng) were mixed in water and electroporated in JC8679 cells as described above.

EXAMPLE 4
Insertion of a reporter gene (luciferase) in the CELO genome i) Preparation of a left hand end fragment containing a CMV luciferase construct The EcoRI fragment designated 7R1 (nucleotides from positions 79 to 8877) was cloned into a pSP65 derivative designated pAAALM (described in WO 95/33062). The plasmid was transformed into the DAM methylase negative bacterial strain JM110 in order to allow cleavage of the ClaI sites in the fragment. The plasmid was purified, cut with ClaI (at position 1083) and NcoI (at position 4334), treated with Klenow enzyme to fill the overhanging ends and ligated to a blunt CMV/luciferase/β-globin cleavage/polyadenylation signal (Plank et al., 1992). The resulting plasmid was designated p7R1_1083-4334Luc.

ii) Recombination of the luciferase left hand end fragment into a complete (full length) CELO sequence The plasmid p7R1_1083-4334Luc was cleaved with Eco47 III, which cleaves at the CELO nucleotides 937, 1292, 2300 and 8406 (the sites at nucleotide 1292 and 2300 are absent from p7R1_1083-4334Luc) in order to release a large fragment containing the sequence CELOnt937-1083/ CMVLusPA/CELOnt4334-8406. This fragment was recombined in pCELO7. pCELO7 was cleaved at the single PmeI site at CELO nt7433 and exhaustively dephosphorylated with calf intestinal phosphatase. The linearised pCELO7 was mixed with an approximately 3 to 5 molar excess of CELOnt937-1083/CMVLucPA/CELOnt4334-8406. The mixture was electroporated into the bacterial strain JC8679 and ampicillin-resistant colonies were examined on plasmids which contain the desired recombinant DNA. The correct plasmid was identified, characterised by restriction enzyme analysis and designated pCELOLucI.

iii) A CELO virus expressing luciferase was prepared by transfecting pCELOLucI into primary embryonic chicken kidney cells as described above.

EXAMPLE 5
Preparation of a CELO vector from a copy of the CELO virus genome contained on a plasmid The region between the DraIII site (originally contained at nt 34,426 in the CELO virus genome) and the XhoI site (originally contained at nt 36,648 in CELO virus genome) were removed from the plasmid pAALMH3 which contains the HindIII fragment from nt 33,920 to nt 38,738, cloned in pAALM. Then it was treated with T4-DNA polymerase to produce blunt ends and ligated with the CMV/luciferase/β-globin fragment (cf. Example 4). In this way the plasmid p7H3Δ34426-36648 Luc was obtained. The CELO/ luciferase/CELO fragment was cut on a HindIII fragment and inserted into the CELO genome of pCELO7 by recombination via the FseI site occurring only once at position 35,694. This yielded the plasmid pCELOΔ 34426-36648Luc. Digestion with SpeI and transfection into embryonic chicken kidney cells yielded a virus CELOΔ 34426-36648Luc. Then further insertions were carried out replacing the luciferase sequence with other genes of interest, using the once occurring PacI site which was introduced with the luciferase sequence.

Figure 6:
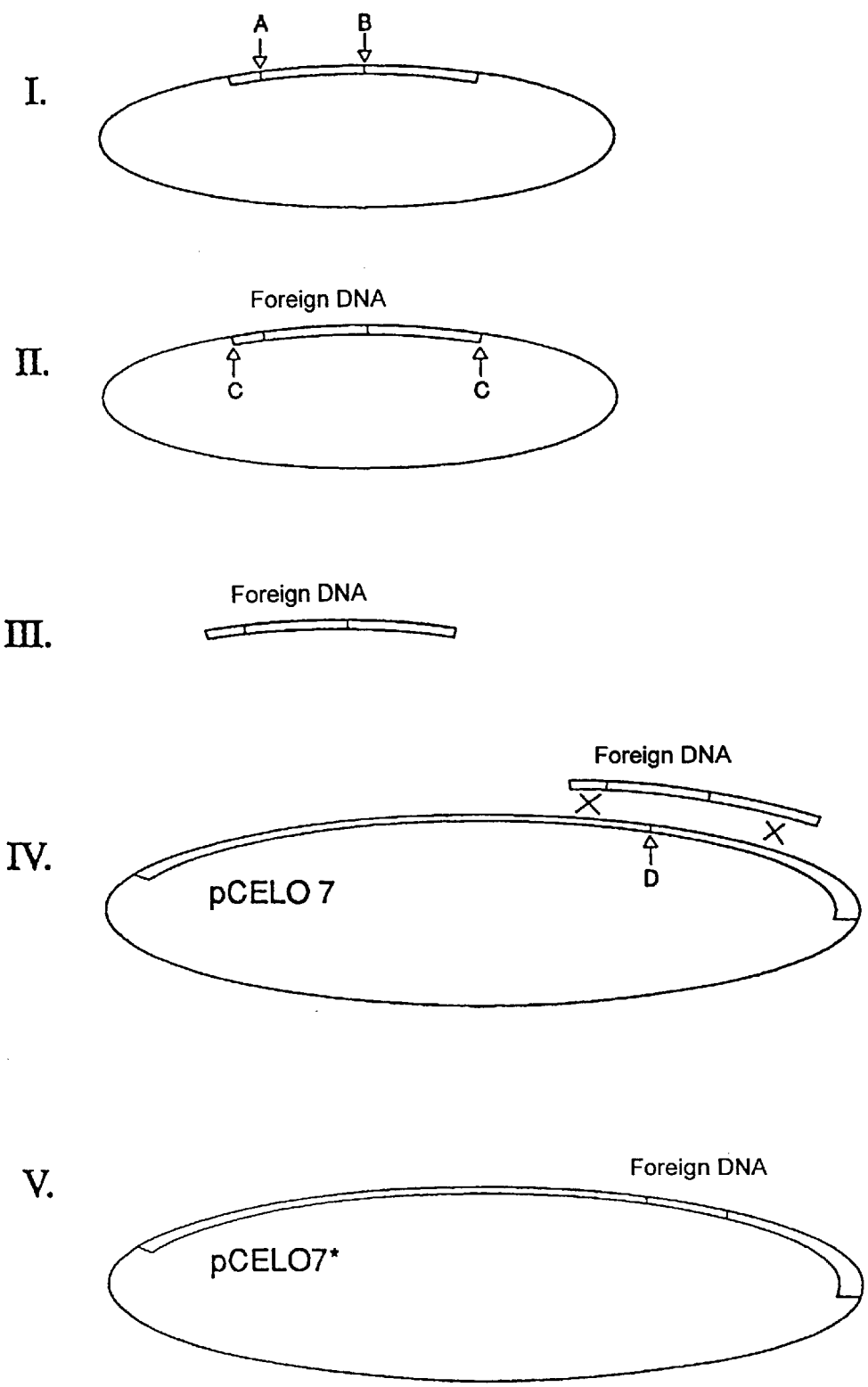
FIG. 6: Preparation of a CELO vector from a copy of the CELO virus genome contained on a plasmid

FIG. 6 shows the cloning strategy used in this Example in general form: a small CELO fragment is subcloned into a plasmid (containing restriction site C); the restriction sites A and B which occur only once in this plasmid are used to replace the sequence with foreign DNA. As the next step, the entire fragment containing the foreign DNA between CELO sequence is cut from the plasmid and mixed with the plasmid which contains the entire CELO DNA and which has been cut with a restriction enzyme (D) which cleaves the CELO-DNA only once. With this mixture, bacteria (e.g. of the strain JC8679; Oliner et al., 1993; or another bacterial strain with a similar capacity for recombination) are transformed; recombination yields the desired plasmid containing the foreign DNA as an insert in the CELO virus genome.

EXAMPLE 6

Preparation of a quail cell line which complements the 7R1 deletions and/or the 9R1 deletions in CELO The plasmids pX7R1 and pX9R1 (described in WO 95/33062) were introduced into primary embryonic quail kidney or liver cells by transferrinfection as described in WO 93/07283. Four days after transfection the cells were trypsinised and seeded at ⅕ of the original density. The cells were fed twice a week with FCK medium. Clonal lines were expanded and clones which carried either the 7R1, 9R1 plasmid or both plasmids were identified by PCR analysis. The RNA expression of the integrated plasmids was determined by Northern analysis.

Figure 7:
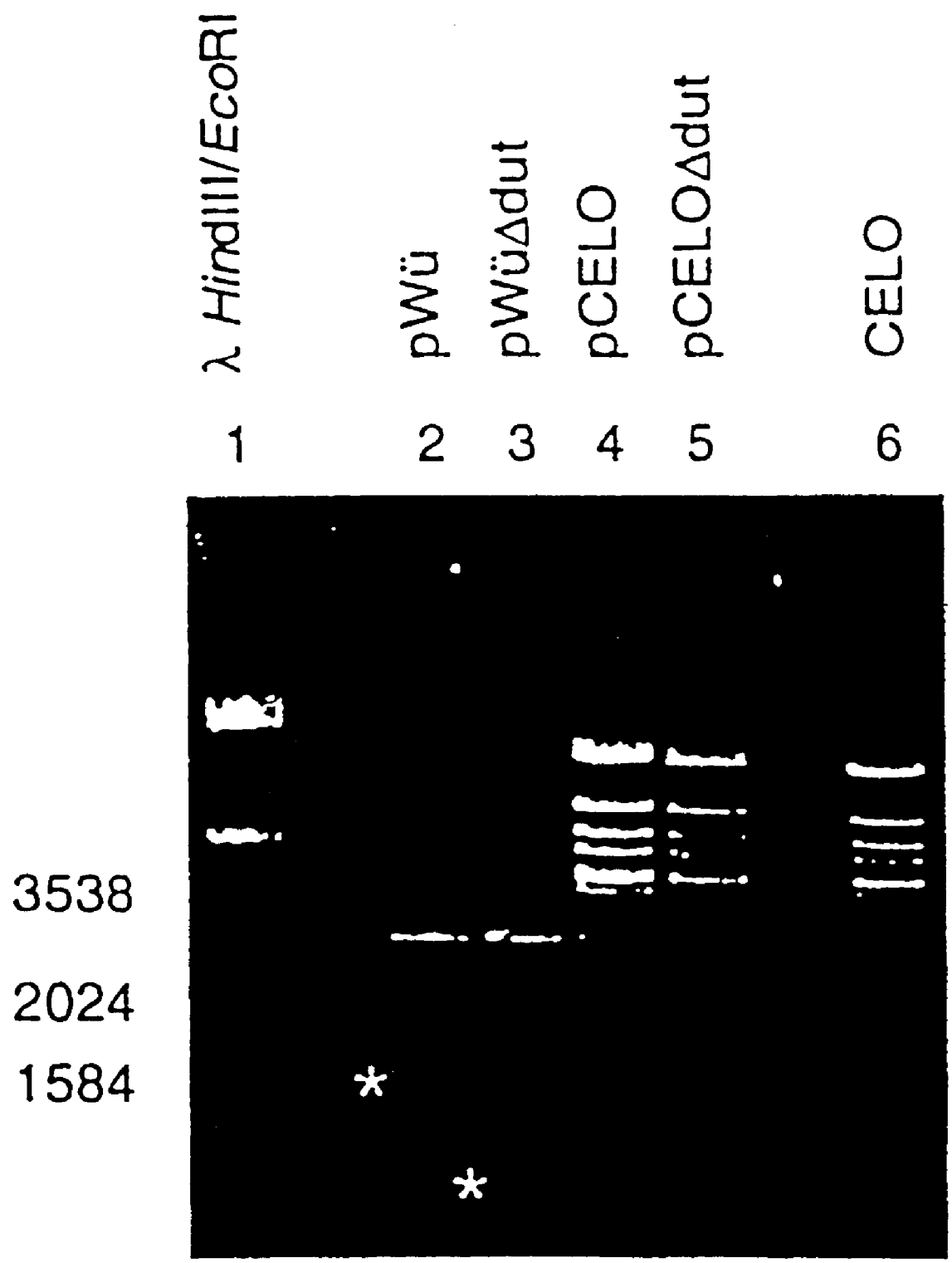
FIG. 7: Identification of bacterial clones which contain a deletion in the dUTPase gene

EXAMPLE 7 a) Preparation of a CELO virus genome with a mutation in the $ORF_{794}$ dUTPase gene A plasmid designated pWuΔdut was produced by removing a 540 bp AflIII-SacI fragment from the $ORF_{794}$ in pWu-H35 (see Example 1 c). In order to product pCELOΔdut, pWuΔdut was linearised with HindIII and dephosphorylated using alkaline shrimp phosphatase. After gel purification the DNA was mixed with purified CELO DNA and used to transform E. coli BJ5183 (Degryse, 1996) to ampicillin resistance. From the ampicillin resistant bacterial colonies obtained the DNA was extracted and E. coli DH5a was transformed therewith. DNA extracted from these bacteria was analysed by restriction mapping in order to identify recombinant virus plasmids. The identity of the clones was determined by restriction mapping (FIG. 7; pWu-H35 is designated "pWu" in the Fig.). The digestion of the Wild type plasmid pWu-H35 with HindIII and SpeI yields fragments of 2944 bp, 1607 bp and 961 bp (track 2). The deletion which changes the dUTPase converts the 1607 bp fragment into a 1071 bp fragment (track 3; the modified fragments are marked with an asterisk). The plasmids which contain the complete sequence coding for CELO or the complete CELO sequence plus the dUTPase mutation were analysed by SpeI/HindIII digestion and showed the same change of the 1607 bp fragment into a 961 bp fragment (tracks 4 and 5).

b) Preparation of recombinant CELO clones from chicken cells

Figure 8:
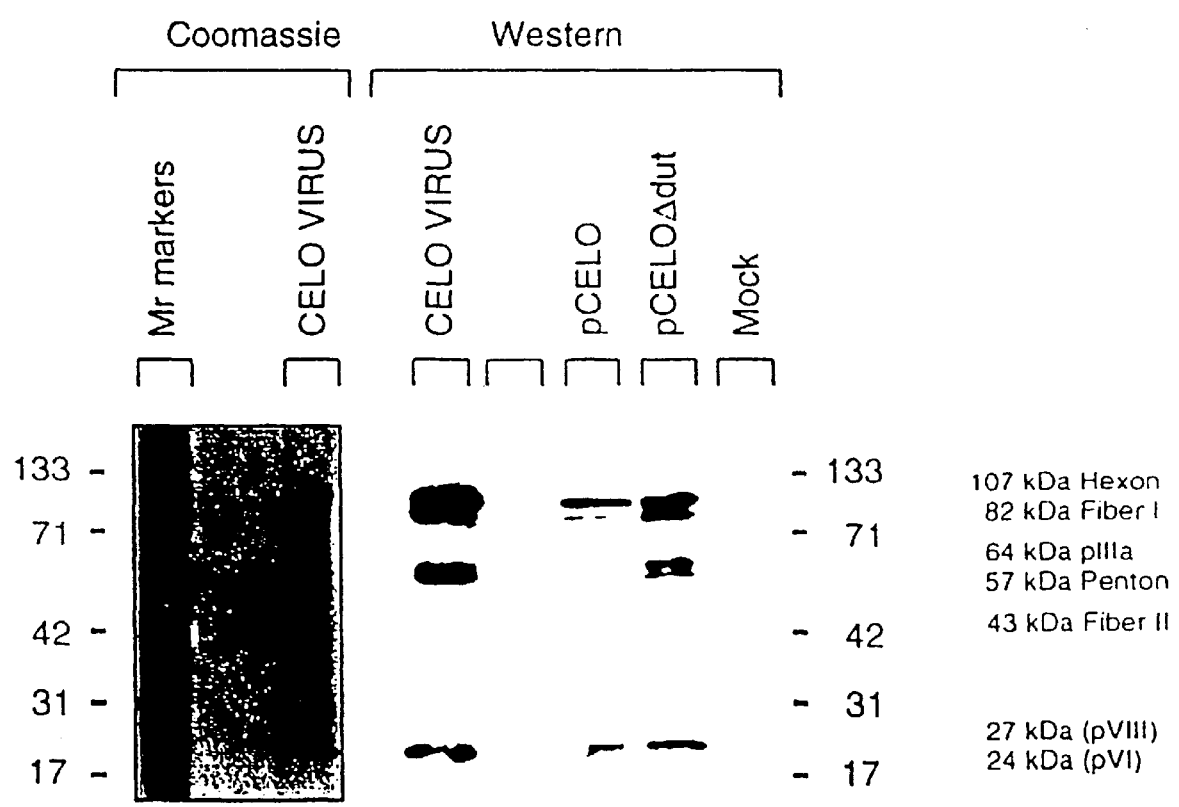
FIG. 8: Comparison of Wild-type CELO and CELO containing a deletion in the dUTPase gene by Western blot analysis.

Either 6 μg pCELO7 (see Example 1 d) or 6 μg of pCELOΔdut (see above, digested with SpeI) were used to transfect primary embryonic chicken kidney cells (approximately 500,000 cells in a 2.5 cm well) using polyethylene amine (PEI)/adenovirus complex. For this, the Qiagen-purified DNA was extracted with Triton X-114 in order to remove lipopolysaccharide as described by Cotten et al., 1994. Transfection complexes were prepared by diluting 6 μg of digested DNA in 250 μl of 20 mM HEPES, pH 7.4. 20 μl of 10 mM PEI (molecular weight 2,000, pH 7) were diluted in 250 μl of 20 mM HEPES, pH 7.4. The PEI solution was added dropwise to the DNA solution, incubated for 20 minutes at ambient temperature and then mixed with 1.5 μl of an adenovirus preparation (psoralen/UV-inactivated adenovirus type 5, cf. WO 1719, $1.5\times10^{12}$ particles/ml). After another 20 minutes the complex was added to the cells in DMEM without serum (250 μl of complex to 1.25 ml of medium). The medium was changed for normal growth medium (with serum) and 4 to 5 days later the cells were harvested, taken up again in 100 μl of HBS and sonicated for 2 minutes. A 10 μl aliquot of this sonicate (virus in passage 1) was used to infect the same number of primary embryonic chicken kidney cells in a 2.5 cm well in a cell culture plate. After another 4 to 5 days the cells were counted in order to determine the cytopathic effect (CPE end point assay or plaque assay, Precious and Russel, 1985). The cells were harvested (virus in passage 2) as in the first step and used to infect fresh chicken cells; harvesting these cells yielded viruses of the third passage, the analysis of which is shown in FIG. 8.

c) Western blots

The virus infected cells were harvested, taken up in HBS and sonicated. Aliquots were mixed with 5×charging buffer (250 mM Tris-Cl, pH 6.8, 500 mM DTT, 10% SDS, 0.5% bromophenol blue, 50% glycerol), heated to 95° C. for 3 minutes and then allowed to run in a 10% polyacrylamide gel. The proteins were transferred onto nitrocellulose, blocked overnight in 5% skimmed milk/TBST (10 mM Tris-Cl, pH 7.4, 150 mM NaCl, 0.05% Tween 20). Viral proteins were shown up using anti-CELO-antisera from rabbits (1:1000) and anti-rabbit-horseradish peroxidase (DAKO; 1:20000) and made visible by ECL (Amersham). CELO virus ($2.5\times10^{12}$ virus particles/ml) was used as the control. The rabbit serum was prepared using CsCl-purified CELO virus and heat-inactivated at 60° C. for 30 minutes.

d) Extraction of virus DNA

Virus infected cells were harvested and taken up in 100 μl of HBS/0.1% SDS/1 g/ml proteinase K, incubated for 1 hour at 56° C. and extracted with phenol/chloroform. The DNA was precipitated with ethanol.

The analyses carried out showed that recombination between the linearised plasmid pWuΔdut and the CELO DNA yielded two types of plasmids. Recombination to the left hand end of the dUTPase mutation yielded a Wild type CELO genome; recombination on the right hand side of the dUTPase mutation yielded a CELO genome which carried the dUTPase mutation.

The infection of primary embryonic chicken cells both with CELO DNA and with CELO-Δdut-DNA produced cytopathic effects which took the form of swollen, detached cells after 36 hours, whereas control cells (treated with lysates of cells which had been transfected with an empty vector (Bluescript pBS, Stratagene)) remained healthy in their morphology.

Western blot analysis showed that CELO viruses and CELO Δdut viruses produced by plasmid DNA are indistinguishable from Wild type virus grown in fertilised, 9 day old hens eggs.

In all, the tests carried out in this example show that pCELO7 codes a viable CELO virus genome. After excision with SpeI and transfection into primary embryonic chicken kidney cells this DNA yields infectious, passagable virus. Lysates of viruses of the 1st and 2nd passage produce a cytopathic effect on primary embryonic chicken kidney cells. It should be noted that these lysates were produced by sonication, which rules out the possibility that the CPE in the secondary and tertiary infections can be put down to the expression of viral genes which originates from the residual plasmid DNA in the lysates; plasmid DNA cannot be expected to withstand the method used to produce the lysates. In addition, it was found that with each round of infection there is a 100 fold amplification of the agent which causes CPE; this conforms to the amplification of a virus but not to the single passage of residual plasmid DNA from the first transfection.

The deletion of 540 bp in the CELO genome with which sequences between an AflIII site at bp 609 and a SacI site at bp 1145 were removed and the open reading frame coding for dUTPase was destroyed, yielded a virus genome which is viable even in primary embryonic chicken cells. With the UTPase gene a virus gene was thus identified which is not necessary for growth in cell culture.

TABLE 1

CELO virus Sequences, published or from data banks

| data bank accession # | authors, publication | size | coordinates in the sequence | differences between published sequences and new sequence (GenBank Accession # U46933) | remarks |
|---|---|---|---|---|---|
|  | Aleström, et al, 1982b | 101 bp | 1–101 | 7 bases different | 5'ITR |
| K00939 | Shinagawa, et al, 1983 | 68 bp | 1–68 | 7 bases different | 5'ITR |
| Z17216, S61107 | Akopian, et al., 1992 | 3576 bp | 1–3576 | 3 bases different 1 missing base 3 additional bases | 92–100% labelled slight differences in these 2 versions |
| Z48167 | unpublished | 3433 bp | 13597–17033 | 6 bases different 4 missing bases 1 additional base | contains genes for penton base and core proteins |
| L13161 | Cai, et al., 1993 | 900 bp | 21023–21922 | no differences | contains protease gene |
| X84724 | Hess, et al., 1995 | 7359 b | 27060–34299 | 2 bases different 6 missing bases 3 additional bases 11 (GCA) repeats (new sequence shows 9) 6 doubtful bases | contains genes for pVIII, fibre 1, fibre 2 |
| M12738 | Larsson, et al., 1986 | 440 bp | 39584–40023 | no differences | contains VA gene |
| Z22864 | unpublished | 3670 bp | 35235–38905 | 2 bases different 4 missing bases 2 additional bases | assigned by the authors: 11.2–19.2% |
| X17217 | Akopian, et al., 1990 | 4898 bp | 38906–43804 | 2 bases different | assigned by the authors: 11.2% |
| K00940 | Shinagawa, et al, 1983 | 68 bp | 43741–43804 | 7 bases different | 3'ITR |
|  | Aleström; et al., 1982b | 124 bp | 43680–43804 | 2 bases different 1 missing base | 3'ITR |

TABLE 2A

Organisation of the CELO Virus Genome

| Protein | ATG | STOP | Cap, cleavage, poly A sites | MW Dalton | Amino acid groups | Remarks |
|---|---|---|---|---|---|---|
| L1 |  |  |  |  |  |  |
| 52K | 12193 | 13329 |  | 42094 | 378 |  |
| IIIa | 13316 | 15043 |  | 63771 | 575 | Protease cleavage site at amino acid 551 |
| L2 |  |  |  |  |  |  |
|  |  |  | 15080 |  |  | Penton base SA |
| Penton base | 15110 | 16657 |  | 56719 | 515 | no RGD |
|  |  |  | 16196 |  |  | poly A-site |
| pVII | 16679 | 16897 |  | 8562 | 72 | Protease cleavage sites at amino acids 27, 40 |
| mu (pX, 11K) | 16929 | 17495 |  | 19787 | 188 | Protease cleavage sites at amino acids 125, 144 |
|  |  |  | 17526 |  |  | poly A-site |
| L3 |  |  |  |  |  |  |
| pVI | 17559 | 18230 |  | 23890 | 223 | Protease cleavage sites at amino acids 28, 212 |
| Hexon | 18289 | 21117 |  | 106704 | 942 |  |
|  |  |  | 18261 |  |  | Hexon SA |
| Protease | 21134 | 21754 |  | 23763 | 206 |  |
|  |  |  | 21102 or 21123 |  |  | Protease SA |
|  |  |  | 21767, 21836 |  |  | L3 poly A-site |

TABLE 2A-continued

Organisation of the CELO Virus Genome

| Protein | ATG | STOP | Cap, cleavage, poly A sites | MW Dalton | Amino acid groups | Remarks |
|---|---|---|---|---|---|---|
| L4 | | | | | | |
| | | | 23608 or 23649 | | | 100K SA |
| 100K | 23680 | 26634 | | 109905 | 984 | |
| pVIII | 27149 | 27886 | | 26876 | 245 | Protease cleavage sites at amino acids 40, 115, 130, 141, 166 |
| | | | 27920 | | | LA poly A-site |
| L5 | | | | | | |
| | | | 28315 or 28341 | | | fibre SA |
| fibre 1 | 28114 | 30495 | | 81526 | 793 | |
| | | | 30509 | | | [GCA]9 repeat |
| | | | 30511 | | | fibre SA |
| fibre 2 | 30536 | 31768 | | 42939 | 410 | |
| | | | 31771 | | | L5 poly A-site |
| VA RNA | | | 39841 to 39751 | | | |
| E2 and IVa2 | | | | | | |
| IVa2 | 6685 | 5366 | | 50366 | 439 | |
| E2b pol | 10268 | 6501 | | 144984 | 1255 | |
| E2b pTP | 11996 | 10269 | | 66089 | 575 | Protease cleavage sites at amino acids 116, 141, 260, 264 |
| DBP | 23224 | 21899 | | 49272 | 441 | |
| | | | 23292 | | | DBP cap site |
| | | | 21824 or 21882 | | | DBP poly A site |

TABLE 2B

Non-assigned open reading frame, larger than 99 amino acid groups

| Right ORFs | | | Left ORFs | | |
|---|---|---|---|---|---|
| ATG | STOP | groups | ATG | STOP | groups |
| 794 | 1330 | 178 | 5094 | 4462 | 210 |
| 1999 | 2829 | 276 | 4568 | 3549 | 339 |
| 3781 | 4095 | 104 | 3374 | 2892 | 160 |
| 5963 | 6373 | 136 | 1514 | 1191 | 107 |
| 33030 | 33476 | 148 | 39705 | 39286 | 139 |
| 33169 | 33483 | 104 | 39256 | 38717 | 179 |
| 35629 | 36024 | 131 | 36144 | 35536 | 202 |
| 37391 | 38239 | 282 | 35599 | 34238 | 453 |
| 40037 | 41002 | 321 | 33707 | 32892 | 271 |
| 41002 | 41853 | 283 | 33058 | 32735 | 107 |
| 41958 | 42365 | 135 | 32429 | 31812 | 251 |

TABLE 3

Recombinant Adenovirus vaccines

| Pathogen | Reference | Comments |
|---|---|---|
| Respiratory Syncytial Virus | Hsu et al., (1994) | Glycoprotein F and G, inserted into the E3 region of Ad 4, 5 or 7 |
| Hepatitis B | Chengalvala et al., (1994) | HBsAg, inserted into the E3 region of Ad 4 oder 7 |
| Pseudorabies | Eloit et al., (1990) | Pseudorabies Glycoprotein gp50, inserted into the E1 region of Ad 5 |
| Herpes Simplex | Zheng et al., (1993) | Tandem repeats of the epitope of gD |
| Herpes Simplex | Gallichan et al., (1993). | Glycoprotein B |

TABLE 3-continued

Recombinant Adenovirus vaccines

| Pathogen | Reference | Comments |
|---|---|---|
| Rotavirus | Both et al., (1993) | Rotavirus antigen, inserted into the E3 region |
| HIV | Natuk et al., (1993) | Ad4, 5 or 7, HIV env, or gag-protease gene |
| SIV | Cheng et al., (1992) | SIV Env Rev, inserted into the E3 region of Ad 5 |
| Rabies | Kalicharran et al., (1992) | Ad5 with rabies glycoprotein |
| Rabies | Charlton et al., (1992) | Ad5 with rabies glycoprotein |
| Human Cytomegalovirus | Marshall et al., (1990) | gB in E3 region of Ad5 |
| Measles virus | Fooks et al., (1995) | N protein in AdE1 Region |

TABLE 4

Characteristics of the CELO Virus Genome.

| Characteristics | Coordinates (Nucleotides) | Category |
|---|---|---|
| Left terminal Repeat | 0–68 | 1 |
| Packaging signal | 70–200 | 1 |
| unknown open reading frame | 0–5365 | 3 |
| L1 | | |
| 52K | 12193–13329 | 2 |
| IIIa | 13316–15043 | 2 |

TABLE 4-continued

Characteristics of the CELO Virus Genome.

| Characteristics | Coordinates (Nucleotides) | Category |
|---|---|---|
| L2 | | |
| penton base SA | 15080 | 2 |
| penton base | 15110–16657 | 2 |
| Poly A site | 16196 | 2 |
| pVII | 16679–16897 | 2 |
| mu (pX, 11K) | 16929–17495 | 2 |
| Poly A site | 17526 | 2 |
| L3 | | |
| pVI | 17559–18230 | 2 |
| Hexon SA | 18261 | 2 |
| Hexon | 18289–21117 | 2 |
| Protease SA | 21102 or 21123 | 2 |
| Protease | 21134–21754 | 2 |
| L3 Poly A site | 21767, 21836 | 2 |
| L4 | | |
| 100K SA | 23608 or 23649 | 2 |
| 100K | 23680–26634 | 2 |
| pVIII | 27149–27886 | 2 |
| LA Poly A site | 27920 | 2 |
| L5 | | |
| fibre SA | 28315 oder 28341 | 2 or 3 |
| fibre 1 | 28114–30495 | 2 or 3 |
| Major Late promoter | 7350–7650 (TATA box at 7488) | 2 or 3 |
| Tripartite Leader | 8651–8700, 8798–8857, 9682–9774 | |
| fibre SA | 30511 | 2 |
| fibre 2 | 30536–31768 | 2 |
| L5 Poly A site | 31771 | 2 |
| VA RNA | 39841 to 39751 | 3 |
| E2 and IVa2 | | |
| IVa2 | 6685–5366 | 3 |
| E2b pol | 10268–6501 | 3 |
| E2b pTP | 11996–10269 | 3 |
| DBP | 23224–21899 | 3 |
| DBP cap site | 23292 | 3 |
| DBP Poly A site | 21824 or 21882 | 3 |
| right end open reading frame | 31771 to 43804 (right end) | 3 |
| right terminal repeat | 43734–43804 (roughly the last 70 bp) | 1 |

Bibliography

Akopian, T. A., et al., 1990, Nucleic Acids Res. 18: 2825. (Corrigendum: Nucleic Acids Res 19: 424).
Akopian, T. A., et al., 1992, Mol. Gen. Microbiol. Virol. 1112: 19–23.
Aleström, P., et al., 1982a, J. Virology 42: 306–310.
Aleström, et al., 1982b, Gene 18: 193–197.
Anderson, J., et al., 1969a, J. Natl. Cancer Inst. 42: 1–7.
Anderson, J., et al., 1969b, J. Natl. Cancer Inst. 43: 575–580.
Anderson, C. W., et al., 1989, Virology 172: 506–512.
Bailey, A. and Mautner, V., 1994. Virology 205: 438–452.
Bennett, D. D. and Wrigth, S. E., 1987, Virus Res. 8: 73–7.
Bett, A. J., Prevec, L. and Graham, F. L., 1993, J. Virol. 67: 5911–5921.
Both et al., 1993, Virology 193: 940–950.
Boulanger, P., et al., 1979, J. Gen. Virol., 44: 783–800.
Bridge, E. and Ketner, G., 1989, J. Virol. 63: 631–638.
Brown, P.H., et al., 1994, Oncogene 9: 791–799.
Cai, F. and Weber, J., 1993, Virology 196: 358–362.
Calnek, B. W. and Cowen, B. S., 1975, Avian Dis. 19: 91–103.
Capado-Kimball and Barbour, 1997, J. Bacteriol. 106: 204–212
Caravokyri, C. and Leppard, K. N., 1995, J. Virol. 69: 6627–6633.
Cavanagh, D., et al., 1988, Virus Res. 11: 141–50.
Charlton et al., 1992, Arch. Virol. 123: 169–179.
Chartier, C., et al., 1996, J. Virol. 70: 4805–4810
Cheng et al., 1992, J. Virol. 66: 6721–6727.
Chengalvala, et al., 1994, J. Gen. Virol. 75: 125–131.
Chiocca, S., et al., 1996, J. Virol. 70: 2939–2949
Chroboczek, J., Bieber, F. and Jacrot, B., 1992, Virology 186: 280–285.
Colby, W. W. and Shenk, T., 1981, J. Virol. 39: 977–980.
Cosset, F. L., et al., 1991, Virology 185: 862–6
Cotten, M., et al., 1993, J. Virol 67: 3777–3785.
Cotten, M., et al., 1994, Virology 205: 254–261
Cotten, M., et al., 1994, Gene Therapy 1: 239–246
Cowen, B., et al., 1978, Avian Diseases 22: 459–470.
Cunningham, C. H., 1975, Dev. Biol. Stand. 28: 546–62.
Davison, A. J., et al., 1993, J. Mol. Biol. 234: 1308–1316.
Degryse, E., 1996, Gene 170: 45–50
Denisova, T. S., Sitnikov, B. S. and Ghibadulin, R. A., 1979, Mol. Biol. (USSR) 13: 1021–1034.
Descombes, P., and Schibler, U., 1991, Cell 67: 569–579
Deshmukh, D. R., et al., 1974, Am. J. Vet. Res. 35: 1463–4.
Eloit et al., 1990, J. Gen. Virol. 71: 2425–2431.
Estes, M. K. and Graham, D. Y., 1985, Adv. Exp. Med. Biol. 185: 201–14.
Everitt, E., et al., 1973, Virology 52: 130–147.
Fooks et al., 1995, Virology 210: 456–465.
Furcinitti, P. S., van Oostrum, J. and Burnett, R. M., 1989, EMBO J. 8: 3563–3570.
Fynan, E. F., et al., 1993, DNA Cell Biol. 12: 785–9.
Gallichan et al., 1993, J. Infect. Dis. 168:622–629.
Gelderblom, H. and Maichle-Lauppe, I., 1982, Arch. Virol. 72: 289–298.
Ghosh-Choudhury, G., Haj-Ahmad, Y. and Graham, F. L., 1987, EMBO J. 6: 1733–1739.
Gillen, J. R., et al., 1974, Mechanisms in Genetic Recombination (R. F. Grell, ed.) Plenum, New York, pp. 123–135
Gooding, L. R., 1992, Cell 71: 5–7.
Gouvea, V. and Schnitzer, T. J., 1982, Infect. Immun. 38: 731–8.
Gouvea, V., et al., 1983, Virology 126: 240–7.
Gräble, M. and Hearing, P., 1990, J. Virol. 64: 2047–2056.
Gräble, M. and Hearing, P., 1992, J. Virol. 66: 723–731.
Graham, F. L., 1990, Trends in Biotechnology 8: 85–87.
Graham, F. L., et al., 1975, Cold Spring Harbor Symp. Quant. Biol. 39: 637–650.
Graham, F. L., et al., 1977, J. Gen. Virol. 36: 59–74.
Green, M., et al., 1967, Proc. Natl. Acad. Sci. USA 57: 1302–1309.
Green, N. M.,et al., 1983, EMBO J. 2: 1357–1365.
Guilhot, C., et al., 1993, Oncogene 8: 619–624.
Haffer, K., 1984, Avian Dis. 28: 669–76.
Hanahan, D., 1983, J. Mol. Biol. 166: 557–580
Hertmann, I., et al., 1979, Avian Dis. 23: 863–9.
Hertmann, I., et al., 1980, Prog. Clin. Biol. Res. 47: 125–32.
Hess, M., et al., 1995, J. Mol. Biol. 252: 379–385.
Hosokawa, K. and Sung, M. T., 1976, J. Virol. 17: 924–934.
Hsu, et al., 1994, Vaccine 12: 607–612.
Huang, D. D., et al., 1987, Avian Dis. 31:446–54.
Ignjatovic, J. and McWaters, P. G., 1991, J. Gen. Virol. 72: 2915–22.
Javier, R., Raska, K. J. and Shenk, T., 1992, Science 257: 1267–1271.
Javier, R. T., 1994, J. Virol. 68: 3917–3924.
Jia, W., et al., 1995, Arch. Virol. 140: 259–271.
Johnson, D. C., et al., 1988, Virology 164: 1–14.
Jones, N., and Shenk, T., 1978, Cell 13: 181–188.
Jones, R. F., Asch, B. B. and Yohn, D. S., 1970, Cancer Res. 30: 1580–1585.

Kalicharran et al., 1992, Can J. Vet Res. 56: 28–33.
Kawamura, H., Sato, T., Tsubahara, H. and Isogai, S., 1963, Jap. Nat. Inst. Anim. Health Quart. 3: 1–10.
Keeler, C. L., et al., 1991, Avian Dis. 35: 920–9.
Kidd, A. H.,et al., 1993 Virology 192: 73–84.
Kodihalli, S., et al., 1994, Vaccine 12: 1467–1472.
Kozarsky, K. F. and Wilson, J. M., 1993, Current Opinion in Genetics and Development 3: 499–503.
Kusters, J. G., et al., 1990, Vaccine 8: 605–8.
Larsson, S., Bellett, A. J. and Akusjarvi, G., 1986, J. Virol. 58: 600–609.
Laver, W. G., Younghusband, H. B. and Wrigley, N. G., 1971, Virology 457, 598–614. Lenstra, J. A., et al., 1989, Mol. Immunol. 26: 7–15.
Li, P., Bellett, A. J. D. and Parish, C. R., 1983, J. Gen. Virol. 64: 1375–1379.
Li, P., Bellett, A. J. D. and Parish, C. R., 1984a, J. Gen. Virol. 65:1803–1815.
Li, P., Bellett, A. J. D. and Parish, C. R., 1984b, J. Virol. 52: 638–649.
Li, P., Bellett, A. J. D. and Parish, C. R., 1984c, J. Virol. 65: 1817–1825.
Maizel, J. V., et al., 1968, Virology 36: 126–136.
Malkinson, M., et al., 1992, Arch. Virol. 127: 169–84.
Mancini, L. O., et al., 1970a, Arch. für gesamte Virusforschung 30: 257–260.
Mancini, L. O., et all, 1970b, Arch. für gesamte Virusforschung 30: 261–262.
Mangel, W., et al., 1993, Nature 36.1: 274–275.
Maniatis, T., et al., 1989, Molecular cloning, A laboratory Manual, Second Edition. Cold Spring Harbor University Press, Cold Spring Harbor, N.Y.
Marshall, et al., 1990, J. Infect. Dis. 162: 1177–1181.
Mautner, V., 1989, Adenoviridae. in: Porterfield ed. Andrewes' Viruses of Vertebrates. pp. 249–282. London: Baillierre Tindall.
McFerran, J. B. and Adair, B. M., 1977, Avian Pathology 6: 189–217.
McCracken, R. M. and Adair, B. M., 1993, Avian adenoviruses. in "Viral Infections of Vertebrates" (volume 3. Viral Infections of Birds) Eds. J. B. McFerran and M. S. McNulty, Elsevier Scientific Publishers. Amsterdam.
Mittal, S. K., et al., 1995, J. Gen. Virol. 76: 93–102.
Moran, E., 1993, the FASEB J. 7: 880–885.
Moran, E., 1994, Seminars in Virology 5: 327–340.
Morrison, T, et al., 1990, Microb. Pathog. 9: 387–96
Moscovici, C., et al., 1977, Cell 11: 95–103.
Natuk, et al., 1993, AIDS Res. Hum Retroviruses. 9: 395–404
Ni, Y., and Kemp, M. C., 1992, J. Gen. Virol. 73: 3107–13.
Nicholas, R. A., et al., 1987, Arch. Virol. 96: 283–7.
Oliner, J. D., et al., 1993, Nucleic Acids Research 21: 5192–5197
Pieniazek, N. J., et al., 1990, Nucl. Acids Res. 18: 1901.
Plank, C., et al., 1992, Bioconjugate Chemistry 3: 533–539
Precious, B. and Russell, W. C., 1985, Virology, ed. Mahy, B. W. J., IRL Press, Oxford, Washington, D.C., 193-205.
Rao, L., et al., 1992, Proc. Natl. Acad. Sci. USA 89: 7742–7746.
Raviprakash, K. S., et al., 1989, J. Virol. 63: 5455–5458.
Roberts,R. J., et al., 1986, A consensus sequence for the adenovirus-2 genome. (in) Doerfler, W. (Ed.); Adenovirus DNA: 1–51; Martinus Nijhoff Publishing, Boston.
Ruley, H. E., 1983, Nature 304: 602–606.
Sarma, P. S., Huebner, R. J. and Lane, W. T., 1965, Science 149: 1108.
Schnitzlein, W. M., et al., 1988, Virus Res. 10: 65–75.
Scott, S. D., et al., 1989, J. Gen. Virol. 70: 3055–65.
Shafren, D. R. and Tannock, G. A., 1991, J. Gen. Virol. 72: 2713–9.
Sheppard, M. and Trist, H., 1992, Virology 188: 881–886.
Shinagawa, M., et al., 1983, Virology 125: 491–495.
Stouten, P. F. W., et al., 1992, J. Mol. Biol. 226: 1073–1084.
Tagaya, Y., et al., 1989, Embo J. 8: 757–764.
Taylor, J., et al., 1995, Vaccine 13: 539–549.
Traenckner, E., B-M., et al., 1995, Embo J. 14: 2876–2883.
Trapnell, B. C. and Gorziglia, M., 1994, Current Opinion in Biotechnology 5: 617–625.
Treanor, J. J., et al., 1991, Vaccine 9: 495–501.
Tripathy, D. N. and Schnitzlein, W. M., 1991, Avian Dis. 35: 186–91.
Van den Ende, M., Don, P. and Kipps, A., 1949, J. Gen. Microbiol. 3: 174–183.
Van der Eb, A. J., et al., 1980, Cold Spring Harbor Symp. Quant. Biol. 44: 383–399.
Vrati, S., et al., 1995, Virology 209: 400–408.
Wagner, E., et al., 1992, Proc. Natl. Acad. Sci. USA 89: 6099–6103.
Weber, J. M., 1995, Current Topics in Microbiology and Immunology 199/I. eds. W. Doerfler and P. Böhm. Springer-Verlag, Heidelberg-Berlin.
Weber, J. and Anderson, C. W., 1988, J. Virol. 62: 1741–1745.
Webster, A., Hay, R. and Kemp, G., 1993, Cell 72: 97–104.
Webster, A., Leith, I. R. and Hay, R. T., 1994, J. Virol. 68: 7292–7300.
Weinberg, D. H. and Ketner, G., 1983, Proc. Natl. Acad. Sci. USA 80: 5383–5386.
White, E., 1994, Seminars in Virology 5: 341–348.
Wold, W. S. M. and Gooding, L. R., 1991, Virology 184, 1–8.
Yates, V. J., and Fry, D. E., 1957, Amer. J. Vet. Res. 18: 657–660.
Zheng, et al., 1993, Vaccine 11: 1191–1198.

What is claimed is:

1. A fowl adenovirus type 1 (CELO) virus DNA comprising the left and right inverted terminal repeats and the packaging signal of the CELO virus genome, wherein said CELO virus DNA contains a deletion of all or part of, an insertion in, or a mutation in, one or more non-essential regions selected from the group consisting of:

(a) nucleotides from about 794 to about 1,330 of SEQ ID NO:1; and (b) nucleotides from about 28,114 to about 30,495 of SEQ ID NO:1.

2. The CELO virus DNA of claim 1, wherein said deletion, insertion or mutation occurs within nucleotides from about 794 to about 1,330 of SEQ ID NO:1.

3. The CELO virus DNA of claim 2, wherein said CELO virus DNA contains a deletion of nucleotides from about 794 to about 1,330 of SEQ ID NO:1.

4. A fowl adenovirus type 1 (CELO) virus DNA comprising the left and right inverted terminal repeats and the packaging signal of the CELO virus genome, wherein said CELO virus DNA contains a deletion of part of, an insertion in, or a mutation in, a non-essential region consisting of nucleotides from about 31,800 to about 43,734 of SEQ ID NO:1, and wherein said CELO virus DNA yields CELO virus particles in suitable cells with or without complementation.

5. The CELO virus DNA of claim 4, wherein said CELO virus DNA further contains a deletion, insertion or mutation within nucleotides from about 794 to about 1,330 of SEQ ID NO:1.

6. The CELO virus DNA of claim 1, wherein said deletion, insertion or mutation occurs within nucleotides from about 28,114 to about 30,495 of SEQ ID NO:1.

7. The CELO virus DNA of claim 6, wherein said CELO virus DNA contains a deletion of nucleotides from about 28,114 to about 30,495 of SEQ ID NO:1.

8. The CELO virus DNA of claim 5, wherein said CELO virus DNA contains a deletion of nucleotides from about 794 to about 1,330 of SEQ ID NO:1.

9. The CELO virus DNA of claim 4, wherein said CELO virus DNA further contains a deletion, insertion or mutation within nucleotides from about 28,114 to about 30,495 of SEQ ID NO:1.

10. The CELO virus DNA of claim 1, wherein said deletion, insertion or mutation occurs within nucleotides from about 794 to about 1,330 and nucleotides from about 28,114 to about 30,495 of SEQ ID NO:1.

11. The CELO virus DNA of claim 10, wherein said CELO virus DNA contains a deletion of nucleotides from about 794 to about 1,330 and nucleotides from about 28,114 to about 30,495 of SEQ ID NO:1.

12. The CELO virus DNA of claim 9, wherein said CELO virus DNA contains a deletion of nucleotides from about 28,114 to about 30,495 of SEQ ID NO:1.

13. The CELO virus DNA of claim 4, wherein CELO virus DNA further contains a deletion, insertion or mutation within nucleotides from about 794 to about 1,330 and nucleotides from about 28,114 to about 30,495 of SEQ ID NO:1.

14. The CELO virus DNA of claim 13, wherein said CELO virus DNA contains a deletion of nucleotides from about 794 to about 1,330 and nucleotides from about 28,114 to about 30,495 of SEQ ID NO:1.

15. The CELO virus DNA of claim 4, wherein said CELO virus genome comprises nucleotides 1 to 43,804 in SEQ ID NO:1.

16. The CELO virus DNA of claim 4, wherein said CELO virus DNA is contained on a plasmid which replicates in bacteria or yeast and which yields virus particles after being introduced into cells.

17. The CELO virus DNA of claim 1, wherein said CELO virus genome comprises nucleotides 1 to 43,804 in SEQ ID NO:1.

18. The CELO virus DNA of claim 1, wherein said CELO virus DNA is contained on a plasmid which replicates in bacteria or yeast and which yields virus particles after being introduced into cells.

19. The CELO virus DNA of claim 18, wherein said CELO virus DNA contains a deletion of a gene which is necessary for the formation of mature virus particles, and wherein said CELO virus DNA, after being introduced into cells together with a plasmid which complements said deleted gene, yields mature virus particles.

20. The CELO virus DNA of claim 1, wherein said CELO virus DNA contains foreign DNA.

21. The CELO virus DNA of claim 20, wherein said foreign DNA encodes a protein.

22. The CELO virus DNA of claim 20, wherein said foreign DNA is inserted in a deleted section.

23. The CELO virus DNA of claim 19, wherein said CELO virus DNA contains foreign DNA.

24. The CELO virus DNA of claim 23, wherein said foreign DNA encodes a protein.

25. The CELO virus DNA of claim 23, wherein said foreign DNA is inserted in a deleted section.

26. The CELO virus DNA of claim 21, wherein said foreign DNA codes for a therapeutically active protein.

27. The CELO virus DNA of claim 26, wherein said foreign DNA codes for an immunostimulatory protein.

28. The CELO virus DNA of claim 27, wherein said foreign DNA codes for a cytokine.

29. The CELO virus DNA of claim 26, wherein said foreign DNA codes for a protein selected from the group consisting of IL-1, IL-2, IL-6, IL-12, GM-CSF, an interferon, IκB, a glucocorticoid receptor, a catalase, manganese superoxide dismutase, glutathione peroxidase, LIP, LAP, ADF, Bcl-2, adenovirus E1B19K, Mcl-2, BAX, IRF-2, ICE protease, cJun, TAM-67, adenovirus E1A, p53, factor VIII, factor IX, erythropoietin, cystic fibrosis transmembrane regulator, dystrophin, globin, the LDL receptor and β-glucuronidase.

30. The CELO virus DNA of claim 20, wherein said foreign DNA codes for a tumor antigen or an immunogenic fragment thereof.

31. The CELO virus DNA of claim 20, wherein said foreign DNA codes for an antigen from a human pathogen.

32. The CELO virus DNA of claim 20, wherein said foreign DNA codes for an antigen from an animal pathogen.

33. The CELO virus DNA of claim 32, wherein said foreign DNA codes for an antigen from a bird pathogen.

34. The CELO virus DNA of claim 20, wherein said foreign DNA codes for a ligand for mammalian cells.

35. The CELO virus DNA of claim 16, wherein said CELO virus DNA contains a deletion of a gene which is necessary for the formation of mature virus particles, and wherein said CELO virus DNA, after being introduced into cells together with a plasmid which complements said deleted gene, yields mature virus particles.

36. The CELO virus DNA of claim 20, wherein said CELO virus DNA contains said foreign DNA on a section comprising nucleotides from about 28,114 to about 30,495 of SEQ ID NO:1, which contains the fibre 1 gene.

37. The CELO virus DNA of claim 20, wherein said CELO virus DNA contains said foreign DNA in the region of the reading frame at nucleotide 794 of SEQ ID NO:1 which codes for dUTPase.

38. The CELO virus DNA of claim 1, wherein said left terminal repeat comprises nucleotides 1 to 68 in SEQ ID NO:1, said packaging signal comprises nucleotides 70 to 200 in SEQ ID NO:1, and said right terminal repeat comprises nucleotides 43,734 to 43,804 in SEQ ID NO:1.

39. The CELO virus DNA of claim 20, wherein said foreign DNA is operably associated with a regulatory sequence.

40. The CELO virus DNA of claim 23, wherein said foreign DNA is operably associated with a regulatory sequence.

41. The CELO virus DNA of claim 39, wherein said regulatory sequence is selected from the group consisting of promoters and enhancers.

42. The CELO virus DNA of claim 41, wherein said promoter is selected from the group consisting of the CMV immediate early promoter, the Rous Sarcoma Virus LTR, the adenovirus major late promoter and the CELO virus major late promoter.

43. A host cell comprising the CELO virus DNA of claim 1.

44. A host cell comprising the CELO virus DNA of claim 20.

45. A host cell comprising the CELO virus DNA of claim 23.

46. A host cell comprising the CELO virus DNA of claim 39.

47. A host cell comprising the CELO virus DNA of claim 40.

48. A method for producing a protein comprising culturing the host cell of claim 44 under conditions such that said protein is expressed, and recovering said protein.

49. A method for producing a protein comprising culturing the host cell of claim 45 under conditions such that said protein is expressed, and recovering said protein.

50. A fowl adenovirus type 1 (CELO) virus DNA comprising the left and right inverted terminal repeats and the packaging signal of the CELO virus genome,
wherein said CELO virus DNA contains a deletion of nucleotides within the region from about 201 to about 5,000 of SEQ ID NO:1, and wherein said CELO virus DNA yields CELO virus particles in suitable cells with or without complementation.

51. The CELO virus DNA of claim 50, wherein said CELO virus genome comprises nucleotides 1 to 43,804 in SEQ ID NO:1.

52. The CELO virus DNA of claim 50, wherein said CELO virus DNA is contained on a plasmid which replicates in bacteria or yeast and which yields virus particles after being introduced into cells.

53. The CELO virus DNA of claim 52, wherein said CELO virus DNA contains a deletion of a gene which is necessary for the formation of mature virus particles, and wherein said CELO virus DNA, after being introduced into cells together with a plasmid which complements said deleted gene, yields mature virus particles.

54. The CELO virus DNA of claim 50, wherein said CELO virus DNA contains foreign DNA.

55. The CELO virus DNA of claim 54, wherein said foreign DNA encodes a protein.

56. The CELO virus DNA of claim 54, wherein said foreign DNA is inserted in the deleted section.

57. The CELO virus DNA of claim 53, wherein said CELO virus DNA contains foreign DNA.

58. The CELO virus DNA of claim 57, wherein said foreign DNA encodes a protein.

59. The CELO virus DNA of claim 57, wherein said foreign DNA is inserted in the deleted section.

60. The CELO virus DNA of claim 55, wherein said foreign DNA codes for a therapeutically active protein.

61. The CELO virus DNA of claim 60, wherein said foreign DNA codes for an immunostimulatory protein.

62. The CELO virus DNA of claim 61, wherein said foreign DNA codes for a cytokine.

63. The CELO virus DNA of claim 60, wherein said foreign DNA codes for a protein selected from the group consisting of IL-1, IL-2, IL-6, IL-12, GM-CSF, an interferon, IκB, a glucocorticoid receptor, a catalase, manganese superoxide dismutase, glutathione peroxidase, LIP, LAP, ADF, Bcl-2, adenovirus E1B19K, Mcl-2, BAX, IRF-2, ICE protease, cjun, TAM-67, adenovirus E1A, p53, factor VIII, factor IX, erythropoietin, cystic fibrosis transmembrane regulator, dystrophin, globin, the LDL receptor and β-glucuronidase.

64. The CELO virus DNA of claim 54, wherein said foreign DNA codes for a tumor antigen or an immunogenic fragment thereof.

65. The CELO virus DNA of claim 54, wherein said foreign DNA codes for an antigen from a human pathogen.

66. The CELO virus DNA of claim 54, wherein said foreign DNA codes for an antigen from an animal pathogen.

67. The CELO virus DNA of claim 66, wherein said foreign DNA codes for an antigen from a bird pathogen.

68. The CELO virus DNA of claim 54, wherein said foreign DNA codes for a ligand for mammalian cells.

69. The CELO virus DNA of claim 50, wherein said left terminal repeat comprises nucleotides 1 to 68 in SEQ ID NO:1, said packaging signal comprises nucleotides 70 to 200 in SEQ ID NO:1, and said right terminal repeat comprises nucleotides 43,734 to 43,804 in SEQ ID NO:1.

70. The CELO virus DNA of claim 54, wherein said foreign DNA is operably associated with a regulatory sequence.

71. The CELO virus DNA of claim 57, wherein said foreign DNA is operably associated with a regulatory sequence.

72. The CELO virus DNA of claim 70, wherein said regulatory sequence is selected from the group consisting of promoters and enhancers.

73. The CELO virus DNA of claim 72, wherein said promoter is selected from the group consisting of the CMV immediate early promoter, the Rous Sarcoma Virus LTR, the adenovirus major late promoter and the CELO virus major late promoter.

74. A host cell comprising the CELO virus DNA of claim 50.

75. A host cell comprising the CELO virus DNA of claim 54.

76. A host cell comprising the CELO virus DNA of claim 57.

77. A host cell comprising the CELO virus DNA of claim 70.

78. A host cell comprising the CELO virus DNA of claim 71.

79. A method for producing of a protein comprising culturing the host cell of claim 54 under conditions such that said protein is expressed, and recovering said protein.

80. A method for producing of a protein comprising culturing the host cell of claim 57 under conditions such that said protein is expressed, and recovering said protein.

81. Process for preparing recombinant CELO virus DNA according to claim 1, characterized in that the CELO virus genome or sections thereof are contained on a plasmid and are genetically manipulated.

82. Process according to claim 81, characterized in that the CELO virus genome or sections thereof contained on a plasmid are manipulated in a region which is different from the left and right inverted terminal repeat and from the packaging signal.

83. Process according to claim 81, characterized in that insertions, insertions and deletions, or deletions are carried out.

84. Process according to claim 82, characterized in that insertions, insertions and deletions, or deletions are carried out.

85. Process according to claim 83, characterized in that a foreign gene is inserted in a naturally occurring or artificially introduced restriction cutting site on a section of the CELO virus DNA which contains a sequence which is not necessary for the replication of the virus in the host cell or which can be complemented.

86. Process according to claim 85, characterized in that in addition to the insertion, a deletion is carried out in another region of the CELO virus DNA which contains a sequence which is not necessary for the replication of the virus in the host cell or which can be complemented.

87. Process according to claim 81, characterized in that the manipulation is carried out by recombination.

88. Process according to claim 82, characterized in that the manipulation is carried out by recombination.

89. Process according to claim 87, characterized in that DNA molecules obtained by polymerase chain reaction are recombined.

90. Process according to claim 87, characterized in that DNA molecules obtained by ligation are recombined.

91. Process according to claim 87, characterized in that DNA molecules obtained by cloning in bacteria are recombined.

92. Process for preparing recombinant CELO virus DNA according to claim 91, comprising:
(a) cloning a CELO virus DNA fragment containing two restriction sites into a bacterial plasmid;
(b) inserting foreign DNA between these restriction sites which occur only once on the plasmid;
(c) excising the fragment containing the foreign DNA from the plasmid and mixing said fragment with a plasmid which contains the complete CELO virus DNA and which has been cut at a restriction cutting site which occurs only once;
(d) transforming the bacteria with this mixture of DNA molecules and growing the bacteria; and
(e) obtaining a plasmid by recombination of the DNA molecules which contains the entire CELO virus DNA with the foreign DNA as an insert.

93. Process according to claim 85, characterized in that a reporter gene is inserted as the foreign DNA.

94. Process according to claim 87, characterized in that a reporter gene is inserted as the foreign DNA.

95. Process according to claim 93, characterized in that the reporter gene has a restriction cutting site into which foreign DNA which codes for a therapeutically active protein is inserted in an additional step.

96. Process according to claim 93, characterized in that the reporter gene has a restriction cutting site into which foreign DNA which codes for a tumor antigen or a fragment thereof is inserted in an additional step.

97. Process according to claim 93, characterized in that the reporter gene has a restriction cutting site into which foreign DNA which codes for an antigen derived from a human pathogen is inserted in an additional step.

98. Process according to claim 93, characterized in that the reporter gene has a restriction cutting site into which foreign DNA which codes for an antigen derived from an animal pathogen is inserted in an additional step.

99. Process according to claim 93, characterized in that the reporter gene has a restriction cutting site into which foreign DNA which codes for a ligand for mammalian cells is inserted in an additional step.

100. Process according to claim 94, characterized in that the reporter gene has a restriction cutting site into which foreign DNA which codes for a therapeutically active protein is inserted in an additional step.

101. Process according to claim 94, characterized in that the reporter gene has a restriction cutting site into which foreign DNA which codes for a tumor antigen or a fragment thereof is inserted in an additional step.

102. Process according to claim 94, characterized in that the reporter gene has a restriction cutting site into which foreign DNA which codes for an antigen derived from a human pathogen is inserted in an additional step.

103. Process according to claim 94, characterized in that the reporter gene has a restriction cutting site into which foreign DNA which codes for an antigen derived from an animal pathogen is inserted in an additional step.

104. Process according to claim 94, characterized in that the reporter gene has a restriction cutting site into which foreign DNA which codes for a ligand for mammalian cell is inserted in an additional step.

105. Process for preparing CELO virus which comprises:
(a) transforming avian cells with a plasmid containing CELO virus DNA of claim 1, thereby obtaining transformed cells;
(b) cultivating said transformed cells (a), thereby obtaining a cell culture; and
(c) harvesting said cell culture (b), thereby preparing CELO virus.

106. Process according to claim 105, characterized in that the CELO virus DNA lacks sequences which are necessary for the formation of mature virus particles, the process which further comprises complementing said sequences.

107. Process according to claim 106, characterized in that the avian cells used are helper cells which complement said sequences which are necessary for the formation of mature virus particles.

108. Process according to claim 106, characterized in that the avian cells are also transformed with a plasmid which complements said sequences necessary for the formation of mature virus particles.

109. Process according to claim 106, characterized in that the avian cells are also infected with a helper virus which complements said sequences necessary for the formation of mature virus particles.

110. The CELO virus DNA of claim 4, wherein said CELO virus DNA contains foreign DNA.

111. The CELO virus DNA of claim 110, wherein said foreign DNA encodes a protein.

112. The CELO virus DNA of claim 110, wherein said foreign DNA is inserted in a deleted section.

113. The CELO virus DNA of claim 35, wherein said CELO virus DNA contains foreign DNA.

114. The CELO virus DNA of claim 113, wherein said foreign DNA encodes a protein.

115. The CELO virus DNA of claim 113, wherein said foreign DNA is inserted in a deleted section.

116. The CELO virus DNA of claim 111, wherein said foreign DNA codes for a therapeutically active protein.

117. The CELO virus DNA of claim 116, wherein said foreign DNA codes for an immunostimulatory protein.

118. The CELO virus DNA of claim 117, wherein said foreign DNA codes for a cytokine.

119. The CELO virus DNA of claim 116, wherein said foreign DNA codes for a protein selected from the group consisting of IL-1, IL-2, IL-6, IL-12, GM-CSF, an interferon, IκB, a glucocorticoid receptor, a catalase, manganese superoxide dismutase, glutathione peroxidase, LIP, LAP, ADF, Bcl-2, adenovirus E1B19K, Mcl-2, BAX, IRF-2, ICE protease, cjun, TAM-67, adenovirus E1A, p53, factor VIII, factor IX, erythropoietin, cystic fibrosis transmembrane regulator, dystrophin, globin, the LDL receptor and β-glucuronidase.

120. The CELO virus DNA of claim 110, wherein said foreign DNA codes for a tumor antigen or an immunogenic fragment thereof.

121. The CELO virus DNA of claim 110, wherein said foreign DNA codes for an antigen from a human pathogen.

122. The CELO virus DNA of claim 110, wherein said foreign DNA codes for an antigen from an animal pathogen.

123. The CELO virus DNA of claim 122, wherein said foreign DNA codes for an antigen from a bird pathogen.

124. The CELO virus DNA of claim 110, wherein said foreign DNA codes for a ligand for mammalian cells.

125. The CELO virus DNA of claim 110, wherein said CELO virus DNA contains said foreign DNA at about the FseI cutting site which is located at position 35,693 of SEQ ID NO:1.

126. The CELO virus DNA of claim 4, wherein said left terminal repeat comprises nucleotides 1 to 68 in SEQ ID NO:1, said packaging signal comprises nucleotides 70 to 200 in SEQ ID NO:1, and said right terminal repeat comprises nucleotides 43,734 to 43,804 in SEQ ID NO:1.

127. The CELO virus DNA of claim 110, wherein said foreign DNA is operably associated with a regulatory sequence.

128. The CELO virus DNA of claim 113, wherein said foreign DNA is operably associated with a regulatory sequence.

129. The CELO virus DNA of claim 127, wherein said regulatory sequence is selected from the group consisting of promoters and enhancers.

130. The CELO virus DNA of claim 129, wherein said promoter is selected from the group consisting of the CMV immediate early promoter, the Rous Sarcoma Virus LTR, the adenovirus major late promoter and the CELO virus major late promoter.

131. A host cell comprising the CELO virus DNA of claim 4.

132. A host cell comprising the CELO virus DNA of claim 110.

133. A host cell comprising the CELO virus DNA of claim 113.

134. A host cell comprising the CELO virus DNA of claim 127.

135. A host cell comprising the CELO virus DNA of claim 128.

136. A method for producing a protein comprising culturing the host cell of claim 132 under conditions such that said protein is expressed, and recovering said protein.

137. A method for producing a protein comprising culturing the host cell of claim 133 under conditions such that said protein is expressed, and recovering said protein.

138. A process for preparing recombinant CELO virus DNA according to claim 4, characterized in that the CELO virus genome or sections thereof are contained on a plasmid and are genetically manipulated.

139. The process according to claim 138, characterized in that the CELO virus genome or sections thereof contained on a plasmid are manipulated in a region which is different from the left and right inverted terminal repeat and from the packaging signal.

140. The process according to claim 138, characterized in that insertions, insertions and deletions, or deletions are carried out.

141. The process according to claim 139, characterized in that insertions, insertions and deletions, or deletions are carried out.

142. The process according to claim 140, characterized in that a foreign gene is inserted in a naturally occurring or artificially introduced restriction cutting site on a section of the CELO virus DNA which contains a sequence which is not necessary for the replication of the virus in the host cell or which can be complemented.

143. The process according to claim 142, characterized in that in addition to the insertion, a deletion is carried out in another region of the CELO virus DNA which contains a sequence which is not necessary for the replication of the virus in the host cell or which can be complemented.

144. The process according to claim 138, characterized in that the manipulation is carried out by recombination.

145. The process according to claim 139, characterized in that the manipulation is carried out by recombination.

146. The process according to claim 144, characterized in that DNA molecules obtained by polymerase chain reaction are recombined.

147. The process according to claim 144, characterized in that DNA molecules obtained by ligation are recombined.

148. The process according to claim 144, characterized in that DNA molecules obtained by cloning in bacteria are recombined.

149. The process for preparing recombinant CELO virus DNA according to claim 148, comprising:
    (a) cloning a CELO virus DNA fragment containing two restriction sites into a bacterial plasmid;
    (b) inserting foreign DNA between these restriction sites which occur only once on the plasmid;
    (c) excising the fragment containing the foreign DNA from the plasmid and mixing said fragment with a plasmid which contains the complete CELO virus DNA and which has been cut at a restriction cutting site which occurs only once;
    (d) transforming the bacteria with this mixture of DNA molecules and growing the bacteria; and
    (e) obtaining a plasmid by recombination of the DNA molecules which contains the entire CELO virus DNA with the foreign DNA as an insert.

150. The process according to claim 142, characterized in that a reporter gene is inserted as the foreign DNA.

151. The process according to claim 144, characterized in that a reporter gene is inserted as the foreign DNA.

152. The process according to claim 150, characterized in that the reporter gene has a restriction cutting site into which foreign DNA which codes for a therapeutically active protein is inserted in an additional step.

153. The process according to claim 150, characterized in that the reporter gene has a restriction cutting site into which foreign DNA which codes for a tumor antigen or a fragment thereof is inserted in an additional step.

154. The process according to claim 150, characterized in that the reporter gene has a restriction cutting site into which foreign DNA which codes for an antigen derived from a human pathogen is inserted in an additional step.

155. The process according to claim 150, characterized in that the reporter gene has a restriction cutting site into which foreign DNA which codes for an antigen derived from an animal pathogen is inserted in an additional step.

156. The process according to claim 150, characterized in that the reporter gene has a restriction cutting site into which foreign DNA which codes for a ligand for mammalian cells is inserted in an additional step.

157. The process according to claim 151, characterized in that the reporter gene has a restriction cutting site into which foreign DNA which codes for a therapeutically active protein is inserted in an additional step.

158. The process according to claim 151, characterized in that the reporter gene has a restriction cutting site into which foreign DNA which codes for a tumor antigen or a fragment thereof is inserted in an additional step.

159. The process according to claim 151, characterized in that the reporter gene has a restriction cutting site into which foreign DNA which codes for an antigen derived from a human pathogen is inserted in an additional step.

160. The process according to claim 151, characterized in that the reporter gene has a restriction cutting site into which foreign DNA which codes for an antigen derived from an animal pathogen is inserted in an additional step.

161. The process according to claim 151, characterized in that the reporter gene has a restriction cutting site into which foreign DNA which codes for a ligand for mammalian cells is inserted in an additional step.

162. A process for preparing CELO virus which comprises:
   (a) transforming avian cells with a plasmid containing CELO virus DNA of claim 4, thereby obtaining transformed cells;
   (b) cultivating said transformed cells (a), thereby obtaining a cell culture; and
   (c) harvesting said cell culture (b), thereby preparing CELO virus.

163. The process according to claim 162, characterized in that the CELO virus DNA lacks sequences which are necessary for the formation of mature virus particles and complementing said sequences.

164. The process according to claim 163, characterized in that the avian cells used are helper cells which complement said sequences which are necessary for the formation of mature virus particles.

165. The process according to claim 163, characterized in that the avian cells are also transformed with a plasmid which complements said sequences necessary for the formation of mature virus particles.

166. The process according to claim 163, characterized in that the avian cells are also infected with a helper virus which complements said sequences necessary for the formation of mature virus particles.

* * * * *

UNITED STATES PATENT AND TRADEMARK OFFICE
CERTIFICATE OF CORRECTION

PATENT NO.    : 6,335,016 B1
DATED         : January 1, 2002
INVENTOR(S)   : Baker et al.

It is certified that error appears in the above-identified patent and that said Letters Patent is hereby corrected as shown below:

Column 177,
Line 57, please delete "cjun" and insert therein -- cJun --.

Column 180,
Line 53, please delete "cjun" and insert therein -- cJun --.

Signed and Sealed this

Twelfth Day of November, 2002

Attest:

JAMES E. ROGAN
Attesting Officer     Director of the United States Patent and Trademark Office